United States Patent [19]
Burns et al.

[11] Patent Number: 6,060,038
[45] Date of Patent: May 9, 2000

[54] RADIOLABELED FARNESYL-PROTEIN TRANSFERASE INHIBITORS

[75] Inventors: Hugh D. Burns, Harleysville; Wai-Si Eng, Maple Glen; Raymond E. Gibson, Holland, all of Pa.

[73] Assignee: Merck & Co., Inc., Rahway, N.J.

[21] Appl. No.: 09/074,346

[22] Filed: May 7, 1998

Related U.S. Application Data

[60] Provisional application No. 60/046,539, May 15, 1997.

[51] Int. Cl.$^7$ .......................... A61K 51/04; C07D 241/00
[52] U.S. Cl. .................... 424/1.81; 424/1.85; 424/1.89; 544/336; 544/386; 544/392; 544/406
[58] Field of Search .................. 424/1.81, 1.85, 424/1.89, 1.65; 544/224, 358, 366, 386, 392, 406, 336; 548/311.1, 335.3, 343.5, 517; 435/15; 436/504; 514/18, 317, 400, 450, 252, 255; 549/266, 271, 293, 320

[56] References Cited

U.S. PATENT DOCUMENTS

| | | | |
|---|---|---|---|
| 4,960,815 | 10/1990 | Moos | 424/1.11 |
| 4,994,258 | 2/1991 | Burns et al. | 424/1.11 |
| 5,141,851 | 8/1992 | Brown et al. | 435/15 |
| 5,238,922 | 8/1993 | Graham et al. | 514/18 |
| 5,340,828 | 8/1994 | Graham et al. | 514/357 |
| 5,352,705 | 10/1994 | Deana et al. | 514/630 |
| 5,439,918 | 8/1995 | De Solms et al. | 514/307 |
| 5,504,212 | 4/1996 | De Solms et al. | 546/336 |
| 5,534,537 | 7/1996 | Ciccarone et al. | 514/397 |
| 5,571,835 | 11/1996 | Anthony et al. | 514/428 |
| 5,578,629 | 11/1996 | Ciccarone et al. | 514/397 |
| 5,609,849 | 3/1997 | Kung | 424/1.85 |

FOREIGN PATENT DOCUMENTS

| | | | |
|---|---|---|---|
| WO 95/25086 | 9/1995 | WIPO | C07C 237/20 |
| WO 96/00736 | 1/1996 | WIPO | C07K 5/078 |
| WO 96/30343 | 10/1996 | WIPO . | |

OTHER PUBLICATIONS

Gibbs, J.B. et al., "Selective Inhibition of Farnesyl–Protein Transferase Blocks Ras Processing in Vivo," The Journal of Biological Chemistry, vol. 268, No. 11, pp. 7617–7620 (1993).

Goldstein, J.L. et al., "Nonfarnesylated Tetrapeptide Inhibitors of Protein Farnesyltransferase," The Journal of Biological Chemistry, vol. 266, No. 24, pp. 15575–15578 (1991).

Graham, S.L., "Inhibitors of protein farnesylation: a new approach to cancer chemotherapy ," Exp. Opin. Ther. Patents vol. 5 (12), pp. 1269–1285 (1995).

James, G., et al., "Polylysine and CVIM Sequences of K–RasB Dictate Specificity of Prenylation and Confer Resistance to Benzodiazepine Peptidomimetic in Vitro," The Journal of Biological Chemistry, vol. 270, No. 11, pp. 6221–6226 (1995).

Kohl, N.E., et al., "Inhibition of farnesyltransferase induces regression of mammary and salivary carcinomas in ras transgenic mice," Nature Medicine, vol. 1, No. 8, pp. 792–797 (1995).

Kohl, N.E. et al., "Protein farnesyltransferase inhibitors block the growth of ras–dependent tumors in nude mice", Proc. Natl. Acad. Sci. USA, Med. Sciences, vol. 91, pp. 9141–9145 (1994).

Kohl, N.E. et al., "Selective Inhibition of ras–Dependent Transformation by a Farnesyltransferase Inhibitor", Science, vol. 260, pp. 1934–1937 (1993).

Pompliano, D.L., "Steady–State Kinetic Mechanism of Ras Farnesyl: Protein Transferase," Biochemistry, vol. 31, pp. 3800–3807 (1992).

Sepp–Lorenzino, L., et al., "A Pepitodomimetic Inhibitor of Farnesyl:Protein Transferase Blocks the Anchorage–dependent and –independent Growth of Human Tumor Cell Lines," Cancer Research, vol. 55, pp. 5302–5309 (1995).

Graham, S.L. et al., "Inhibitors of protein farnesylation," Exp. Opin. Ther. Patents, vol. 6 (12), pp. 1295–1304 (1996).

*Primary Examiner*—Jose' G. Dees
*Assistant Examiner*—Michael G. Hartley
*Attorney, Agent, or Firm*—Dianne Pecoraro; Mark R. Daniel

[57] ABSTRACT

The present invention is directed toward radiolabeled farnesyl-protein transferase inhibitor compounds which are useful to label FPTase in assays, whether cell-based, tissue-based or in whole animal. The tracers can also be used in competitive binding assays to obtain information on the interaction of unlabeled FTIs with FPTase.

8 Claims, No Drawings

RADIOLABELED FARNESYL-PROTEIN TRANSFERASE INHIBITORS

The priority of U.S. Provisional Application Ser. No. 60/046,539, filed on May 15, 1997, now abandoned, is claimed.

BACKGROUND OF THE INVENTION

Noninvasive, nuclear imaging techniques can be used to obtain basic and diagnostic information about the physiology and biochemistry of a variety of living subjects including experimental animals, normal humans and patients. These techniques rely on the use of sophisticated imaging instrumentation which is capable of detecting radiation emitted from radiotracers administered to such living subjects. The information obtained can be reconstructed to provide planar and tomographic images which reveal distribution of the radiotracer as a function of time. Use of appropriately designed radiotracers can result in images which contain information on the structure, function and most importantly, the physiology and biochemistry of the subject. Much of this information cannot be obtained by other means. The radiotracers used in these studies are designed to have defined behaviors in vivo which permit the determination of specific information concerning the physiology or biochemistry of the the subject or the effects that various diseases or drugs have on the physiology or biochemistry of the the subject. Currently, radiotracers are available for obtaining useful information concerning such things as cardiac function, myocardial blood flow, lung perfusion, liver function, brain blood flow, regional brain glucose and oxygen metabolism.

Compounds can be labeled with either positron or gamma emitting radionuclides. For imaging, the most commonly used positron emitting radionuclidesare $^{11}C$, $^{18}F$, $^{15}O$ and $^{13}N$, all of which are accelerator produced, and have half lifes of 20, 110, 2 and 10 min. respectively. Since the half-lives of these radionuclides are so short, it is only feasible to use them at institutions which have an accelerator on site for their production, thus limiting their use. Several gamma emitting radiotracers are available which can be used by essentially any hospital in the U.S. and in most hospitals worldwide. The most widely used of these are $^{99m}Tc$, $^{201}Tl$, and $^{123}I$. $^{123}I$ is particularly useful as a radiotracer for imaging applications because of its ability to form covalent bonds with carbon which, in many cases, are stable in vivo and which have well-understood effects on physiochemical properties of small molecules.

In the past decade, one of the most active areas of nuclear medicine research has been the development of receptor imaging radiotracers. These tracers bind with high affinity and specificity to selective hormone receptors and neuroreceptors. Successful examples include radiotracers for imagining the following receptor systems: estrogen, muscarinic, dopamine D1 and D2, and opiate.

Currently available chemotherapeutic drugs for treating neoplastic diseases act by disrupting fundamental mechanisms concerned with cell growth, mitotic activity, differentiation and function. The capacity of these drugs to interfere with normal mitosis and cell division in rapidly proliferating tissues is the basis for their therapeutic application as well as toxic properties. As a result, clinical doses of antitumor drugs are a compromise between efficacy and toxicity such that therapeutic doses are usually set close to the toxic levels in order to maximize efficacy. In a similar manner, dose selection for clinical evaluation of new antitumor drugs is a function of the toxicity of the drug where doses used in Phase II and III trials are often the maximally tolerated doses.

The Ras proteins (Ha-Ras, Ki4a-Ras, Ki4b-Ras and N-Ras) are part of a signalling pathway that links cell surface growth factor receptors to nuclear signals initiating cellular proliferation. Mutated ras genes (Ha-ras, Ki4a-ras, Ki4b-ras and N-ras) are found in many human cancers, including colorectal carcinoma, exocrine pancreatic carcinoma, and myeloid leukemias. The protein products of these genes are defective in their GTPase activity and constitutively transmit a growth stimulatory signal.

At least 3 post-translational modifications are involved with Ras membrane localization, required for normal and oncogenic function, and all 3 modifications occur at the C-terminus of Ras. The Ras C-terminus contains a sequence motif termed a "CAAX" or "Cys-Aaa$^1$-Aaa$^2$-Xaa" box, which, depending on the specific sequence, serves as a signal sequence for the enzymes farnesyl-protein transferase or geranylgeranyl-protein transferase, which catalyze the alkylation of the cysteine residue of the CAAX motif with a $C_{15}$ or $C_{20}$ isoprenoid, respectively. (S. Clarke., *Ann. Rev. Biochem.* 61:355–386 (1992); W. R. Schafer and J. Rine, *Ann. Rev. Genetics* 30:209–237 (1992)). The Ras protein is one of several proteins that are known to undergo post-translational farnesylation. Other farnesylated proteins include the Ras-related GTP-binding proteins such as Rho, fungal mating factors, the nuclear lamins, and the gamma subunit of transducin. James, et al., *J. Biol. Chem.* 269, 14182 (1994) have identified a peroxisome associated protein Pxf which is also farnesylated. James, et al., have also suggested that there are farnesylated proteins of unknown structure and function in addition to those listed above.

Inhibition of farnesyl-protein transferase has been shown to block the growth of Ras-transformed cells in soft agar and to modify other aspects of their transformed phenotype. Recently, it has been shown that an inhibitor of farnesyl-protein transferase blocks the growth of ras-dependent tumors in nude mice (N. E. Kohl et al., *Proc. Natl. Acad. Sci U.S.A.*, 91:9141–9145 (1994) and induces regression of mammary and salivary carcinomas in ras transgenic mice (N. E. Kohl et al., *Nature Medicine*, 1:792–797 (1995).

Farnesyl transferase inhibitors (FTIs) represent a new pharmacological approach to the treatment of cancer that is mechanism-based and does not rely on a cytotoxic mechanism of action. Ideally, therapeutically effective doses of FTIs will not be limited by cytotoxic side effects and these compounds will have a much larger therapeutic window than currently available antitumor drugs.

Farnesyl-protein transferase inhibitors may also be useful for inhibiting other proliferative diseases, both benign and malignant, wherein Ras proteins are aberrantly activated as a result of oncogenic mutation in other genes (i.e., the Ras gene itself is not activated by mutation to an oncogenic form) with said inhibition being accomplished by the administration of an effective amount of the instant composition to a mammal in need of such treatment. For example, a component of NF-1 is a benign proliferative disorder.

Use of farnesyl-protein transferase inhibitors in the prevention of restenosis after percutaneous transluminal coronary angioplasty by inhibiting neointimal formation has recently been described (C. Indolfi et al. *Nature medicine*, 1:541–545(1995)). It has been disclosed that farnesyl-protein transferase inhibitors may also be useful in the treatment and prevention of polycystic kidney disease (D. L. Schaffner et al. *American Journal of Pathology*, 142:1051–1060 (1993) and B. Cowley, Jr. et al. *FASEB Journal*, 2:A3160 (1988)).

It has recently been reported that farnesyl-protein transferase inhibitors are inhibitors of proliferation of vascular smooth muscle cells and are therefore useful in the prevention and therapy of arteriosclerosis and diabetic disturbance of blood vessels (JP H7-112930).

In contrast to cytotoxic chemotherapeutic agents, a more rational approach for estimating clinically-effective doses can be used with FTIs, i.e. it may not be necessary to titrate doses in a patient until toxic effects are observed if that dose is considerably higher than needed to provide the desired effect on tumor growth. Alternatively, if dose-limiting toxicity is observed with the clinical FTI, the dose may not be sufficient to inhibit the enzyme to the extent needed to block tumor growth. Demonstration of clinical efficacy using inhibition of tumor growth or regression in tumor size as an endpoint will require considerable time (weeks to months) and, therefore, dose selection for these trials is very important. Plasma drug concentrations are often used for clinical dose selection, however this endpoint may be a poor surrogate for the drug concentration at the pharmacological target, especially when the site of action is intracellular, such as is the case with farnesyl transferase. PET (Positron Emission Tomography) radiotracers and imaging technology may provide a powerful method for clinical evaluation and dose selection of FTIs. Using a carbon-11 or fluorine-18 labeled radiotracer that enters cells and provides a farnesyl transferase (FPTase) enzyme-specific image in tumors and other tissues, the dose required to saturate FPTase can be determined by the blockade of the PET radiotracer image in humans. The rationale for this approach is as follows: anti-tumor efficacy of FTIs is a consequence of the extent of enzyme inhibition, which in turn is a function of the degree of drug-enzyme occupancy.

It is, therefore, an object of this invention to develop radiolabeled farnesyl-protein transferase inhibitor compounds that would be useful not only in traditional imaging applications, but would also be useful in assays, both in vitro and in vivo, for labeling the enzyme and for competing with unlabeled farnesyl-protein transferase inhibitors (FTIs). It is a further object of this invention to develop novel assays which comprise such radiolabeled compounds.

It is also the object of this invention to provide for a radiolabeled farnesyl-protein transferase inhibitor compound which is optimized for in vivo imaging and is therefore useful for determining the appropriate clinical doses of an FTI which will be used to assess antitumor efficacy in humans.

SUMMARY OF THE INVENTION

The present invention is directed toward radiolabeled farnesyl-protein transferase inhibitor compounds which are useful to label FPTase in assays, whether cell-based, tissue-based or whole animal. The tracers can also be used in competitive binding assays to obtain information on the interaction of unlabeled FTIs with FPTase.

DETAILED DESCRIPTION OF THE INVENTION

The present invention is directed toward radiolabeled farnesyl-protein transferase inhibitor compounds which are useful for labeling farnesyl-protein transferase (FPTase) in assays, whether cell-based, tissue-based or in whole animal. Such radiolabeled compounds can also be used in competitive binding assays to obtain information on the interaction of unlabeled FTIs with FPTase. The in vitro and in vivo assays utilizing the instant radiolabeled compounds are useful in identification of novel compounds that are highly selective inhibitors of FPTase and are therefore useful in the treatment of cancer. The radiolabeled compounds may also be useful in autoradiography and as diagnostic imaging agents.

Suitable radionuclides that may be incorporated in the instant compounds include $^{3}H$ (also written as T), $^{11}C$, $^{18}F$, $^{125}I$, $^{82}Br$, $^{123}I$, $^{131}I$, $^{75}Br$, $^{15}O$, $^{13}N$, $^{211}At$ or $^{77}Br$. The radionuclide that is incorporated in the instant radiolabeled compounds will depend on the specific analytical or pharmaceutical application of that radiolabeled compound. Thus, for in vitro FPTase labeling and competition assays, inhibitor compounds that incorporate $^{3}H$, $^{125}I$ or $^{82}Br$ will generally be most useful. For diagnostic imaging agents, inhibitor compounds that incorporate a radionuclide selected from $^{11}C$, $^{18}F$, $^{123}I$, $^{131}I$, $^{75}Br$, $^{76}Br$ or $^{77}Br$ are preferred. In certain applications incorporation of a chelating radionuclide such as $Tc^{99m}$ may also be useful.

The labeled farnesyl-protein transferase inhibitor should bind with a high affinity to FPTase. Preferably, the labeled inhibitor has an $IC_{50} \leq 10$ nM, and most preferably the labeled inhibitor has an $IC_{50} \leq 5$ nM.

Because the FPTase that is interacting with the labeled inhibitor is generally cellular FPTase, the labeled inhibitor of the instant invention must be diffuseable across the cell membrane and remain diffuseable after binding to FPTase to avoid intracellular accumulation of labeled inhibitor which might contribute to greater assay background noise. Therefore, it is preferred that the labeled inhibitor have a lipophilicity (partition coefficient) in the range of about 0.5 to about 3.5 and preferably in the range of about 1.0 to about 3.0. It is also preferred that the labeled inhibitor chosen is generally free from nonspecific intracellular interactions that would alter the compounds permeability or effect its FPTase binding affinity. Therefore, while many farnesyl-protein transferase inhibitors have been described that incorporate a thiol moiety, the nonspecific interactions associated with such a moiety disfavor those inhibitors. Similarly, ester prodrugs which exhibit potent intercellular FPTase inhibitory activity only upon conversion to their corresponding acid within the cell are also disfavored because the conversion to the active acid would alter the permeability of the labeled inhibitor.

Radiolabeled FPTase inhibitor compounds, when labeled with the appropriate radionuclide, are potentially useful for diagnostic imaging, basic research, and radiotherapeutic applications. Specific examples of possible diagnostic imaging applications include:

1. Location of primary and metastatic tumors of the pancreas; exocrine tumors;
2. Diagnosis and staging of colorectal carcinoma.
3. Diagnosis and staging of myeloid leukemia.
4. Diagnosis and staging of neurological tumors.
5. Diagnosis and staging of the benign proliferative disorder associated with NF-1.
6. Diagnosis of neointimal formation resulting from percutaneous transluminal coronary angioplasty.
7. Diagnosis and staging of polycystic kidney disease.

Specific examples of possible radiotherapeutic applications include:

1. Radioimmunoassay of FPTase inhibitors.
2. Radioimmunoassay to determine the concentration of FPTase in a tissue sample.
3. Autoradiography to determine the distribution of FPTase in a mammal or an organ or tissue sample thereof.

For the use of the instant compounds as diagnostic imaging agents the radiolabeled compounds may be administered to mammals, preferably humans, in a pharmaceutical composition, either alone or, preferably, in combination with pharmaceutically acceptable carriers or diluents, optionally with known adjuvants, such as alum, in a pharmaceutical composition, according to standard pharmaceutical practice. Such compositions can be administered orally or parenterally, including the intravenous, intramuscular, intraperitoneal, subcutaneous, rectal and topical routes of administration. Preferably, administration is intravenous.

For intramuscular, intraperitoneal, subcutaneous and intravenous use, sterile solutions of the labeled compound are usually prepared, and the pH of the solutions should be suitably adjusted and buffered. For intravenous use, the total concentration of solutes should be controlled in order to render the preparation isotonic. For oral use of a diagnostic imaging combination according to this invention, the selected combination or compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredients are combined with emulsifying and suspending agents. If desired, certain sweetening and/or flavoring agents may be added.

Suitable compositions of this invention include aqueous solutions comprising compounds of this invention and pharmacologically acceptable carriers, e.g., saline, at a pH level, e.g., 7.4. The solutions may be introduced into a patient's bloodstream by local bolus injection.

As used herein, the term "composition" is intended to encompass a product comprising the specified ingredients in the specific amounts, as well as any product which results, directly or indirectly, from combination of the specific ingredients in the specified amounts.

When a radiolabeled compound according to this invention is administered into a human subject, the amount required for diagnostic imaging will normally be determined by the prescribing physician with the dosage generally varying according to the age, weight, and response of the individual patient, as well as the quantity of emission from the radionuclide. However, in most instances, an effective amount will be the amount of compound sufficient to produce emissions in the range of from about 1–5 mCi.

In one exemplary application, administration occurs in an amount of radiolabeled compound of between about 0.005 μg of body weight to about 50 μg/kg of body weight per day, preferably of between 0.02 μg/kg of body weight to about 3 μg/kg of body weight. A particular analytical dosage that comprises the instant composition includes from about 0.5 μg to about 100 μg of a labeled farnesyl-protein transferase inhibitor. Preferably, the dosage comprises from about 1 μg to about 50 μg of a radiolabeled farnesyl-protein transferase inhibitor.

The following illustrative procedure may be utilized when preforming PET imaging studies on patients in the clinic:

The patient is fasted for at least 12 hours allowing water intake ad libitum, and is premedicated with 0.3–0.4 mL Acepromazine injected i.m. on the day of the experiment. A 20 G two inch venous catheter is inserted into the contralateral ulnar vein for radiotracer administration.

The patient is positioned in the PET camera and a tracer dose of $[^{15}O]H_2O$ administered via i.v. catheter. The image thus obtained is used to insure that the patient is positioned correctly to include liver, kidneys, tumors and pancreas. Subsequently the $[^{11}C]$ radiolabeled farnesyl-protein transferase inhibitor (<20 mCi) is administered via i.v. catheter. Following the acquisition of the total radiotracer image, an infusion is begun of the farnesyl-protein transferase inhibitor which is being clinically evaluated (clinical candidate) at one of three dose rates (0.1, 1 or 10 mpk/day). After infusion for 2.5 hrs, the $[^{11}C]$ radiolabeled farnesyl-protein transferase inhibitor is again injected via the catheter. Images are again acquired for up to 90 min. Within ten minutes of the injection of radiotracer and at the end of the imaging session, 1 ml blood samples are obtained for determining the plasma concentration of the clinical candidate.

For uninhibited distribution of radiotracer, regions of interest (ROIs) are drawn on the reconstructed image includes the tumor, kidney cortex and a region of liver which is removed from the gallbladder images. These regions are used to generate time activity curves obtained in the absence of inhibitor or in the presence of the clinical candidate at the various infusion doses examined. Data are expressed as radioactivity per unit time per unit volume (,Ci/cc/mCi injected dose). Inhibition curves are generated from the data obtained in a region of interest obtained starting at 70 min. post-injection of radiotracer. At this time, clearance of non-specific binding has reached steady state. The $ID_{50}$ values were obtained by curve fitting the dose-rate/inhibition curves with equation iii:

$$B = A_0 - A_0 * I/(ID_{50}+I) + NS \qquad \text{(iii)}$$

where B is the %-Dose/g of radiotracer in tissues for each dose of clinical candidate, $A_0$ is the specifically bound radiotracer in a tissue in the absence of clinical candidate, I is the injected dose of inhibitor, $ID_{50}$ is the dose of clinical candidate which inhibits 50% of specific radiotracer binding to FPTase, and NS is the amount of non-specifically bond radiotracer.

Examples of radiolabeled farnesyl protein transferase inhibiting compounds include the following:

(a) a compound represented by formula (I-a) through (I-c):

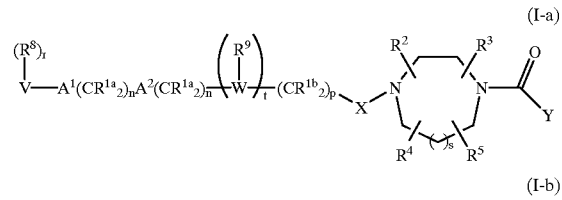

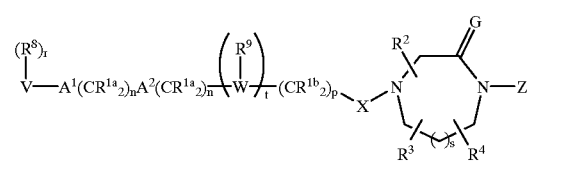

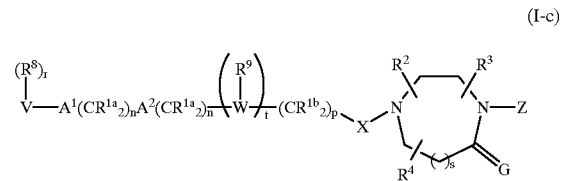

-continued wherein with respect to formula (I-a):

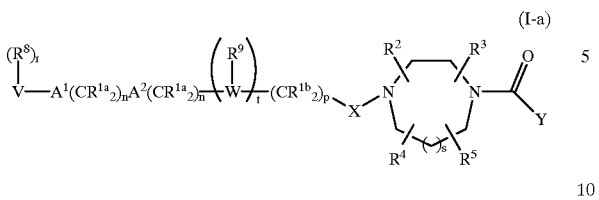
(I-a)

or a pharmaceutically acceptable salt thereof, $R^{1a}$ and $R^{1b}$ are independently selected from:

a) hydrogen, b) aryl, heterocycle, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, CN, NO$_2$, $(R^{10})_2N$—$C(NR^{10})$—, $R^{10}C(O)$—, $R^{10}OC(O)$—, N$_3$, —N$(R^{10})_2$, or $R^{11}OC(O)NR^{10}$—, c) $C_1$–$C_6$ alkyl unsubstituted or substituted by aryl, heterocyclyl, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, N$_3$, —N$(R^{10})_2$, or $R^{11}OC(O)$—NR$^{10}$—;

$R^2$ and $R^3$ are independently selected from: H; unsubstituted or substituted $C_{1-8}$ alkyl, unsubstituted or substituted $C_{2-8}$ alkenyl, unsubstituted or substituted $C_{2-8}$ alkynyl, unsubstituted or substituted aryl, unsubstituted or substituted heterocycle,

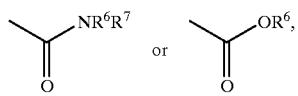

wherein the substituted group is substituted with one or more of:

1) aryl or heterocycle, unsubstituted or substituted with:
   a) $C_{1-4}$ alkyl,
   b) (CH$_2$)$_p$OR$^6$,
   c) (CH$_2$)$_p$NR$^6$R$^7$,
   d) halogen,
   e) a radionuclide,
2) $C_{3-6}$ cycloalkyl,
3) OR$^6$,
4) SR$^6$, S(O)R$^6$, SO$_2$R$^6$,

5) —NR$^6$R$^7$,

6) 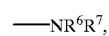

7) 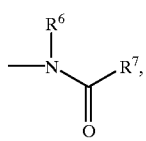

8) 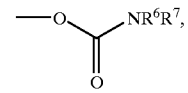

9) 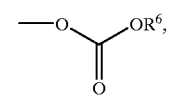

10) 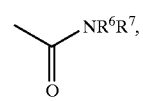

11) —SO$_2$—NR$^6$R$^7$,

12) 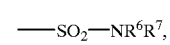

13) 

14) 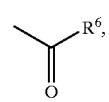

15) a radionuclide; or $R^2$ and $R^3$ are attached to the same C atom and are combined to form (CH$_2$)$_u$—wherein one of the carbon atoms is optionally replaced by a moiety selected from: O, S(O)$_m$, —NC(O)—, and —N(COR$^{10}$)—;

$R^4$ and $R^5$ are independently selected from H and CH$_3$; and any two of $R^2$, $R^3$, $R^4$ and $R^5$ are optionally attached to the same carbon atom;

$R^6$, $R^7$ and $R^{7a}$ are independently selected from: H; $C_{1-4}$ alkyl, $^{11}$C-methyl, $C_{3-6}$ cycloalkyl, heterocycle, aryl, aroyl, heteroaroyl, arylsulfonyl, heteroarylsulfonyl, unsubstituted or substituted with:
   a) $C_{1-4}$ alkoxy,
   b) aryl or heterocycle,
   c) halogen,
   d) HO,
   e) 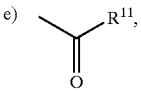
   f) —SO$_2$R$^{11}$
   g) N(R$^{10}$)$_2$,
   h) $^{11}$C-methyl, or
   i) a radionuclide; or
$R^6$ and $R^7$ may be joined in a ring;
$R^7$ and $R^{7a}$ may be joined in a ring;
$R^8$ is independently selected from:
   a) hydrogen,
   b) aryl, heterocycle, $C_3$–$C_{10}$ cycloalkyl, $C_2$–$C_6$ alkenyl, $C_2$–$C_6$ alkynyl, perfluoroalkyl, F, Cl, Br, $R^{10}O$—, $R^{11}S$ (O)$_m$—, R$^{10}$C(O)NR$^{10}$—, CN, NO$_2$, R$^{10}$$_2$N—C(NR$^{10}$)—, R$^{10}$C(O)—, R$^{10}$OC(O)—, N$_3$, —N(R$^{10}$)$_2$, or R$^{10}$C(O)NR$^{10}$—, c) C$_1$–C$_6$ alkyl unsubstituted or substituted by aryl, heterocycle, C$_3$–C$_{10}$ cycloalkyl, C$_2$–C$_6$ alkenyl, C$_2$–C$_6$ alkynyl, perfluoroalkyl, F, Cl, Br, R$^{10}$O—, R$^{11}$S(O)$_m$—, R$^{10}$C(O)NH—, CN, H$_2$N—C(NH)—, R$^{10}$C(O)—, R$^{10}$OC(O)—, N$_3$, —N(R$^{10}$)$_2$, or R$^{10}$OC(O)NH—, and d) a radionuclide;

R$^9$ is selected from:

a) hydrogen, b) C$_2$–C$_6$ alkenyl, C$_2$–C$_6$ alkynyl, perfluoroalkyl, F, Cl, Br, R$^{10}$O—, R$^{11}$S(O)$_m$—, R$^{10}$C(O)NR$^{10}$—, CN, NO$_2$, (R$^{10}$)$_2$N—C—(NR$^{10}$)—, R$^{10}$C(O)—, R$^{10}$OC(O)—, N$_3$, —N(R$^{10}$)$_2$, or R$^{11}$OC(O)NR$^{10}$—, and c) C$_1$–C$_6$ alkyl unsubstituted or substituted by perfluoroalkyl, F, Cl, Br, R$^{10}$O—, R$^{11}$S(O)$_m$—, R$^{10}$C(O)NR$^{10}$—, CN, (R$^{10}$)$_2$N—C(NR$^{10}$)—, R$^{10}$C(O)—, R$^{10}$OC(O)—, N$_3$, —N(R$^{10}$)$_2$, or R$^{11}$OC(O)NR$^{10}$—;

R$^{10}$ is independently selected from hydrogen, C$_1$–C$_6$ alkyl, $^3$H-methyl, $^{11}$C-methyl, benzyl and aryl;

R$^{11}$ is independently selected from C$_1$–C$_6$ alkyl and aryl;

A$^1$ and A$^2$ are independently selected from: a bond, —CH=CH—, —C≡C—, —C(O)—, —C(O)NR$^{10}$—, —NR$^{10}$C(O)—, O, —N(R$^{10}$)—, —S(O)$_2$N(R$^{10}$)—, —N(R$^{10}$)S(O)$_2$—, or S(O)$_m$;

V is selected from:

a) hydrogen, b) heterocycle, c) aryl, d) C$_1$–C$_{20}$ alkyl wherein from 0 to 4 carbon atoms are replaced with a a heteroatom selected from O, S, and N, and e) C$_2$–C$_{20}$ alkenyl, provided that V is not hydrogen if A$^1$ is S(O)$_m$ and V is not hydrogen if A$^1$ is a bond, n is 0 and A$^2$ is S(O)$_m$;

W is a heterocycle;

X is —CH$_2$—, —C(=O)—, or —S(=O)$_m$—;

Y is aryl, heterocycle, unsubstituted or substituted with one or more of:

1) C$_{1-4}$ alkyl, unsubstituted or substituted with:
 a) C$_{1-4}$ alkoxy,
 b) NR$^6$R$^7$,
 c) C$_{3-6}$ cycloalkyl,
 d) aryl or heterocycle,
 e) HO,
 f) —S(O)$_m$R$^6$,
 g) —C(O)NR$^6$R$^7$, or
 h) a radionuclide;

2) aryl or heterocycle, 3) halogen,

4) OR$^6$,

5) NR$^6$R$^7$,

6) CN,

7) NO$_2$,

8) CF$_3$;

9) —S(O)$_m$R$^6$,

10) —C(O)NR$^6$R$^7$,

11) C$_3$–C$_6$ cycloalkyl, or 12) a radionuclide;

| | |
|---|---|
| m is | 0, 1 or 2; |
| n is | 0, 1, 2, 3 or 4; |
| p is | 0, 1, 2, 3 or 4; |
| r is | 0 to 5, provided that r is 0 when V is hydrogen; |
| s is | 0 or 1; |
| t is | 0 or 1; and |
| u is | 4 or 5; | and wherein at least one radionuclide or $^3$H-methyl is present in the molecule;

with respect to formula (I-b):

(I-b)

$$(R^8)_r \;\; V\!\!-\!\!A^1(CR^{1a}_2)_n A^2(CR^{1a}_2)_n\!\!-\!\!W\!\!-\!\!_t(CR^{1b}_2)_p\!\!-\!\!X \overset{R^2}{\underset{R^3 \; R^4_s}{\diagup\!\!\!\diagdown}} N\!\!-\!\!Z$$

or a pharmaceutically acceptable salt thereof,

R$^{1a}$, R$^{1b}$, R$^{10}$, R$^{11}$, m, R$^2$, R$^3$, R$^6$, R$^7$, p, R$^{7a}$, u, R$^8$, A$^1$, A$^2$, V, W, X, n, p, r, s, t and u are as defined above with respect to formula (I-a);

R$^4$ is selected from H and CH$_3$;

and any two of R$^2$, R$^3$ and R$^4$ are optionally attached to the same carbon atom;

R$^9$ is selected from:

a) hydrogen, b) alkenyl, alkynyl, perfluoroalkyl, F, Cl, Br, R$^{10}$O—, R$^{11}$S(O)$_m$—, R$^{10}$C(O)NR$^{10}$—, CN, NO$_2$, (R$^{10}$)$_2$N—C—(NR$^{10}$)—, R$^{10}$C(O)—, R$^{10}$OC(O)—, N$_3$, —N(R$^{10}$)$_2$, or R$^{10}$C(O)NR$^{10}$—, and c) C$_1$–C$_6$ alkyl unsubstituted or substituted by perfluoroalkyl, F, Cl, Br, R$^{10}$O—, R$^{11}$S(O)$_m$—, R$^{10}$C(O)NR$^{10}$—, CN, (R$^{10}$)$_2$N—C(NR$^{10}$)—, R$^{10}$C(O)—, R$^{10}$OC(O)—, N$_3$, —N(R$^{10}$)$_2$, or R$^{11}$OC(O)NR$^{10}$—;

G is H$_2$ or O;

Z is aryl, heteroaryl, arylmethyl, heteroarylmethyl, arylsulfonyl, heteroarylsulfonyl, unsubstituted or substituted with one or more of the following:

1) C$_{1-4}$ alkyl, unsubstituted or substituted with:
 a) C$_{1-4}$ alkoxy,
 b) NR$^6$R$^7$,
 c) C$_{3-6}$ cycloalkyl,
 d) aryl or heterocycle,
 e) HO,
 f) —S(O)$_m$R$^6$,
 g) —C(O)NR$^6$R$^7$, or
 h) a radionuclide;

2) aryl or heterocycle, 3) halogen,

4) OR$^6$,

5) NR$^6$R$^7$,

6) CN,

7) NO$_2$,

8) CF$_3$;

9) —S(O)$_m$R$^6$,

10) —C(O)NR$^6$R$^7$,

11) C$_3$–C$_6$ cycloalkyl, or 12) a radionuclide;
and wherein at least one radionuclide or $^3$H-methyl is present in the molecule;
with respect to formula(I-c):

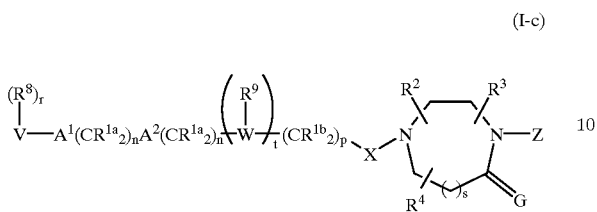

(I-c)

or a pharmaceutically acceptable salt thereof,
$R^{1a}$, $R^{1b}$, $R^{10}$, $R^{11}$, m, $R^2$, $R^3$, $R^6$, $R^7$, p, u, $R^{7a}$, $R^8$, $A^1$, $A^2$, V, W, X, n, r and t are as defined above with respect to formula (I-a);
$R^4$ is selected from H and $CH_3$;
and any two of $R^2$, $R^3$ and $R^4$ are optionally attached to the same carbon atom;
G is O;
Z is aryl, heteroaryl, arylmethyl, heteroarylmethyl, arylsulfonyl, heteroarylsulfonyl, unsubstituted or substituted with one or more of the following:
1) $C_{1-4}$ alkyl, unsubstituted or substituted with:
  a) $C_{1-4}$ alkoxy,
  b) $NR^6R^7$,
  c) $C_{3-6}$ cycloalkyl,
  d) aryl or heterocycle,
  e) HO,
  f) —S(O)$_m$R$^6$, or
  g) —C(O)NR$^6$R$^7$,
2) aryl or heterocycle,
3) halogen,
4) OR$^6$,
5) NR$^6$R$^7$,
6) CN,
7) NO$_2$,
8) CF$_3$;
9) —S(O)$_m$R$^6$,
10) —C(O)NR$^6$R$^7$,
11) $C_3$–$C_6$ cycloalkyl, or
12) a radionuclide; and
s is 1;
and wherein at least one radionuclide or $^3$H-methyl is present in the molecule;
(b) a compound represented by formula (I-d):

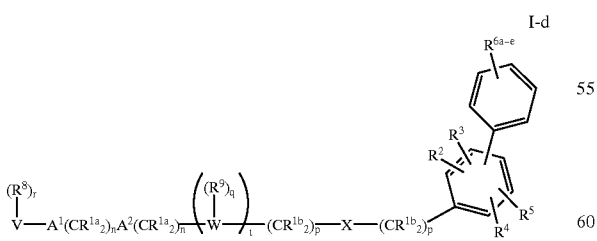

I-d wherein:
$R^{1a}$ and $R^{1b}$ are independently selected from:
a) hydrogen,
b) aryl, heterocycle, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)$ NR$^{10}$—, $R^{11}C(O)O$—, $(R^{10})_2NC(O)$—, $R^{10}{}_2N$—C(NR$^{10}$)—, CN,
NO$_2$, $R^{10}C(O)$—, N$_3$, —N(R$^{10})_2$, or $R^{11}OC(O)NR^{10}$—,
c) unsubstituted or substituted $C_1$–$C_6$ alkyl wherein the substituent on the substituted $C_1$–$C_6$ alkyl is selected from unsubstituted or substituted aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2NC(O)$—, $R^{10}{}_2N$—C(NR$^{10}$)—, CN, $R^{10}C(O)$—, N$_3$, —N(R$^{10})_2$, and $R^{11}OC(O)$—NR$^{10}$—;
$R^2$, $R^3$, $R^4$ and $R^5$ are independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{11}C(O)O$—, $R^{10}{}_2N$—C(NR$^{10}$)—, CN, NO$_2$, $R^{10}C(O)$—, N$_3$, —N(R$^{10})_2$, or $R^{11}OC(O)NR^{10}$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2$ NC(O)—, $R^{10}{}_2N$—C(NR$^{10}$)—, CN, $R^{10}C(O)$—, N$_3$, —N(R$^{10})_2$, and $R^{11}OC(O)$—NR$^{10}$—, and
e) a radionuclide;
$R^{6a}$, $R^{6b}$, $R^{6c}$, $R^{6d}$ and $R^{6e}$ are independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{11}C(O)O$—, $R^{10}{}_2N$—C(NR$^{10}$)—, CN, NO$_2$, $R^{10}C(O)$—, N$_3$, —N(R$^{10})_2$, or $R^{11}OC(O)NR^{10}$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2$ NC(O)—, $R^{10}{}_2N$—C(NR$^{10}$)—, CN, $R^{10}C(O)$—, N$_3$, —N(R$^{10})_2$, and $R^{11}OC(O)$—NR$^{10}$—, and
e) a radionuclide;
any two of $R^{6a}$, $R^{6b}$, $R^{6c}$, $R^{6d}$ and $R^{6e}$ on adjacent carbon atoms are combined to form a diradical selected from —CH═CH—CH═CH—, —CH═CH—CH$_2$—, —(CH$_2$)$_4$— and —(CH$_2$)$_3$—;
$R^7$ is selected from: H; $C_{1-4}$ alkyl, $C_{3-6}$ cycloalkyl, heterocycle, aryl, aroyl, heteroaroyl, arylsulfonyl, heteroarylsulfonyl, unsubstituted or substituted with:
a) $C_{1-4}$ alkoxy,
b) aryl or heterocycle,
c) halogen,
d) HO, e)

f) —SO$_2$R$^{11}$
g) N(R$^{10}$)$_2$ or h) $C_{1-4}$ perfluoroalkyl;

$R^8$ is independently selected from:
a) hydrogen,
b) aryl, substituted aryl, heterocycle, substituted heterocycle, $C_3$–$C_{10}$ cycloalkyl, $C_2$–$C_6$ alkenyl, $C_2$–$C_6$ alkynyl, perfluoroalkyl, F, Cl, Br, $R^{10}O$—, $R^{11}S(O)_m$—, $R^{10}C(O)NR^{10}$—, $(R^{10})_2NC(O)$—, $R^{10}{}_2N$—$C(NR^{10})$—, CN, $NO_2$, $R^{10}C(O)$—, $N_3$, —$N(R^{10})_2$, or $R^{11}OC(O)NR^{10}$—,
c) $C_1$–$C_6$ alkyl unsubstituted or substituted by aryl, cyanophenyl, heterocycle, $C_3$–$C_{10}$ cycloalkyl, $C_2$–$C_6$ alkenyl, $C_2$–$C_6$ alkynyl, perfluoroalkyl, F, Cl, Br, $R^{10}O$—, $R^{11}S(O)_m$—, $R^{10}C(O)NH$—, $(R^{10})_2NC(O)$—, $R^{10}{}_2N$—$C(NR^{10})$—, CN, $R^{10}C(O)$—, $N_3$, —$N(R^{10})_2$, or $R^{10}OC(O)NH$—, and
d) a radionuclide;

$R^9$ is independently selected from:
a) hydrogen,
b) $C_2$–$C_6$ alkenyl, $C_2$–$C_6$ alkynyl, $C_1$–$C_6$ perfluoroalkyl, F, Cl, Br, $R^{10}O$—, $R^{11}S(O)_m$—, $R^{10}C(O)NR^{10}$—, $(R^{10})_2 NC(O)$—, $R^{10}{}_2N$—$C(NR^{10})$—, CN, $NO_2$, $R^{10}C(O)$—, $N_3$, —$N(R^{10})_2$, or $R^{11}OC(O)NR^{10}$—, and
c) $C_1$–$C_6$ alkyl unsubstituted or substituted by $C_1$–$C_6$ perfluoroalkyl, F, Cl, Br, $R^{10}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$—, $N_3$, —$N(R^{10})_2$, or $R^{11}OC(O)NR^{10}$—;

$R^{10}$ is independently selected from hydrogen, $C_1$–$C_6$ alkyl, 2,2,2-trifluoroethyl, $^3$H-methyl, $^{11}$C-methyl, benzyl and aryl;

$R^{11}$ is independently selected from $C_1$–$C_6$ alkyl and aryl;

$R^{12}$ is independently selected from hydrogen, $C_1$–$C_6$ alkyl, $C_1$–$C_6$ aralkyl, $C_1$–$C_6$ substituted aralkyl, $C_1$–$C_6$ heteroaralkyl, $C_1$–$C_6$ substituted heteroaralkyl, aryl, substituted aryl, heteroaryl, substituted heteraryl, $C_1$–$C_6$ perfluoroalkyl, 2-aminoethyl and 2,2,2-trifluoroethyl;

$A^1$ and $A^2$ are independently selected from: a bond, —CH═CH—, —C≡C—, —C(O)—, —C(O)NR$^{10}$—, NR$^{10}$C(O)—, O, —N(R$^{10}$)—, —S(O)$_2$N(R$^{10}$)—, —N(R$^{10}$)S(O)$_2$— or S(O)$_m$—;

V is selected from:
a) hydrogen,
b) heterocycle,
c) aryl,
d) $C_1$–$C_{20}$ alkyl wherein from 0 to 4 carbon atoms are replaced with a a heteroatom selected from O, S, and N, and
e) $C_2$–$C_{20}$ alkenyl,
provided that V is not hydrogen if $A^1$ is S(O)$_m$ and V is not hydrogen if $A^1$ is a bond, n is 0 and $A^2$ is S(O)$_m$;

W is a heterocycle;

X is a bond, —CH═CH—, O, —C(═O)—, —C(O)NR$^7$—, —NR$^7$C(O)—, —C(O)O—, —OC(O)—, —C(O)NR$^7$C(O)—, —NR$^7$—, —S(O)$_2$N(R$^{10}$)—, —N(R$^{10}$)S(O)$_2$— or —S(═O)$_m$—;

m is 0,1 or 2;

n is independently 0, 1, 2, 3 or 4;

p is independently 0, 1, 2, 3 or 4;

q is 0,1,2 or 3;

r is 0 to 5, provided that r is 0 when V is hydrogen; and t is 0 or 1; and wherein at least one radionuclide or $^3$H-methyl is present in the molecule;

(c) a compound represented by formula (I-e):

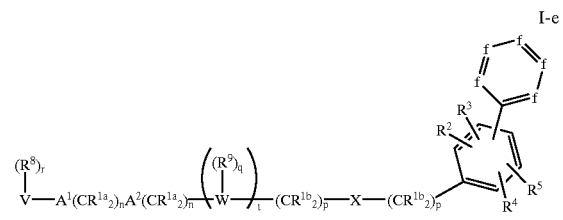

wherein:

$R^{1a}$, $R^{1b}$, $R^2$, $R^3$, $R^4$, $R^5$, $R^7$, $R^8$, $R^9$, $R^{10}$, $R^{11}$, $A^1$, $A^2$, V, W, m, n, p, q, r and t are as previously defined with respect to formula (I-d);

from 1–3 of f(s) are independently N, and the remaining f's are independently CR$^6$; and each $R^6$ is independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{11}C(O)O$—, $R^{10}{}_2N$—$C(NR^{10})$—, CN, $NO_2$, $R^{10}C(O)$—, $N_3$, —$N(R^{10})_2$, or $R^{11}OC(O)NR^{10}$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2$ NC(O)—, $R^{10}{}_2N$—$C(NR^{10})$—, CN, $R^{10}C(O)$—, $N_3$, —$N(R^{10})_2$, and $R^{11}OC(O)$—$NR^{10}$—, and
e) a radionuclide; or
any two of $R^6$ on adjacent carbon atoms are combined to form a diradical selected from —CH═CH—CH═CH—, —CH═CH—CH$_2$—, —(CH2)$_4$— and —(CH$_2$)$_3$—;

and wherein at least one radionuclide or $^3$H-methyl is present in the molecule;

(d) a compound represented by formula (I-f):

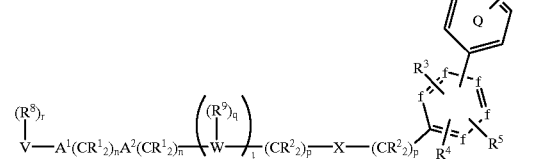

wherein:

$R^3$, $R^4$, $R^5$, $R^{6a-e}$, $R^7$, $R^8$, $R^9$, $R^{10}$, $R^{11}$, $A^1$, $A^2$, V, W, m, n, p, q, r and t are as previously defined with respect to formula (I-d);

from 1–2 of f(s) are independently N, and the remaining f's are independently CH; and $R^1$ and $R^2$ are independently selected from:
a) hydrogen,
b) aryl, heterocycle, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $R^{11}C(O)O$—, $(R^{10})_2NC(O)$—, $R^{10}{}_2N$—$C(NR^{10})$—, CN, $NO_2$, $R^{10}C(O)$—, $N_3$, —$N(R^{10})_2$,or $R^{11}OC(O)NR^{10}$—,
c) unsubstituted or substituted $C_1$–$C_6$ alkyl wherein the substituent on the substituted $C_1$–$C_6$ alkyl is selected from unsubstituted or substituted aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2NC(O)$—, $R^{10}_2N$—$C(NR^{10})$—, CN, $R^{10}C(O)$—, $N_3$, —$N(R^{10})_2$, and $R^{11}OC(O)$—$NR^{10}$—;

and wherein at least one radionuclide or $^3$H-methyl is present in the molecule;

(e) a compound represented by formula (I-g):

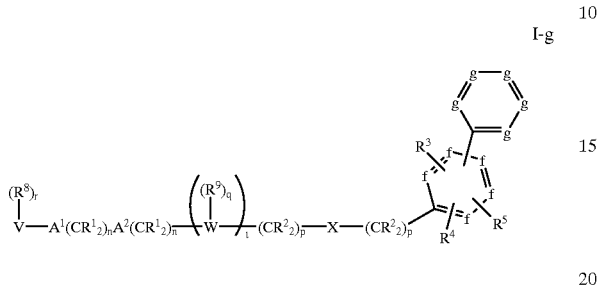

I-g wherein:

$R^3$, $R^4$, $R^5$, $R^7$, $R^8$ $R^9$, $R^{10}$, $R^{11}$, $A^1$, $A^2$, V, W, m, n, p, q, r and t are as previously defined with respect to formula (I-d);

from 1–2 of f(s) are independently N, and the remaining f's are independently CH;

from 1–3 of g(s) are independently N, and the remaining g's are independently $CR^6$;

$R^1$ and $R^2$ are independently selected from:

a) hydrogen, b) aryl, heterocycle, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $R^{11}C(O)O$—, $(R^{10})_2NC(O)$—, $R^{10}_2N$—$C(NR^{10})$—, CN, $NO_2$, $R^{10}C(O)$—, $N_3$, —$N(R^{10})_2$, or $R^{11}OC(O)NR^{10}$—, c) unsubstituted or substituted $C_1$–$C_6$ alkyl wherein the substituent on the substituted $C_1$–$C_6$ alkyl is selected from unsubstituted or substituted aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2NC(O)$—, $R^{10}_2N$—$C(NR^{10})$—, CN, $R^{10}C(O)$—, $N_3$, —$N(R^{10})_2$, and $R^{11}OC(O)$—$NR^{10}$—; and each $R^6$ is independently selected from:

a) hydrogen, b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{11}C(O)O$—, $R^{10}_2N$—$C(NR^{10})$—, CN, $NO_2$, $R^{10}C(O)$—, $N_3$, —$N(R^{10})_2$, or $R^{11}OC(O)NR^{10}$—, c) unsubstituted $C_1$–$C_6$ alkyl, d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2$ NC(O)—, $R^{10}_2N$—$C(NR^{10})$—, CN, $R^{10}C(O)$—, $N_3$, —$N(R^{10})_2$, and $R^{11}OC(O)$—$NR^{10}$—, and e) a radionuclide; or any two of $R^6$ on adjacent carbon atoms are combined to form a diradical selected from —CH═CH—CH═CH—, —CH═CH—$CH_2$—, —$(CH_2)_4$— and —$(CH_2)_3$—;

and wherein at least one radionuclide or $^3$H-methyl is present in the molecule;

(f) a compound represented by formula (I-h):

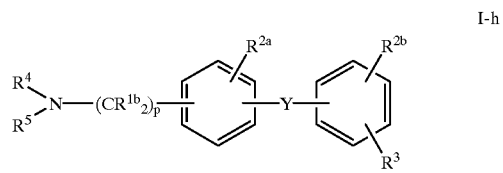

I-h wherein:

$R^{1a}$ and $R^{1b}$ are independently selected from:

a) hydrogen, b) unsubstituted or substituted aryl, unsubstituted or substituted heterocycle, unsubstituted or substituted $C_3$–$C_6$ cycloalkyl, $C_2$–$C_6$ alkenyl, $C_2$–$C_6$ alkynyl, $R^8O$—, $R^9S(O)_m$—, $R^8C(O)NR^8$—, CN, $NO_2$, $(R^8)_2N$—$C(NR^8)$—, $R^8C(O)$—, $R^8OC(O)$—, $N_3$, —$N(R^8)_2$, or $R^9OC(O)NR^8$—, c) $C_1$–$C_6$ alkyl unsubstituted or substituted by unsubstituted or substituted aryl, unsubstituted or substituted heterocyclic, unsubstituted or substituted $C_3$–$C_6$ cycloalkyl, $C_2$–$C_6$ alkenyl, $C_2$–$C_6$ alkynyl, $R^8O$—, $R^9S(O)_m$—, $R^8C(O)NR^8$—, CN, $(R^8)_2N$—$C(NR^8)$—, $R^8C(O)$—, $R^8OC(O)$—, $N_3$, —$N(R^8)_2$, or $R^9OC(O)NR^8$—;

$R^{2a}$, $R^{2b}$ and $R^3$ are independently selected from:

a) hydrogen, b) $C_1$–$C_6$ alkyl unsubstituted or substituted by $C_2$–$C_6$ alkenyl, $R^8O$—, $R^9S(O)_m$—, $R^8C(O)NR^8$—, CN, $N_3$, $(R^8)_2N$—$C(NR^8)$, $R^8C(O)$—, $R^8OC(O)$—, —$N(R^8)_2$, or $R^9OC(O)NR^8$—, c) unsubstituted or substituted aryl, unsubstituted or substituted heterocycle, unsubstituted or substituted cycloalkyl, alkenyl, $R^8O$—, $R^9S(O)_m$—, $R^8C(O)NR^8$—, CN, $NO_2$, $(R^8)_2N$—$C(NR^8)$—, $R^8C(O)$—, $R^8OC(O)$—, $N_3$, —$N(R^8)_2$, halogen or $R^9OC(O)NR^8$—, d) $C_1$–$C_6$ alkyl substituted with an unsubstituted or substituted group selected from aryl, heterocyclic and $C_3$–$C_{10}$ cycloalkyl, and e) a radionuclide;

$R^4$ and $R^5$ are independently selected from:

a) hydrogen, and b)

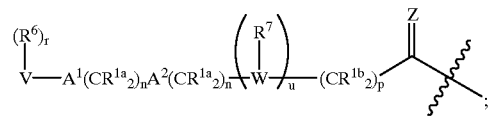

;

$R^6$ is independently selected from:

a) hydrogen, b) unsubstituted or substituted aryl, unsubstituted or substituted heterocycle, unsubstituted or substituted $C_3$–$C_6$ cycloalkyl, $C_2$–$C_6$ alkenyl, $C_2$–$C_6$ alkynyl, $C_1$–$C_6$ perfluoroalkyl, F, Cl, Br, $R^8O$—, $R^9S(O)_m$—, $R^8C(O)NR^8$—, CN, $NO_2$, $R^8_2N$—$C(NR^8)$—, $R^8C(O)$—, $R^8OC(O)$—, $N_3$, —$N(R^8)_2$, or $R^9OC(O)NR^8$—, and c) $C_1$–$C_6$ alkyl unsubstituted or substituted by unsubstituted or substituted aryl, unsubstituted or substituted heterocycle, unsubstituted or substituted $C_3$–$C_6$ cycloalkyl, $C_2$–$C_6$ alkenyl, $C_2$–$C_6$ alkynyl, $C_1$–$C_6$ perfluoroalkyl, F, Cl, Br, $R^8O$—, $R^9S(O)_m$—, $R^8C(O)$ NH—, CN, H$_2$N—C(NH)—, R$^8$C(O), R$^8$OC(O)—, N$_3$, —N(R$^8$)$_2$,or R$^8$OC(O)NH—, and d) a radionuclide;

R$^7$ is selected from:

a) hydrogen, b) C$_2$–C$_6$ alkenyl, C$_2$–C$_6$ alkynyl, C$_1$–C$_6$ perfluoroalkyl, F, Cl, Br, R$^8$O—, R$^9$S(O)$_m$—, R$^8$C(O)NR$^8$—, CN, NO$_2$, (R$^8$)$_2$N—C—(NR$^8$)—, R$^8$C(O)—, R$^8$OC(O)—, N$_3$, —N(R$^8$)$_2$,or R$^9$OC(O)NR$^8$—, and c) C$_1$–C$_6$ alkyl unsubstituted or substituted by C$_1$–C$_6$ perfluoroalkyl, F, Cl, Br, R$^8$O—, R$^9$S(O)$_m$—, R$^8$C(O)NR$^8$—, CN, (R$^8$)$_2$N—C(NR$^8$)—, R$^8$C(O)—, R$^8$OC(O)—, N$_3$, —N(R$^8$)$_2$,or R$^9$OC(O)NR$^8$—;

R$^8$ is independently selected from hydrogen, C$_1$–C$_6$ alkyl, $^3$H-methyl, 11C-methyl, substituted or unsubstituted C$_1$–C$_6$ aralkyl and substituted or unsubstituted aryl;

R$^9$ is independently selected from C$_1$–C$_6$ alkyl and aryl;

R$^{10}$ is independently selected from hydrogen, C$_1$–C$_6$ alkyl, substituted or unsubstituted C$_1$–C$_6$ aralkyl and substituted or unsubstituted aryl;

A$^1$ and A$^2$ are independently selected from: a bond, —CH=CH—, —C≡C—, —C(O)—, —C(O)NR$^8$—, —NR$^8$C(O)—, O, —N(R$^8$)—, —S(O)$_2$N(R$^8$)—, —N(R$^8$)S(O)$_2$—, or S(O)$_m$;

V is selected from:

a) hydrogen, b) heterocycle, c) aryl, d) C$_1$–C$_{20}$ alkyl wherein from 0 to 4 carbon atoms are replaced with a a heteroatom selected from O, S, and N, and e) C$_2$–C$_{20}$ alkenyl, provided that V is not hydrogen if A$^1$ is S(O)$_m$ and V is not hydrogen if A$^1$ is a bond, n is 0 and A$^2$ is S(O)$_m$;

W is a heterocycle;

Y is selected from: a bond, —C(R$^{10}$)=C(R$^{10}$)—, —C≡C—, —C(O)—, —C(R$^{10}$)$_2$—, —C(OR$^{10}$)R$^{10}$—, —CN(R$^{10}$)$_2$R$^{10}$—, —OC(R$^{10}$)$_2$—, —NR$^{10}$C(R$^{10}$)$_2$—, —C(R$^{10}$)$_2$O—, —C(R$^{10}$)$_2$NR$^{10}$—, —C(O)NR$^{10}$—, —NR$^{10}$C(O)—, O, —NC(O)R$^{10}$—, —NC(O)OR$^{10}$—, —S(O)$_2$N(R$^{10}$)—, —N(R$^{10}$)S(O)$_2$—, or S(O)$_m$;

Z is H$_2$ or O;

| | |
|---|---|
| m is | 0, 1 or 2; |
| n is | 0, 1, 2, 3 or 4; |
| p is | 0, 1, 2, 3 or 4; |
| r is | 0 to 5, provided that r is 0 when V is hydrogen; and |
| u is | 0 or 1; and | wherein at least one radionuclide or $^3$H-methyl is present in the molecule;

(g) a compound represented by formula (I-i):

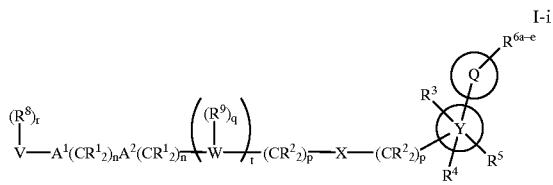

I-i wherein:

Q is a 4, 5, 6 or 7 membered heterocyclic ring which comprises a nitrogen atom through which Q is attached to Y and 0–2 additional heteroatoms selected from N, S and O, and which also comprises a carbonyl, thiocarbonyl, —C(=NR$^{13}$)— or sulfonyl moiety adjacent to the nitrogen atom attached to Y;

Y is a 5, 6 or 7 membered carbocyclic ring wherein from 0 to 3 carbon atoms are replaced by a heteroatom selected from N, S and O, and wherein Y is attached to Q through a carbon atom;

R$^1$ and R$^2$ are independently selected from:

a) hydrogen, b) aryl, heterocycle, C$_3$–C$_{10}$ cycloalkyl, C$_2$–C$_6$ alkenyl, C$_2$–C$_6$ alkynyl, R$^{10}$O—, R$^{11}$S(O)$_m$—, R$^{10}$C(O)NR$^{10}$—, R$^{11}$C(O)O—, (R$^{10}$)$_2$NC(O)—, R$^{10}$$_2$N—C(NR$^{10}$)—, CN, NO$_2$, R$^{10}$C(O)—, N$_3$, —N(R$^{10}$)$_2$,or R$^{11}$OC(O)NR$^{10}$—, c) unsubstituted or substituted C$_1$–C$_6$ alkyl wherein the substituent on the substituted C$_1$–C$_6$ alkyl is selected from unsubstituted or substituted aryl, heterocyclic, C$_3$–C$_{10}$ O cycloalkyl, C$_2$–C$_6$ alkenyl, C$_2$–C$_6$ alkynyl, R$^{10}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, R$^{10}$C(O)—, N$_3$, —N(R$^{10}$)$_2$, and R$^{11}$OC(O)—NR$^{10}$—;

R$^3$, R$^4$ and R$^5$ are independently selected from:

a) hydrogen, b) unsubstituted or substituted aryl, unsubstituted or substituted heterocycle, C$_3$–C$_{10}$ cycloalkyl, C$_2$–C$_6$ alkenyl, C$_2$–C$_6$ alkynyl, halogen, C$_1$–C$_6$ perfluoroalkyl, R$^{12}$O—, R$^{11}$S(O)$_m$—, R$^{10}$C(O)NR$^{10}$—, (R$^{10}$)$_2$NC(O)—, R$^{11}$C(O)O—, R$^{10}$$_2$N—C(NR$^{10}$)—, CN, NO$_2$, R$^{10}$(O)—, N$_3$, —N(R$^{10}$)$_2$,or R$^{11}$OC(O)NR$^{10}$—, c) unsubstituted C$_1$–C$_6$ alkyl, d) substituted C$_1$–C$_6$ alkyl wherein the substituent on the substituted C$_1$–C$_6$ alkyl is selected from unsubstituted or substituted aryl, unsubstituted or substituted heterocyclic, C$_3$–C$_{10}$ cycloalkyl, C$_2$–C$_6$ alkenyl, C$_2$–C$_6$ alkynyl, R$^{12}$O—, R$^{11}$S(O)$_m$—, R$^{10}$C(O)NR$^{10}$—, (R$^{10}$)$_2$ NC(O)—, R$^{10}$$_2$N—C(NR$^{10}$)—, CN, R$^{10}$C(O)—, N$_3$, —N(R$^{10}$)$_2$, and R$^{11}$OC(O)—NR$^{10}$—, and e) a radionuclide;

R$^{6a}$, R$^{6b}$, R$^{6c}$, R$^{6d}$ and R$^{6e}$ are independently selected from:

a) hydrogen, b) unsubstituted or substituted aryl, unsubstituted or substituted heterocycle, C$_3$–C$_{10}$ cycloalkyl, C$_2$–C$_6$ alkenyl, C$_2$–C$_6$ alkynyl, halogen, C$_1$–C$_6$ perfluoroalkyl, R$^{12}$O—, R$^{11}$S(O)$_m$—, R$^{10}$C(O)NR$^{10}$—, (R$^{10}$)$_2$NC(O)—, R$^{11}$S(O)$_2$NR$^{10}$—, (R$^{10}$)$_2$NS(O)$_2$—, R$^{11}$C(O)O—, R$^{10}$$_2$N—C(NR$^{10}$)—, CN, NO$_2$, R$^{10}$C(O)—, N$_3$, —N(R$^{10}$)$_2$, or R$^{11}$OC(O)NR$^{10}$—, c) unsubstituted C$_1$–C$_6$ alkyl, d) substituted C$_1$–C$_6$ alkyl wherein the substituent on the substituted C$_1$–C$_6$ alkyl is selected from unsubstituted or substituted aryl, unsubstituted or substituted heterocyclic, C$_3$–C$_{10}$ cycloalkyl, C$_2$–C$_6$ alkenyl, C$_2$–C$_6$ alkynyl, R$^{12O}$—, R$^{11}$S(O)$_m$—, R$^{10}$C(O)NR$^{10}$—, (R$^{10}$)$_2$ NC(O)—, R$^{11}$S(O)$_2$NR$^{10}$—, (R$^{10}$)$_2$NS(O)$_2$—, R$^{10}$$_2$N—C(NR$^{10}$)—, CN, R$^{10}$C(O)—, N$_3$, —N(R$^{10}$)$_2$, and R$^{11}$OC(O)—NR$^{10}$—, and e) a radionuclide; or any two of R$^{6a}$, R$^{6b}$, R$^{6c}$, R$^{6d}$ and R$^{6e}$ on adjacent carbon atoms are combined to form a diradical selected from —CH=CH—CH=CH—, —CH=CH—CH$_2$—, —(CH$_2$)$_4$— and —(CH$_2$)$_3$—;

R$^7$ is selected from:

H; C$_{1-4}$ alkyl, C$_{3-6}$ cycloalkyl, heterocycle, aryl, aroyl, heteroaroyl, arylsulfonyl, heteroarylsulfonyl, unsubstituted or substituted with:

a) $C_{1-4}$ alkoxy,
b) aryl or heterocycle, c) 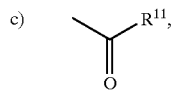

d) —$SO_2R^{11}$
e) $N(R^{10})_2$ or
f) $C_{1-4}$ perfluoroalkyl;

$R^8$ is independently selected from:
a) hydrogen,
b) aryl, substituted aryl, heterocycle, substituted heterocycle, $C_3$–$C_{10}$ cycloalkyl, $C_2$–$C_6$ alkenyl, $C_2$–$C_6$ alkynyl, perfluoroalkyl, F, Cl, Br, $R^{10}O$—, $R^{11}S(O)_m$—, $R^{10}C(O)NR^{10}$—, $(R^{10})_2NC(O)$—, $R^{11}S(O)_2NR^{10}$—, $(R^{10})_2NS(O)_2$—, $R^{10}_2N$—$C(NR^{10})$—, CN, $NO_2$, $R^{10}C(O)$—, $N_3$, —$N(R^{10})_2$, or $R^{11}OC(O)NR^{10}$—,
c) $C_1$–$C_6$ alkyl unsubstituted or substituted by aryl, cyanophenyl, heterocycle, $C_3$–$C_{10}$ cycloalkyl, $C_2$–$C_6$ alkenyl, $C_2$–$C_6$ alkynyl, perfluoroalkyl, F, Cl, Br, $R^{10}O$—, $R^{11}S(O)_m$—, $R^{10}C(O)NR^{10}$—, $(R^{10})_2NC(O)$—, $R^{11}S(O)_2NR^{10}$—, $(R^{10})_2NS(O)_2$—, $R^{10}_2N$—$C(NR^{10})$—, CN, $R^{10}C(O)$—, $N_3$, —$N(R^{10})_2$, or $R^{10}OC(O)NH$—, and
d) a radionuclide;

$R^9$ is independently selected from:
a) hydrogen, sb) alkenyl, alkynyl, perfluoroalkyl, F, Cl, Br, $R^{10}O$—, $R^{11}S(O)_m$—, $R^{10}C(O)NR^{10}$—, $(R^{10})_2NC(O)$—, $R^{10}_2N$—$C(NR^{10})$—, CN, $NO_2$, $R^{10}C(O)$—, $N_3$, —$N(R^{10})_2$, or $R^{11}OC(O)NR^{10}$—, and
c) $C_1$–$C_6$ alkyl unsubstituted or substituted by perfluoroalkyl, F, Cl, Br, $R^{10}O$—, $R^{11}S(O)_m$—, $R^{10}C(O)NR^{10}$—, $(R^{10})_2NC(O)$—, $R^{10}_2N$—$C(NR^{10})$—, CN, $R^{10}C(O)$—, $N_3$, —$N(R^{10})_2$, or $R^{11}OC(O)NR^{10}$—;

$R^{10}$ is independently selected from hydrogen, $C_1$–$C_6$ alkyl, benzyl, $^3$H-methyl, $^{11}$C-methyl, 2,2,2-trifluoroethyl and aryl;

$R^{11}$ is independently selected from $C_1$–$C_6$ alkyl and aryl;

$R^{12}$ is independently selected from hydrogen, $C_1$–$C_6$ alkyl, $C_1$–$C_6$ aralkyl, $C_1$–$C_6$ substituted aralkyl, $C_1$–$C_6$ heteroaralkyl, $C_1$–$C_6$ substituted heteroaralkyl, aryl, substituted aryl, heteroaryl, substituted heteraryl, $C_1$–$C_6$ perfluoroalkyl, 2-aminoethyl and 2,2,2-trifluoroethyl;

$R^{13}$ is selected from hydrogen, $C_1$–$C_6$ alkyl, cyano, $C_1$–$C_6$ alkylsulfonyl and $C_1$–$C_6$ acyl;

$A^1$ and $A^2$ are independently selected from: a bond, —CH=CH—, —C≡C—, —C(O)—, —C(O)NR$^{10}$—, —NR$^{10}$C(O)—, O, —N(R$^{10}$)—, —S(O)$_2$N(R$^{10}$)—, —N(R$^{10}$)S(O)$_2$—, or S(O)$_m$;

V is selected from:
a) hydrogen,
b) heterocycle,
c) aryl,
d) $C_1$–$C_{20}$ alkyl wherein from 0 to 4 carbon atoms are replaced with a heteroatom selected from O, S, and N, and
e) $C_2$–$C_{20}$ alkenyl,
provided that V is not hydrogen if $A^1$ is $S(O)_m$ and V is not hydrogen if $A^1$ is a bond, n is 0 and $A^2$ is $S(O)_m$;

W is a heterocycle;

X is a bond, —CH=CH—, O, —C(=O)—, —C(O)NR$^7$—, —NR$^7$C(O)—, —C(O)O—, —OC(O)—, —C(O)NR$^7$C(O)—, —NR$^7$—, —S(O)$_2$N(R$^{10}$)—, —N(R$^{10}$)S(O)$_2$—or —S(=O)$_m$—;

m is 0, 1 or 2;
n is independently 0, 1, 2, 3 or 4;
p is independently 0, 1, 2, 3 or 4;
q is 0, 1, 2 or 3;
r is 0 to 5, provided that r is 0 when V is hydrogen; and
t is 0 or 1;

and wherein at least one radionuclide or $^3$H-methyl is present in the molecule;

(h) a compound represented by formula (I-j):

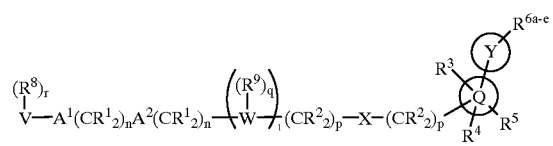

wherein:

$R^1$, $R^2$, $R^3$, $R^4$, $R^5$, $R^{6a-e}$, $R^7$, $R^8$, $R^9$, $R^{10}$, $R^{11}$, $R^{12}$, $R^{13}$, $A^1$, $A^2$, V, W, m, n, p, q, r and t are as previously defined with respect to formula (I-j);

Q is a 4, 5, 6 or 7 membered heterocyclic ring which comprises a nitrogen atom through which Q is attached to Y and 0–2 additional heteroatoms selected from N, S and O, and which also comprises a carbonyl, thiocarbonyl, —C(=NR$^{13}$)— or sulfonyl moiety adjacent to the nitrogen atom attached to Y, provided that Q is not

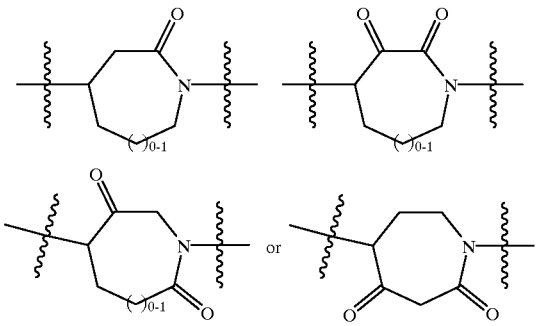

Y is a 5, 6 or 7 membered carbocyclic ring wherein from 0 to 3 carbon atoms are replaced by a heteroatom selected from N, S and O, and wherein Y is attached to Q through a carbon atom;

and wherein at least one radionuclide or $^3$H-methyl is present in the molecule;

or a pharmaceutically acceptable salt thereof.

Preferably, the radiolabeled farnesyl protein transferase inhibiting compound is selected from:

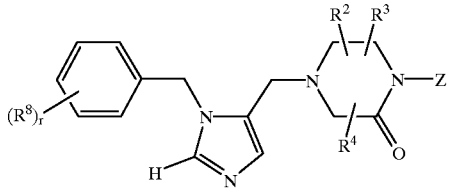

$R^2$ and $R^3$ are independently selected from: H; unsubstituted or substituted $C_{1-8}$ alkyl, unsubstituted or substituted $C_{2-8}$ alkenyl, unsubstituted or substituted $C_{2-8}$ alkynyl, unsubstituted or substituted aryl, unsubstituted or substituted heterocycle,

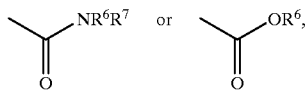

wherein the substituted group is substituted with one or more of:

1) aryl or heterocycle, unsubstituted or substituted with:
   a) $C_{1-4}$ alkyl,
   b) $(CH_2)_pOR^6$,
   c) $(CH_2)_pNR^6R^7$,
   d) halogen,
   e) a radionuclide,
2) $C_{3-6}$ cycloalkyl,
3) $OR^6$,
4) $SR^6$, $S(O)R^6$, $SO_2$, $R^6$,

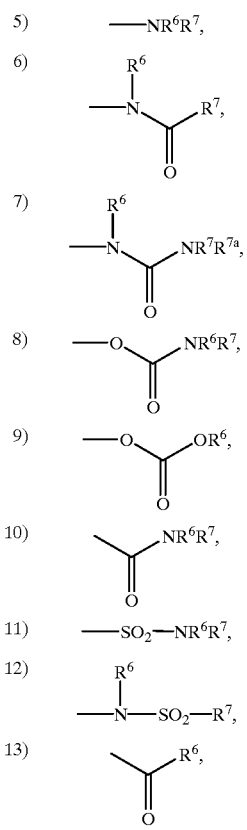

-continued

14) ⟶OR⁶, or 15) a radionuclide; or $R^4$ is selected from H and $CH_3$; and any two of $R^2$, $R^3$ and $R^4$ are optionally attached to the same carbon atom;

$R^6$, $R^7$ and $R^{7a}$ are independently selected from: H; $C_{1-4}$ alkyl, $^{11}C$-methyl, $C_{3-6}$ cycloalkyl, heterocycle, aryl, aroyl, heteroaroyl, arylsulfonyl, heteroarylsulfonyl, unsubstituted or substituted with:

a) $C_{1-4}$ alkoxy,
b) aryl or heterocycle,
c) halogen,
d) HO, e) 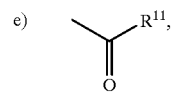

f) —$SO_2R^{11}$
g) $N(R^{10})_2$,
h) $^{11}C$-methyl, or
i) a radionuclide; or
$R^6$ and $R^7$ may be joined in a ring;
$R^7$ and $R^{7a}$ may be joined in a ring;
$R^8$ is independently selected from:
a) hydrogen,
b) aryl, heterocycle, $C_3$–$C_{10}$ cycloalkyl, $C_2$–$C_6$ alkenyl, $C_2$–$C_6$ alkynyl, perfluoroalkyl, F, Cl, Br, $R^{10}O$—, $R^{11}S(O)_m$—, $R^{10}C(O)NR^{10}$—, CN, $NO_2$, $R^{10}_2N$—C($NR^{10}$)—, $R^{10}C(O)$—, $R^{10}OC(O)$—, $N_3$, —$N(R^{10})_2$, or $R^{11}OC(O)NR^{10}$—,
c) $C_1$–$C_6$ alkyl unsubstituted or substituted by aryl, heterocycle, $C_3$–$C_{10}$ cycloalkyl, $C_2$–$C_6$ alkenyl, $C_2$–$C_6$ alkynyl, perfluoroalkyl, F, Cl, Br, $R^{10}O$—, $R^{11}S(O)_m$—, $R^{10}C(O)NH$—, CN, $H_2N$—C(NH)—, $R^{10}C(O)$—, $R^{10}OC(O)$—, $N_3$, —$N(R^{10})_2$, or $R^{10}OC(O)NH$—, and
d) a radionuclide;
$R^{10}$ is independently selected from hydrogen, $C_1$–$C_6$ alkyl, $^3H$-methyl, $^{11}C$-methyl, benzyl and aryl;
$R^{11}$ is independently selected from $C_1$–$C_6$ alkyl and aryl;
Z is phenyl, unsubstituted or substituted with one or more of:

1) $C_{1-4}$ alkyl, unsubstituted or substituted with:
   a) $C_{1-4}$ alkoxy,
   b) $NR^6R^7$,
   c) $C_{3-6}$ cycloalkyl,
   d) aryl or heterocycle,
   e) HO,
   f) —$S(O)_mR^6$,
   g) —$C(O)NR^6R^7$, or
   h) a radionuclide;
2) aryl or heterocycle,
3) halogen,
4) $OR^6$,
5) $NR^6R^7$,
6) CN,
7) $NO_2$, 8) CF$_3$;
9) —S(O)$_m$R$^6$,
10) —C(O)NR$^6$R$^7$,
11) C$_3$–C$_6$ cycloalkyl, or
12) a radionuclide;

| | |
|---|---|
| m is | 0, 1 or 2; and |
| r is | 0 to 5; and | wherein at least one radionuclide or $^3$H-methyl is present in the molecule;

or a pharmaceutically acceptable salt thereof.

Examples of compounds which selectively inhibit farnesyl protein transferase and may be radiolabeled as described hereinbelow include the following:

1-[1-(4-cyanobenzyl)imidazol-5-ylmethyl]-4-(2,3-dimethylphenyl)-2(S)-(2-methoxyethyl)piperazin-5-one;
(S)-1-(3-chlorophenyl)-4-[1-(4-cyanobenzyl)-5-imidazolylmethyl]-5-[2-(methanesulfonyl)ethyl]-2-piperazinone;
(S)-1-(3-chlorophenyl)-4-[1-(4-cyanobenzyl)-5-imidazolylmethyl]-5-[2-(ethanesulfonyl)ethyl]-2-piperazinone;
(R)-1-(3-chlorophenyl)-4-[1-(4-cyanobenzyl)-5-imidazolylmethyl]-5-[2-(ethanesulfonyl)methyl]-2-piperazinone;
(±)-5-(2-Butynyl)-1-(3-chlorophenyl)-4-[1-(4-cyanobenzyl)-5-imidazolylmethyl]-2-piperazinone;
1-(3-chlorophenyl)-4-[1-(4-cyanobenzyl)-5-imidazolylmethyl]-2-piperazinone;
5(S)-n-Butyl-4-[1-(4-cyanobenzyl)-5-imidazolylmethyl]-1-(2-methylphenyl)piperazin-2-one;
4-[1-(4-cyanobenzyl)-5-imidazolylmethyl]-5(S)-(2-fluoroethyl)-1-(3-chlorophenyl)piperazin-2-one;
4-[5-(4-cyanobenzyl)-1-imidazolylethyl]-1-(3-chlorophenyl)piperazin-2-one;
5(S)-n-Butyl-4-[1-(4-cyanobenzyl)-5-imidazolylmethyl]-1-phenylpiperazin-2-one;
5(S)-(2-fluroethyl)-4-[1-(4-cyanobenzyl)-5-imidazolylmethyl]-1-(3-methoxyphenyl)piperazin-2-one;
5(S)-(2-(methylsulfonyl)ethyl)-1-(3-iodophenyl)-4-[1-(4-cyanobenzyl)-5-imidazolylmethyl]-2-piperazinone;
5(S)-(2-(methylsulfonyl)ethyl)-1-(3-iodo5-fluoromethylphenyl)-4-[1-(4-cyanobenzyl)-5-imidazolylmethyl]-2-piperazinone;
1-(2-Phenyl-N-Oxopyrid-5-ylmethyl)-5-(4-cyanobenzyl)imidazole; 1-(2-(3-Trifluoromethoxyphenyl)-pyrid-5-ylmethyl)-5-(4-cyanobenzyl)imidazole;
1-(2-(2-Trifluoromethylphenyl)-pyrid-5-ylmethyl)-5-(4-cyanobenzyl)imidazole;
4-{3-[4-(-2-Oxo-2-H-pyridin-1-yl)benzyl]-3-H-imidazol-4-ylmethyl]benzonitrile;
4-{1-[4-(5-chloro-2-oxo-2H-pyridin-1-yl)-benzyl]-1H-pyrrol-2-ylmethyl}-benzonitrile;
4-[1-(2-Oxo-2H-[1,2']bipyridinyl-5'-ylmethyl)-1H-pyrrol-2-ylmethyl]-benzonitrile;
4-[1-(5-chloro-2-oxo-2H-[1,2']bipyridinyl-5'-ylmethyl)-1H-pyrrol-2-ylmethyl]-benzonitrile;
4-[3-(2-Oxo-1-phenyl-1,2-dihydropyridin-4-ylmethyl)-3H-imidazol-4-ylmethyl]benzonitrile;
4-{3-[1-(3-chloro-phenyl)-2-oxo-1,2-dihydropyridin-4-ylmethyl]-3H-imidazol-4-ylmethyl}benzonitrile;

TABLE 1

| X | Y |
|---|---|
| CH$_2$SO$_2$Et | CF$_3$ |
| CH$_2$SO$_2$Ph | CF$_3$ |
| CH$_2$SO$_2$Me | Cl |
| CH$_2$SO$_2$Et | Cl |
| CONHEt | CF$_3$ |
| CH$_2$SO$_2$Ph | Cl |
| CONHMe | Cl |
| CONHEt | Cl |
| CONHc-Pr | Cl |
| CONHc-Pr | CF$_3$ |
| NHCOMe | Cl |
| CONMe$_2$ | CF$_3$ |
| SO$_2$Et | Cl |
| CH$_2$SMe | Cl |
| (±) C≡CMe | Cl |

TABLE 2

| X | Y |
|---|---|
| CH$_2$ | 3-Cl |
| CH$_2$ | 2-Br |
| CH$_2$ | 3-F |
| CH$_2$ | 3-Br |

TABLE 3

| X | Y |
|---|---|
| 2-Me | H |

TABLE 4
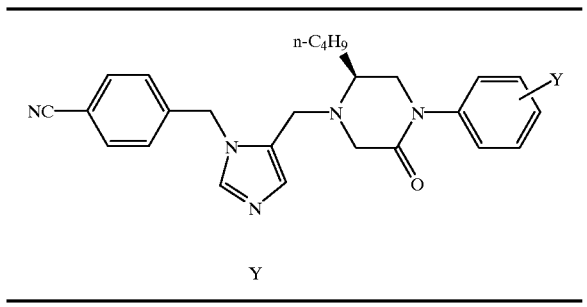
| Y |
|---|
| 3-SO$_2$Me |
| 3-CH$_3$ |
| 3-OCH$_3$ |
| H |
| 3-F |
TABLE 5
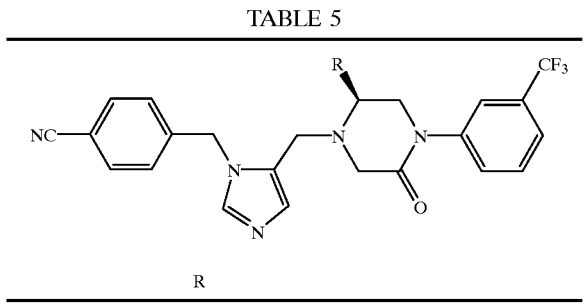
| R |
|---|
| CH$_2$CH$_2$OCH$_2$CF$_3$ |
| CH$_2$CH$_2$N$_3$ |
| CH$_2$CH$_2$NHCOCH$_3$ |
| CH$_2$CH$_2$NHCOC$_2$H$_5$ |
| CH$_2$CH$_2$SO$_2$CH(CH$_3$)$_2$ |
| CH$_2$CH$_2$S(O)CH(CH$_3$)$_2$ |
TABLE 6
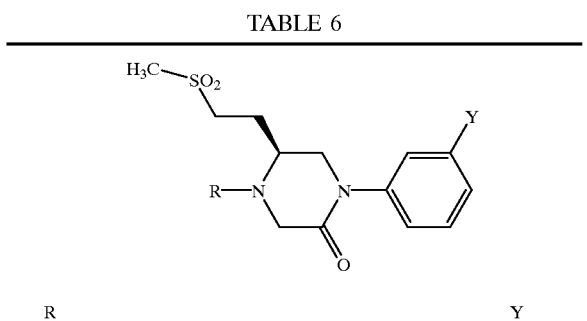
| R | Y |
|---|---|
| 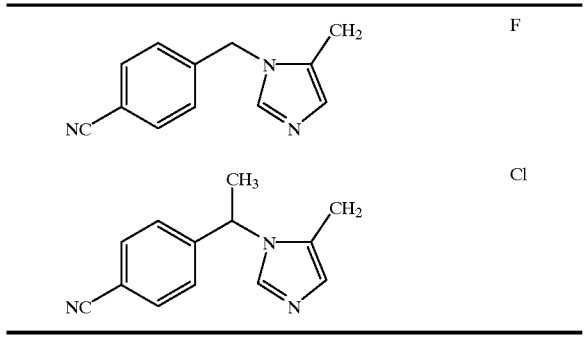 | F |
|  | Cl |
TABLE 7
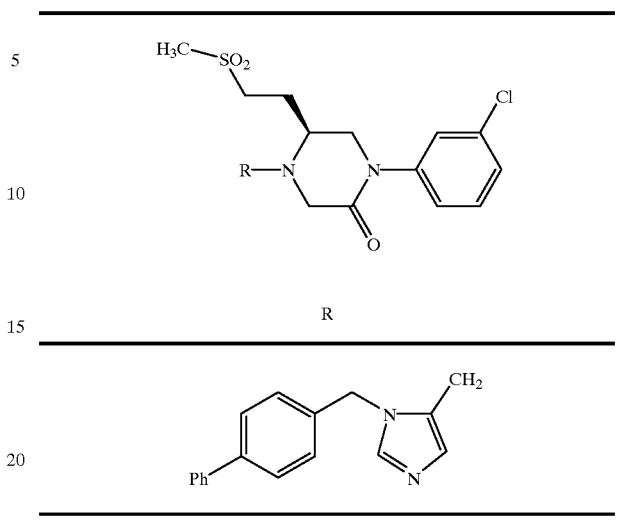
| R |
|---|
| 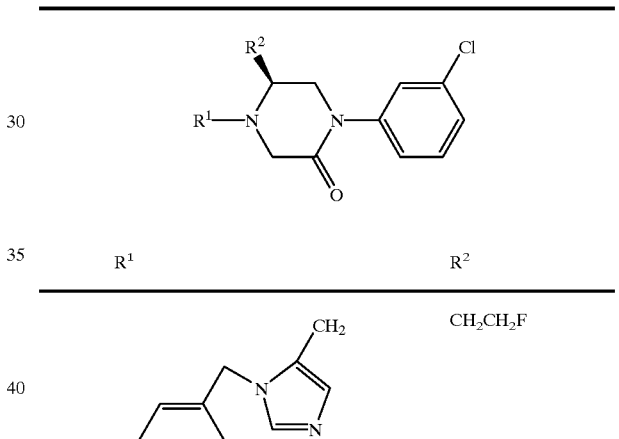 |
TABLE 8
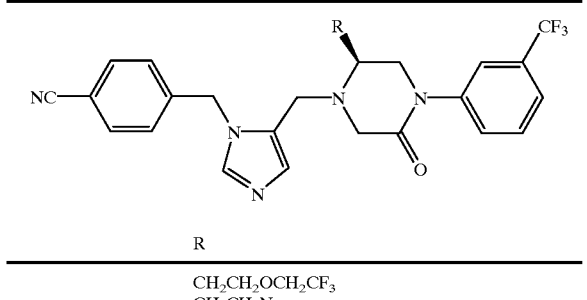
| R$^1$ | R$^2$ |
|---|---|
| 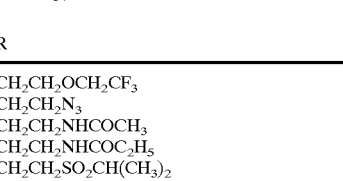 | CH$_2$CH$_2$F |
TABLE 9
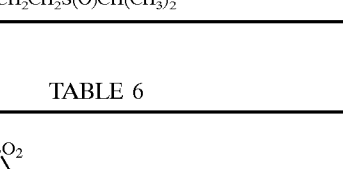
| R | Y |
|---|---|
| 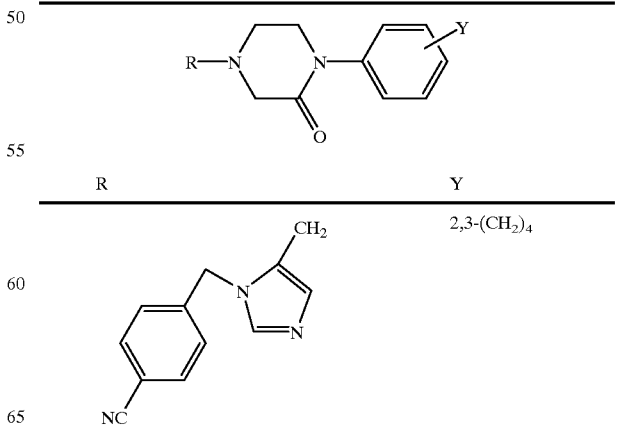 | 2,3-(CH$_2$)$_4$ |

TABLE 9-continued
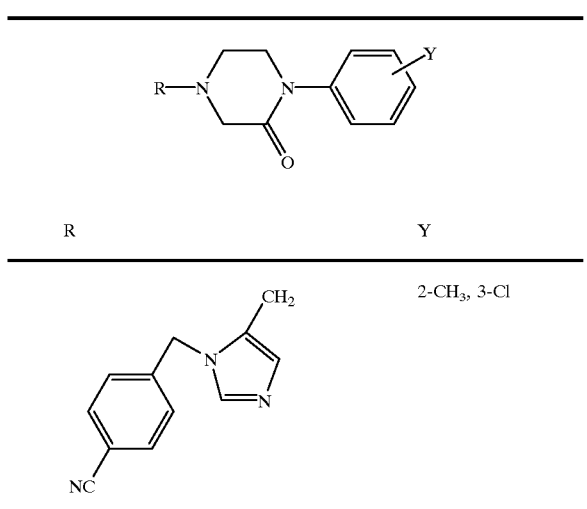
| R | Y |
|---|---|
| (structure shown) | 2-CH$_3$, 3-Cl |
TABLE 10
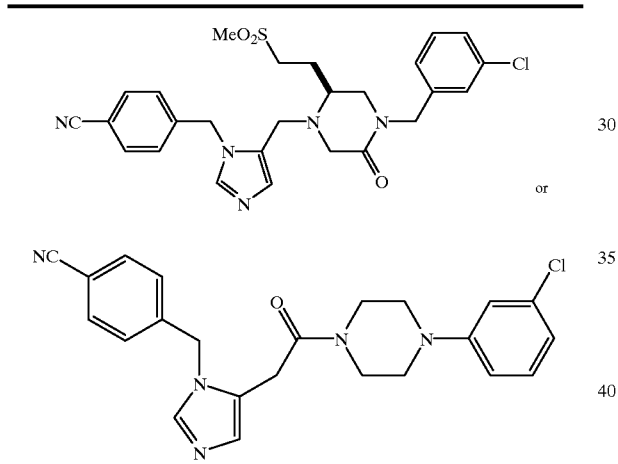
or a pharmaceutically acceptable salt or optical isomer thereof.
Specific examples of radiolabeled farnesyl-protein transferase inhibitors include:
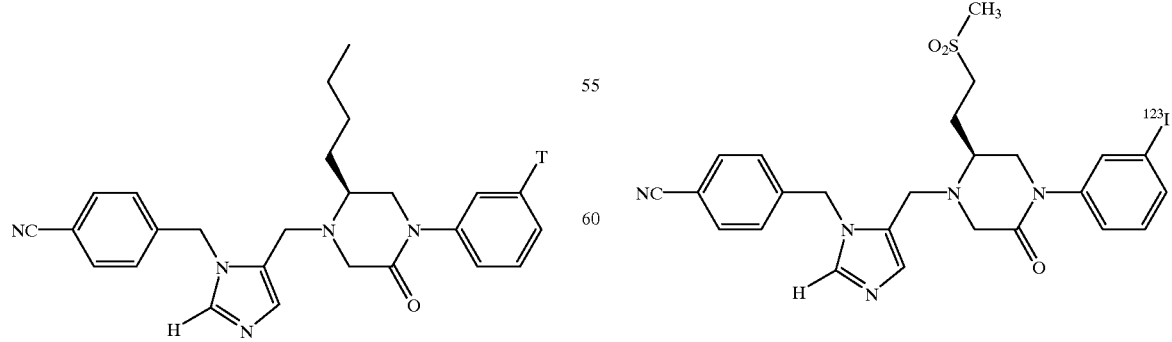
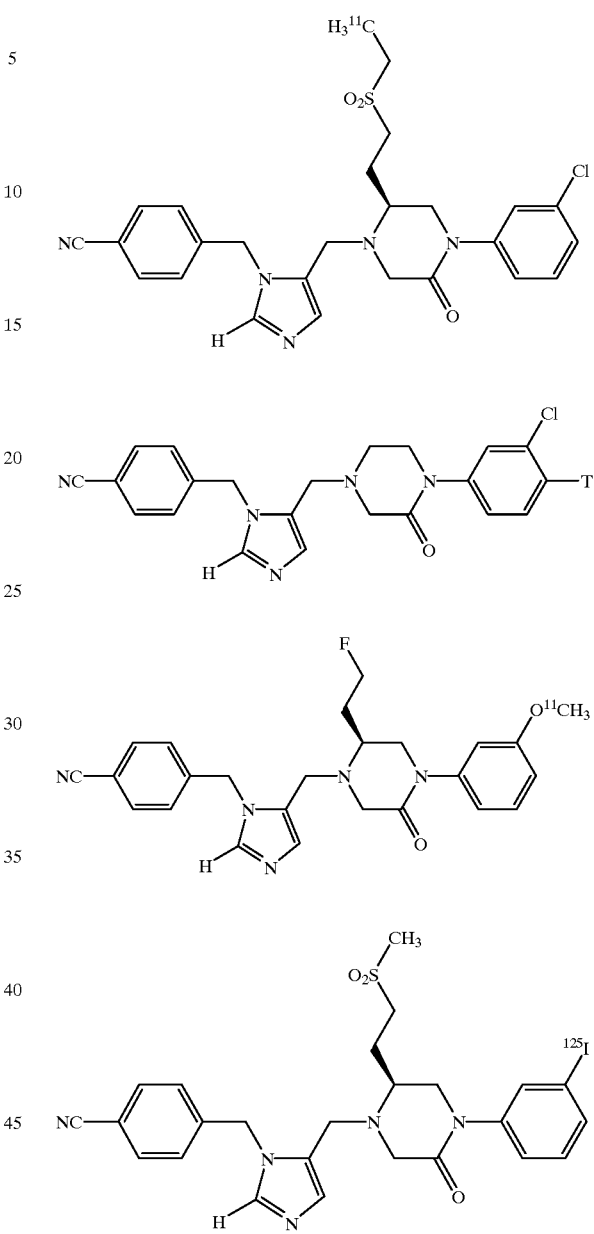

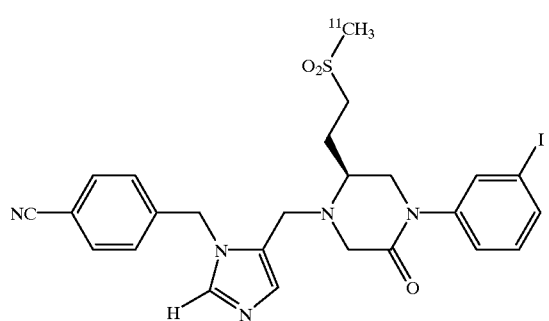
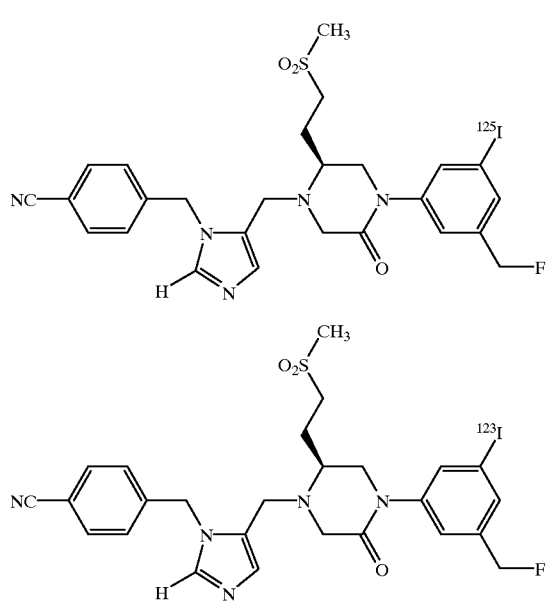

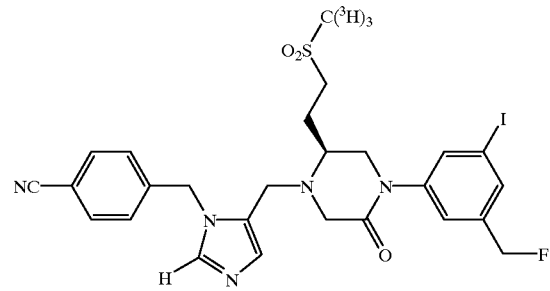

or a pharmaceutically acceptable salt thereof.

Preferably the radiolabeled farnesyl-protein transferase inhibitor is the compound of the formula

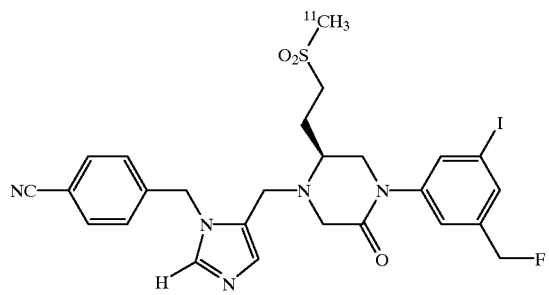

or a pharmaceutically acceptable salt thereof, which has been radiolabeled with a radionuclide selected from $^{3}$H, $^{11}$C, $^{18}$F, $^{125}$I and $^{123}$I.

Compounds which are described as inhibitors of farnesyl-protein transferase and may therefore be useful in radiolabeled form in the present invention, and methods of synthesis thereof, can be found in the following patents, pending applications and publications, which are herein incorporated by reference:

WO 95/32987 published on Dec. 7, 1995;
European Pat. Publ. 0 618 221;
European Pat. Publ. 0 675 112;
WO 95/08542;
WO 95/11917;
WO 95/12612;
WO 95/12572;
WO 95/10514;
WO 95/10515;
WO 95/10516;
WO 95/24612;
WO 95/34535;
WO 96/22278;
WO 96/24611;
WO 96/24612;
WO 96/05168;
WO 96/05169;
WO 96/00736 and U.S. Pat. No. 5,571,792 granted on Nov. 5, 1996;
WO 96/17861;
WO 96/33159;
WO 96/34850;

WO 96/34851;
WO 96/30017;
WO 96/30018;
WO 96/30362;
WO 96/30363;
WO 96/31111;
WO 96/31477;
WO 96/31478;
WO 96/31501; and
U.S. Pat. No. 5,532,359 granted on Jul. 2, 1996.

Compounds which are inhibitors of farnesyl-protein transferase and may therefore be useful in radiolabeled form in the present invention, and methods of synthesis thereof, can be found in the following patents, pending applications and publications, which are herein incorporated by reference:

WO 96/30343 (Oct. 3, 1996); U.S. Ser. No. 08/412,829 filed on Mar. 29, 1995; and U.S. Ser. No. 08/470,690 filed on Jun. 6, 1995; and U.S. Ser. No. 08/600,728 filed on Feb. 28, 1996;
WO 96/37204 (Nov. 28, 1996); U.S. Ser. No. 08/449,038 filed on May 24, 1995;
U.S. Ser. No. 08/648,330 filed on May 15, 1996;
WO 96/39137 (Dec. 12, 1996); U.S. Ser. No. 08/468,160 filed on Jun. 6, 1995;
U.S. Ser. No. 08/652,055 filed on May 23, 1996;
U.S. Ser. No. 08/749,254 filed on Nov. 15, 1996.
U.S. Ser. No. 60/010,798 filed on Jan. 30, 1996; U.S. Ser. No. 08/786,516, filed on Jan. 21, 1997;
U.S. Ser. No. 60/010,799 filed on Jan. 30, 1996; U.S. Ser. No. 08/786,520, filed on Jan. 21, 1997;
U.S. Ser. No. 60/010,860 filed on Jan. 30, 1996; U.S. Ser. No. 08/784,556, filed on Jan. 21, 1997;
U.S. Ser. No. 60/011,081 filed on Jan. 30, 1996; U.S. Ser. No. 08/786,519, filed on Jan. 21, 1997;
U.S. Ser. No. 60/010,798 filed on Jan. 30, 1996; U.S. Ser. No. 08/786,516, filed on Jan. 21, 1997;
U.S. Ser. No. 60/014,587 filed on Apr. 3, 1996; U.S. Ser. No. 08/823,921, filed on Mar. 25, 1997;
U.S. Ser. No. 60/014,589 filed on Apr. 3, 1996; U.S. Ser. No. 08/823,923, filed on Mar. 25, 1997;
U.S. Ser. No. 60/014,592 filed on Apr. 3, 1996; U.S. Ser. No. 08/834,671, filed on Apr. 1, 1997;
U.S. Ser. No. 60/014,593 filed on Apr. 3, 1996; U.S. Ser. No. 08/827,485, filed on Mar. 27, 1997;
U.S. Ser. No. 60/014,594 filed on Apr. 3, 1996; U.S. Ser. No. 08/823,920, filed on Mar. 25, 1997;
U.S. Ser. No. 60/014,668 filed on Apr. 3, 1996; U.S. Ser. No. 08/824,588 filed on Mar. 26, 1997;
U.S. Ser. No. 60/014,775 filed on Apr. 3, 1996; U.S. Ser. No. 08/826,292, filed on Mar. 27, 1997;
U.S. Ser. No. 60/014,776 filed on Apr. 3, 1996; U.S. Ser. No. 08/824,427, filed on Mar. 26, 1997;
U.S. Ser. No. 60/014,777 filed on Apr. 3, 1996; U.S. Ser. No. 08/826,317, filed on Mar. 27, 1997;
U.S. Ser. No. 60/014,791 filed on Apr. 3, 1996; U.S. Ser. No. 08/831,308, filed on Apr. 1, 1997;
U.S. Ser. No. 60/014,792 filed on Apr. 3, 1996; U.S. Ser. No. 08/827,482, filed on Mar. 27, 1997;
U.S. Ser. No. 60/014,793 filed on Apr. 3, 1996; U.S. Ser. No. 08/823,934, filed on Mar. 25, 1997;
U.S. Ser. No. 60/014,794 filed on Apr. 3, 1996; U.S. Ser. No. 08/834,675, filed on Apr. 1, 1997;
U.S. Ser. No. 60/014,798 filed on Apr. 3, 1996; U.S. Ser. No. 08/823,929, filed on Mar. 25, 1997;
U.S. Ser. No. 60/014,774 filed on Apr. 3, 1996; U.S. Ser. No. 08/826,291, filed on Mar. 27, 1997;
U.S. Ser. No. 60/022,332 filed on Jul. 24, 1996; U.S. Ser. No. 08/823,919, filed on Mar. 25, 1997;
U.S. Ser. No. 60/022,340 filed on Jul. 24, 1996; U.S. Ser. No. 08/827,486, filed on Mar. 27, 1997;
U.S. Ser. No. 60/022,341 filed on Jul. 24, 1996; U.S. Ser. No. 08/826,251, filed on Mar. 26, 1997;
U.S. Ser. No. 60/022,342 filed on Jul. 24, 1996; U.S. Ser. No. 08/825,293, filed on Mar. 27, 1997;
U.S. Ser. No. 60/022,558 filed on Jul. 24, 1996; U.S. Ser. No. 08/827,476 filed on Mar. 27, 1997;
U.S. Ser. No. 60/022,582 filed on Jul. 24, 1996; U.S. Ser. No. 08/829,922, filed on Apr. 1, 1997;
U.S. Ser. No. 60/022,586 filed on Jul. 24, 1996; U.S. Ser. No. 08/827,484, filed on Mar. 27, 1997;
U.S. Ser. No. 60/022,587 filed on Jul. 24, 1996; U.S. Ser. No. 08/831,105, filed on Apr. 1, 1997;
U.S. Ser. No. 60/022,647 filed on Jul. 24, 1996; U.S. Ser. No. 08/827,483, filed on Mar. 27, 1997;
U.S. Ser. No. 60/032,126 filed on Dec. 5, 1996; U.S. Ser. No. 08/984,732, filed on Dec. 4, 1997;
U.S. Ser. No. 60/032,428 filed on Dec. 5, 1996; U.S. Ser. No. 08/985,124, filed on Dec. 4, 1997;
U.S. Ser. No. 60/032,578 filed on Dec. 5, 1996; U.S. Ser. No. 08/985,337, filed on Dec. 4, 1997;
U.S. Ser. No. 60/032,579 filed on Dec. 5, 1996; U.S. Ser. No. 08/985,320, filed on Dec. 4, 1997;
U.S. Ser. No. 60/033,990, filed on Dec. 30, 1996; U.S. Ser. No. 08/995, 744, filed on Dec. 22, 1997; and
U.S. Ser. No. 60/033,991, filed on Dec. 30, 1996; U.S. Ser. No. 08/997,171, filed on Dec. 23, 1997;

All patents, publications and pending patent applications identified are hereby incorporated by reference.

With respect to the compounds of formulas I-a through I-j the following definitions apply:

The term "$^3$H-methyl" represents the moiety —C($^3$H)$_3$.

The term "alkyl" refers to a monovalent alkane (hydrocarbon) derived radical containing from 1 to 15 carbon atoms unless otherwise defined. It may be straight, branched or cyclic. Preferred straight or branched alkyl groups include methyl, ethyl, propyl, isopropyl, butyl and t-butyl. Preferred cycloalkyl groups include cyclopentyl and cyclohexyl.

When substituted alkyl is present, this refers to a straight, branched or cyclic alkyl group as defined above, substituted with 1–3 groups as defined with respect to each variable.

Heteroalkyl refers to an alkyl group having from 2–15 carbon atoms, and interrupted by from 1–4 heteroatoms selected from O, S and N.

The term "alkenyl" refers to a hydrocarbon radical straight, branched or cyclic containing from 2 to 15 carbon atoms and at least one carbon to carbon double bond. Preferably one carbon to carbon double bond is present, and up to four non-aromatic (non-resonating) carbon-carbon double bonds may be present. Examples of alkenyl groups include vinyl, allyl, iso-propenyl, pentenyl, hexenyl, heptenyl, cyclopropenyl, cyclobutenyl, cyclopentenyl, cyclohexenyl, 1-propenyl, 2-butenyl, 2-methyl-2-butenyl, isoprenyl, farnesyl, geranyl, geranylgeranyl and the like. Preferred alkenyl groups include ethenyl, propenyl, butenyl and cyclohexenyl. As described above with respect to alkyl, the straight, branched or cyclic portion of the alkenyl group may contain double bonds and may be substituted when a substituted alkenyl group is provided.

The term "alkynyl" refers to a hydrocarbon radical straight, branched or cyclic, containing from 2 to 15 carbon atoms and at least one carbon to carbon triple bond. Up to three carbon—carbon triple bonds may be present. Preferred alkynyl groups include ethynyl, propynyl and butynyl. As described above with respect to alkyl, the straight, branched or cyclic portion of the alkynyl group may contain triple bonds and may be substituted when a substituted alkynyl group is provided.

Aryl refers to aromatic rings e.g., phenyl, substituted phenyl and like groups as well as rings which are fused, e.g., naphthyl and the like. Aryl thus contains at least one ring having at least 6 atoms, with up to two such rings being present, containing up to 10 atoms therein, with alternating (resonating) double bonds between adjacent carbon atoms. The preferred aryl groups are phenyl and naphthyl. Aryl groups may likewise be substituted as defined below. Preferred substituted aryls include phenyl and naphthyl substituted with one or two groups. With regard to the farnesyl transferase inhibitors, "aryl" is intended to include any stable monocyclic, bicyclic or tricyclic carbon ring(s) of up to 7 members in each ring, wherein at least one ring is aromatic. Examples of aryl groups include phenyl, naphthyl, anthracenyl, biphenyl, tetrahydronaphthyl, indanyl, phenanthrenyl and the like.

The term "heteroaryl" refers to a monocyclic aromatic hydrocarbon group having 5 or 6 ring atoms, or a bicyclic aromatic group having 8 to 10 atoms, containing at least one heteroatom, O, S or N, in which a carbon or nitrogen atom is the point of attachment, and in which one additional carbon atom is optionally replaced by a heteroatom selected from 0 or S, and in which from 1 to 3 additional carbon atoms are optionally replaced by nitrogen heteroatoms. The heteroaryl group is optionally substituted with up to three groups.

Heteroaryl thus includes aromatic and partially aromatic groups which contain one or more heteroatoms. Examples of this type are thiophene, purine, imidazopyridine, pyridine, oxazole, thiazole, oxazine, pyrazole, tetrazole, imidazole, pyridine, pyrimidine, pyrazine and triazine. Examples of partially aromatic groups are tetrahydro-imidazo[4,5-c]pyridine, phthalidyl and saccharinyl, as defined below.

With regard to the farnesyl transferase inhibitors, the term heterocycle or heterocyclic, as used herein, represents a stable 5- to 7-membered monocyclic or stable 8- to 11-membered bicyclic or stable 11–15 membered tricyclic heterocycle ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, 2-oxopiperazinyl, 2-oxopiperidinyl, 2-oxopyrrolidinyl, piperidyl, piperazinyl, pyridyl, pyridyl N-oxide, pyridonyl, pyrazinyl, pyrazolidinyl, pyrazolyl, pyrimidinyl, pyrrolidinyl, pyrrolyl, quinazolinyl, quinolinyl, quinolinyl N-oxide, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, and thienyl. Preferably, heterocycle is selected from imidazolyl, 2-oxopyrrolidinyl, piperidyl, pyridyl and pyrrolidinyl.

With regard to the farnesyl transferase inhibitors, the terms "substituted aryl", "substituted heterocycle" and "substituted cycloalkyl" are intended to include the cyclic group which is substituted with 1 or 2 substitutents selected from the group which includes but is not limited to F, Cl, Br, $CF_3$, $NH_2$, $N(C_1$–$C_6$ alkyl$)_2$, $NO_2$, CN, $(C_1$–$C_6$ alkyl)O—, —OH, $(C_1$–$C_6$ alkyl)S(O)$_m$—, $(C_1$–$C_6$ alkyl)C(O)NH—, $H_2N$—C(NH)—, $(C_1$–$C_6$ alkyl)C(O)—, $(C_1$–$C_6$ alkyl)OC(O)—, $N_3$, $(C_1$–$C_6$ alkyl)OC(O)NH— and $C_1$–$C_{20}$ alkyl.

In the present method, amino acids which are disclosed are identified both by conventional 3 letter and single letter abbreviations as indicated below:

| | | |
|---|---|---|
| Alanine | Ala | A |
| Arginine | Arg | R |
| Asparagine | Asn | N |
| Aspartic acid | Asp | D |
| Asparagine or Aspartic acid | Asx | B |
| Cysteine | Cys | C |
| Glutamine | Gln | Q |
| Glutamic acid | Glu | E |
| Glutamine or Glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The compounds used in the present method may have asymmetric centers and occur as racemates, racemic mixtures, and as individual diastereomers, with all possible isomers, including optical isomers, being included in the present invention. Unless otherwise specified, named amino acids are understood to have the natural "L" stereo-configuration With respect to the farnesyl-protein transferase inhibitors of the formulas I-d and I-f, the substituent illustrated by the structure

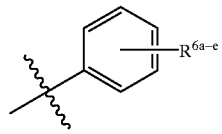

is a simplified representation of a phenyl ring having five (5) substituents (hydrogens and/or non-hydrogens) and may also be represented by the structure With respect to the farnesyl-protein transferase inhibitors of the formulas I-d and I-f, the moiety described as

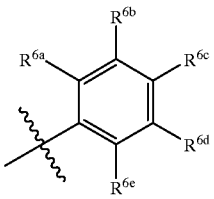

where any two of $R^{6a}$, $R^{6b}$, $R^{6c}$, $R^{6d}$ and $R^{6e}$ on adjacent carbon atoms are combined to form a diradical selected from —CH=CH—CH=CH, —CH=CH—CH—, —(CH$_2$)$_4$— and —(CH$_2$)$_4$— includes the following structures:

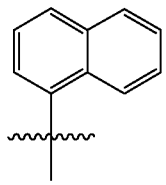 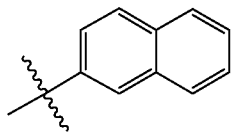

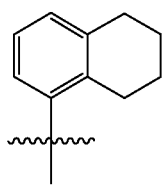 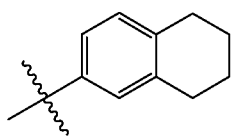

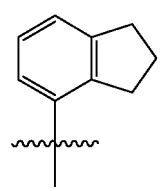 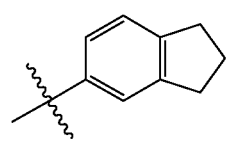

It is understood that such fused ring moieties may be further substituted by the remaining $R^{6a}$, $R^{6b}$, $R^{6c}$, $R^{6d}$ and/or $R^{6e}$ as defined hereinabove.

With respect to the farnesyl-protein transferase inhibitors of the formulas I-e and I-g, the moieties designated by the following structures

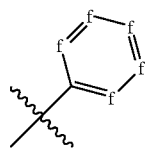 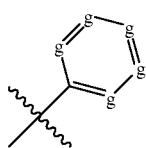

represent an aromatic 6-membered heterocyclic ring and includes the following ring systems:

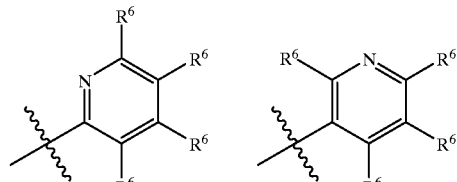

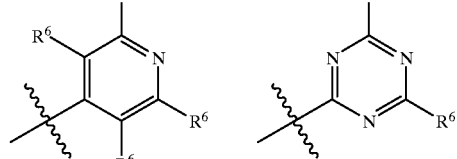

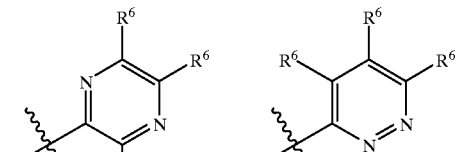

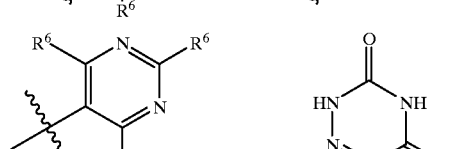

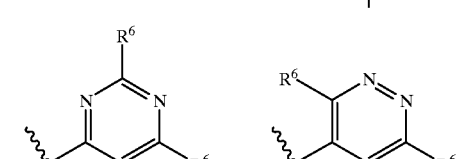

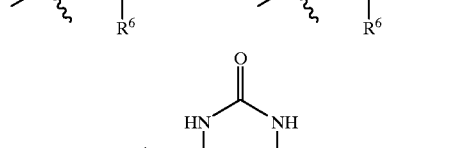

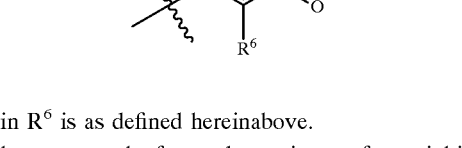

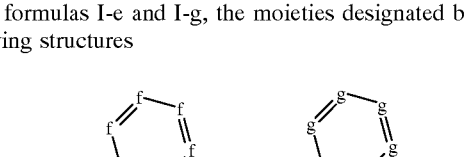

wherein $R^6$ is as defined hereinabove.

With respect to the farnesyl-protein transferase inhibitors of the formulas I-e and I-g, the moieties designated by the following structures

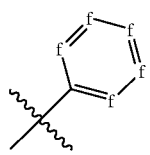 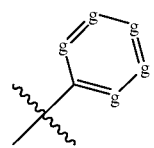

where any two of $R^6$ on adjacent carbon atoms are combined to form a diradical selected from —CH=CH—CH=CH—, —CH=CH—CH—, —(CH$_2$)$_4$— and —(CH$_2$)$_4$— include, but are not limited to the following structures:

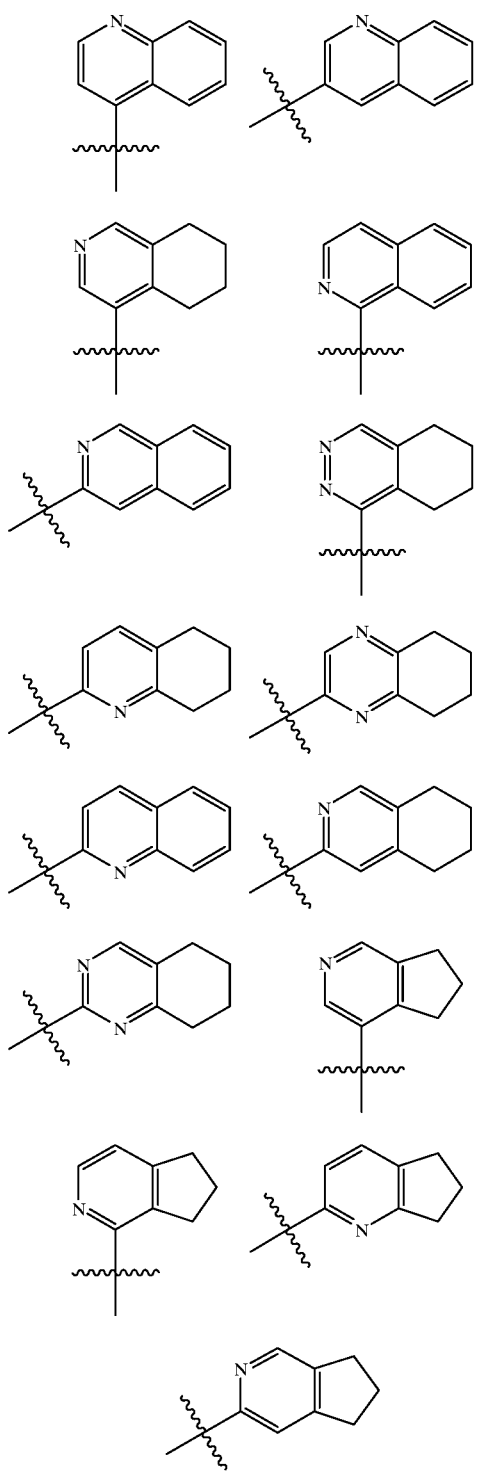

It is understood that such fused ring moieties may be further substituted by the remaining R⁶s as defined hereinabove.

With respect to the farnesyl-protein transferase inhibitors of the formulas I-f and I-g, the moiety designated by the following structure

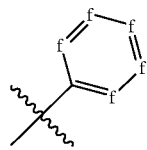

represents an aromatic 6-membered heterocyclic ring and includes the following ring systems:

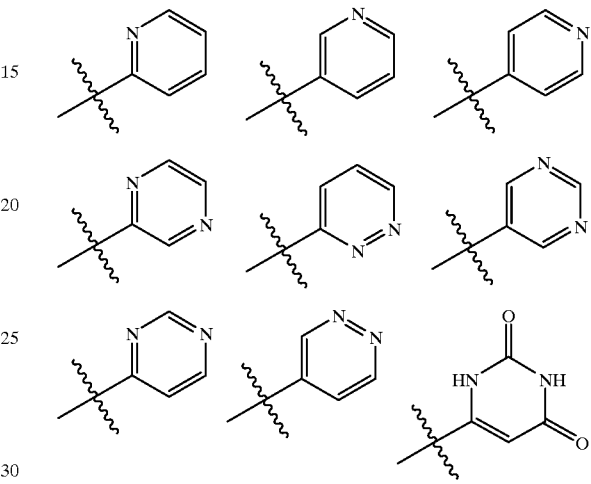

wherein it is understood that one of the ring carbon atoms is substituted with

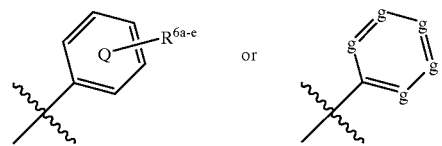

respectively.

With respect to the farnesyl-protein transferase inhibitors of the formula I-i, the substituent illustrated by the structure

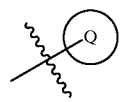

represents a 4, 5, 6 or 7 membered heterocyclic ring which comprises a nitrogen atom through which Q is attached to Y and 0–2 additional heteroatoms selected from N, S and O, and which also comprises a carbonyl, thiocarbonyl, —C(=NR¹³)— or sulfonyl moiety adjacent to the nitrogen atom attached to Y and includes the following ring systems:

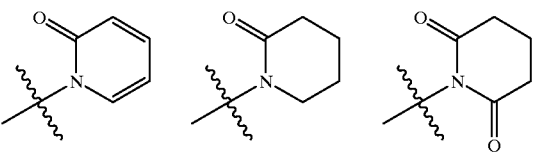

-continued

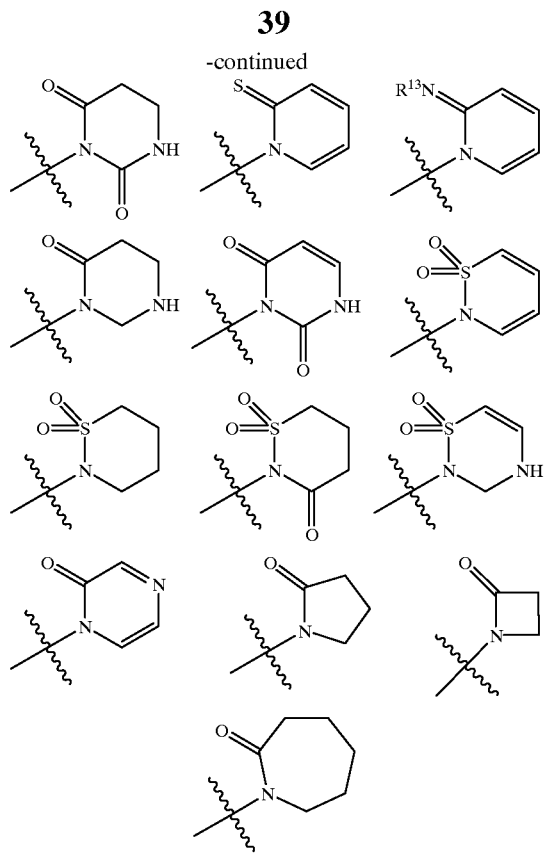

It is understood that such rings may be substituted by $R^{6a}$, $R^{6b}$, $R^{6c}$, $R^{6d}$ and/or $R^{6e}$ as defined hereinabove.

With respect to the farnesyl-protein transferase inhibitors of the formula II-i, the moiety described as

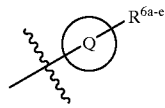

where any two of $R^{6a}$, $R^{6b}$, $R^{6c}$, $R^{6d}$ and $R^{6e}$ on adjacent carbon atoms are combined to form a diradical selected from —CH=CH—CH=CH, —CH=CH—CH—, —(CH$_2$)$_4$— and —(CH$_2$)$_4$— includes, but is not limited to, the following structures:

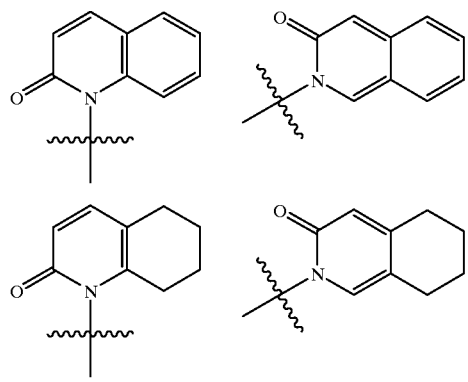

-continued

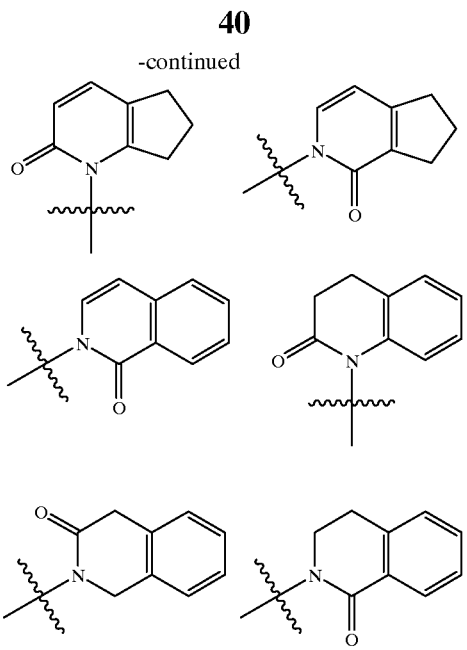

It is understood that such fused ring moieties may be further substituted by the remaining $R^{6a}$, $R^{6b}$, $R^{6c}$, $R^{6d}$ and/or $R^{6e}$ as defined hereinabove.

With respect to the farnesyl-protein transferase inhibitors of the formula I-i, the substituent illustrated by the structure

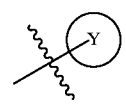

represents a 5, 6 or 7 membered carbocyclic ring wherein from 0 to 3 carbon atoms are replaced by a heteroatom selected from N, S and O, and wherein Y is attached to Q through a carbon atom and includes the following ring systems:

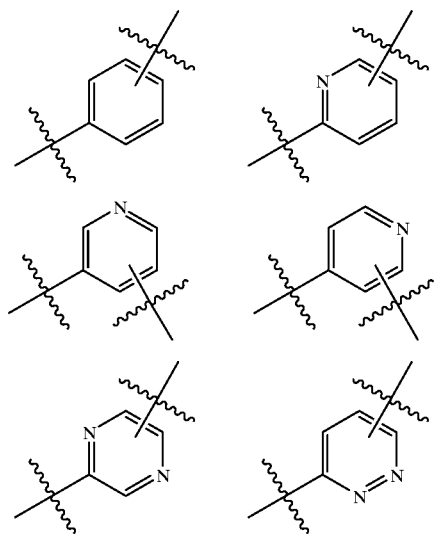

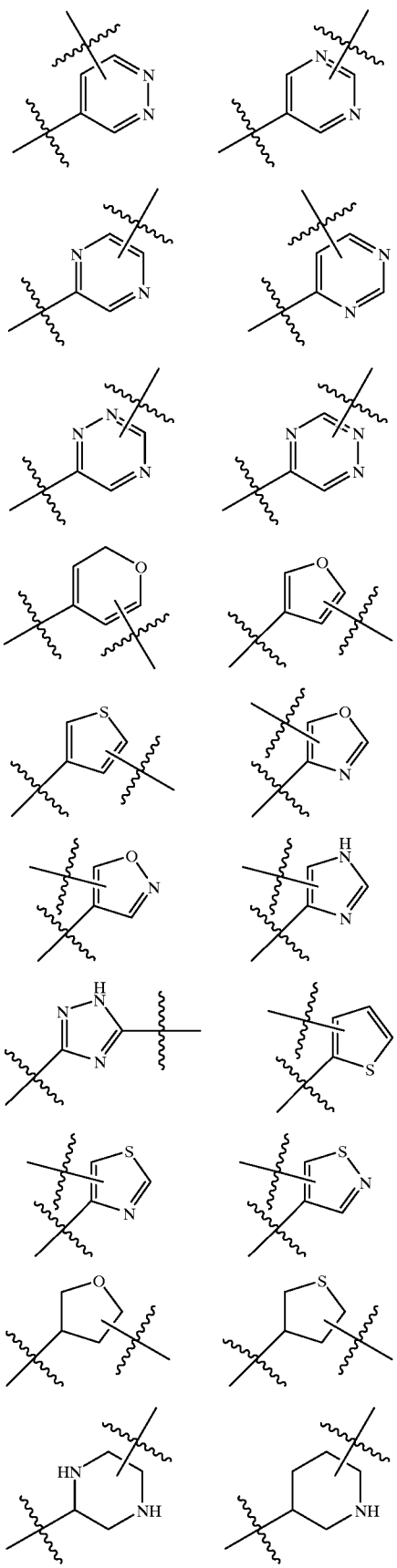

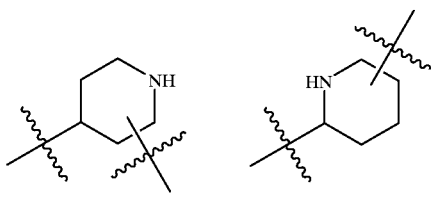

With respect to the farnesyl-protein transferase inhibitors of the formula I-j, the substituent illustrated by the structure

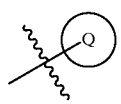

represents a 4, 5, 6 or 7 membered heterocyclic ring which comprises a nitrogen atom through which Q is attached to Y and 0–2 additional heteroatoms selected from N, S and O, and which also comprises a carbonyl, thiocarbonyl, —C(=NR$^{13}$)— or sulfonyl moiety adjacent to the nitrogen atom attached to Y and includes the following ring systems:

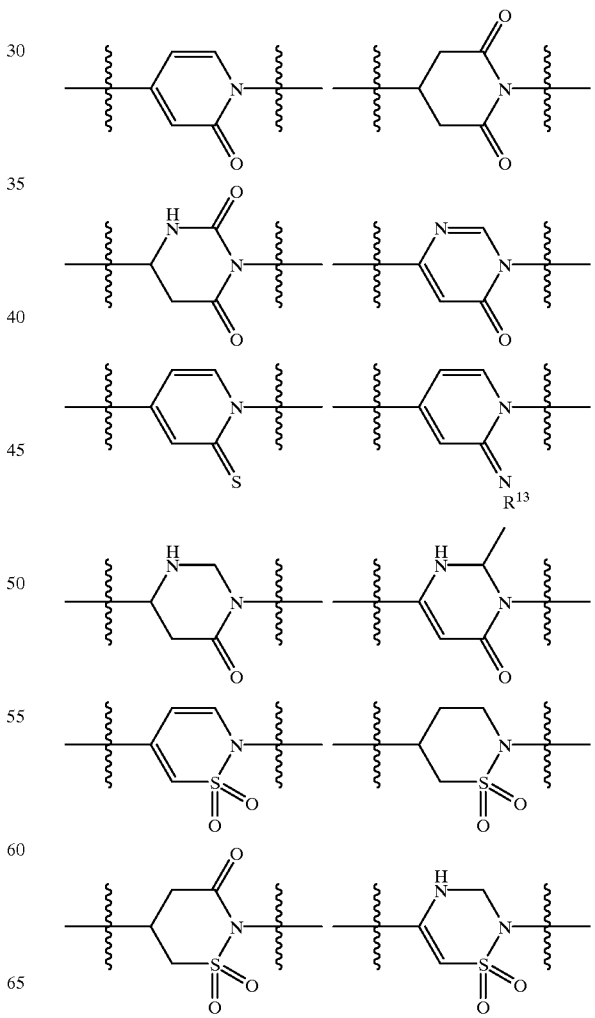

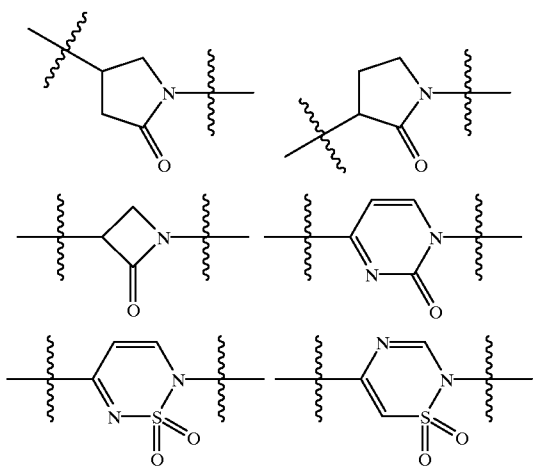

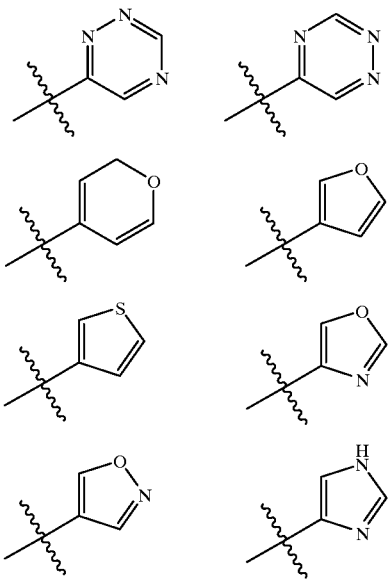

With respect to the farnesyl-protein transferase inhibitors of the formula I-j, the substituent illustrated by the structure

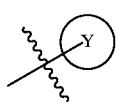

represents a 5-, 6- or 7-membered carbocyclic ring wherein from 0 to 3 carbon atoms are replaced by a heteroatom selected from N, S and O, and wherein Y is attached to Q through a carbon atom and includes the following ring systems:

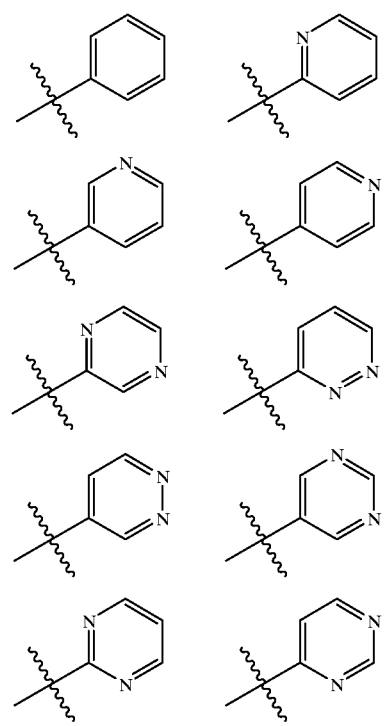

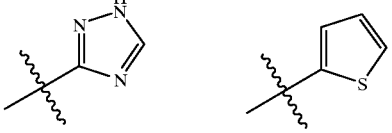

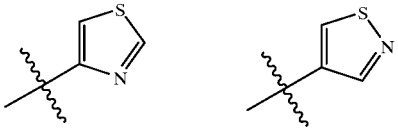

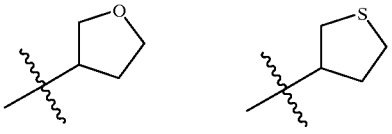

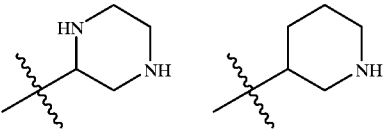

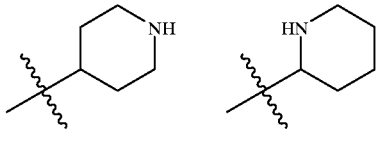

With respect to the farnesyl-protein transferase inhibitors of the formula I-j, the moiety described as

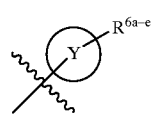

where any two of $R^{6a}$, $R^{6b}$, $R^{6c}$, $R^{6d}$ and $R^{6e}$ on adjacent carbon atoms are combined to form a diradical selected from —CH=CH—CH=CH, —CH=CH—CH—, —(CH$_2$)$_4$— and —(CH$_2$)$_4$— includes, but is not limited to, the following structures:

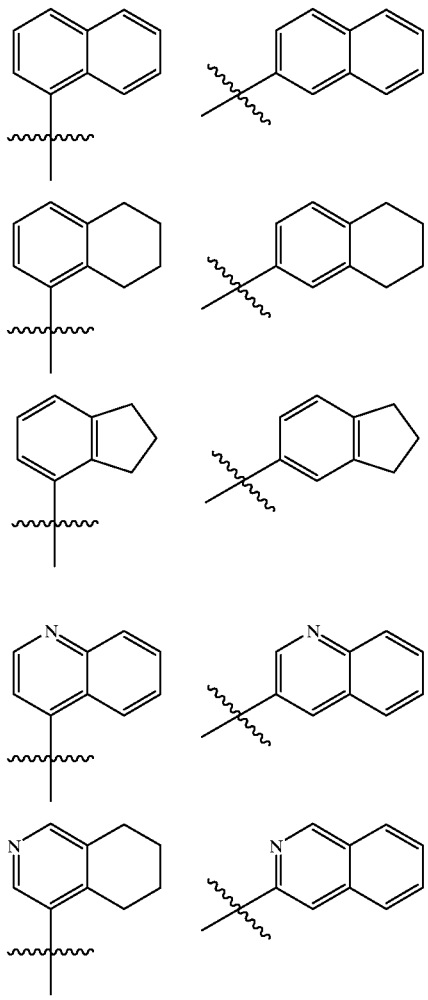

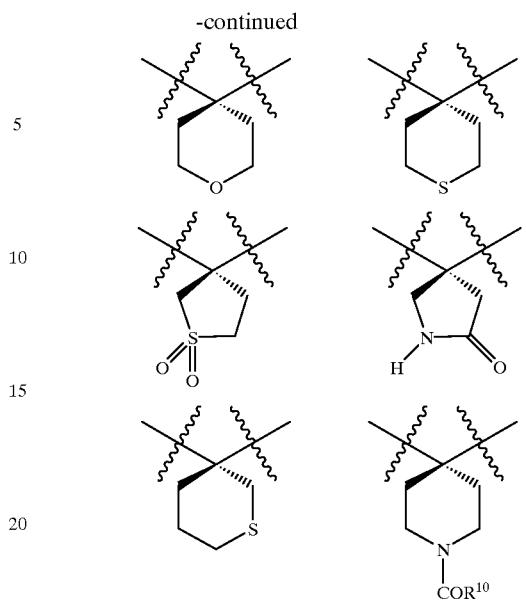

-continued

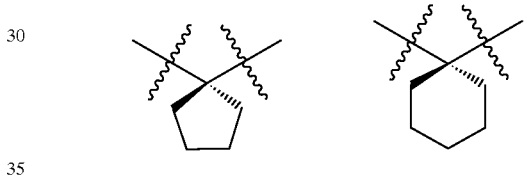

When $R^6$ and $R^7$, $R^7$ and $R^{7a}$, or are combined to form —$(CH_2)_u$—, cyclic moieties are formed. Examples of such cyclic moieties include, but are not limited to:

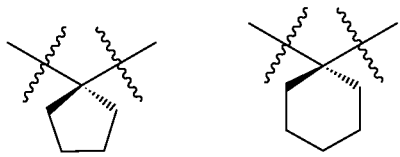

It is understood that such fused ring moieties may be further substituted by the remaining $R^{6a}$, $R^{6b}$, $R^{6c}$, $R^{6d}$ and/or $R^{6e}$ as defined hereinabove.

When $R^2$ and $R^3$ are combined to form —$(CH_2)_u$—, cyclic moieties are formed. Examples of such cyclic moieties include, but are not limited to:

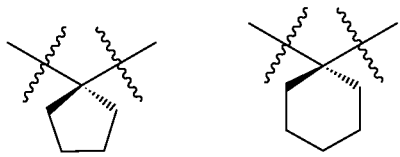

In addition, such cyclic moieties may optionally include a heteroatom(s). Examples of such heteroatom-containing cyclic moieties include, but are not limited to:

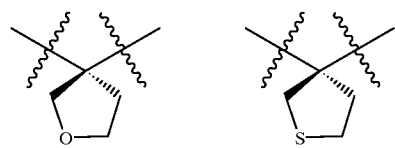

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenyl-acetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

It is intended that the definition of any substituent or variable (e.g., $R^{10}$, Z, n, etc.) at a particular location in a molecule be independent of its definitions elsewhere in that molecule. Thus, —$N(R^{10})_2$ represents —NHH, —$NHCH_3$, —$NHC_2H_5$, etc. It is understood that substituents and substitution patterns on the compounds of the instant invention can be selected by one of ordinary skill in the art to provide compounds that are chemically stable and that can be readily synthesized by techniques known in the art as well as those methods set forth below.

The pharmaceutically acceptable salts of the compounds of this invention can be synthesized from the compounds of this invention which contain a basic moiety by conventional chemical methods. Generally, the salts are prepared by reacting the free base with stoichiometric amounts or with an excess of the desired salt-forming inorganic or organic acid in a suitable solvent or various combinations of solvents.

Abbreviations used in the description of the chemistry and in the Examples that follow are:

| | |
|---|---|
| Ac₂O | Acetic anhydride; |
| Boc | t-Butoxycarbonyl; |
| DBU | 1,8-diazabicyclo[5.4.0]undec-7-ene; |
| DMAP | 4-Dimethylaminopyridine; |
| DME | 1,2-Dimethoxyethane; |
| DMF | Dimethaformamide; |
| EDC | 1-(3-dimethylaminopropyl)-3-ethyl-carbodiimide-hydrochloride; |
| HOBT | 1-Hydroxybenzotriazole hydrate; |
| Et₃N | Triethylamine; |
| EtOAc | Ethyl acetate; |
| FAB | Fast atom bombardment; |
| HOOBT | 3-Hydroxy-1,2,2-benzotriazin-4(3H-one; |
| HPLC | High-performance liquid chromatography; |
| MCPBA | m-Chloroperoxybenzoic acid; |
| MsCl | Methanesulfonyl chloride; |
| NaHMDS | Sodium bis(trimethylsily)amide; |
| Py | Pyridine; |
| TFA | Trifluoroacetic acid; |
| THF | Tetrahydrofuran. |

The compounds are useful in various pharmaceutically acceptable salt forms. The term "pharmaceutically acceptable salt" refers to those salt forms which would be apparent to the pharmaceutical chemist. i.e., those which are substantially non-toxic and which provide the desired pharmacokinetic properties, palatability, absorption, distribution, metabolism or excretion. Other factors, more practical in nature, which are also important in the selection, are cost of the raw materials, ease of crystallization, yield, stability, hygroscopicity and flowability of the resulting bulk drug. Conveniently, pharmaceutical compositions may be prepared from the active ingredients in combination with pharmaceutically acceptable carriers.

Pharmaceutically acceptable salts include conventional non-toxic salts or quarternary ammonium salts formed, e.g., from non-toxic inorganic or organic acids. Non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, sulfanilic, 2-acetoxybenzoic, fumaric, toluenesulfonic, methanesulfonic, ethane disulfonic, oxalic, isethionic, trifluoroacetic and the like.

The pharmaceutically acceptable salts of the present invention can be synthesized by conventional chemical methods. Generally, the salts are prepared by reacting the free base or acid with stoichiometric amounts or with an excess of the desired salt-forming inorganic or organic acid or base, in a suitable solvent or solvent combination.

The instant invention is also directed to an assay that measures the competition between a farnesyl transferase inhibitor test compound and a radiolabeled farnesyl transferase inhibitor for binding to farnesyl transferase binding sites in living cells. Such an assay for example would comprise the steps of:

a) culturing monolayers of the cells;
b) exposing a monolayer of cells to growth media containing the radiolabeled farnesyl transferase inhibitor in the presence or absence of the test compound;
c) washing the cells;
d) counting the radiation emitted by the cells; and
e) comparing the radiation emitted by cells exposed to the radiolabeled farnesyl transferase inhibitor and the test compound to the radiation emitted by cells exposed to only the radiolabeled farnesyl transferase inhibitor.

In an embodiment of the above described assay, the monolayer of cells first exposed to growth media containing only the radiolabeled FTI and then, after this pre-exposure, the cells are exposed to growth media containing the test compound. The period of pre-exposure is preferably from about 5 min. to about 1 hour.

Farnesyl-protein trasferase inhibitor compounds which incorporate a radionuclide may be prepared by first synthesizing an unlabeled inhibitor that optionally incorpoates a iodo or bromo moiety and then exchanging a hydrogen or halogen moiety with an appropriate radionuclide using techniques well known in the art. Syntheses of unlabeled FPTase inhibitors have been generally described in the patent publications cited hereinabove. Syntheses of particular FPTase inhbitors is described below.

The farnesyl transferase inhibitors of formula (I-a) through (I-c) can be synthesized in accordance with Schemes 1–4, in addition to other standard manipulations such as ester hydrolysis, cleavage of protecting groups, etc., as may be known in the literature or exemplified in the experimental procedures. Substituents R, $R^a$ and $R^b$, as shown in the Schemes, represent the substituents $R^2, R^3, R^4$, and $R^5$; however their point of attachment to the ring is illustrative only and is not meant to be limiting. Incorporation of a halogen precursor to a radionuclide moiety may be accomplished, for example, by selection of the appropriate haloaniline in Schemes 1 and 2 and/or the appropriate halogenated benzyl precursor in Scheme 1.

These reactions may be employed in a linear sequence to provide the compounds of the invention or they may be used to synthesize fragments which are subsequently joined by the alkylation reactions described in the Schemes.

Synopsis of Schemes 1–4:

The suitably substituted aldehyde II can be reductively alkylated with an aniline as shown in Scheme 1. The product III can be converted to a piperazinone by acylation with chloroacetyl chloride to give IV, followed by base-induced cyclization to V. Deprotection, followed by reductive alkylation with a protected imidazole carboxaldehyde leads to VII, which can be alkylation with an arylmethylhalide to give the imidazolium salt VIII. Final removal of protecting groups by either solvolysis with a lower alkyl alcohol, such as methanol, or treatment with triethylsilane in methylene chloride in the presence of trifluoroacetic acid gives the final product IX.

N-Aryl piperazines can be prepared as described in Scheme 2. An aryl amine X is reacted with bis -chloroethyl amine hydrochloride (XI) in refluxing n -butanol to furnish compounds XII. The resulting piperazines XII can then be carried on to final products containing the preferred arylmethylimidazolyl substituent as described in Scheme 1.

Scheme 3 illustrates the use of an optionally substituted homoserine lactone XIII to prepare a Boc-protected piperazinone XVI. Intermediate XVI may be deprotected and reductively alkylated or acylated as illustrated in the previous Schemes. Alternatively, the hydroxyl moiety of intermediate XVI may be mesylated and displaced by a suitable nucleophile, such as the sodium salt of ethane thiol, to provide an intermediate XVII. Intermediate XVI may also be oxidized to provide the carboxylic acid on intermediate XVIII, which can be utilized form an ester or amide moiety.

Amino acids of the general formula XX which have a sidechain not found in natural amino acids may be prepared by the reactions illustrated in Scheme 4 starting with the readily prepared imine XIX.

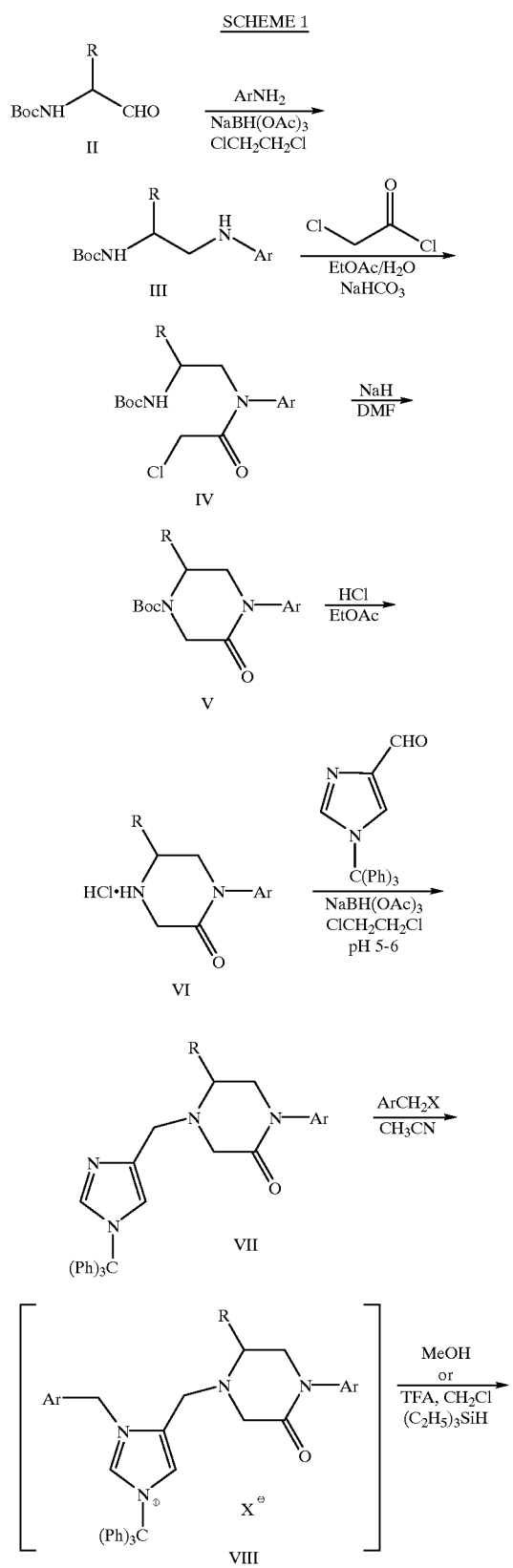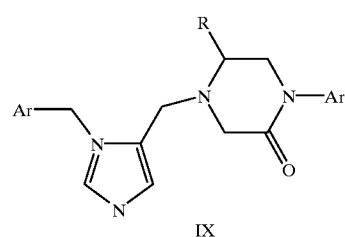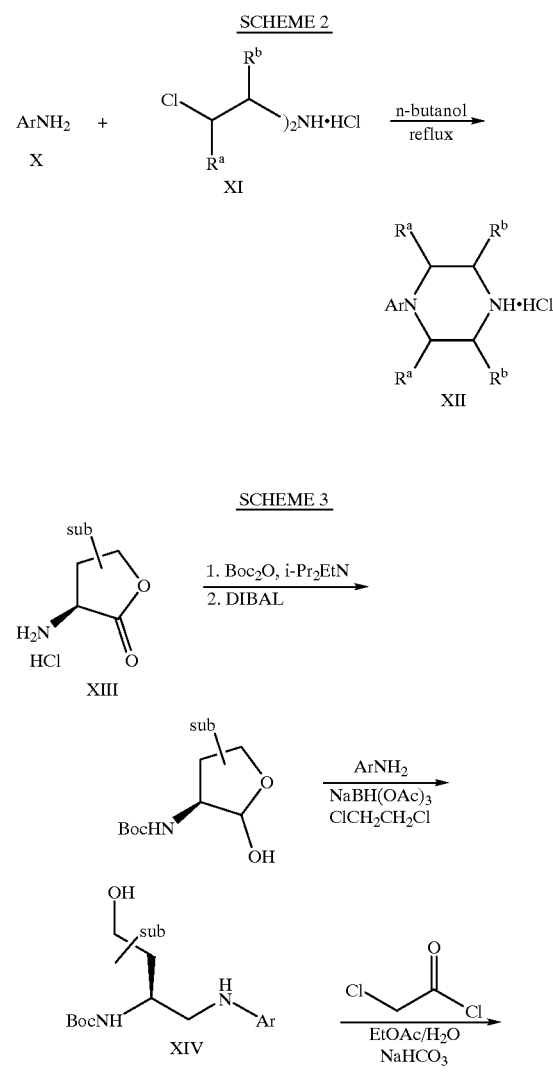

-continued

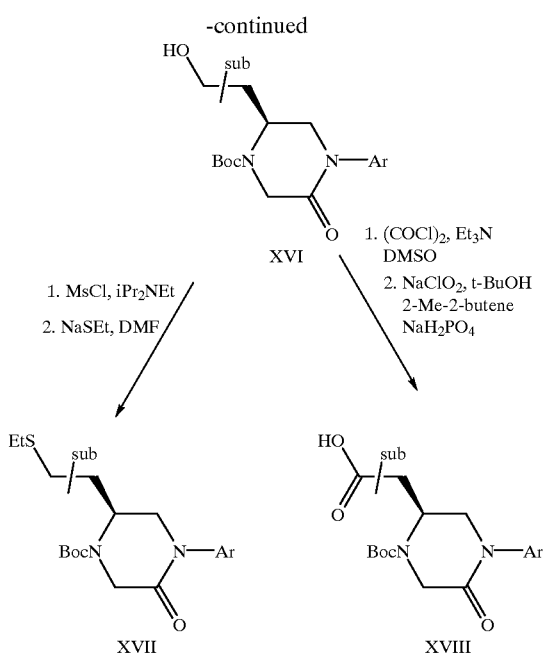

SCHEME 4

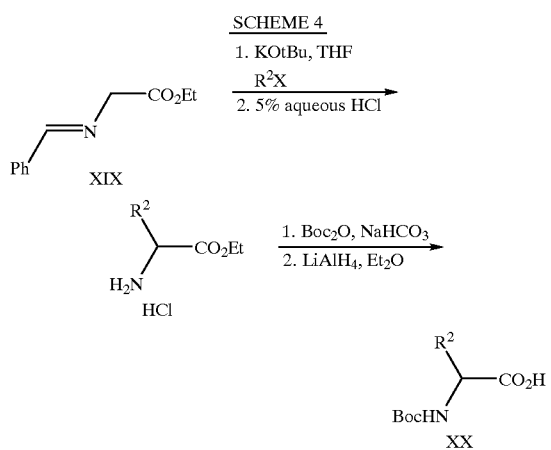

The farnesyl transferase inhibitors of formula (I-d) can be synthesized in accordance with Schemes 5–17, in addition to other standard manipulations such as ester hydrolysis, cleavage of protecting groups, etc., as may be known in the literature or exemplified in the experimental procedures. Substituents $R^2$, $R^6$ and $R^8$, as shown in the Schemes, represent the substituents $R^2$, $R^3$, $R^4$, $R^5$, $R^{6a}$, $R^{6b}$, $R^{6c}$, $R^{6d}$ and $R^8$; although only one such $R^2$, $R^6$ or $R^8$ is present in the intermediates and products of the schemes, it is understood that the reactions shown are also applicable when such aryl or heteroaryl moieties contain multiple substituents. The compounds referred to in the Synopsis of Schemes 5–17 by Roman numerals are numbered starting sequentially with II and ending with XXV. Incorporation of a halogen precursor to a radionuclide moiety may be accomplished, for example, by selection of the appropriate halogenated benzyl precursor in Scheme 5.

These reactions may be employed in a linear sequence to provide the compounds of the invention or they may be used to synthesize fragments which are subsequently joined by the alkylation reactions described in the Schemes. Aryl-aryl coupling is generally described in "Comprehensive Organic Functional Group Transformations," Katritsky et al. eds., pp 472–473, Pergamon Press (1995).

Synopsis of Schemes 5–17:

The requisite intermediates are in some cases commercially available, or can be prepared according to literature procedures, for the most part. Schemes 5–17 illustrate synthesis of the compounds of the formula I-d which incorporate a preferred benzylimidazolyl sidechain. In Scheme 5, for example, a biaryl intermediate that is not commercially available may be synthesized by methods known in the art. Thus, a suitably substituted phenyl boronic acid may be reacted under Suzuki coupling conditions (Pure Appl. Chem., 63:419 (1991)) with a suitably substituted halogenated benzoic acid, such as 4-bromobenzoic acid, to provide the biaryl carboxylic acid II. The acid may be reduced and the triflate of the intermediate alcohol III may be formed in situ and coupled to a suitably substituted benzylimidazolyl IV to provide, after deprotection, the instant compound V.

Schemes 6–9 illustrate other methods of synthesizing the key alcohol intermediates, which can then be processed as described in Scheme 5. Thus, Scheme 6 illustrates the analogous series of biaryl alcohol forming reactions starting with the halogenated biarylaldehyde.

Scheme 7 illustrates the reaction wherein the "terminal" phenyl moiety is employed in the Suzuki coupling as the halogenated reactant. Such a coupling reaction is also compatible when one of the reactants incorporates a suitably protected hydroxyl functionality as illustrated in Scheme 8.

Negishi chemistry (Org. Synth., 66:67 (1988)) may also be employed to form the biaryl component of the instant compounds, as shown in Scheme 9. Thus, a suitably substituted zinc bromide adduct may be coupled to a suitably substituted aryl halide in the presence of nickel (II) to provide the biaryl VII. The aryl halide and the zinc bromide adduct may be selected based on the availability of the starting reagents.

Scheme 10 illustrates the preparation of a suitably substituted biphenylmethyl bromide which could also be utilized in the reaction with the protected imidazole as described in Scheme 5.

As illustrated in Scheme 11, the sequence of coupling reactions may be modified such that the biphenyl bond is formed last. Thus, a suitably substituted imidazole may first be alkylated with a suitably substituted benzyl halide to provide intermediate VIII. Intermediate VIII can then undergo Suzuki type coupling to a suitably substituted phenyl boronic acid.

Scheme 12 illustrates synthesis of an instant compound wherein a non-hydrogen $R^{9b}$ is incorporated in the instant compound. Thus, a readily available 4-substituted imidazole IX may be selectively iodinated to provide the 5-iodoimidazole X. That imidazole may then be protected and coupled to a suitably substituted benzyl moiety to provide intermediate XI. Intermediate XI can then undergo the alkylation reactions that were described hereinabove.

Scheme 13 illustrates synthesis of instant compounds that incorporate a preferred imidazolyl moiety connected to the biaryl via an alkyl amino, sulfonamide or amide linker. Thus, the 4-aminoalkylimidazole XII, wherein the primary amine is protected as the phthalimide, is selectively alkylated then deprotected to provide the amine XIII. The amine XIII may then react under conditions well known in the art with various activated biaryl moieties to provide the instant compounds shown.

Compounds of the instant invention wherein the $A^1(CR^{1a}_2)_nA^2(CR^{1a}_2)n$ linker is oxygen may be synthesized by methods known in the art, for example as shown in Scheme 14. The suitably substituted phenol XIV may be reacted with methyl N-(cyano)methanimidate to provide the 4-phenoxyimidazole XV. After selective protection of one of the imidazolyl nitrogens, the intermediate XVI can undergo alkylation reactions as described for the benzylimidazoles hereinabove.

Scheme 15 illustrates an analogous series of reactions wherein the $(CR^{1b}{}_2)_pX(CR^{1b}{}_2)_p$ linker of the instant compounds is oxygen. Thus, a suitably substituted haloaryl alcohol, such as, is reacted with methyl N-(cyano) methanimidate to provide intermediate XVI. Intermediate XVI is then protected and, if desired to form a compound of a preferred embodiment, alkylated with a suitably protected benzyl. The intermediate XVII can then be coupled to a second aryl moiety by Suzuki chemistry to provide the instant compound.

Compounds of the instant invention wherein the $A^1(CR^{1a}{}_2)_nA^2(CR^{1a}{}_2)_n$ linker is a substituted methylene may be synthesized by the methods shown in Scheme 16. Thus, the N-protected imidazolyl iodide XVIII is reacted, under Grignard conditions with a suitably protected benzaldehyde to provide the alcohol XIX. Acylation, followed by the alkylation procedure illustrated in the Schemes above (in particular, Scheme 5) provides the instant compound XX. If other $R^1$ substituents are desired, the acetyl moiety can be manipulated as illustrated in the Scheme.

Grignard chemistry may also be employed to form a substituted alkyl linker between the biaryl and the preferred W (imidazolyl) as shown in Scheme 17. Similar substituent manipulation as shown in Scheme 16 may be performed on the fully functionalized compound which incorporates an $R^{1b}$ hydroxyl moiety.

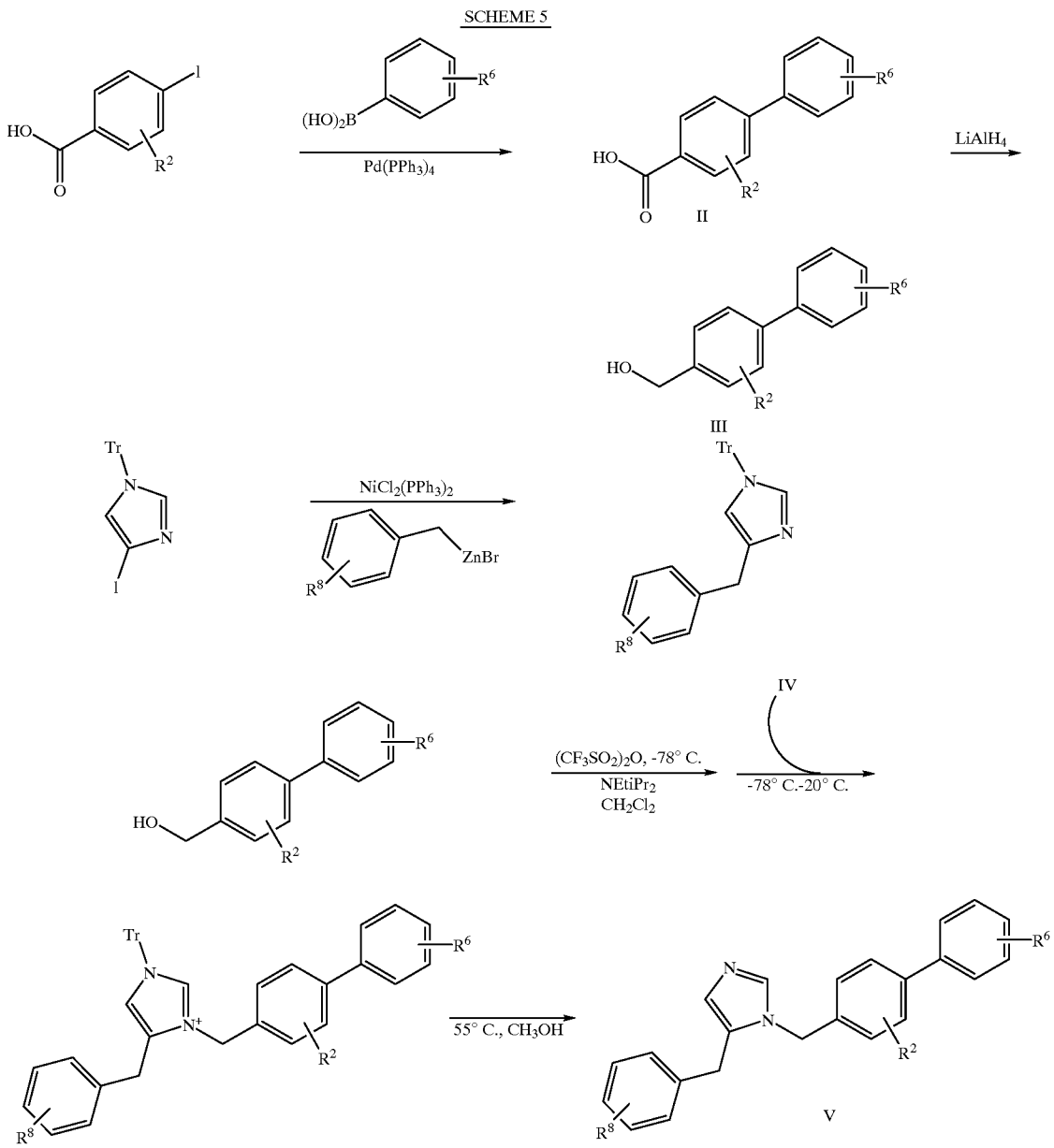

SCHEME 6
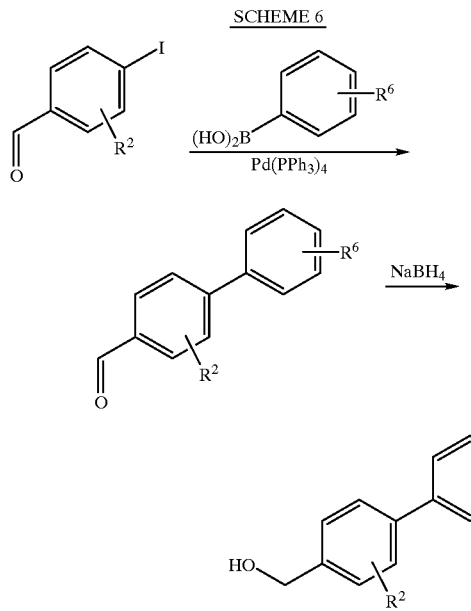
SCHEME 7
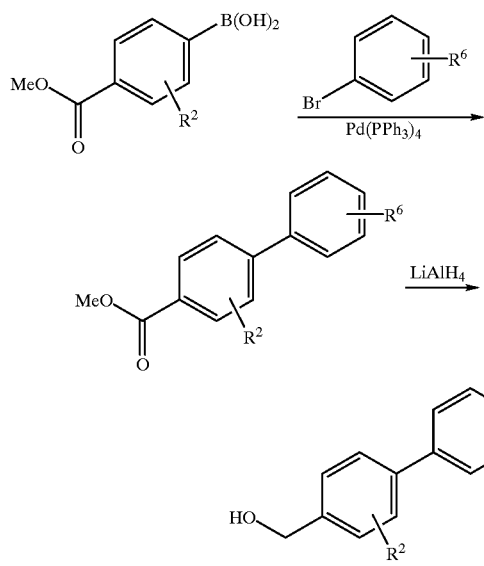
SCHEME 8
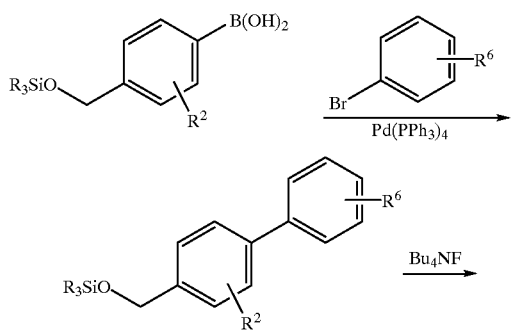
SCHEME 9
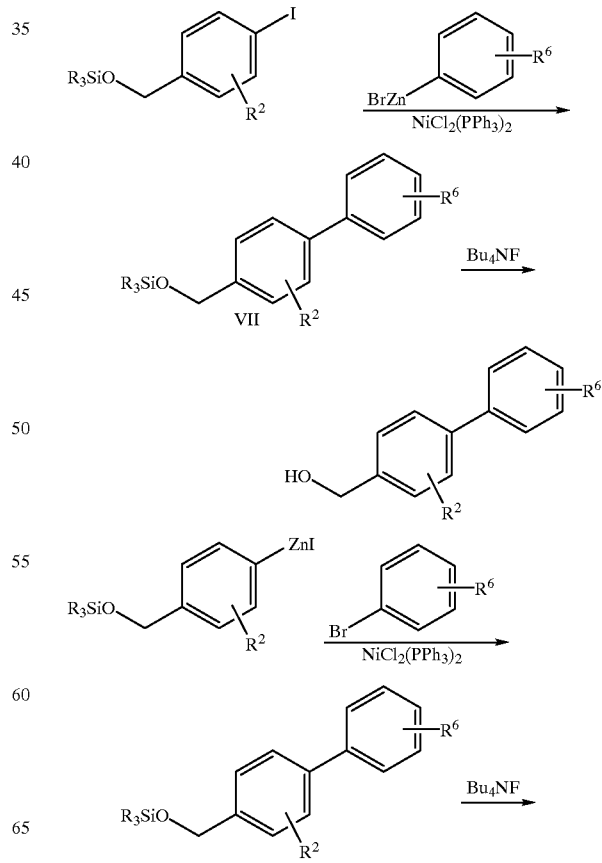
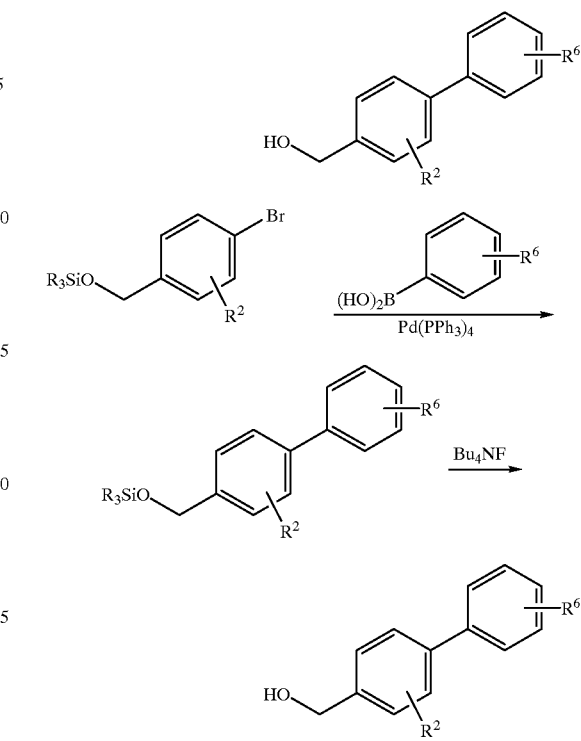

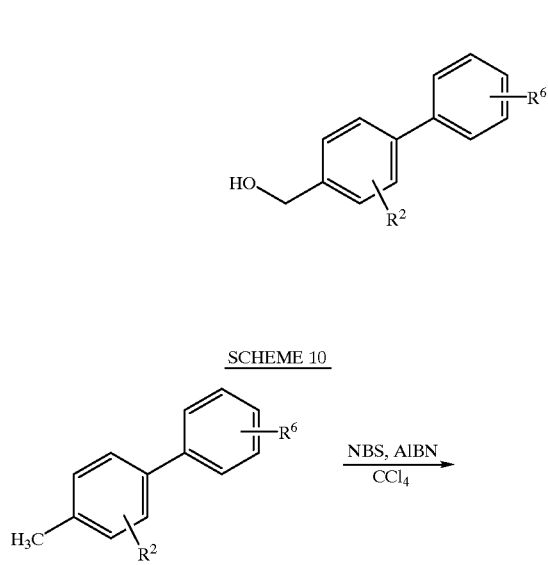
SCHEME 10
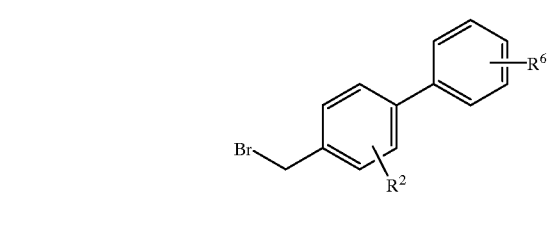
SCHEME 11
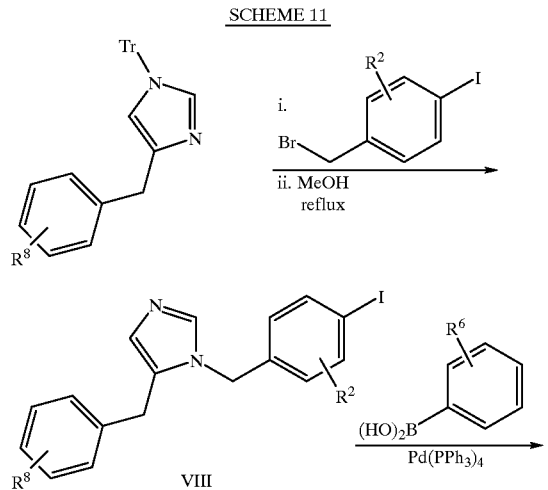
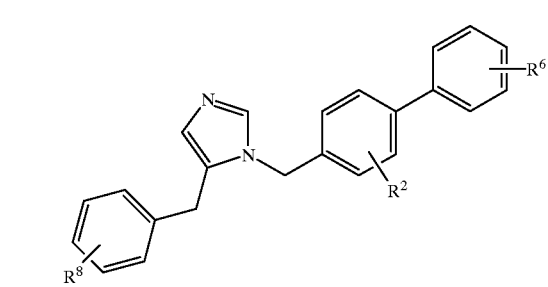
SCHEME 12
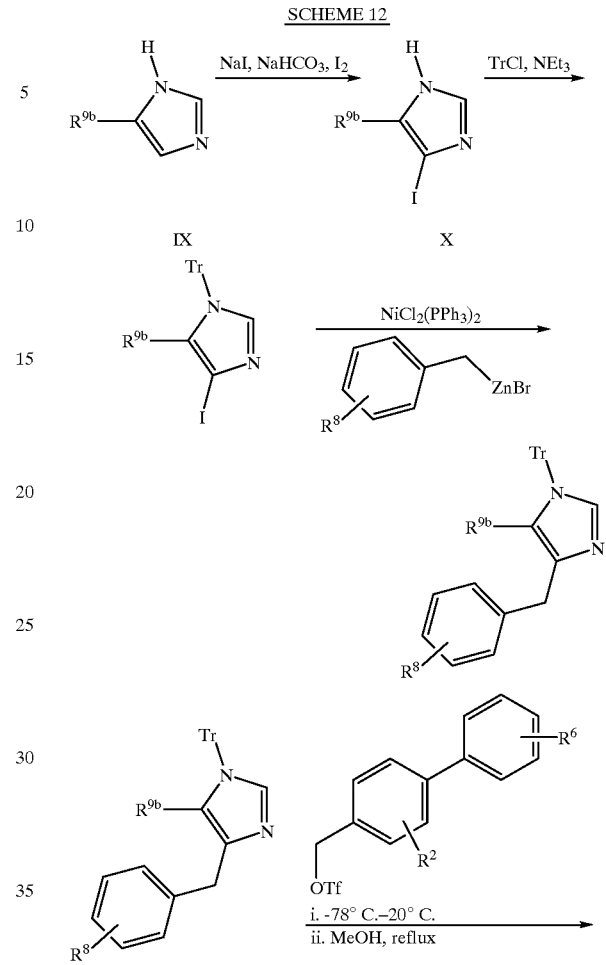
SCHEME 13
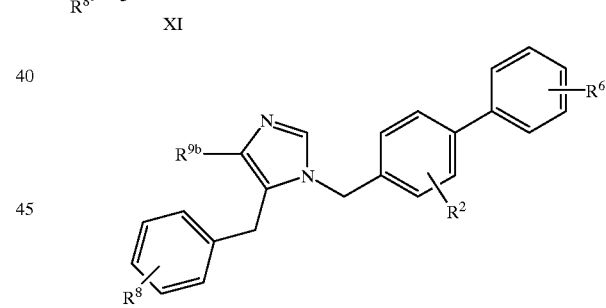
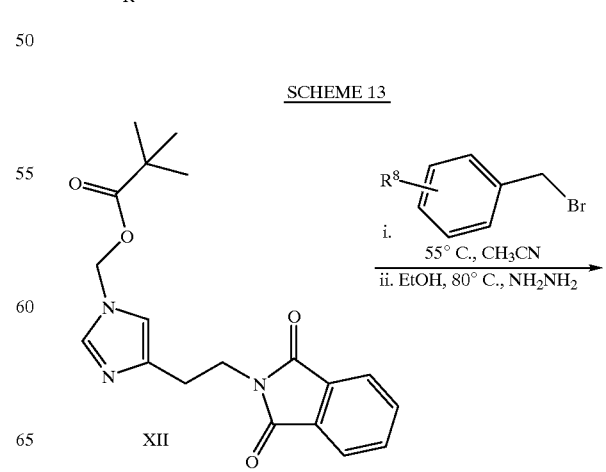

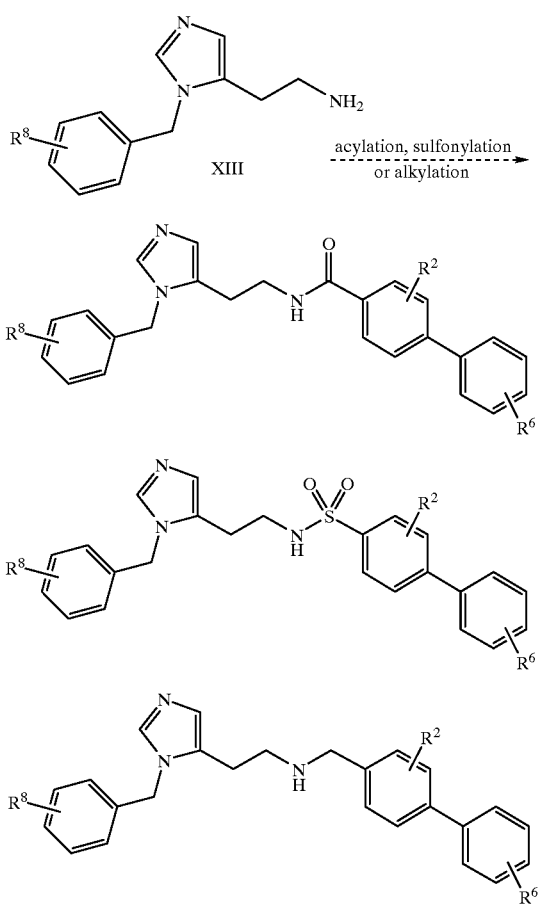
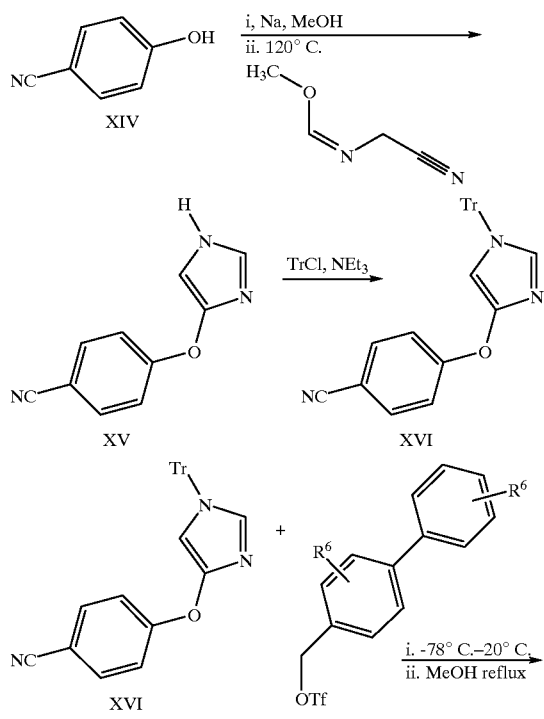
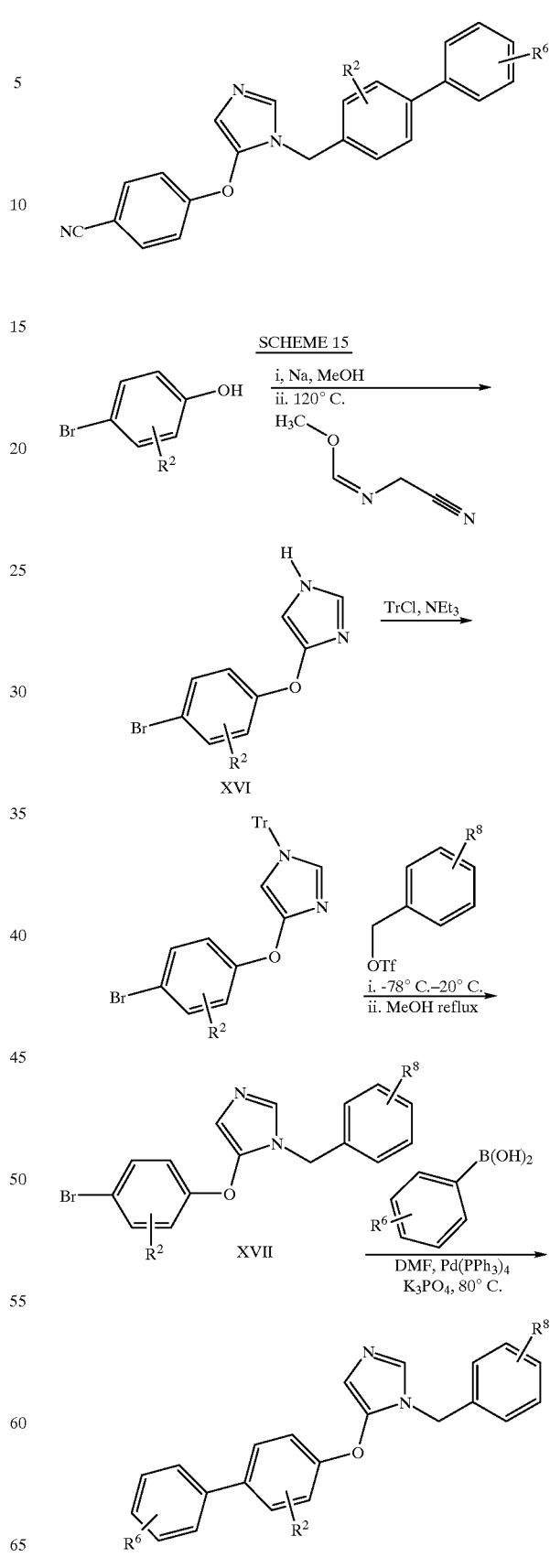

6,060,038

SCHEME 16

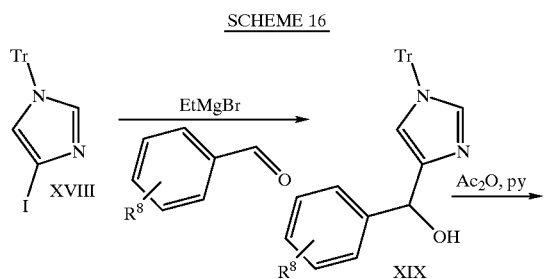

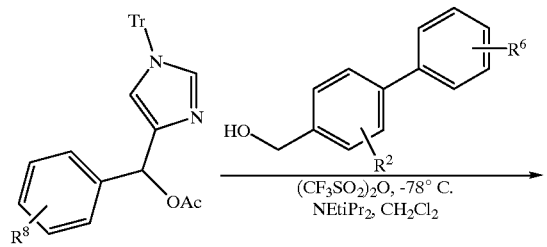

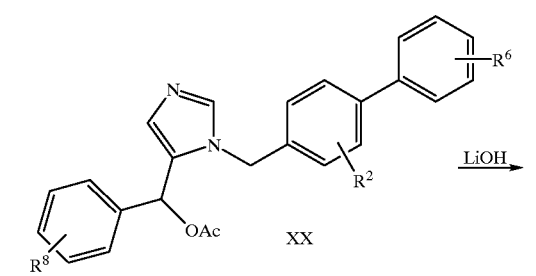

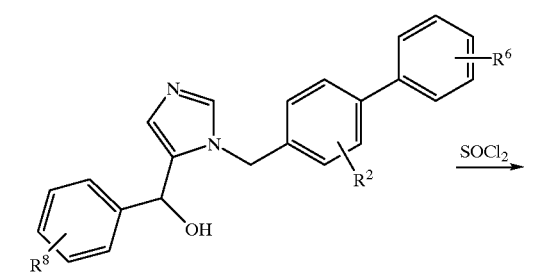

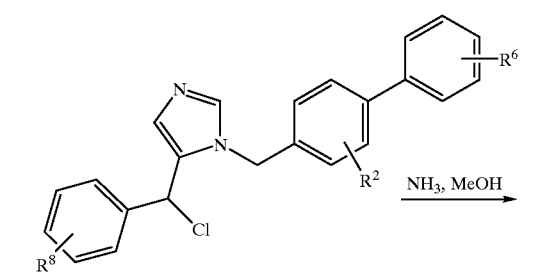

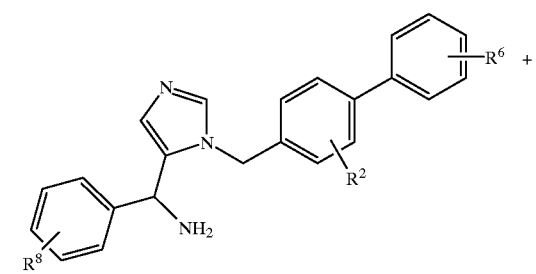

-continued

SCHEME 17

The farnesyl transferase inhibitors of formula (I-e) can be synthesized in accordance with Schemes 18–32, in addition to other standard manipulations such as ester hydrolysis, cleavage of protecting groups, etc., as may be known in the literature or exemplified in the experimental procedures. Substituents $R^2$, $R^6$ and $R^8$, as shown in the Schemes, represent the substituents $R^2$, $R^3$, $R^4$, $R^5$, $R^6$ and $R^8$; although only one such $R^2$, $R^6$ or $R^8$ is present in the intermediates and products of the schemes, it is understood that the reactions shown are also applicable when such aryl or heteroaryl moieties contain multiple substituents. The compounds referred to in the Synopsis of Schemes 18–32 by Roman numerals are numbered starting sequentially with II and ending with XXV. Incorporation of a halogen precursor to a radionuclide moiety may be accomplished, for example, by selection of the appropriate halogenated benzyl precursor in Scheme 18.

These reactions may be employed in a linear sequence to provide the compounds of the invention or they may be used to synthesize fragments which are subsequently joined by the alkylation reactions described in the Schemes. Other reactions useful in the preparation of heteroaryl moieties are described in "Comprehensive Organic Chemistry, Volume 4: Heterocyclic Compounds" ed. P. G. Sammes, Oxford (1979) and references therein. Aryl-aryl coupling is generally described in "Comprehensive Organic Functional Group Transformations," Katritsky et al. eds., pp 472–473, Pergamon Press (1995).

Synopsis of Schemes 18–32:

The requisite intermediates are in some cases commercially available, or can be prepared according to literature procedures, for the most part. Schemes 18–32 illustrate synthesis of the instant arylheteroaryl compound which incorporate a preferred benzylimidazolyl sidechain. Thus, in Scheme 37, for example, a arylheteroaryl intermediate that is not commercially available may be synthesized by methods known in the art. Thus, a suitably substituted pyridyl boronic acid may be reacted under Suzuki coupling conditions (*Pure Appl. Chem.,* 63:419 (1991)) with a suitably substituted halogenated benzoic acid, such as 4-bromobenzoic acid, to provide the arylheteroaryl carboxylic acid II. The acid may be reduced and the triflate of the intermediate alcohol III may be formed in situ and coupled to a suitably substituted benzylimidazolyl IV to provide, after deprotection, the instant compound V.

Schemes 19–22 illustrate other methods of synthesizing the key alcohol intermediates, which can then be processed as described in Scheme 18. Thus, Scheme 19 illustrates the analogous series of arylheteroaryl alcohol forming reactions starting with the halogenated arylaldehyde.

Scheme 20 illustrates the reaction wherein the "terminal" heteroaryl moiety is employed in the Suzuki coupling as the halogenated reactant. Such a coupling reaction is also compatible when one of the reactants incorporates a suitably protected hydroxyl functionality as illustrated in Scheme 21.

Negishi chemistry (*Org. Synth.,* 66:67 (1988)) may also be employed to form the arylheteroaryl component of the instant compounds, as shown in Scheme 22. Thus, a suitably substituted zinc bromide adduct may be coupled to a suitably substituted aryl halide in the presence of nickel (II) to provide the arylheteroaryl VII. The heteroaryl halide and the zinc bromide adduct may be selected based on the availability of the starting reagents.

Scheme 23 illustrates the preparation of the suitably substituted arylheteroaryl methanol from the pyridyltoluene.

Scheme 24 illustrates the preparation of the suitably substituted pyrazinylaryl methanol starting with alanine.

As illustrated in Scheme 25, the sequence of coupling reactions may be modified such that the arylheteroaryl bond is formed last. Thus, a suitably substituted imidazole may first be alkylated with a suitably substituted benzyl halide to provide intermediate VIII. Intermediate VIII can then undergo Suzuki type coupling to a suitably substituted heteroaryl boronic acid.

Scheme 26 illustrates synthesis of an instant compound wherein a non-hydrogen $R^{9b}$ is incorporated in the instant compound. Thus, a readily available 4-substituted imidazole IX may be selectively iodinated to provide the 5-iodoimidazole X. That imidazole may then be protected and coupled to a suitably substituted benzyl moiety to provide intermediate XI. Intermediate XI can then undergo the alkylation reactions that were described hereinabove.

Scheme 27 illustrates synthesis of instant compounds that incorporate a preferred imidazolyl moiety connected to the arylheteroaryl via an alkyl amino, sulfonamide or amide linker. Thus, the 4-aminoalkylimidazole XII, wherein the primary amine is protected as the phthalimide, is selectively alkylated then deprotected to provide the amine XIII. The amine XIII may then react under conditions well known in the art with various activated arylheteroaryl moieties to provide the instant compounds shown.

Compounds of the instant invention wherein the $A^1(CR^{1a}{}_2)_nA^2(CR^{1a}{}_2)_n$ linker is oxygen may be synthesized by methods known in the art, for example as shown in Scheme 28. The suitably substituted phenol XIV may be reacted with methyl N-(cyano)methanimidate to provide the 4-phenoxyimidazole XV. After selective protection of one of the imidazolyl nitrogens, the intermediate XVI can undergo alkylation reactions as described for the phenylmethylimidazoles hereinabove.

Scheme 29 illustrates an analogous series of reactions wherein the $(CR^{1b}{}_2)_pX(CR^{1b}{}_2)_p$ linker of the instant compounds is oxygen. Thus, a suitably substituted haloaryl alcohol, such as 4-bromophenol, is reacted with methyl N-(cyano)methanimidate to provide intermediate XVI. Intermediate XVI is then protected and, if desired to form a compound of a preferred embodiment, alkylated with a suitably protected benzyl. The intermediate XVII can then be coupled to a heteroaryl moiety by Suzuki chemistry to provide the instant compound.

Compounds of the instant invention wherein the $A^1(CR^{1a}{}_2)_nA^2(CR^{1a}{}_2)_n$ linker is a substituted methylene may be synthesized by the methods shown in Scheme 30. Thus, the N-protected imidazolyl iodide XVIII is reacted, under Grignard conditions with a suitably protected benzaldehyde to provide the alcohol XIX. Acylation, followed by the alkylation procedure illustrated in the Schemes above (in particular, Scheme 18) provides the instant compound XX. If other $R^1$ substituents are desired, the acetyl moiety can be manipulated as illustrated in the Scheme.

Addition of various nucleophiles to an imidazolyl aldehyde may also be employed to form a substituted alkyl linker between the arylheteroaryl and the preferred W (imidazolyl) as shown in Scheme 31. Thus a halogenated arylheteroaryl, such as 4-(3-pyridyl)bromobenzene, may undergo metal halogen exchange followed by reaction with a suitably substituted imidazolyl aldehyde and acteylation to form the alcohol. Then, similar substituent manipulation as shown in Scheme 30 may be performed on a fully functionalized compound which incorporates an $R^2$ hydroxyl moiety.

Scheme 32 illustrates the synthesis of a suitably substituted pyrimidinebromobenzene, which may be employed in the reaction illustrated in Scheme 30. This reaction and other reactions useful in the preparation of heteroaryl moieties are described in "Comprehensive Organic Chemistry, Volume 4: Heterocyclic Compounds" ed. P. G. Sammes, Oxford (1979).

SCHEME 18

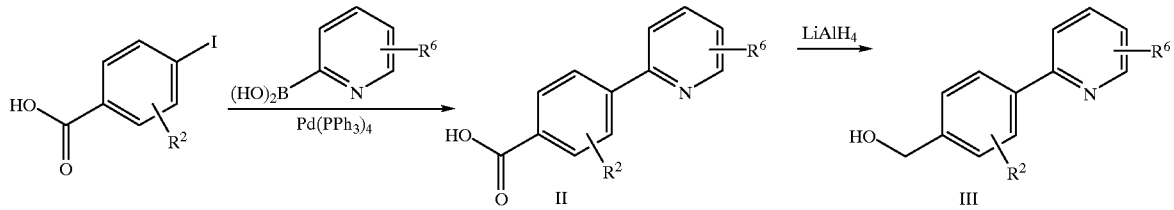

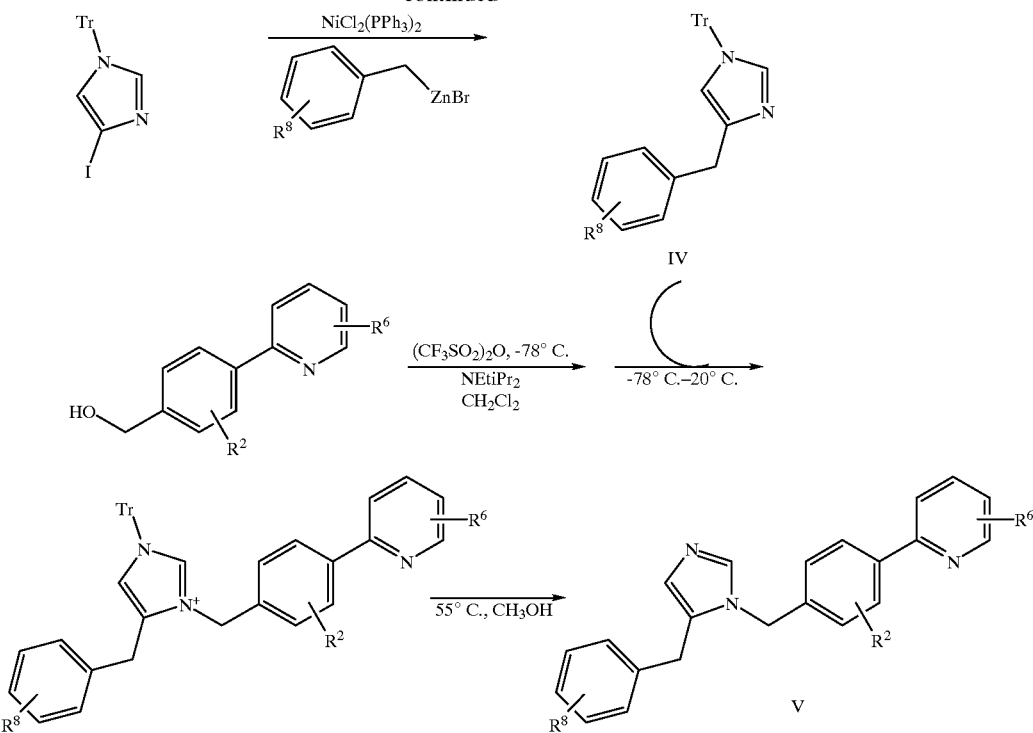
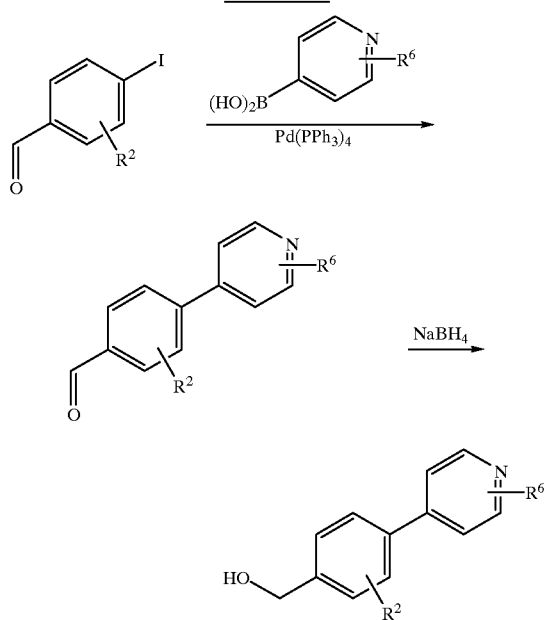
SCHEME 19
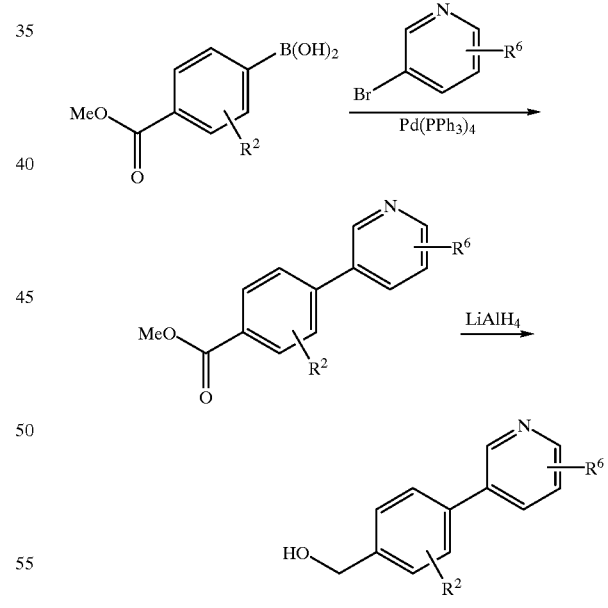
SCHEME 20
SCHEME 21
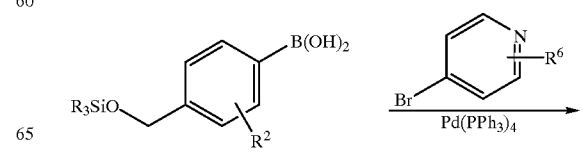

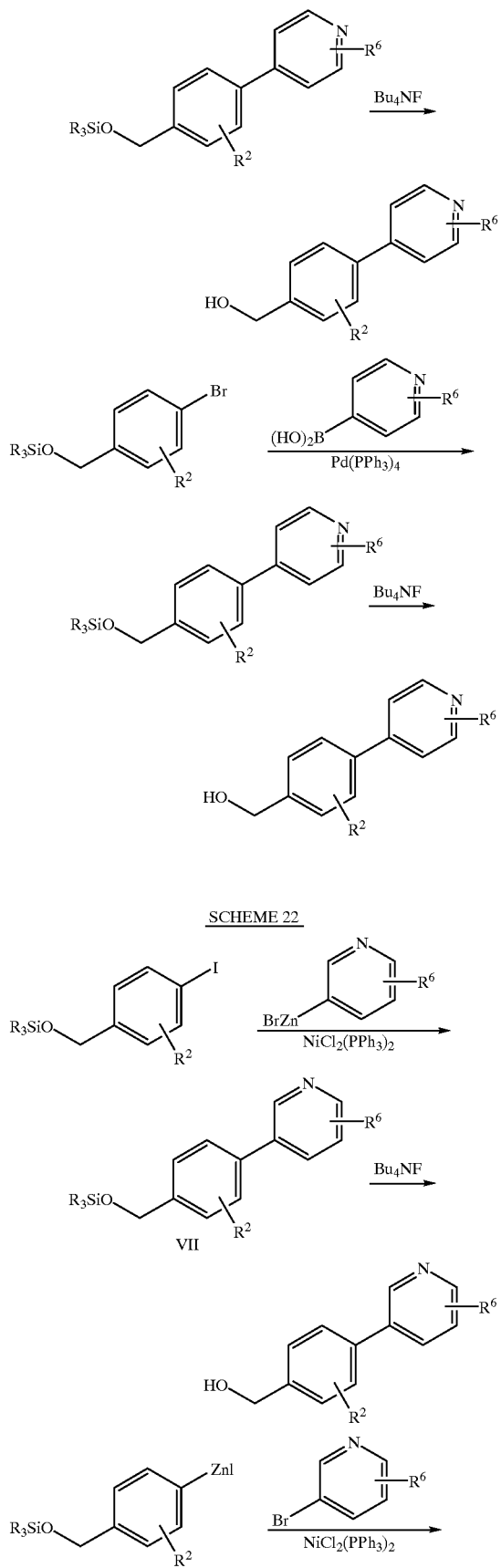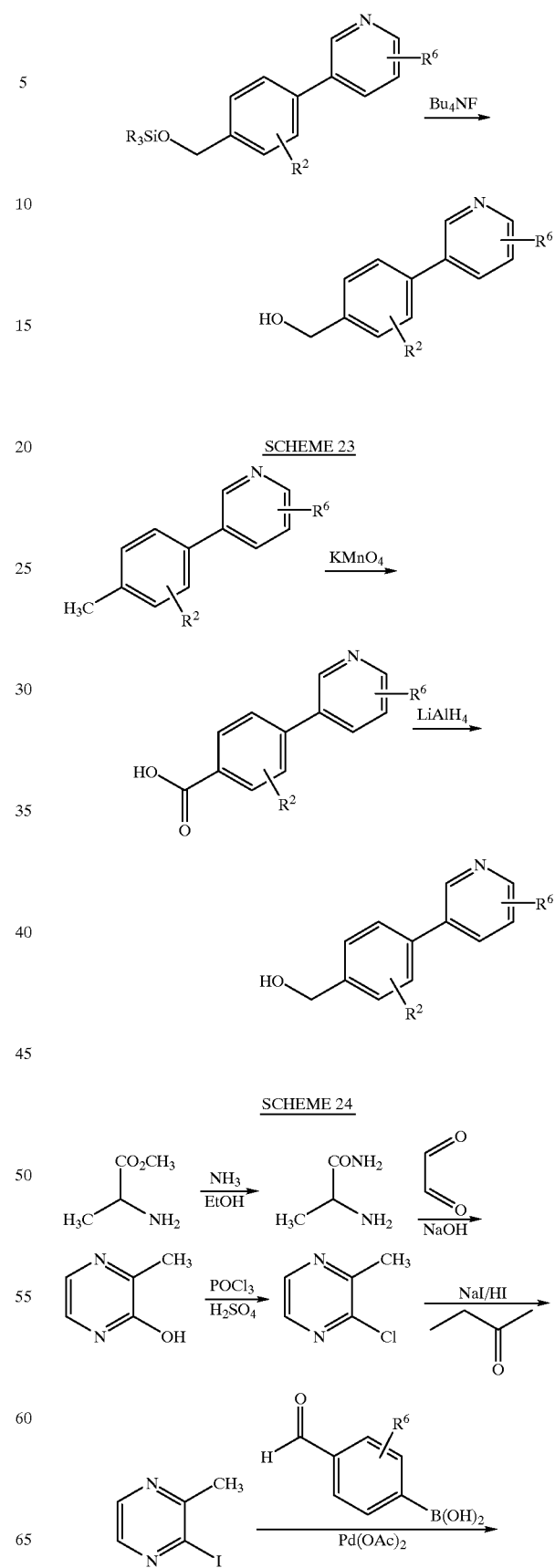

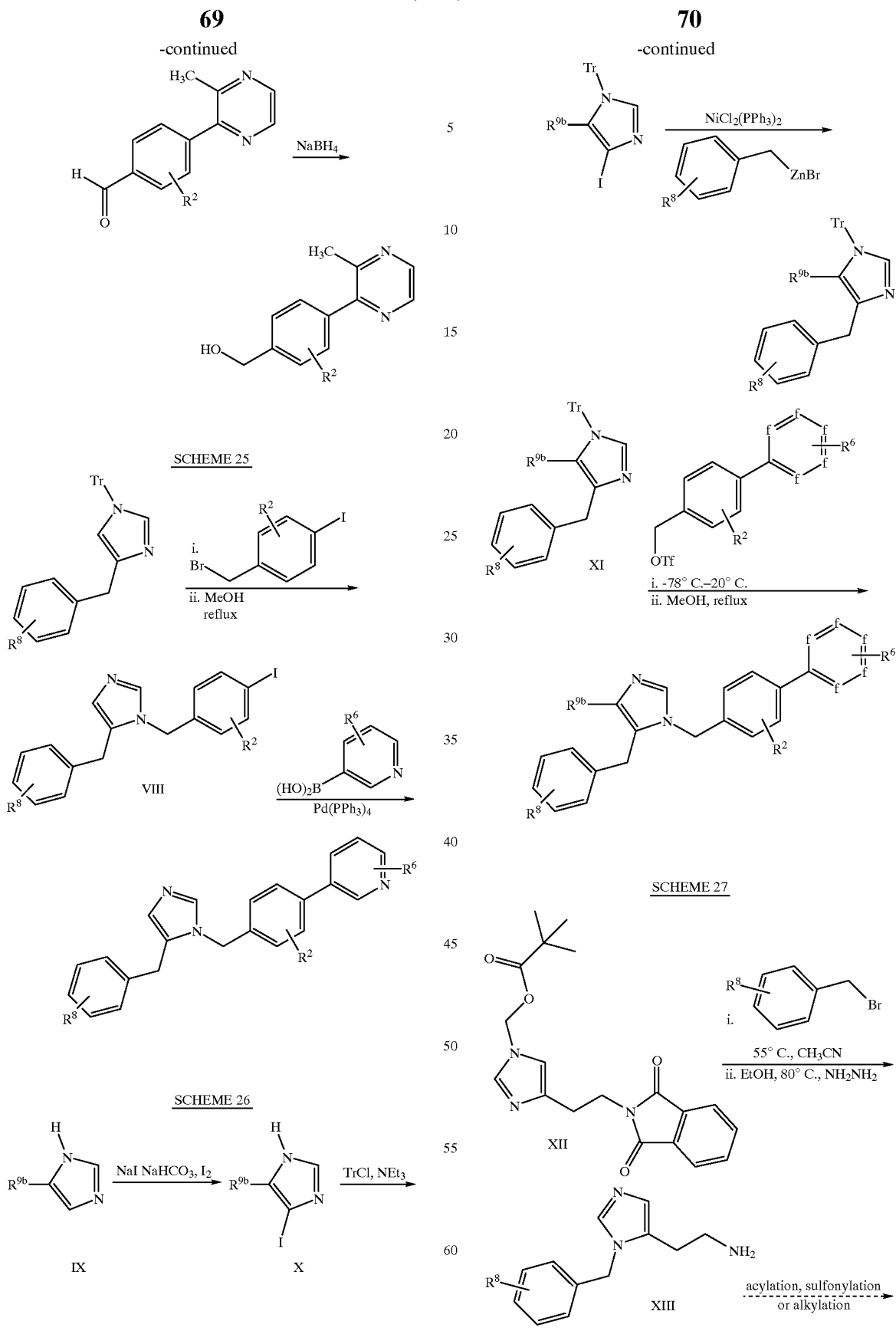

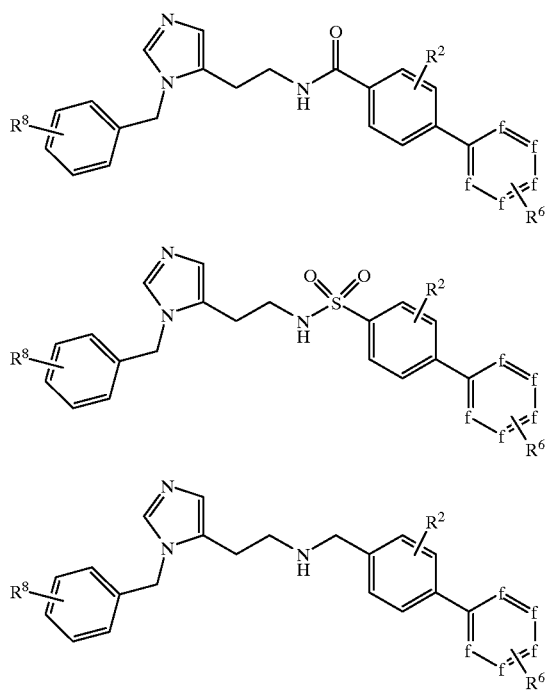
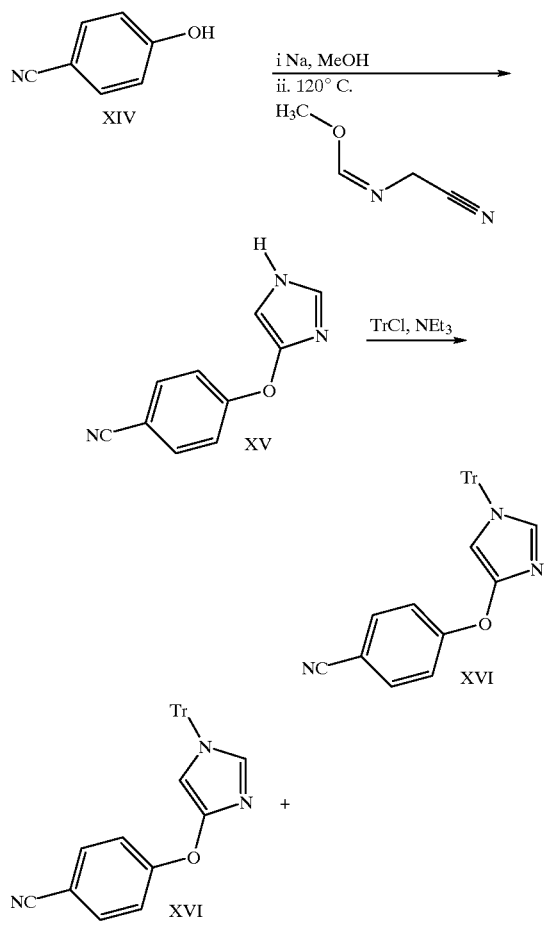
SCHEME 28
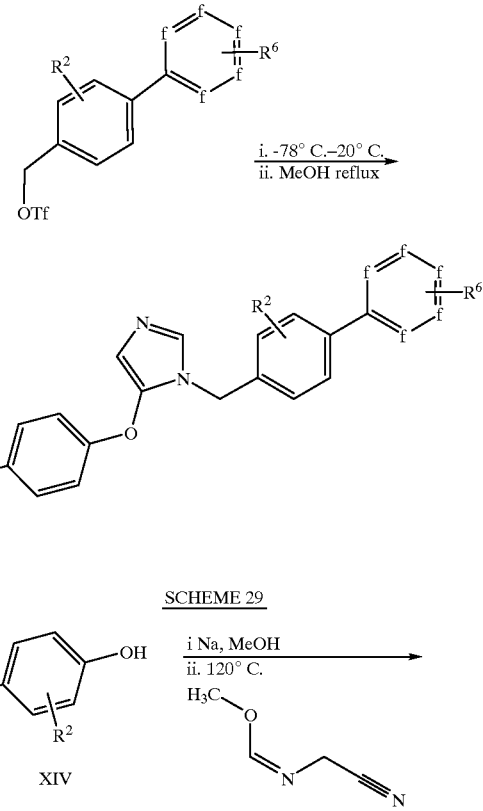
SCHEME 29
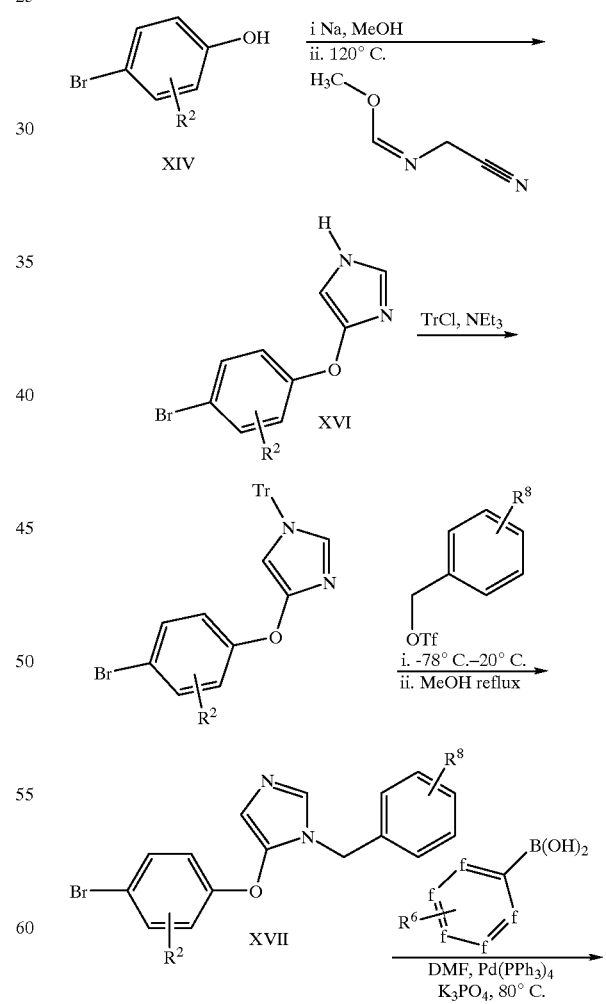

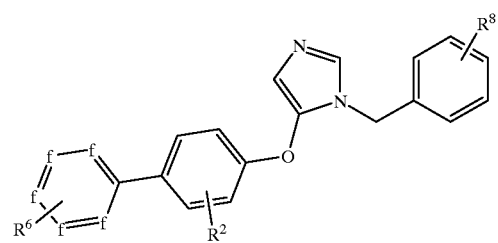
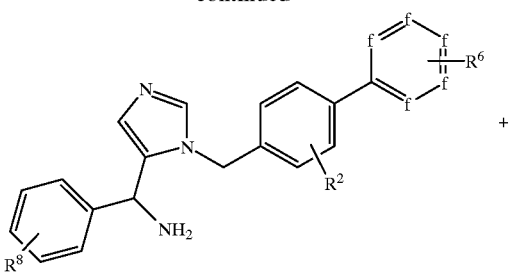
SCHEME 30
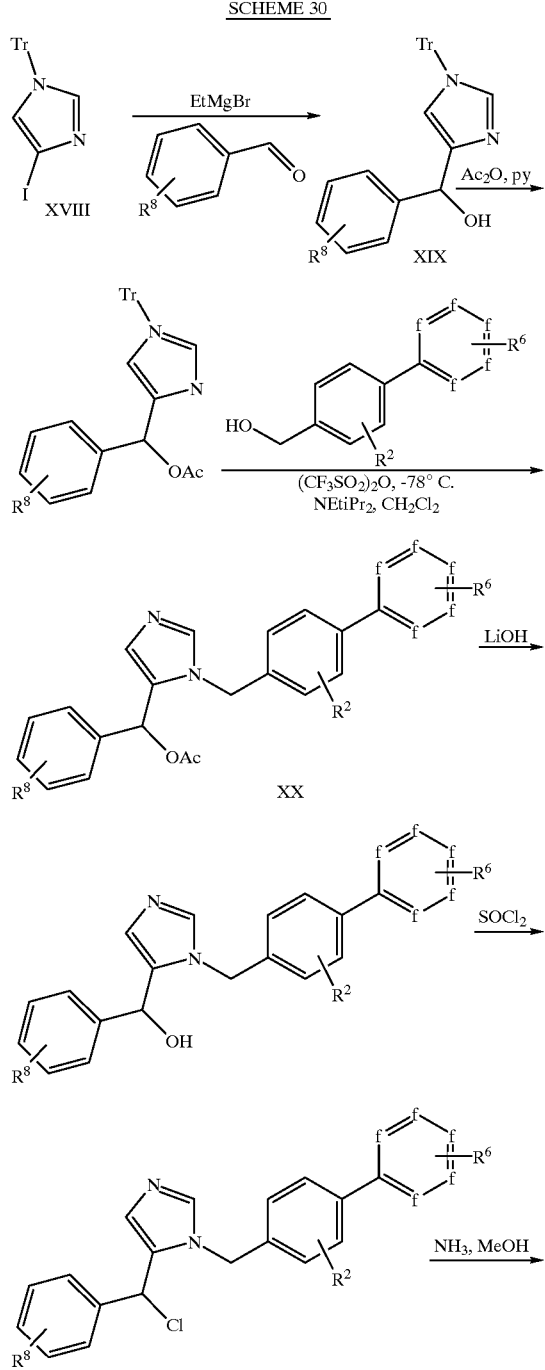
SCHEME 31
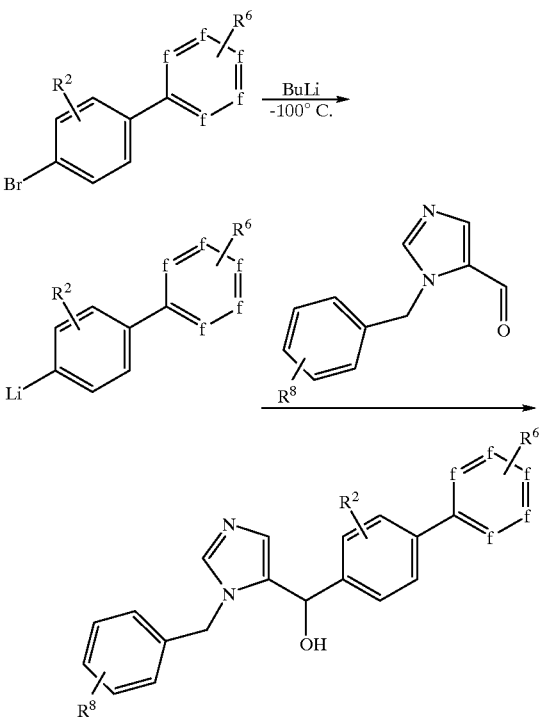
SCHEME 32
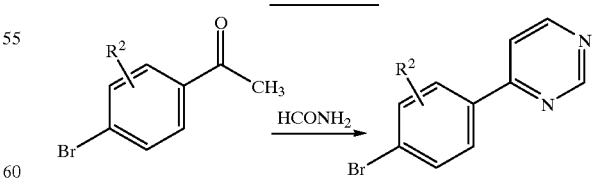
The farnesyl transferase inhibitors of formula (I-f) can be synthesized in accordance with Schemes 33–44, in addition to other standard manipulations such as ester hydrolysis, cleavage of protecting groups, etc., as may be known in the literature or exemplified in the experimental procedures.

Substituents $R^3$, $R^6$ and $R^8$, as shown in the Schemes, represent the substituents $R^3$, $R^4$, $R^5$, $R^{6a}$, $R^{6b}$, $R^{6c}$, $R^{6d}$, $R^{6e}$ and $R^8$; although only one such $R^3$, $R^6$ or $R^8$ is present in the intermediates and products of the schemes, it is understood that the reactions shown are also applicable when such aryl or heteroaryl moieties contain multiple substituents. The compounds referred to in the Synopsis of Schemes 33–44 by Roman numerals are numbered starting sequentially with II and ending with XXX. Incorporation of a halogen precursor to a radionuclide moiety may be accomplished, for example, by selection of the appropriate halogenated benzyl precursor in Scheme 33.

These reactions may be employed in a linear sequence to provide the compounds of the invention or they may be used to synthesize fragments which are subsequently joined by the alkylation reactions described in the Schemes. The reactions described in the Schemes are illustrative only and are not meant to be limiting. Other reactions useful in the preparation of heteroaryl moieties are described in "Comprehensive Organic Chemistry, Volume 4: Heterocyclic Compounds" ed. P. G. Sammes, Oxford (1979) and references therein. Aryl-aryl coupling is generally described in "Comprehensive Organic Functional Group Transformations," Katritsky et al. eds., pp 472–473, Pergamon Press (1995).

Synopsis of Schemes 33–44:

The requisite intermediates are in some cases commercially available, or can be prepared according to literature procedures, for the most part. Schemes 33–44 illustrate synthesis of the instant arylheteroaryl compound which incorporate a preferred benzylimidazolyl sidechain. Thus, in Scheme 33, for example, a arylheteroaryl intermediate that is not commercially available may be synthesized by methods known in the art. Thus, a suitably substituted phenyl boronic acid may be reacted under Suzuki coupling conditions (*Pure Appl. Chem.*, 63:419 (1991)) with a suitably substituted halogenated nicotinic acid, such as 4-bromonicotinic acid, to provide the arylheteroaryl carboxylic acid II. The acid may be reduced and the triflate of the intermediate alcohol III may be formed in situ and coupled to a suitably substituted benzylimidazolyl IV to provide, after deprotection, the instant compound V.

Schemes 34–35 illustrate other methods of synthesizing the key alcohol intermediates, which can then be processed as described in Scheme 33. Thus, Scheme 34 illustrates the analogous series of arylheteroaryl alcohol forming reactions starting with the methyl nicotinate boronic acid and the "terminal" phenyl moiety employed in the Suzuki coupling as the halogenated reactant. Such a coupling reaction is also compatible when one of the reactants incorporates a suitably protected hydroxyl functionality as illustrated in Scheme 35.

Negishi chemistry (*Org. Synth.*, 66:67 (1988)) may also be employed to form the arylheteroaryl component of the instant compounds, as shown in Scheme 36. Thus, a suitably substituted zinc bromide adduct may be coupled to a suitably substituted heteroaryl halide in the presence of nickel (II) to provide the arylheteroaryl VII. The heteroaryl halide and the zinc bromide adduct may be selected based on the availability of the starting reagents.

Scheme 37 illustrates the preparation of a suitably substituted 3-hydroxymethyl-5-phenyl pyridine which could also be utilized in the reaction with the protected imidazole as described in Scheme 33. An Alternative preparation of a suitably substituted 5-hydroxymethyl-2-phenyl pyridine is also illustrated.

As illustrated in Scheme 38, the sequence of coupling reactions may be modified such that the aryl-heteroaryl bond is formed last. Thus, a suitably substituted imidazole may first be alkylated with a suitably substituted benzyl halide to provide intermediate VIII. Intermediate VIII can then undergo Suzuki type coupling to a suitably substituted phenyl boronic acid.

Scheme 39 illustrates synthesis of an instant compound wherein a non-hydrogen $R^{9b}$ is incorporated in the instant compound. Thus, a readily available 4-substituted imidazole IX may be selectively iodinated to provide the 5-iodoimidazole X. That imidazole may then be protected and coupled to a suitably substituted benzyl moiety to provide intermediate XI. Intermediate XI can then undergo the alkylation reactions that were described hereinabove.

Scheme 40 illustrates synthesis of instant compounds that incorporate a preferred imidazolyl moiety connected to the biaryl via an alkyl amino, sulfonamide or amide linker. Thus, the 4-aminoalkylimidazole XII, wherein the primary amine is protected as the phthalimide, is selectively alkylated then deprotected to provide the amine XIII. The amine XIII may then react under conditions well known in the art with various activated arylheteroaryl moieties to provide the instant compounds shown.

Compounds of the instant invention wherein the $A^1(CR^1{}_2)_nA^2(CR^1{}_2)_n$ linker is oxygen may be synthesized by methods known in the art, for example as shown in Scheme 41. The suitably substituted phenol XIV may be reacted with methyl N-(cyano)methanimidate to provide the 4-phenoxyimidazole XV. After selective protection of one of the imidazolyl nitrogens, the intermediate XVI can undergo alkylation reactions as described for the benzylimidazoles hereinabove.

Scheme 42 illustrates an analogous series of reactions wherein the $(CR^2{}_2)_pX(CR^2{}_2)_p$ linker of the instant compounds is oxygen. Thus, a suitably substituted halopyridinol, such as 3-chloro-2-pyridinol, is reacted with methyl N-(cyano)methanimidate to provide intermediate XVI. Intermediate XVI is then protected and, if desired to form a compound of a preferred embodiment, alkylated with a suitably protected benzyl. The intermediate XVII can then be coupled to a aryl moiety by Suzuki chemistry to provide the instant compound.

Compounds of the instant invention wherein the $A^1(CR^1{}_2)_nA^2(CR^1{}_2)n$ linker is a substituted methylene may be synthesized by the methods shown in Scheme 43. Thus, the N-protected imidazolyl iodide XVIII is reacted, under Grignard conditions with a suitably protected benzaldehyde to provide the alcohol XIX. Acylation, followed by the alkylation procedure illustrated in the Schemes above (in particular, Scheme 33) provides the instant compound XX. If other $R^1$ substituents are desired, the acetyl moiety can be manipulated as illustrated in the Scheme.

Addition of various nucleophiles to an imidazolyl aldehyde may also be employed to form a substituted alkyl linker between the biheteroaryl and the preferred W (imidazolyl) as shown in Scheme 44. Thus a sutiably substituted phenyl lithium can be reacted with pyridine to form the 2-substituted N-lithio-1,2-dihydropyridine XXa. Intermediate XXa can then react with a aldehyde to provide a suitably substituted instant compound. Similar substituent manipulation as shown in Scheme 43 may be performed on the fully functionalized compound which incorporates an $R^2$ hydroxyl moiety.

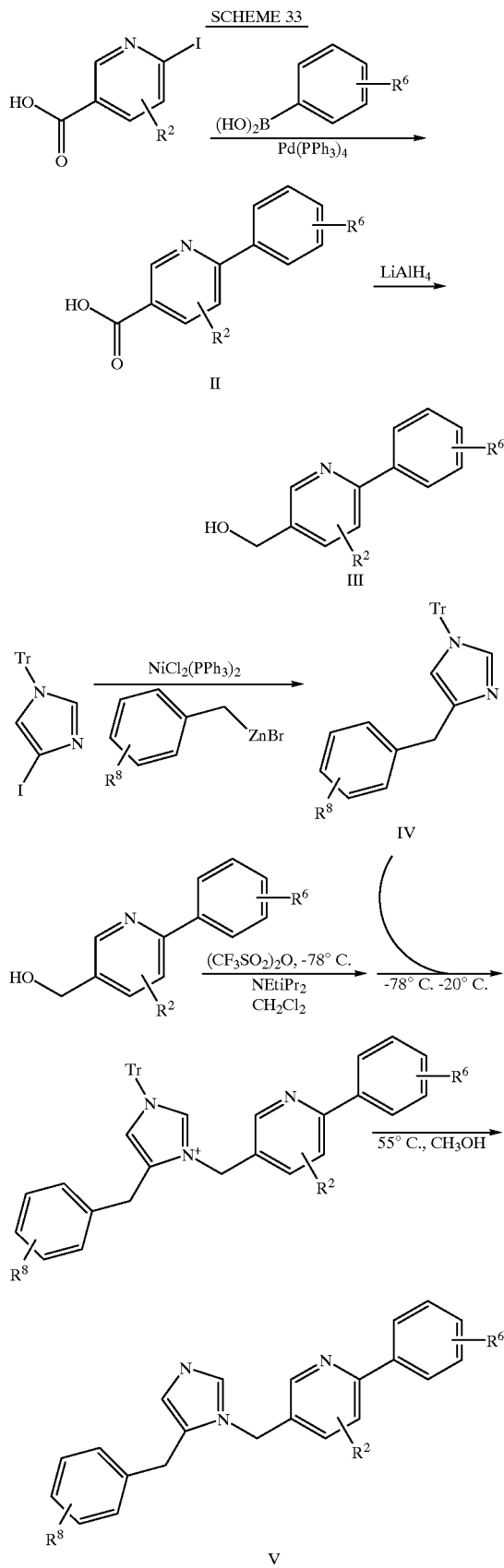

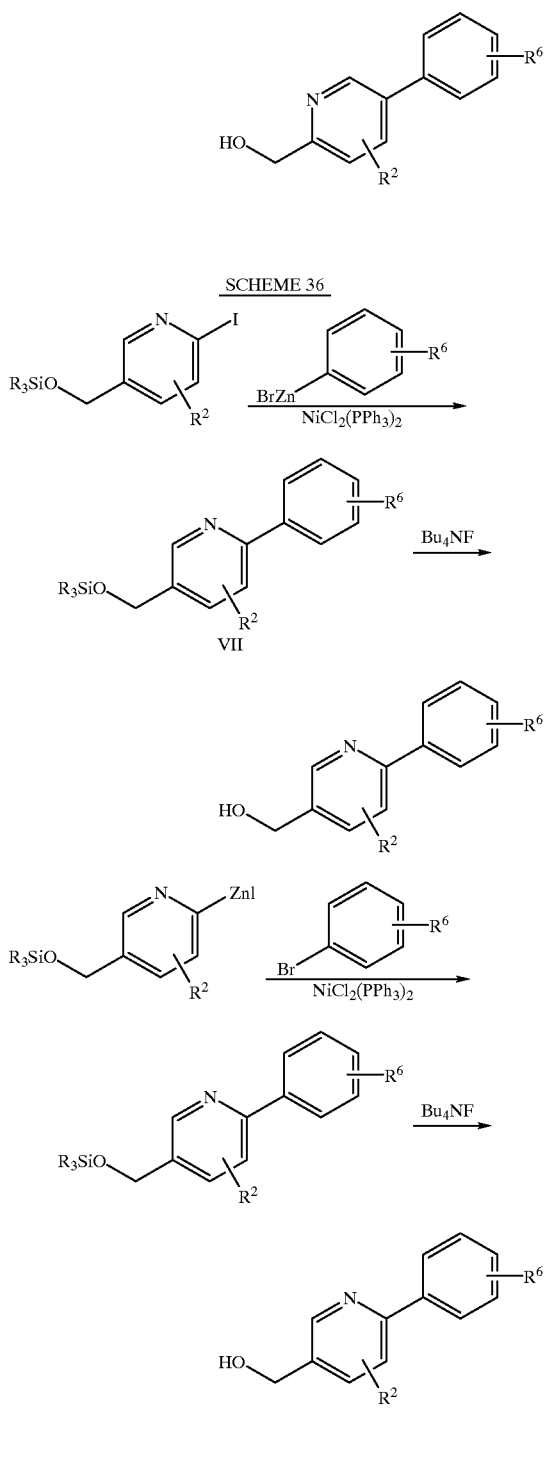
SCHEME 36
SCHEME 37
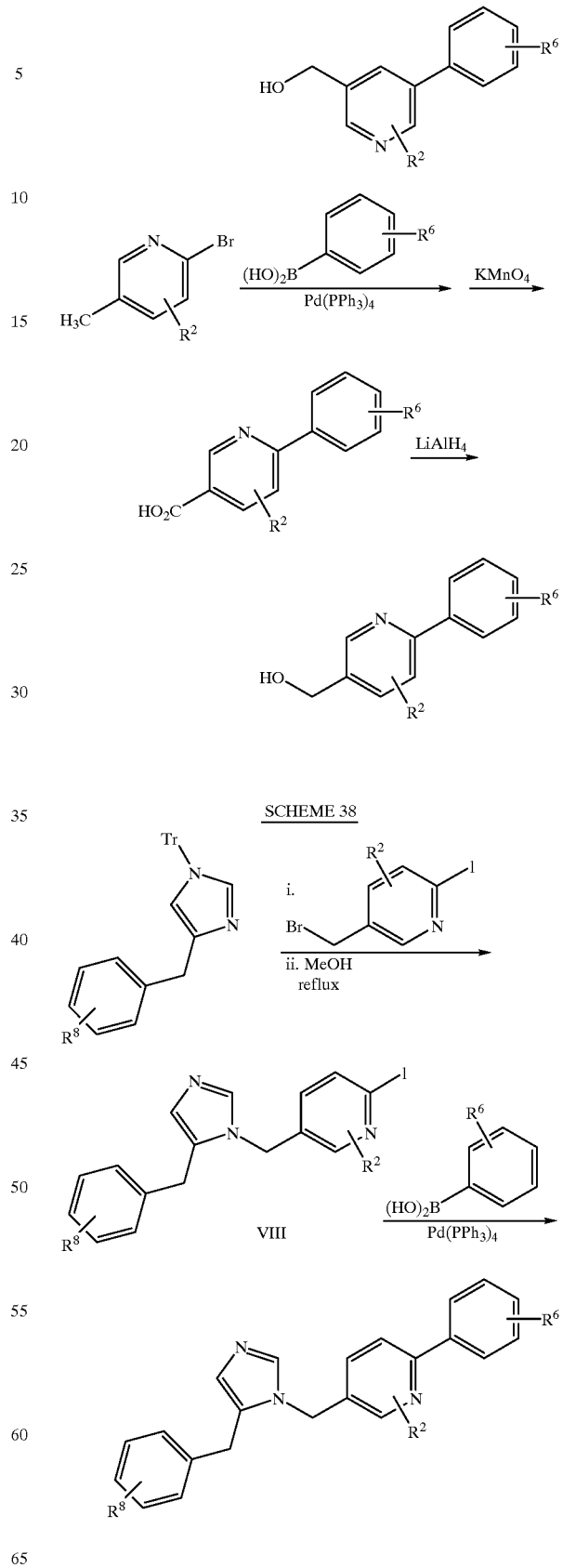
SCHEME 38

SCHEME 39
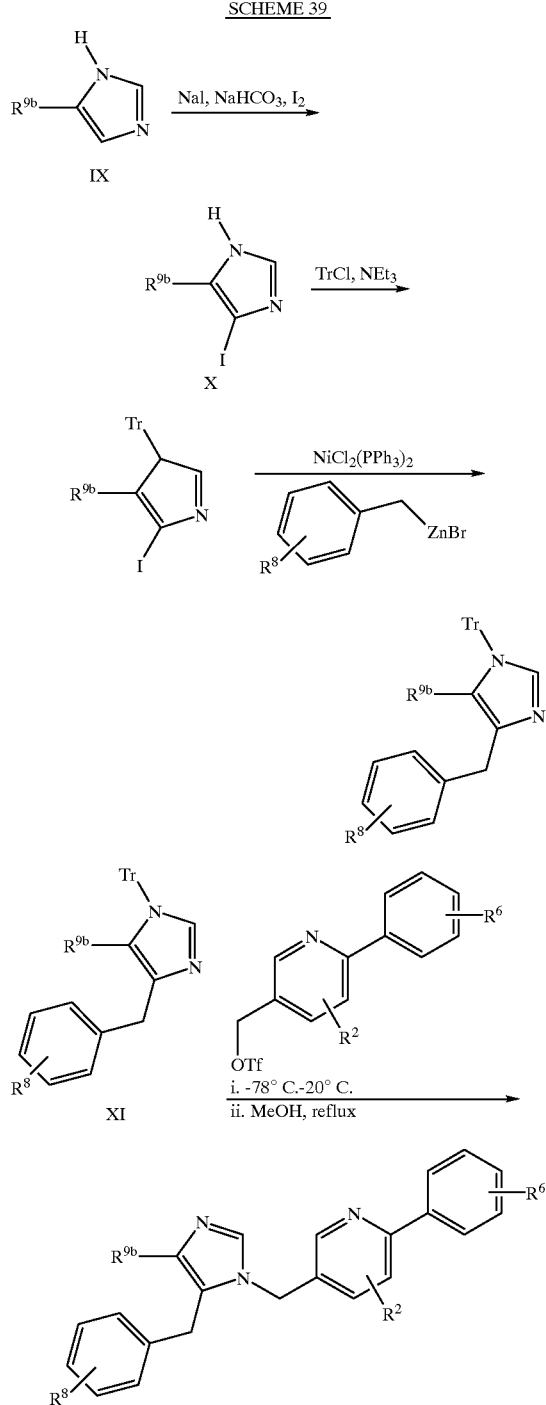
SCHEME 40
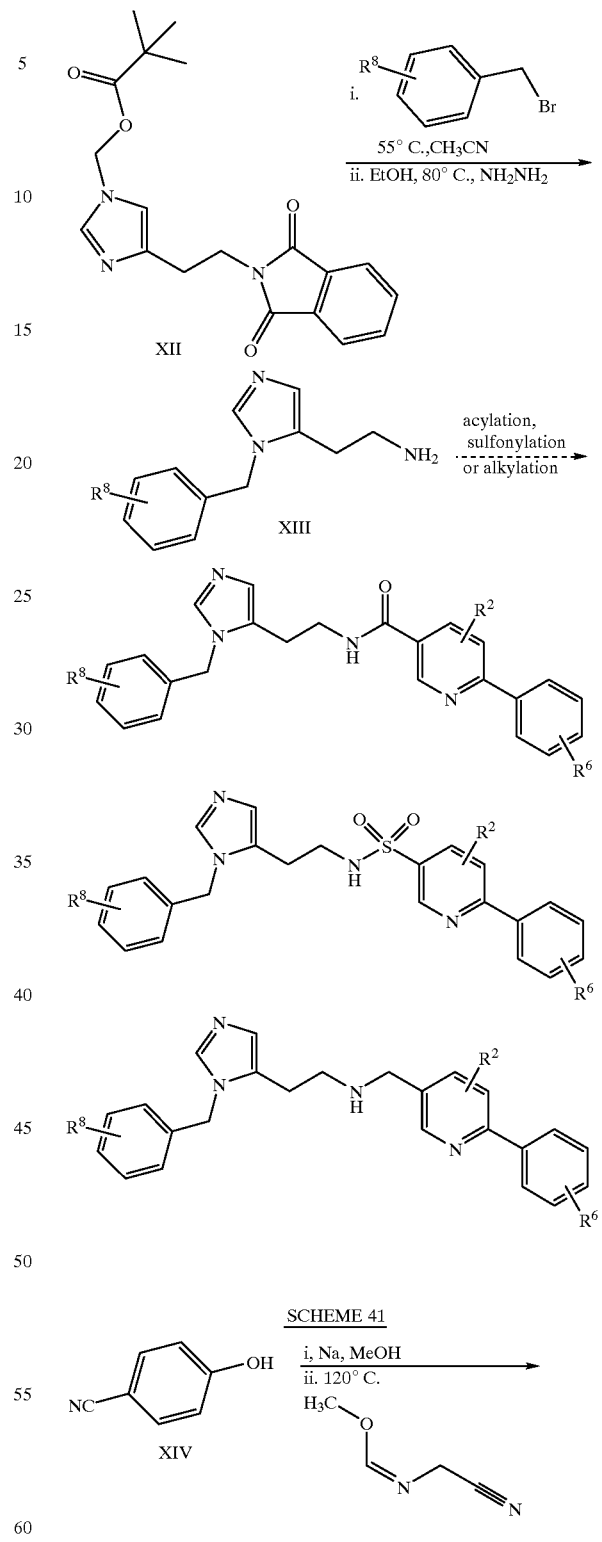
SCHEME 41

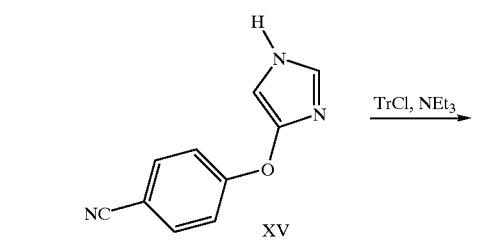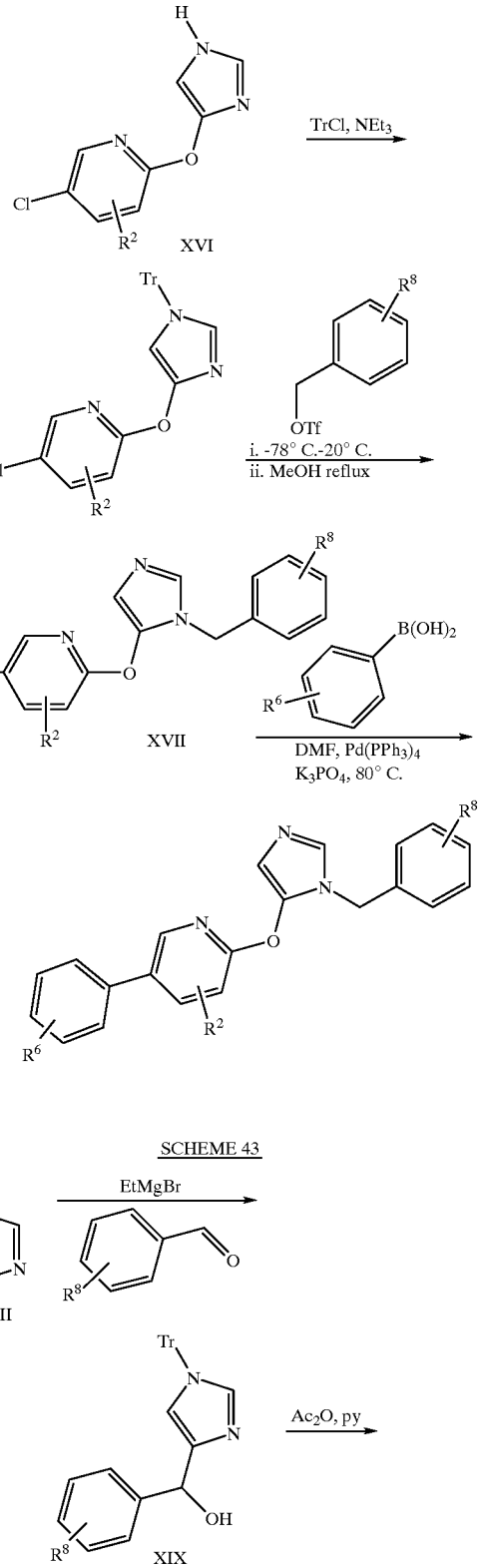

-continued

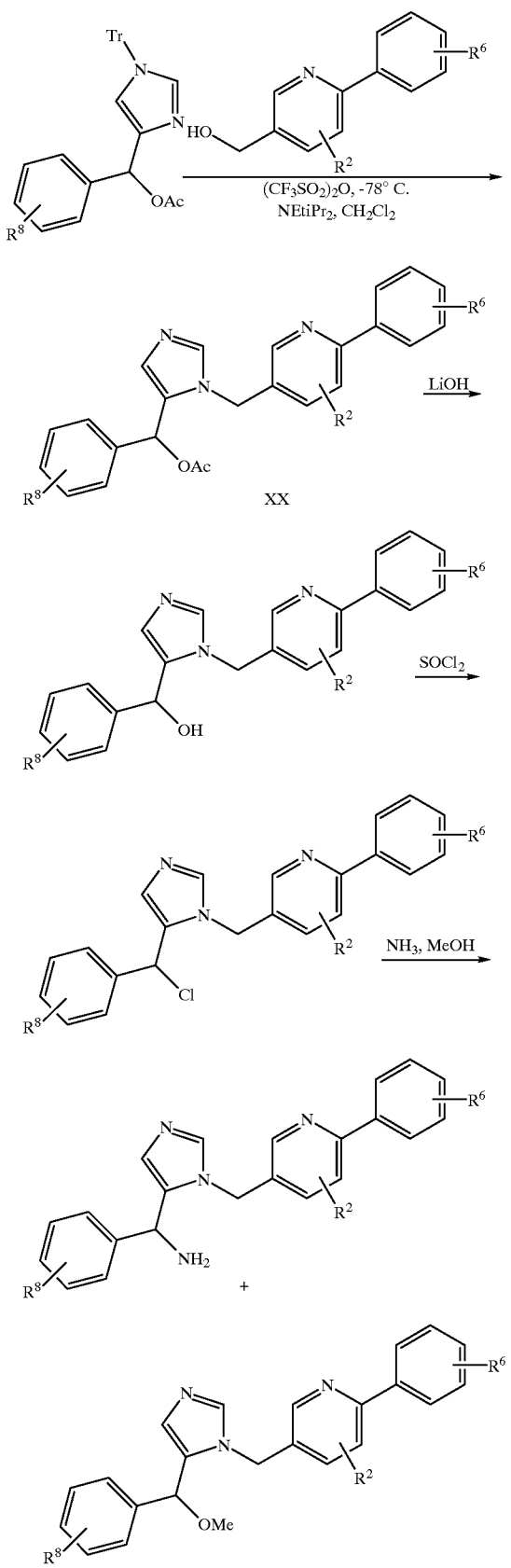

XX

SCHEME 44

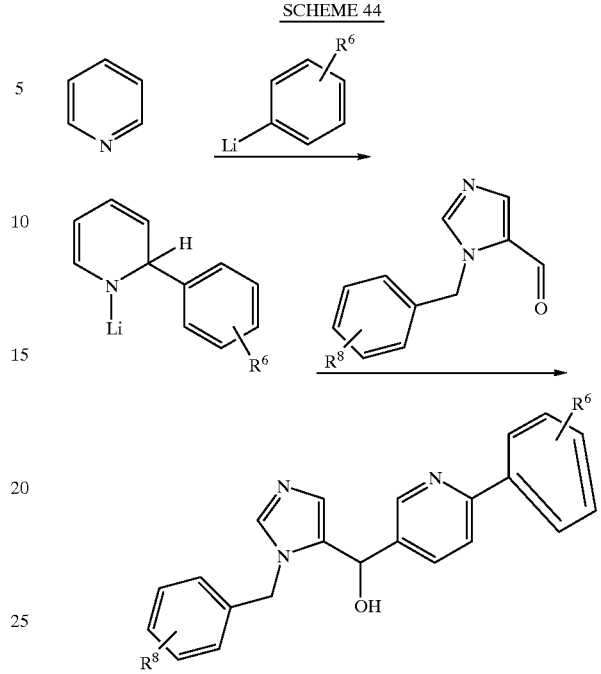

The farnesyl transferase inhibitors of formula (I-g) can be synthesized in accordance with Schemes 45–56, in addition to other standard manipulations such as ester hydrolysis, cleavage of protecting groups, etc., as may be known in the literature or exemplified in the experimental procedures. Substituents $R^3$, $R^6$ and $R^8$, as shown in the Schemes, represent the substituents $R^3$, $R^4$, $R^5$, $R^6$ and $R^8$; although only one such $R^3$, $R^6$ or $R^8$ is present in the intermediates and products of the schemes, it is understood that the reactions shown are also applicable when such aryl or heteroaryl moieties contain multiple substituents. The compounds referred to in the Synopsis of Schemes 45–56 by Roman numerals are numbered starting sequentially with II and ending with XX. Incorporation of a halogen precursor to a radionuclide moiety may be accomplished, for example, by selection of the appropriate halogenated benzyl precursor in Scheme 45.

These reactions may be employed in a linear sequence to provide the compounds of the invention or they may be used to synthesize fragments which are subsequently joined by the alkylation reactions described in the Schemes. The reactions described in the Schemes are illustrative only and are not meant to be limiting. Other reactions useful in the preparation of heteroaryl moieties are described in "Comprehensive Organic Chemistry, Volume 4: Heterocyclic Compounds" ed. P. G. Sammes, Oxford (1979) and references therein. Aryl-aryl coupling is generally described in "Comprehensive Organic Functional Group Transformations," Katritsky et al. eds., pp 472–473, Pergamon Press (1995).

Synopsis of Schemes 45–56:

The requisite intermediates are in some cases commercially available, or can be prepared according to literature procedures, for the most part. Schemes 45–56 illustrate synthesis of the instant biheteroaryl compound which incorporate a preferred benzylimidazolyl sidechain. Thus, in Scheme 45, for example, a biheteroaryl intermediate that is not commercially available may be synthesized by methods known in the art. Thus, a suitably substituted pyridyl boronic acid may be reacted under Suzuki coupling conditions (*Pure Appl. Chem.*, 63:419 (1991)) with a suitably substituted halogenated nicotinic acid, such as 4-bromo-nicotinic acid, to provide the biheteroaryl carboxylic acid II. The acid may be reduced and the triflate of the intermediate alcohol III may be formed in situ and coupled to a suitably substituted benzylimidazolyl IV to provide, after deprotection, the instant compound V.

Schemes 46–49 illustrate other methods of synthesizing the key alcohol intermediates, which can then be processed as described in Scheme 45. Thus, Scheme 46 illustrates the analogous series of biheteroaryl alcohol forming reactions starting with the methyl nicotinate boronic acid and the "terminal" heteroaryl moiety employed in the Suzuki coupling as the halogenated reactant. Such a coupling reaction is also compatible when one of the reactants incorporates a suitably protected hydroxyl functionality as illustrated in Scheme 47.

Negishi chemistry (*Org. Synth.*, 66:67 (1988)) may also be employed to form the biheteroaryl component of the instant compounds, as shown in Scheme 48. Thus, a suitably substituted zinc bromide adduct may be coupled to a suitably substituted heteroaryl halide in the presence of nickel (II) to provide the biheteroaryl VII. The heteroaryl halide and the zinc bromide adduct may be selected based on the availability of the starting reagents.

Scheme 49 illustrates the preparation of the pyridylmethanol intermediate starting with the 3-methyl pyridine.

As illustrated in Scheme 50, the sequence of coupling reactions may be modified such that the heteroaryl-heteroaryl bond is formed last. Thus, a suitably substituted imidazole may first be alkylated with a suitably substituted benzyl halide to provide intermediate VIII. Intermediate VIII can then undergo Suzuki type coupling to a suitably substituted pyridyl boronic acid.

Scheme 51 illustrates synthesis of an instant compound wherein a non-hydrogen $R^{9b}$ is incorporated in the instant compound. Thus, a readily available 4-substituted imidazole IX may be selectively iodinated to provide the 5-iodoimidazole X. That imidazole may then be protected and coupled to a suitably substituted benzyl moiety to provide intermediate XI. Intermediate XI can then undergo the alkylation reactions that were described hereinabove.

Scheme 52 illustrates synthesis of instant compounds that incorporate a preferred imidazolyl moiety connected to the biaryl via an alkyl amino, sulfonamide or amide linker. Thus, the 4-aminoalkylimidazole XII, wherein the primary amine is protected as the phthalimide, is selectively alkylated then deprotected to provide the amine XIII. The amine XIII may then react under conditions well known in the art with various activated biheteroaryl moieties to provide the instant compounds shown.

Compounds of the instant invention wherein the $A^1(CR^1{}_2)_nA^2(CR^1{}_2)_n$ linker is oxygen may be synthesized by methods known in the art, for example as shown in Scheme 53. The suitably substituted phenol XIV may be reacted with methyl N-(cyano)methanimidate to provide the 4-phenoxyimidazole XV. After selective protection of one of the imidazolyl nitrogens, the intermediate XVI can undergo alkylation reactions as described for the benzylimidazoles hereinabove.

Scheme 54 illustrates an analogous series of reactions wherein the $(CR^2{}_2)_pX(CR^2{}_2)_p$ linker of the instant compounds is oxygen. Thus, a suitably substituted halopyridinol, such as 3-chloro-2-pyridinol, is reacted with methyl N-(cyano)methanimidate to provide intermediate XVI. Intermediate XVI is then protected and, if desired to form a compound of a preferred embodiment, alkylated with a suitably protected benzyl. The intermediate XVII can then be coupled to a heteroaryl moiety by Suzuki chemistry to provide the instant compound.

Compounds of the instant invention wherein the $A^1(CR^1{}_2)_nA^2(CR^1{}_2)_n$ linker is a substituted methylene may be synthesized by the methods shown in Scheme 55. Thus, the N-protected imidazolyl iodide XVIII is reacted, under Grignard conditions with a suitably protected benzaldehyde to provide the alcohol XIX. Acylation, followed by the alkylation procedure illustrated in the Schemes above (in particular, Scheme 45) provides the instant compound XX. If other $R^1$ substituents are desired, the acetyl moiety can be manipulated as illustrated in the Scheme.

Scheme 56 illustrates the use of halogenated 2-aminopyrimidine in the preparation of compounds of the instant invention.

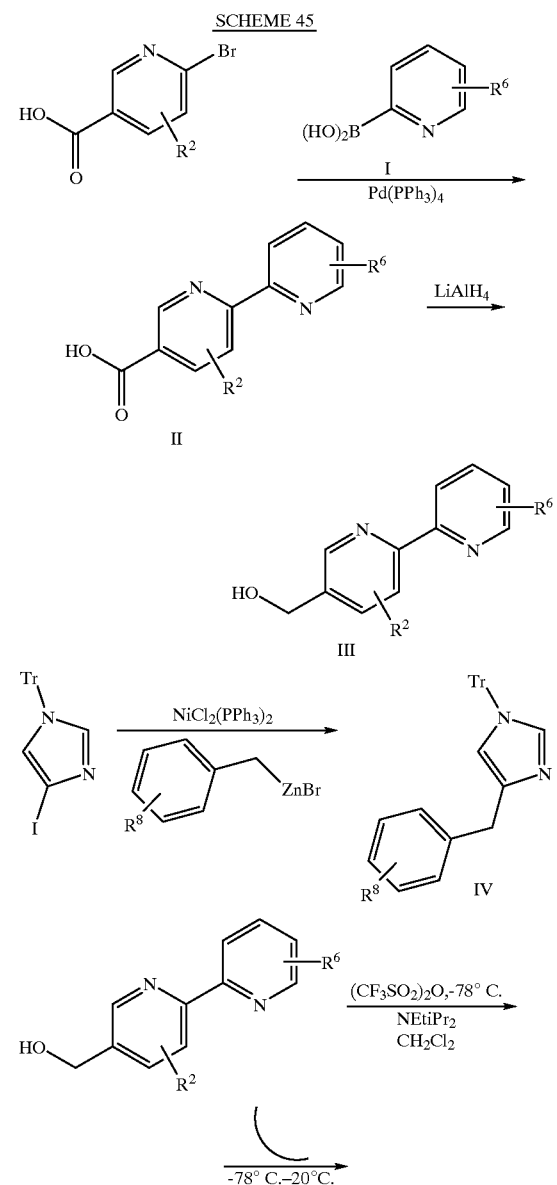

89
-continued
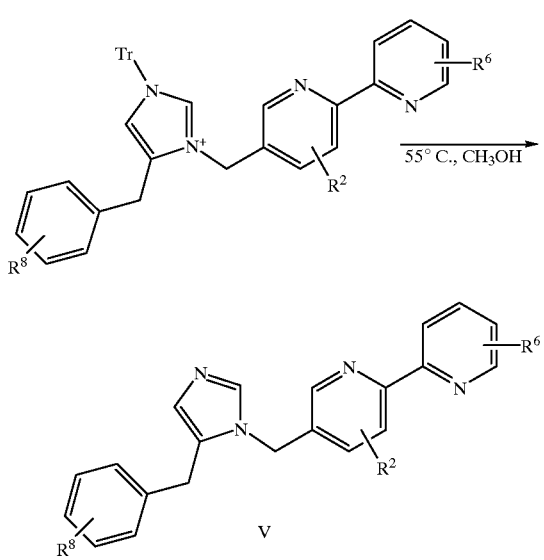
SCHEME 46
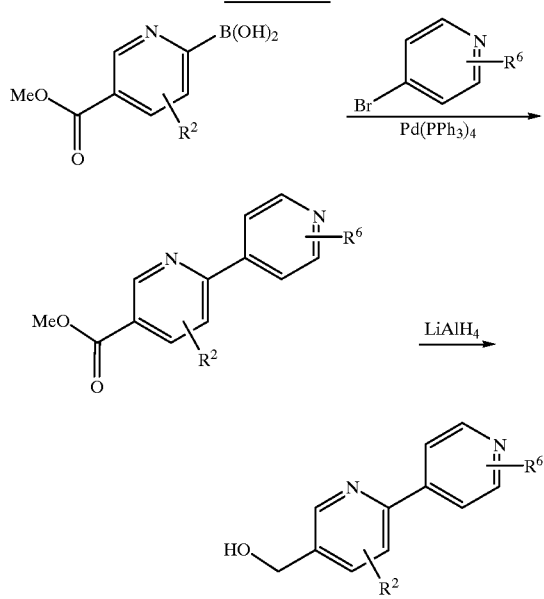
SCHEME 47
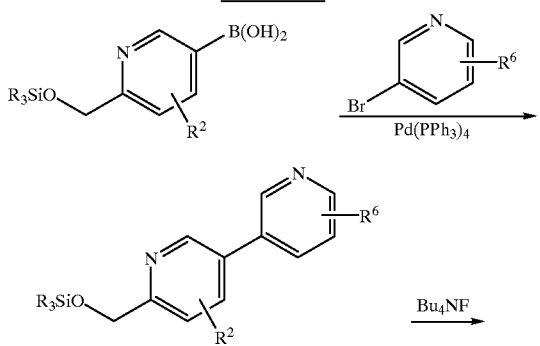
90
-continued
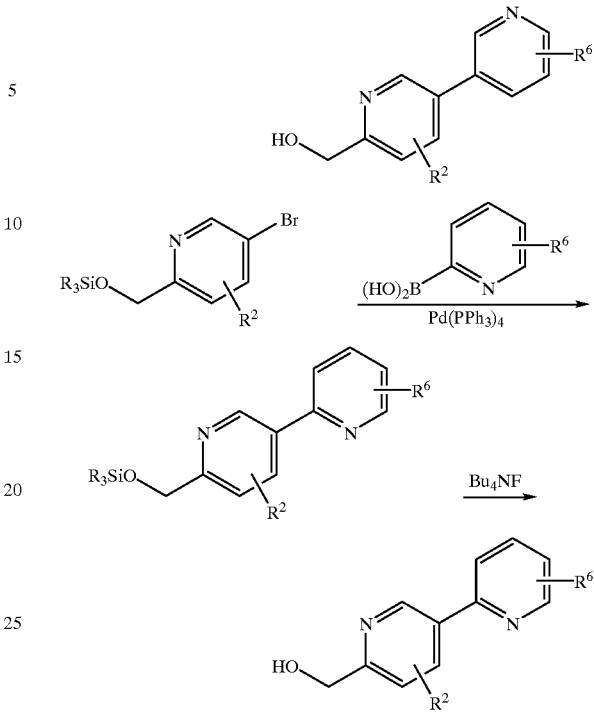
SCHEME 48
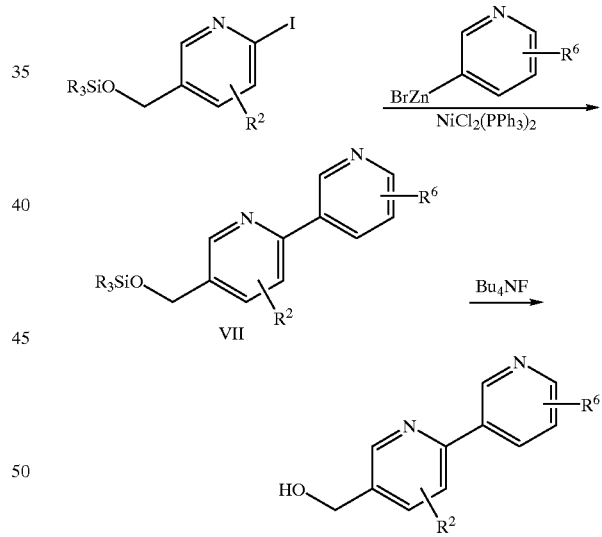
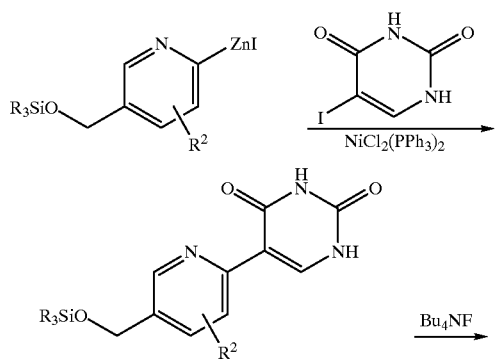

-continued
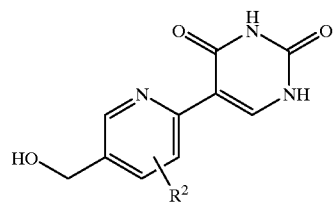
SCHEME 49
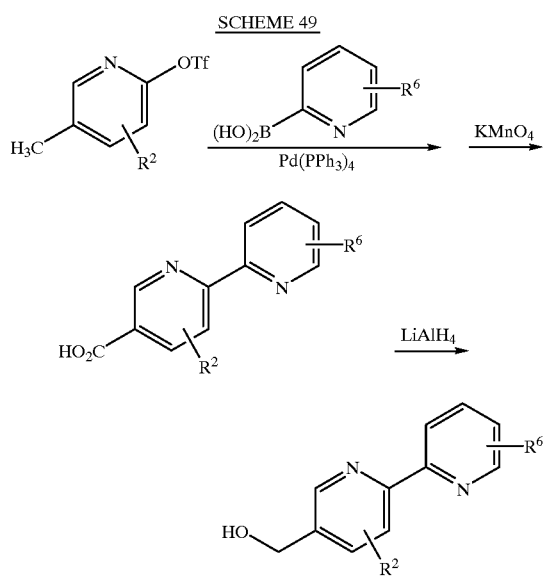
SCHEME 50
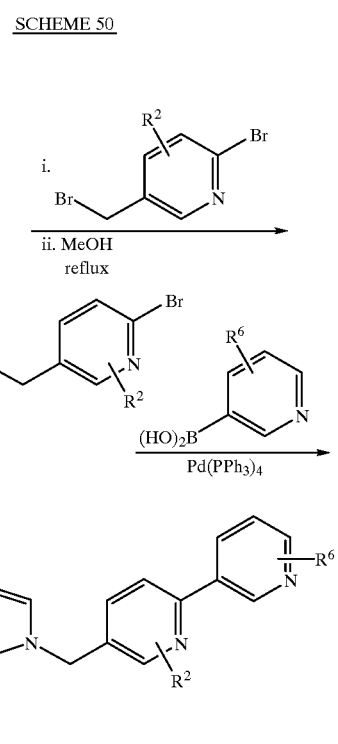
SCHEME 51
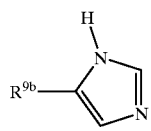
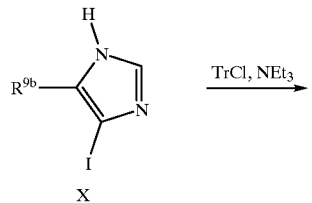
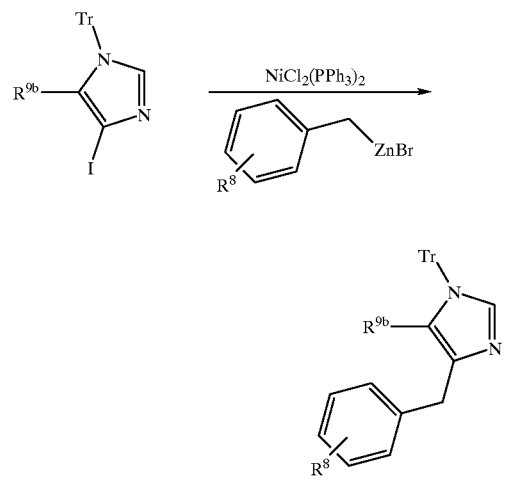
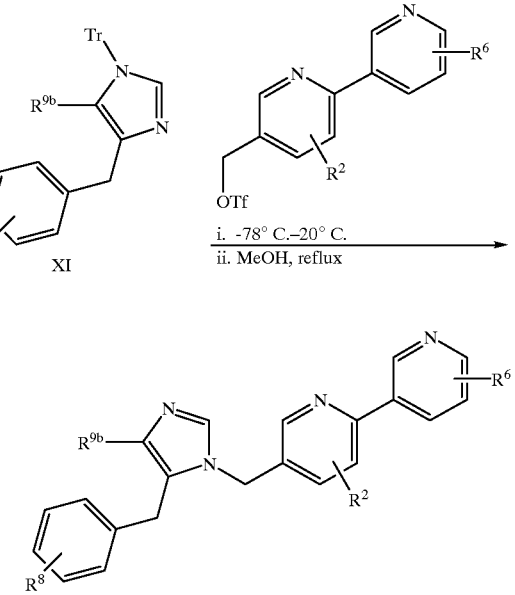

SCHEME 52
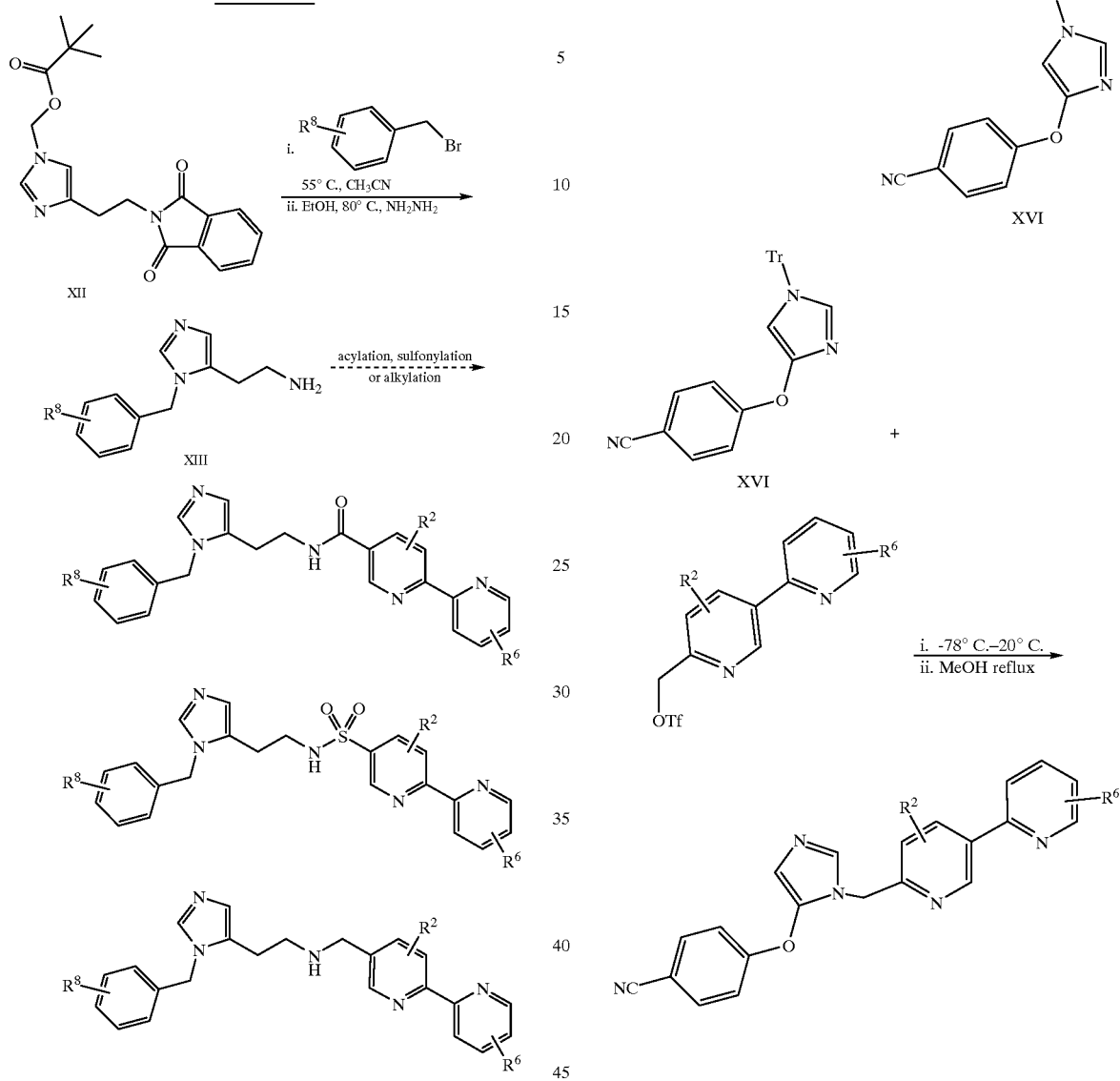
SCHEME 53
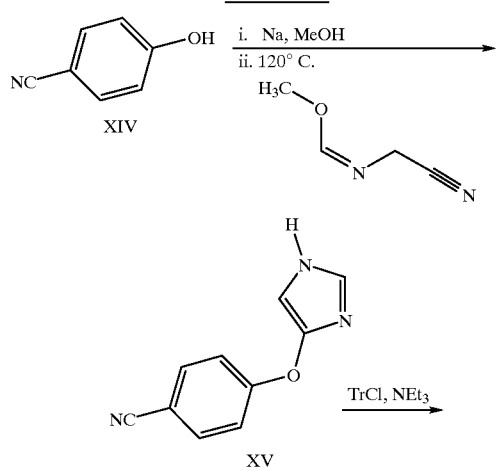
SCHEME 54
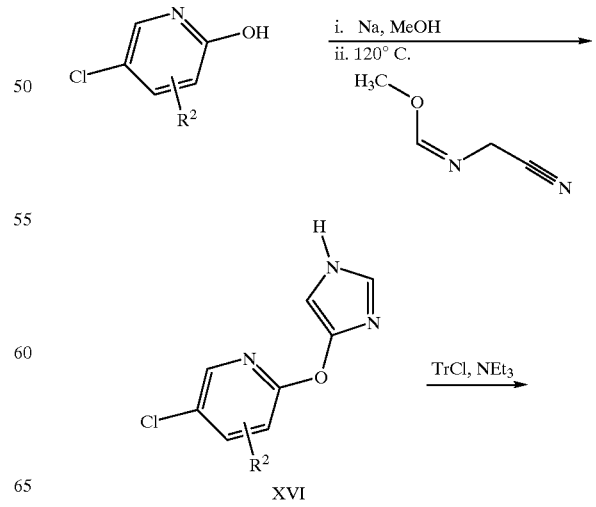

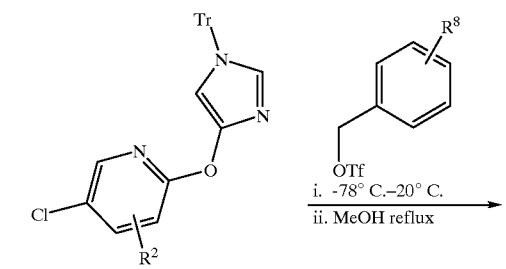
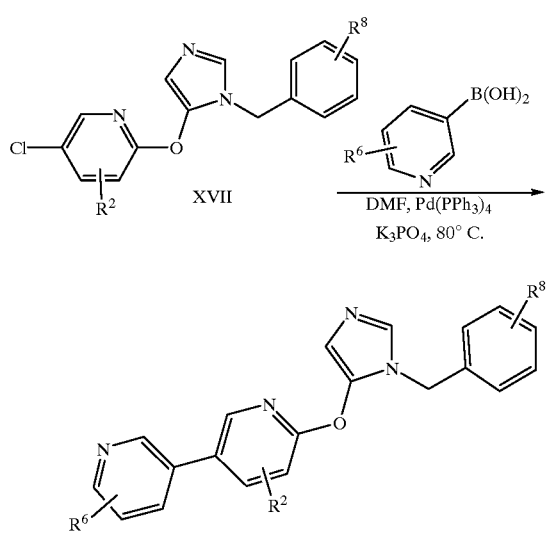
SCHEME 55
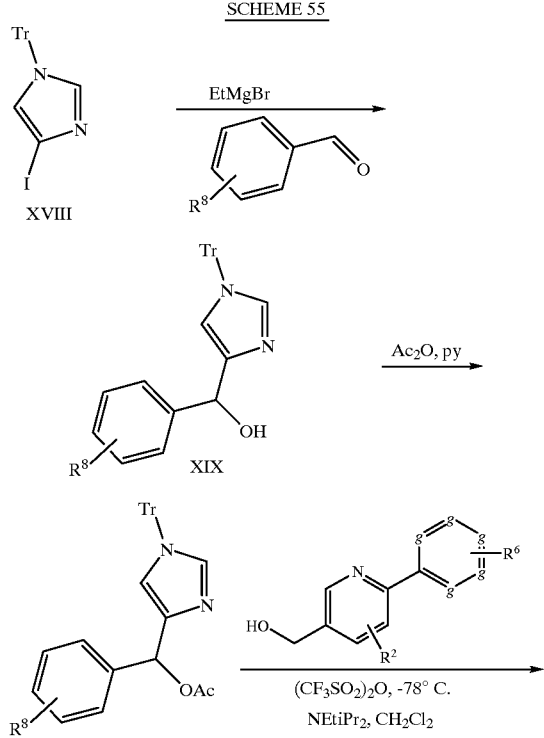
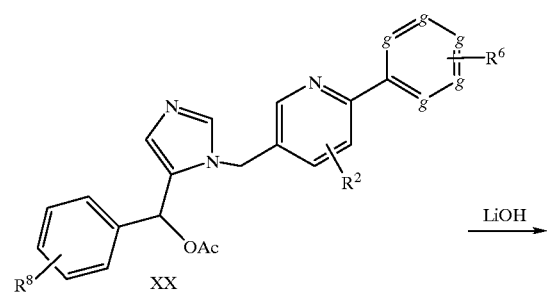
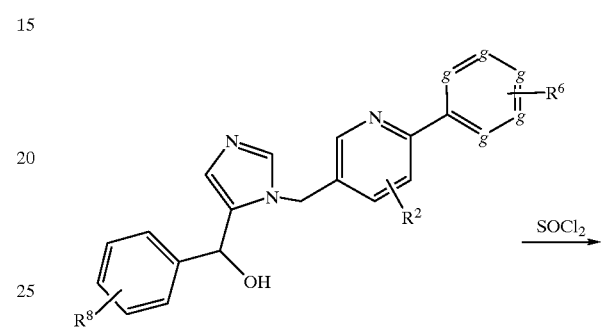
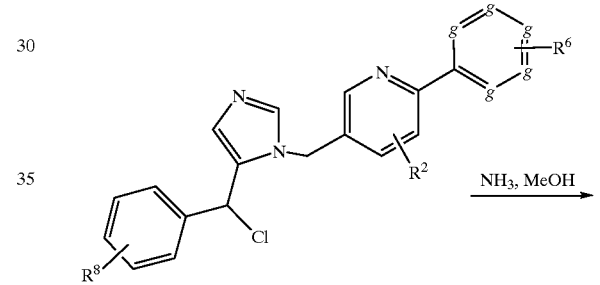
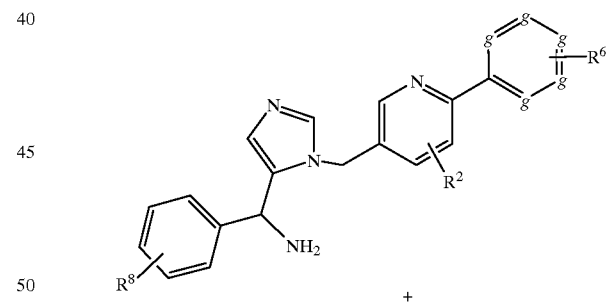
+
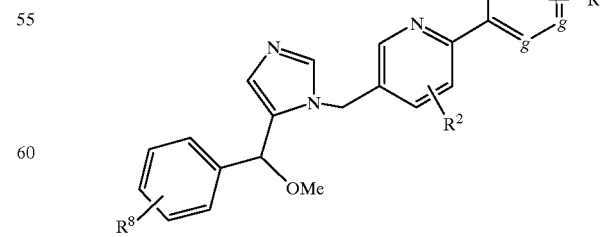

SCHEME 56

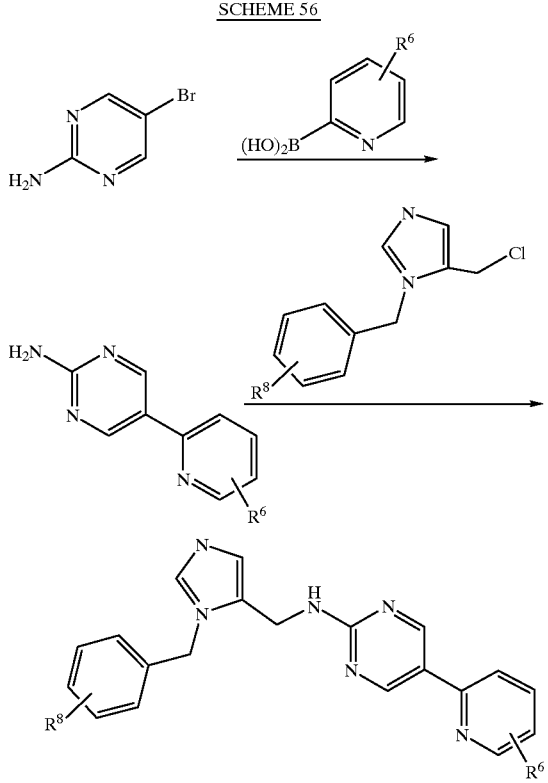

The farnesyl transferase inhibitors of formula (I-i) can be synthesized in accordance with Schemes 57–66, in addition to other standard manipulations such as ester hydrolysis, cleavage of protecting groups, etc., as may be known in the literature or exemplified in the experimental procedures. Substituents $R^3$, $R^6$ and $R^8$, as shown in the Schemes, represent the substituents $R^3$, $R^4$, $R^5$, $R^{6a}$, $R^{6b}$, $R^{6c}$, $R^{6d}$, $R^{6e}$ and $R^8$; although only one such $R^3$, $R^6$ or $R^8$ is present in the intermediates and products of the schemes, it is understood that the reactions shown are also applicable when such aryl or heterocyclic moieties contain multiple substituents. Incorporation of a halogen precursor to a radionuclide moiety may be accomplished, for example, by selection of the appropriate halogenated benzyl precursor in Scheme 57.

These reactions may be employed in a linear sequence to provide the compounds of the invention or they may be used to synthesize fragments which are subsequently joined by the alkylation reactions described in the Schemes. The reactions described in the Schemes are illustrative only and are not meant to be limiting. Other reactions useful in the preparation of heteroaryl moieties are described in "Comprehensive Organic Chemistry, Volume 4: Heterocyclic Compounds" ed. P. G. Sammes, Oxford (1979) and references therein.

Synopsis of Schemes 57–66:

The requisite intermediates are in some cases commercially available, or can be prepared according to literature procedures. Schemes 57–66 illustrate synthesis of the instant bicyclic compounds which incorporate a preferred benzylimidazolyl side chain. Thus, in Scheme 57, for example, a bicyclic intermediate that is not commercially available may be synthesized by methods known in the art. Thus, a suitably substituted pyridinone 1 may be reacted under coupling conditions with a suitably substituted iodobenzyl alcohol to provide the intermediate alcohol 2. The intermediate alcohol 2 may converted to the corresponding bromide 3. The bromide 3 may be coupled to a suitably substituted benzylimidazolyl 4 to provide, after deprotection, the instant compound 5.

Schemes 58–60 illustrate methods of synthesizing related or analogous key alcohol intermediates, which can then be processed as described in Scheme 57. Thus, Scheme 58 illustrates pyridinonylpyridyl alcohol forming reactions starting with the suitably substituted iodonicotinate 6.

Scheme 59 illustrates preparation of the intermediate alcohol 9 wherein the terminal lactam ring is saturated. Acylation of a suitably substituted 4-aminobenzyl alcohol 7 with a suitably substituted brominated acyl chloride provides the bisacylated intermediate 8. Closure of the lactam ring followed by saponifiaction of the remaining acyl group provides the intermediate alcohol. Preparation of the homologous saturated lactam 10 is illustrated in Scheme 60.

Scheme 61 illustrates the synthesis of the alcohol intermediate 13 which incorporates a terminal pyrazinone moiety. Thus, the amide of a suitably substituted amino acid 11 is formed and reacted with glyoxal to form the pyrazine 12, which then undergoes the Ullmann coupling to form intermediate 13.

Scheme 62 illustrates synthesis of an instant compound wherein a non-hydrogen $R^{9b}$ is incorporated in the instant compound. Thus, a readily available 4-substituted imidazole 14 may be selectively iodinated to provide the 5-iodoimidazole 15. That imidazole may then be protected and coupled to a suitably substituted benzyl moiety to provide intermediate 16. Intermediate 16 can then undergo the alkylation reactions that were described hereinabove.

Scheme 63 illustrates synthesis of instant compounds that incorporate a preferred imidazolyl moiety connected to the bicyclic moiety via an alkyl amino, sulfonamide or amide linker. Thus, the 4-aminoalkylimidazole 17, wherein the primary amine is protected as the phthalimide, is selectively alkylated then deprotected to provide the amine 18. The amine 18 may then react under conditions well known in the art with various activated bicyclic moieties to provide the instant compounds shown.

Compounds of the instant invention wherein the $A^1(CR^1{}_2)_nA^2(CR^1{}_2)_n$ linker is oxygen may be synthesized by methods known in the art, for example as shown in Scheme 64. The suitably substituted phenol 19 may be reacted with methyl N-(cyano)methanimidate to provide the 4-phenoxyimidazole 20. After selective protection of one of the imidazolyl nitrogens, the intermediate 21 can undergo alkylation reactions as described for the benzylimidazoles hereinabove.

Compounds of the instant invention wherein the $A^1(CR^1{}_2)_nA^2(CR^1{}_2)_n$ linker is a substituted methylene may be synthesized by the methods shown in Scheme 65. Thus, the N-protected imidazolyl iodide 22 is reacted, under Grignard conditions with a suitably protected benzaldehyde to provide the alcohol 23. Acylation, followed by the alkylation procedure illustrated in the Schemes above (in particular, Scheme 57) provides the instant compound 24. If other $R^1$ substituents are desired, the acetyl moiety can be manipulated as illustrated in the Scheme.

Scheme 66 illustrates incorporation of an acetyl moiety as the $(CR^2{}_2)_pX(CR^2{}_2)_p$ linker of the instant compounds. Thus the readily available methylphenone 25 undergoes the Ullmann reaction and the acetyl brominated to provide intermediate 26. Reaction with the imidazolyl reagent 4 provides, after deprotection, the instant compound 27.

SCHEME 57
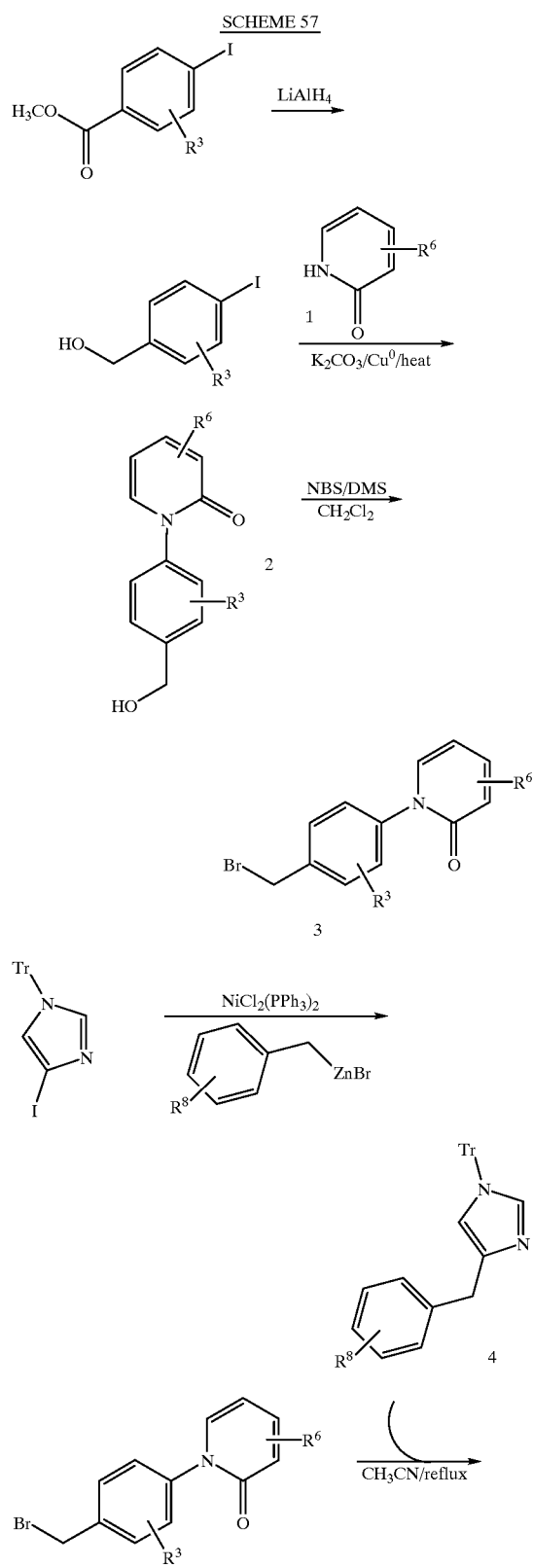
SCHEME 58
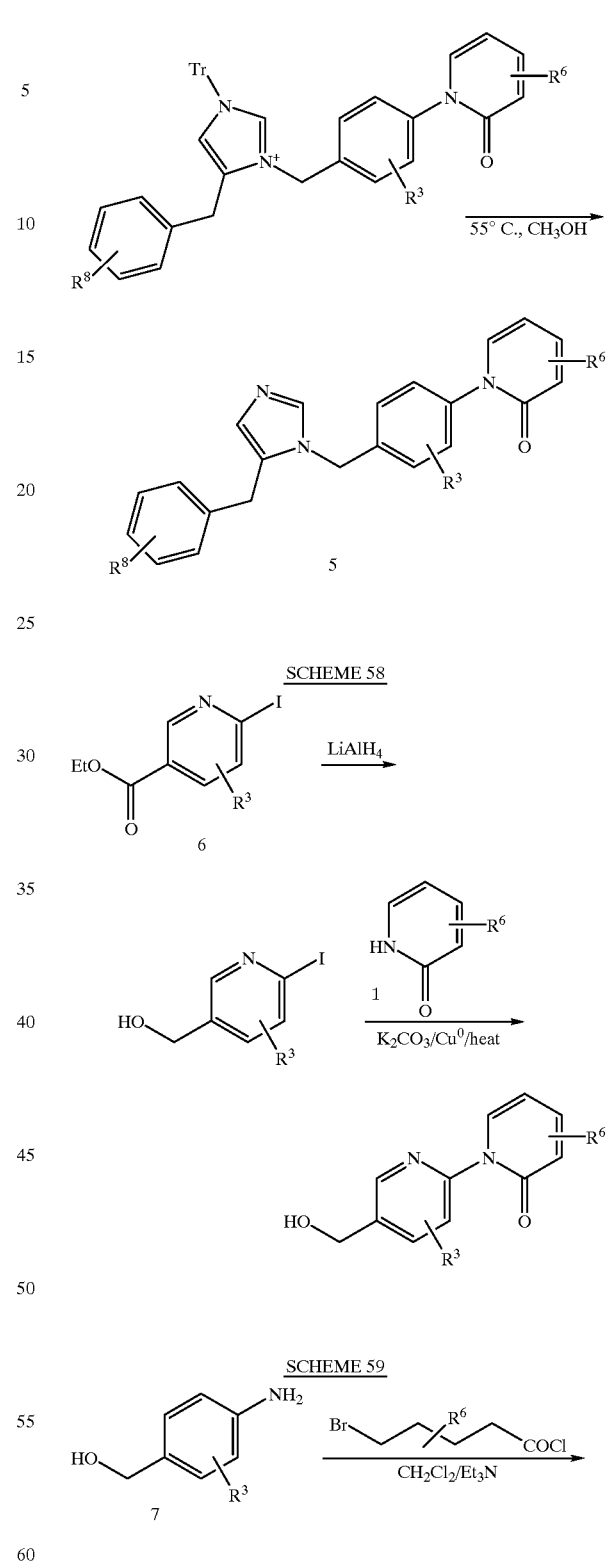
SCHEME 59

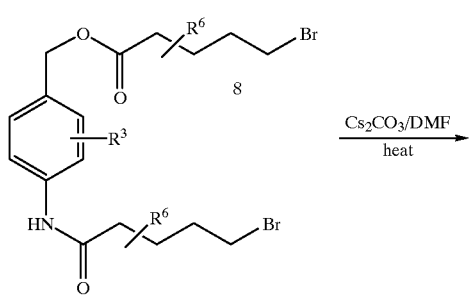
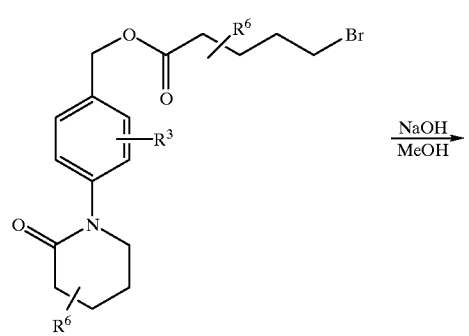
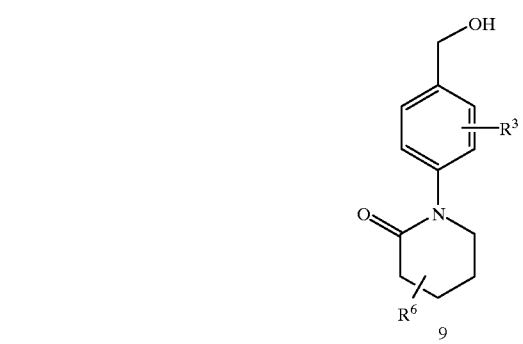
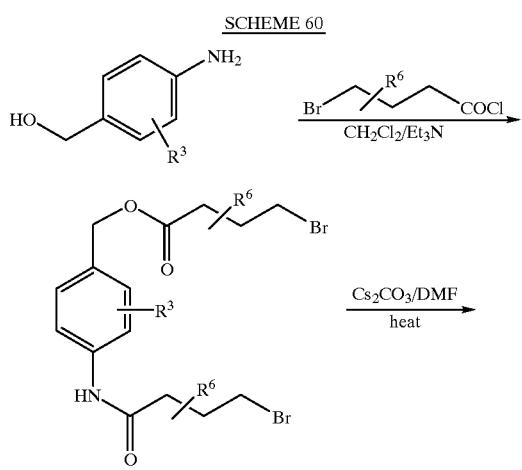
SCHEME 60
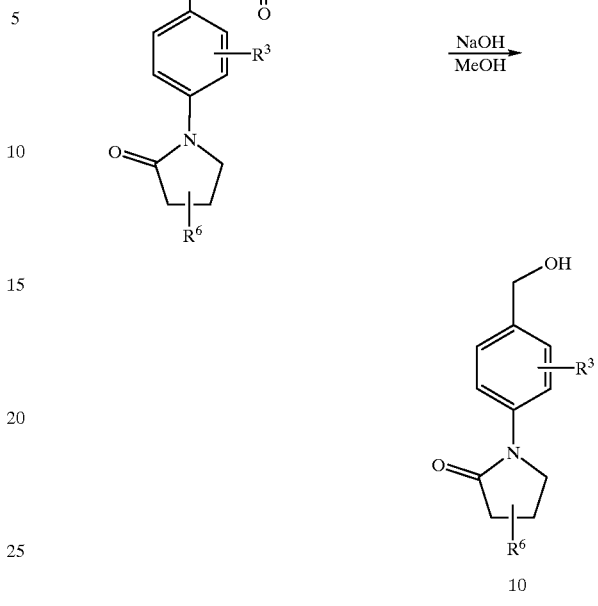
SCHEME 61
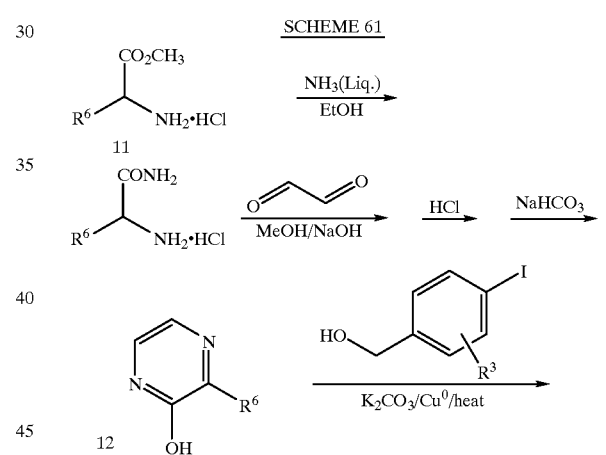
SCHEME 62
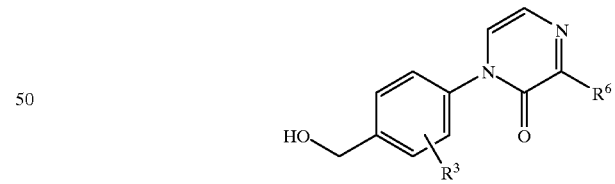

103
-continued
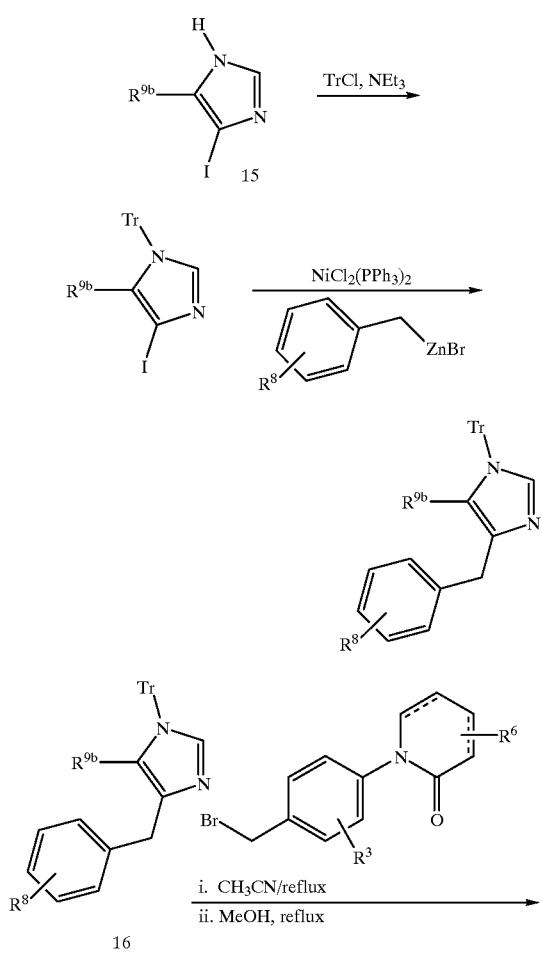
SCHEME 63
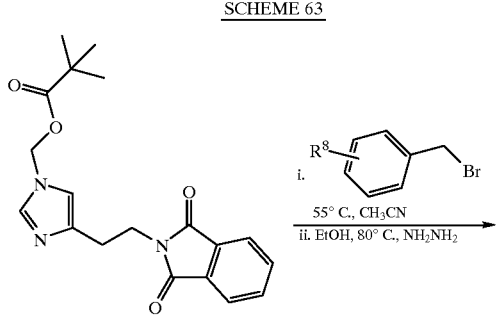
104
-continued
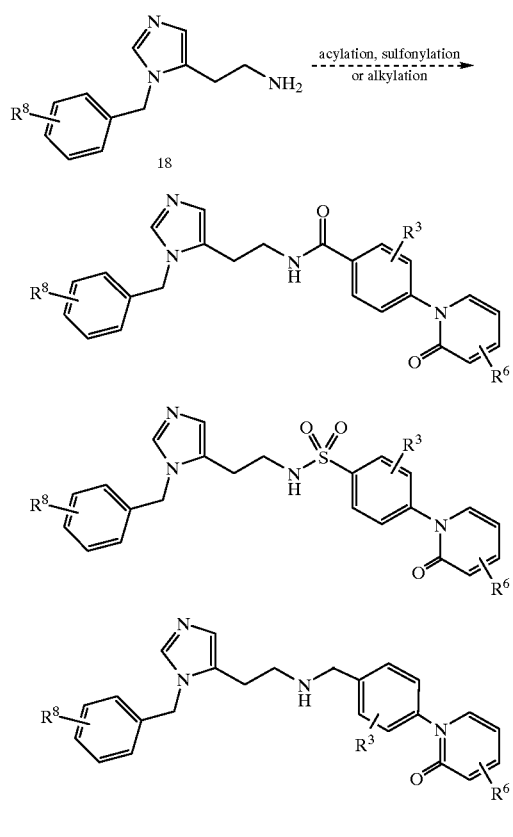
SCHEME 64
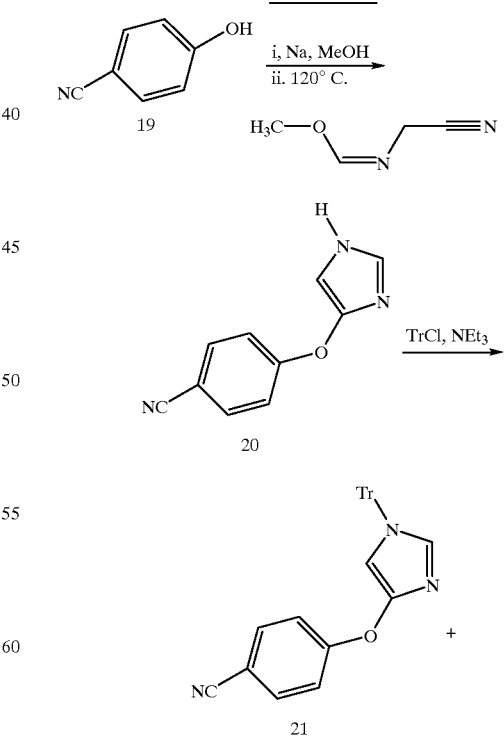

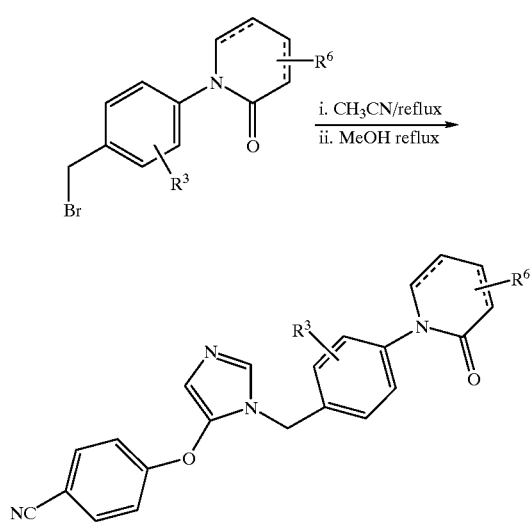
SCHEME 65
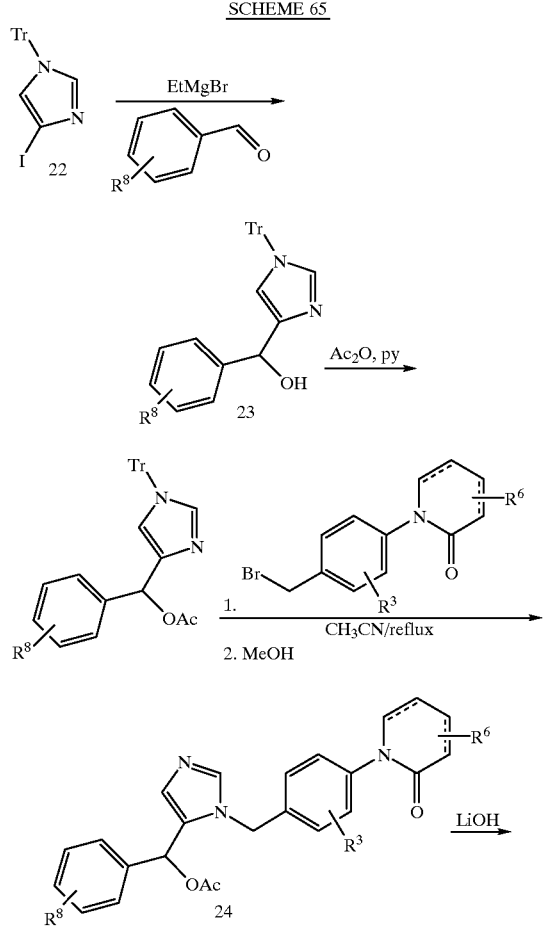
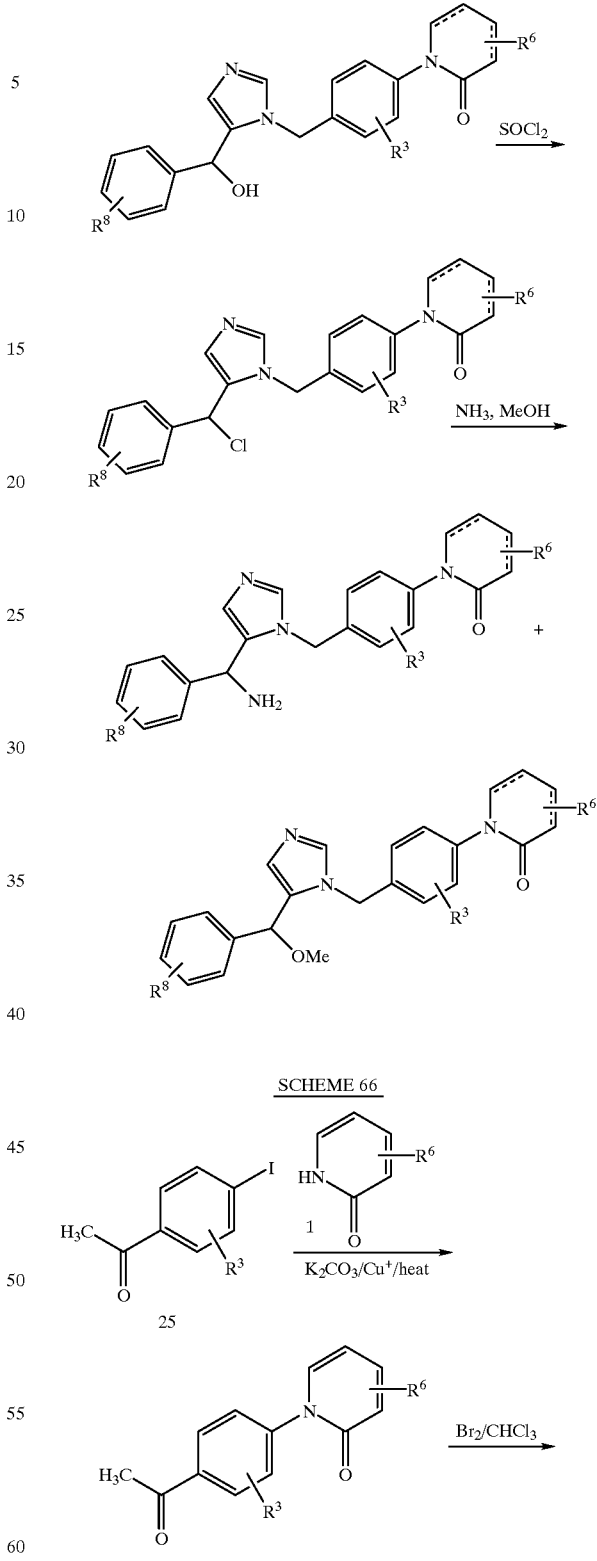
SCHEME 66

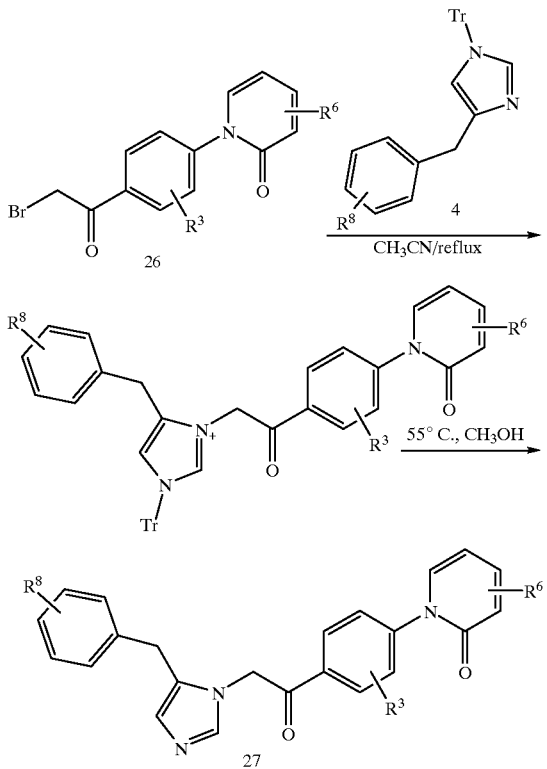

The farnesyl transferase inhibitors of formula (I-j) can be synthesized in accordance with Schemes 67–74, in addition to other standard manipulations such as ester hydrolysis, cleavage of protecting groups, etc., as may be known in the literature or exemplified in the experimental procedures. Substituents $R^3$, $R^6$ and $R^8$, as shown in the Schemes, represent the substituents $R^3$, $R^4$, $R^5$, $R^{6a}$, $R^{6b}$, $R^{6c}$, $R^{6d}$, $R^{6e}$ and $R^8$; although only one such $R^3$, $R^6$ or $R^8$ is present in the intermediates and products of the schemes, it is understood that the reactions shown are also applicable when such aryl or heterocyclic moieties contain multiple substituents. Incorporation of a halogen precursor to a radionuclide moiety may be accomplished, for example, by selection of the appropriate halogenated benzyl precursor in Scheme 67.

These reactions may be employed in a linear sequence to provide the compounds of the invention or they may be used to synthesize fragments which are subsequently joined by the alkylation reactions described in the Schemes. The reactions described in the Schemes are illustrative only and are not meant to be limiting. Other reactions useful in the preparation of heteroaryl moieties are described in "Comprehensive Organic Chemistry, Volume 4: Heterocyclic Compounds" ed. P. G. Sammes, Oxford (1979) and references therein.

Synopsis of Schemes 67–74:

The requisite intermediates are in some cases commercially available, or can be prepared according to literature procedures. Schemes 67–74 illustrate synthesis of the instant bicyclic compounds which incorporate a preferred benzylimidazolyl sidechain. Thus, in Scheme 67, for example, a bicyclic intermediate that is not commercially available may be synthesized by methods known in the art. Thus, a suitably substituted pyridinonyl alcohol 29 may be synthesized starting from the corresponding isonicotinate 28 according to procedures described by Boekelhiede and Lehn (*J. Org. Chem.*, 26:428–430 (1961)). The alcohol is then protected and reacted under Ullmann coupling conditions with a suitably substituted phenyl iodide, to provide the intermediate bicyclic alcohol 30. The intermediate alcohol 30 may converted to the corresponding bromide 31. The bromide 31 may be coupled to a suitably substituted benzylimidazolyl 32 to provide, after deprotection, the instant compound 33.

Schemes 68–69 illustrate methods of synthesizing related or alcohol intermediates, which can then be processed as described in Scheme 67. Thus, Scheme 68 illustrates preparation of a pyridylpyridinonyl alcohol and thienylpyridinonyl alcohol starting with the suitably substituted halogenated heterocycles.

Scheme 69 illustrates preparation of the intermediate bromide 36 wherein the preferred pyridinone is replced by a saturated lactam. Acylation of a suitably substituted aniline 34 with a suitably substituted brominated acyl chloride provides the acylated intermediate 35. Closure of the lactam ring provides the intermediate alcohol, which is converted to the bromide as described above.

Scheme 70 illustrates synthesis of an instant compound wherein a non-hydrogen $R^{9b}$ is incorporated in the instant compound. Thus, a readily available 4-substituted imidazole 37 may be selectively iodinated to provide the 5-iodoimidazole 38. That imidazole 38 may then be protected and coupled to a suitably substituted benzyl moiety to provide intermediate 39. Intermediate 39 can then undergo the alkylation reactions that were described hereinabove.

Scheme 71 illustrates synthesis of instant compounds that incorporate a preferred imidazolyl moiety connected to the biaryl via an alkyl amino, sulfonamide or amide linker. Thus, the 4-aminoalkylimidazole 40, wherein the primary amine is protected as the phthalimide, is selectively alkylated then deprotected to provide the amine 41. The amine 41 may then react under conditions well known in the art with various activated arylheteroaryl moieties to provide the instant compounds shown.

Compounds of the instant invention wherein the $A^1(CR^1_2)_nA^2(CR^1_2)_n$ linker is oxygen may be synthesized by methods known in the art, for example as shown in Scheme 72. The suitably substituted phenol 42 may be reacted with methyl N-(cyano)methanimidate to provide the 4-phenoxyimidazole 43. After selective protection of one of the imidazolyl nitrogens, the intermediate 44 can undergo alkylation reactions as described for the benzylimidazoles hereinabove.

Compounds of the instant invention wherein the $A^1(CR^1_2)_nA^2(CR^1_2)_n$ linker is a substituted methylene may be synthesized by the methods shown in Scheme 73. Thus, the N-protected imidazolyl iodide 45 is reacted, under Grignard conditions with a suitably protected benzaldehyde to provide the alcohol 46. Acylation, followed by the alkylation procedure illustrated in the Schemes above (in particular, Scheme 67) provides the instant compound 47. If other $R^1$ substituents are desired, the acetyl moiety can be manipulated as illustrated in the Scheme.

Scheme 74 illustrates incorporation of an acetyl moiety as the $(CR^2_2)_pX(CR^2_2)_p$ linker of the instant compounds. Thus, the suitably substituted acetyl pyridine 48 is converted to the corresponding pyridinone and undergoes the Ullmann reaction with a suitably substituted phenyl iodide. The acetyl is then brominated to provide intermediate 49. Reaction with the imidazolyl reagent 32 provides, after deprotection, the instant compound 50.

SCHEME 67
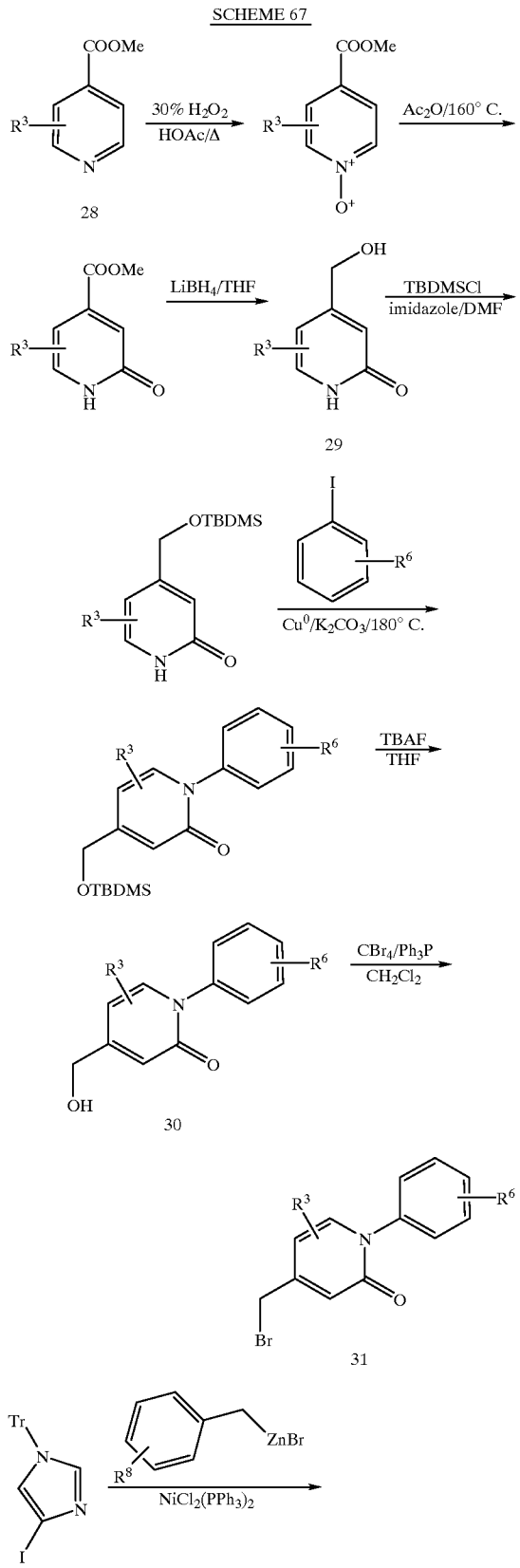
SCHEME 68
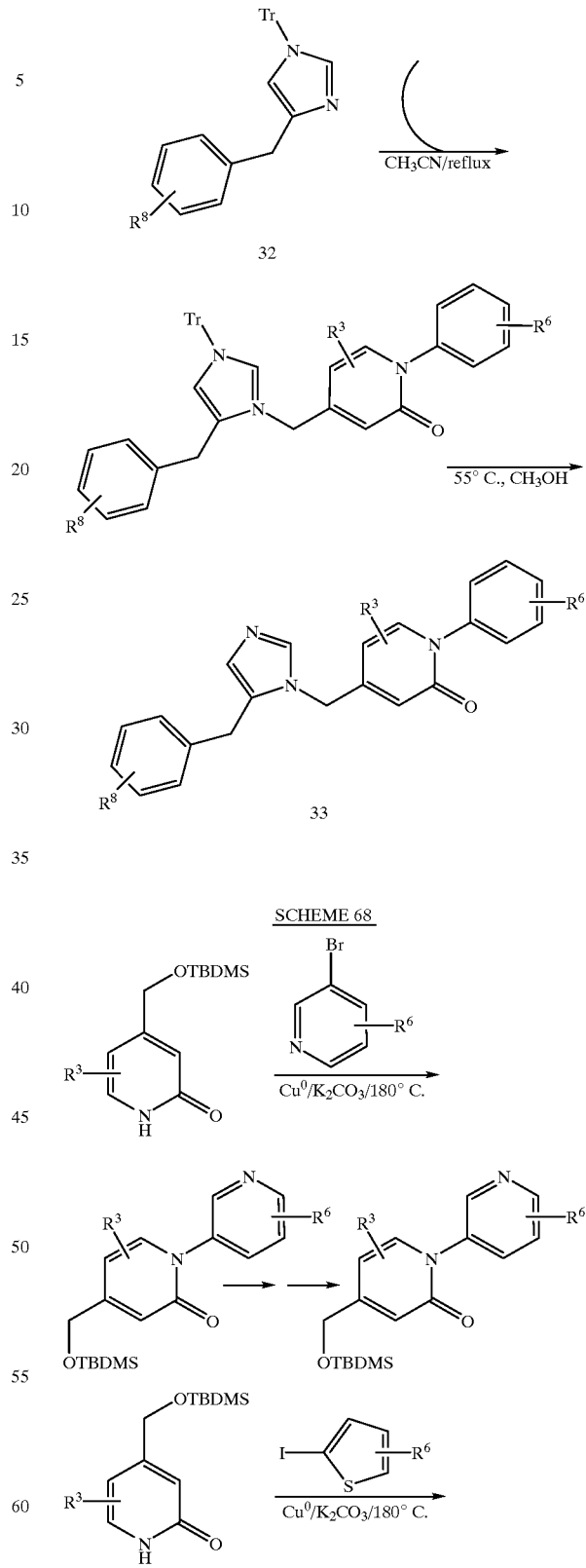

111
-continued
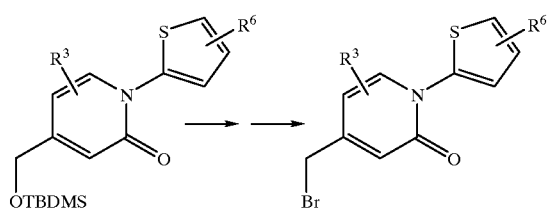
SCHEME 69
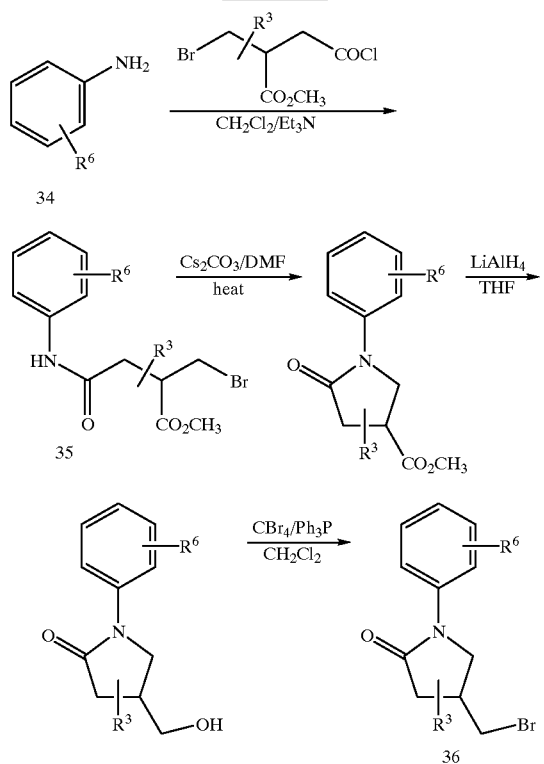
SCHEME 70
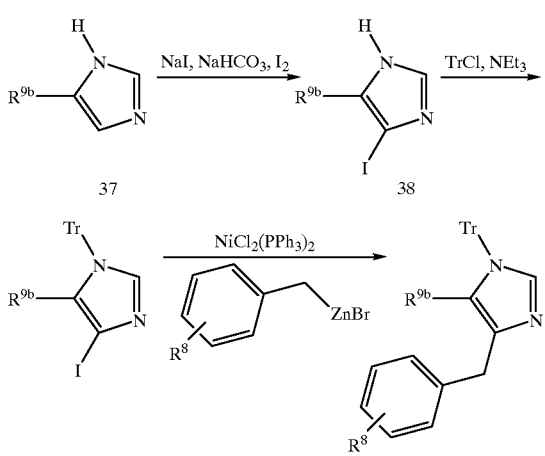
112
-continued
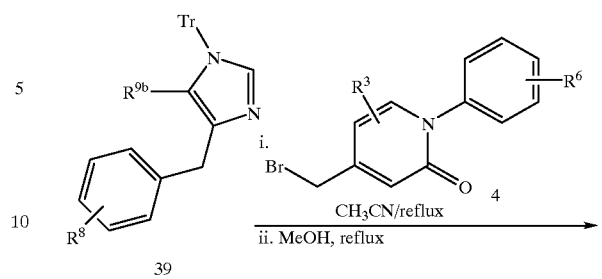
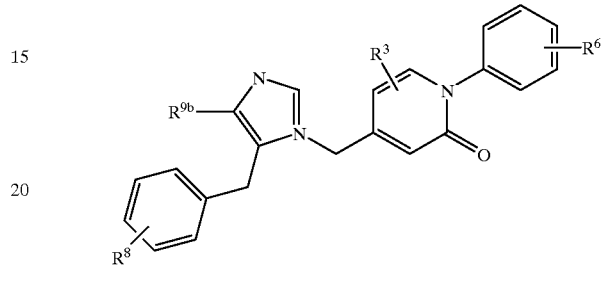
SCHEME 71
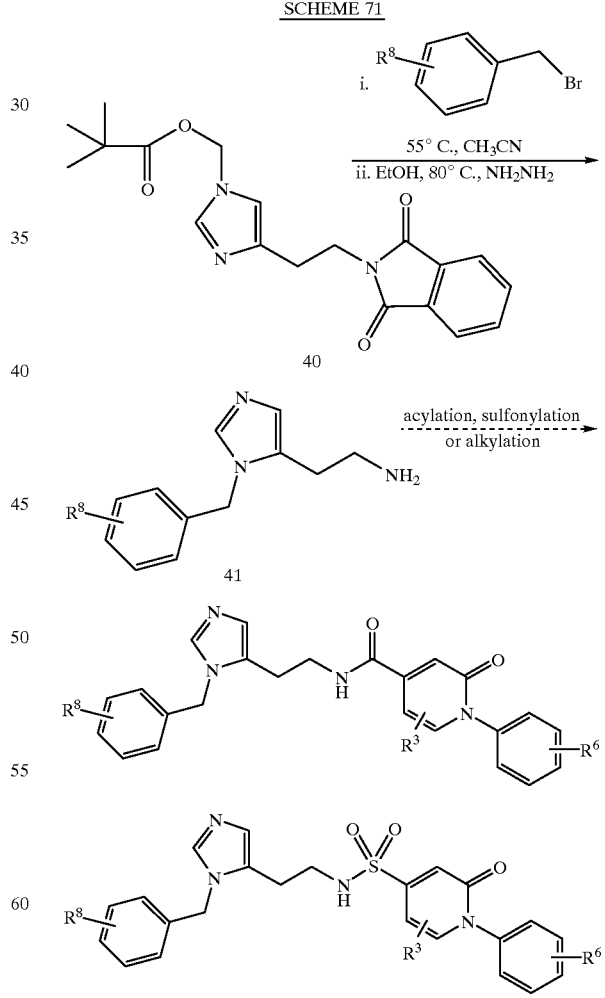

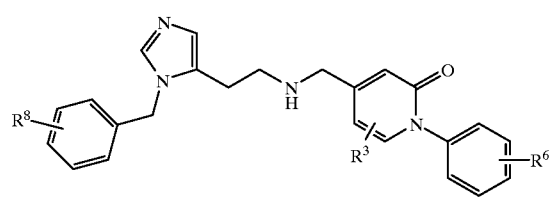
SCHEME 72
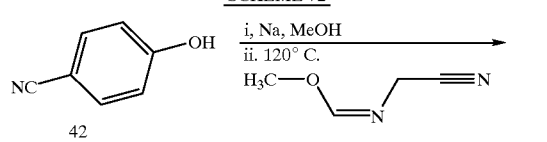
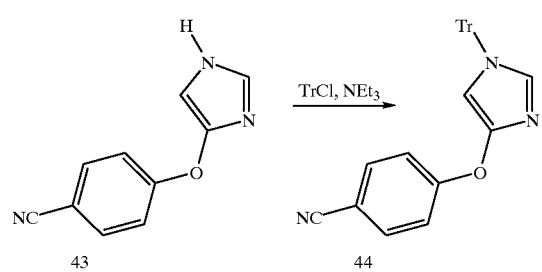
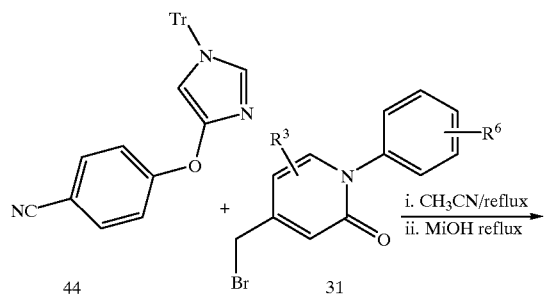
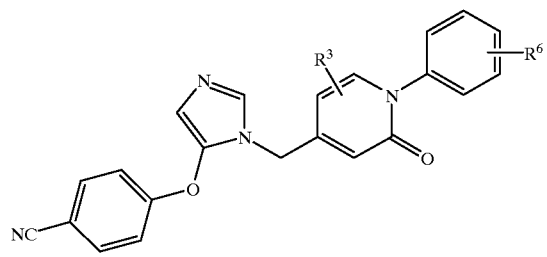
SCHEME 73
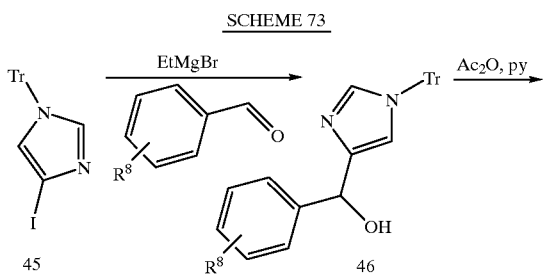
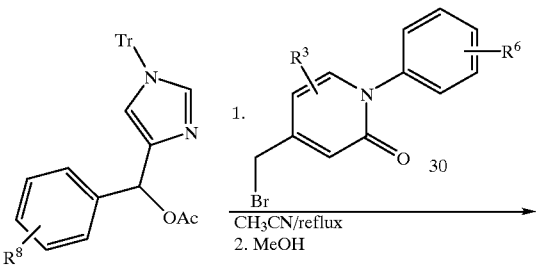
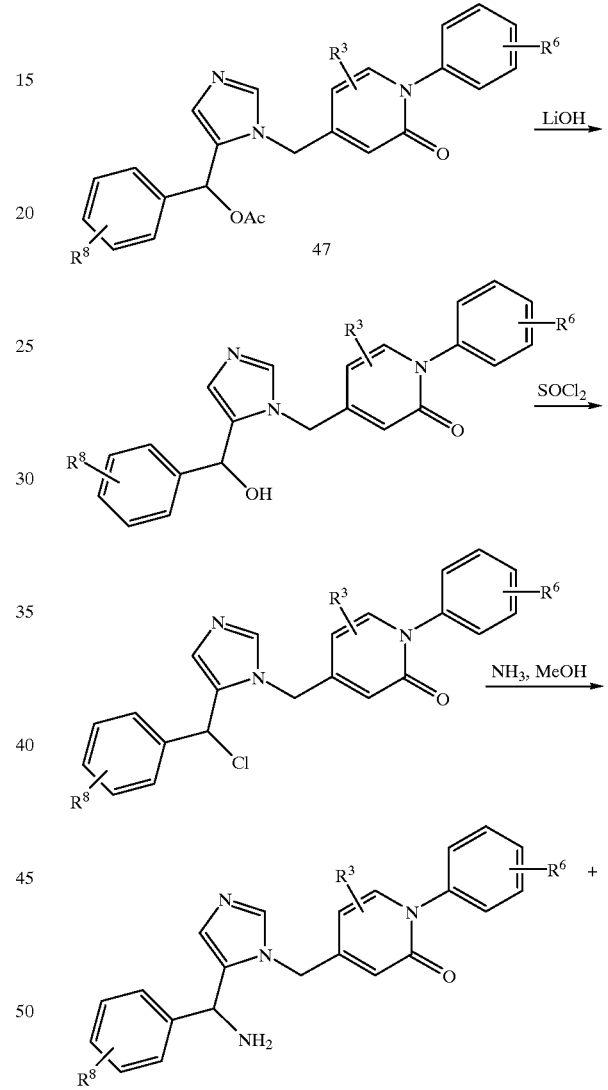
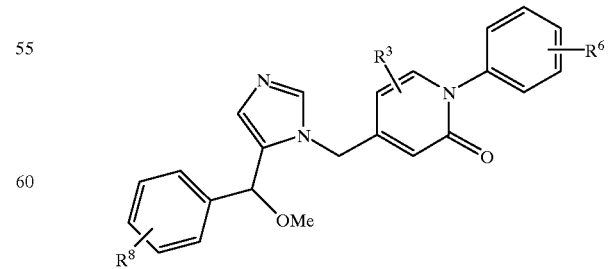

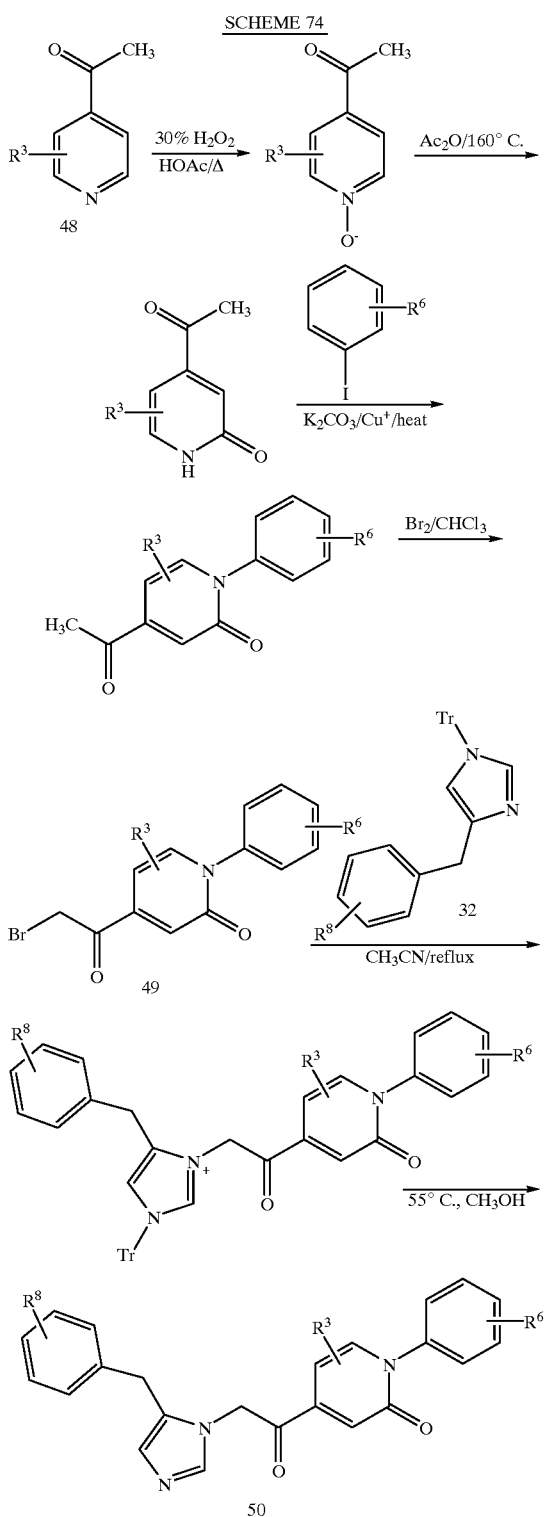

SCHEME 74 may be accomplished, for example, by selection of the appropriate halogenated benzyl precursor in Reaction Scheme R.

These reactions may be employed in a linear sequence to provide the compounds of the invention or they may be used to synthesize fragments which are subsequently joined by the alkylation reactions described in the Reaction Schemes.

Reaction Schemes A–P describe the preparation of appropriately substituted aniline intermediates that may be further functionalized by the methods described in Reaction Schemes Q–S to provide the compounds of the instant invention.

Reaction Schemes A–D illustrate use of Ullman reactions to provide diphenyl ethers, amines and sulfides from readily available fully substituted phenols/thiophenols/anilines and aryl halides. In such syntheses, the desired amine moiety is typically masked as a nitro group which is subsequently reduced by techniques well known in the art. An alternative synthesis of the diphenyl ethers which employs para-nitro fluorobenzene is shown in Reaction Scheme E.

Reaction Scheme F illustrates standard acid-amine coupling to provide the fully substituted N-phenylbenzamides. Reaction Scheme G illustrates formation of the aminomethyl spacer via a reductive amination of a suitably substituted benzaldehyde.

Reaction Scheme H illustrates coupling of suitably substituted anilines with readily available phenylsulfonyl chlorides. Access to aminobenzophenones is illustrated in Reaction Scheme I, which also illustrates the reduction of the carbonyl to provide the unsubstituted methyl spacer. An alternative method of forming the benzophenone intermediates is illustrated in Reaction Scheme J. Also shown in Reaction Scheme J is reductive amination of the resulting carbonyl to provide the amine substituted methyl spacer. Another method of forming the benzophenone intermediates, illustrated in Reaction Scheme K, is a Stille reaction with an aryl stannane.

Reaction Schemes L and M illustrate palladium mediated formation of olefin and acetylene spacer units. Reaction Scheme N illustrates formation of an appropriately substituted benzyl ether. Reaction Scheme P illustrates the use of the Claisen rearrangement to provide methyl spacers having substituents such as a vinyl group which can be further functionalized.

The farnesyl transferase inhibitors of formula (I-h) can be synthesized in accordance with Reaction Schemes A–S, in addition to other standard manipulations such as ester hydrolysis, cleavage of protecting groups, etc., as may be known in the literature or exemplified in the experimental procedures. Some key reactions utilized to form the amino-diphenyl moiety of the instant compounds are shown. Incorporation of a halogen precursor to a radionuclide moiety

REACTION SCHEME A

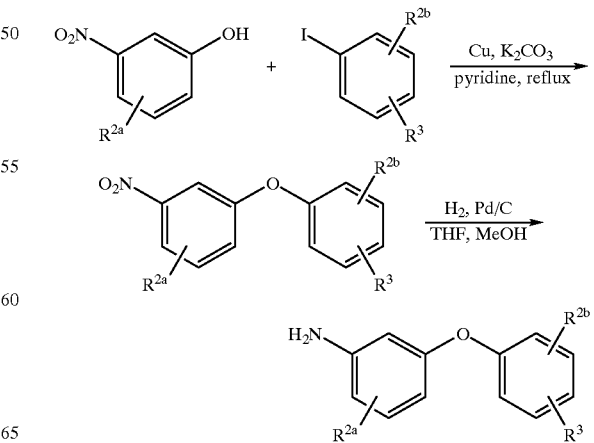

REACTION SCHEME B
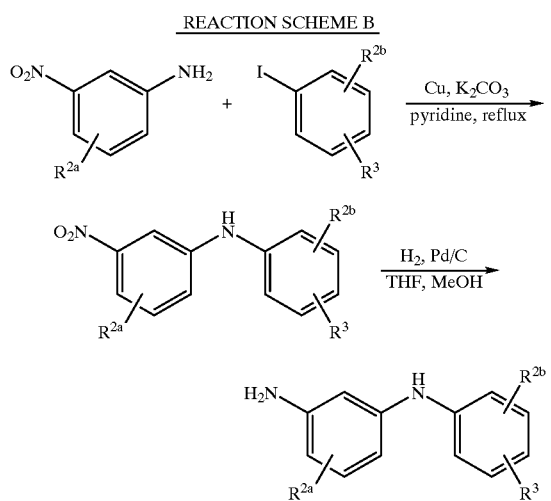
REACTION SCHEME E
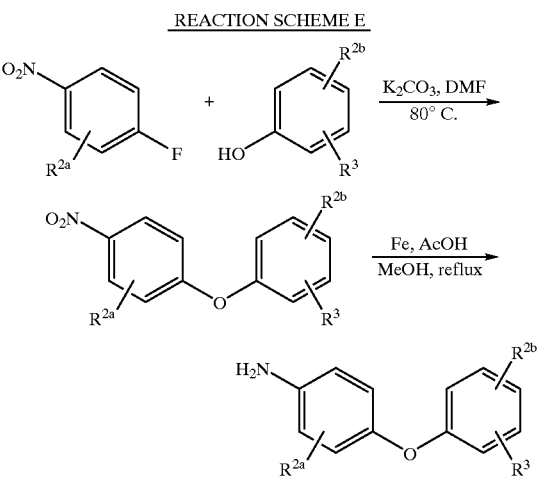
REACTION SCHEME C
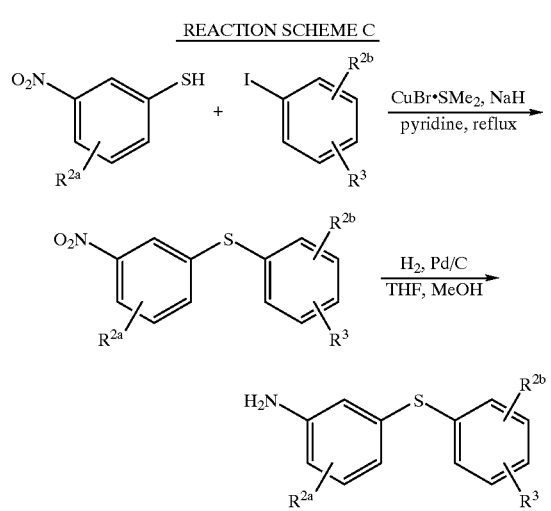
REACTION SCHEME F
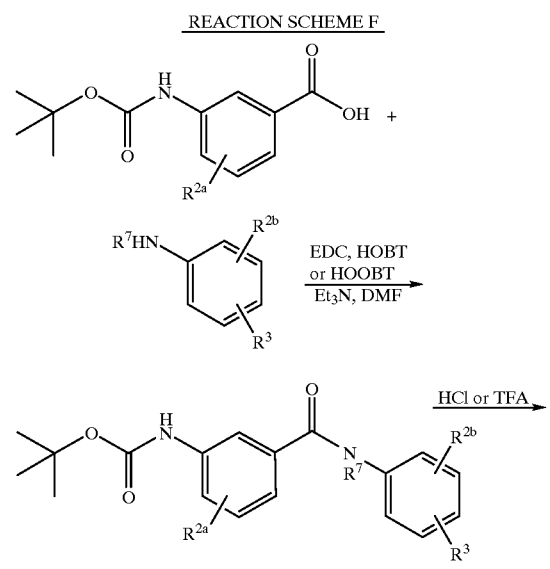
REACTION SCHEME D
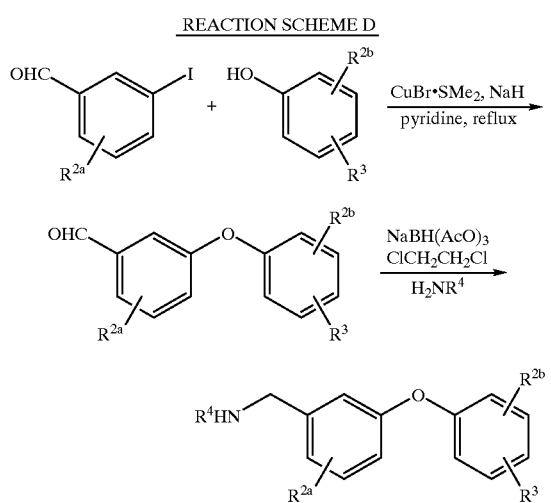
REACTION SCHEME G
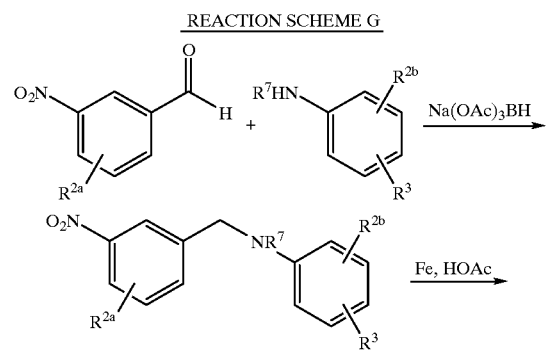

119
-continued
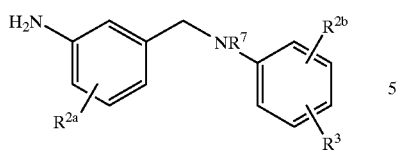
REACTION SCHEME H
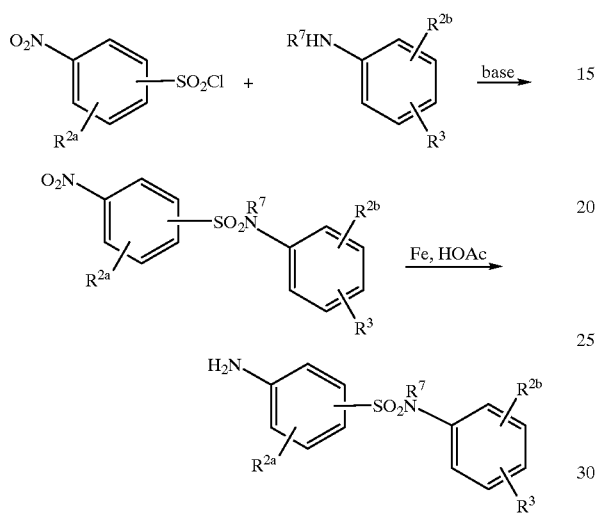
REACTION SCHEME I
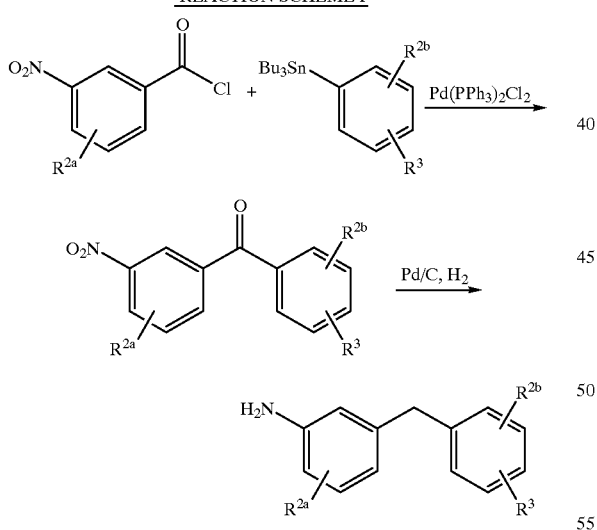
REACTION SCHEME J
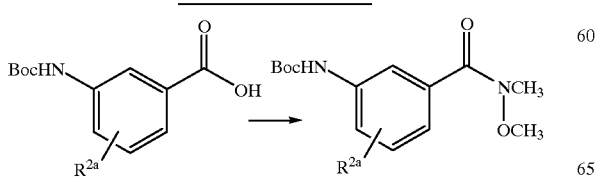
120
-continued
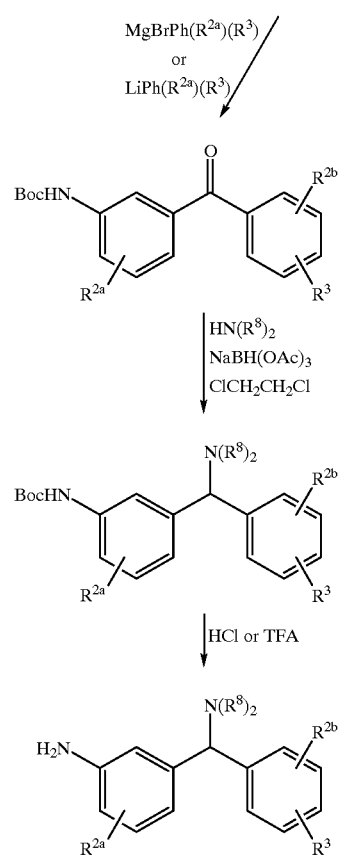
REACTION SCHEME K
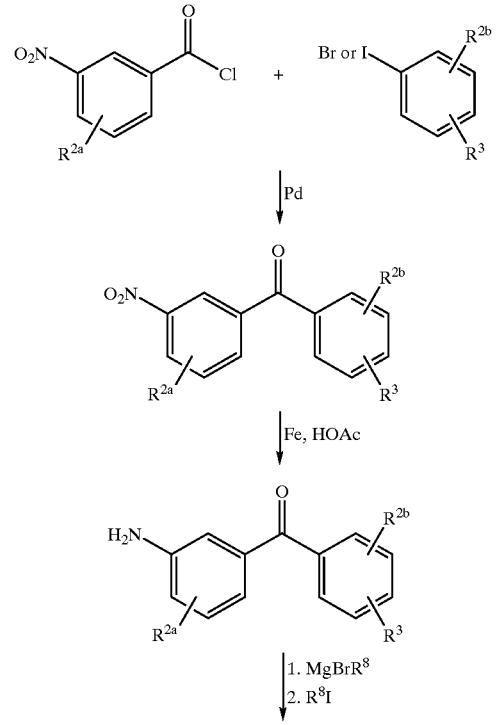

121
-continued
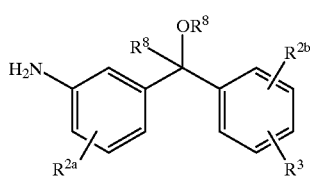
122
-continued
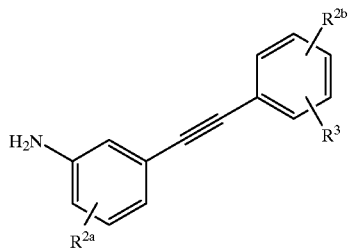
REACTION SCHEME L
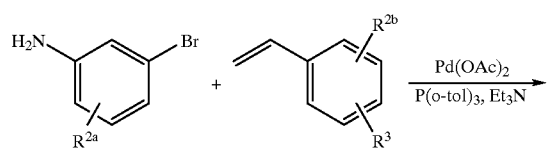
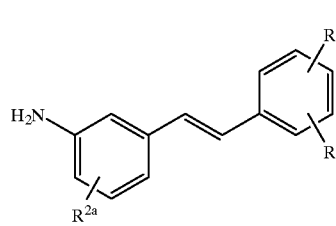
REACTION SCHEME M
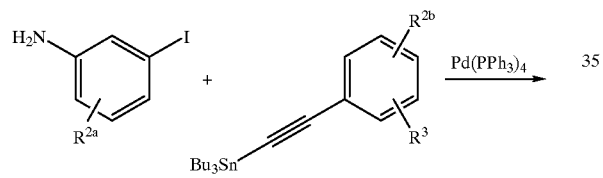
REACTION SCHEME N
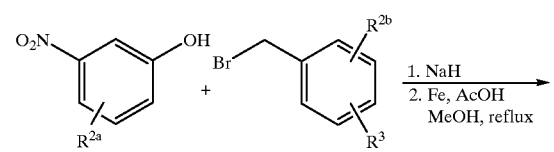
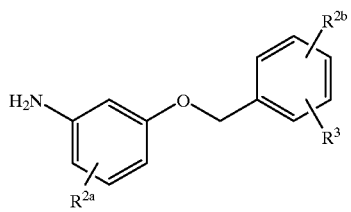
REACTION SCHEME P
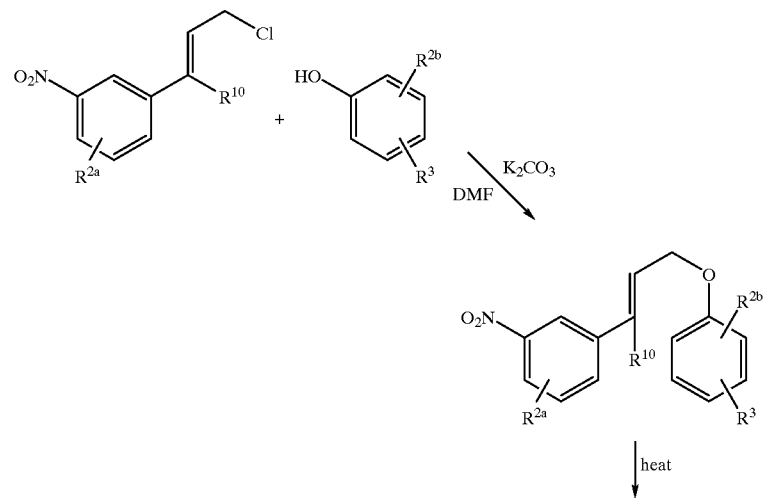

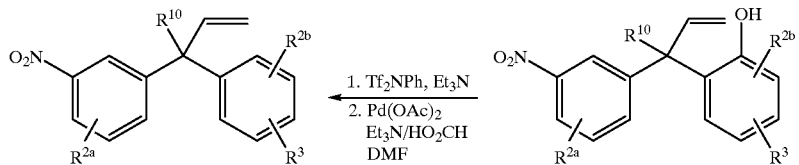

Reaction Schemes Q–S illustrate reactions wherein the non-sulfhydryl-containing moiety(ies) of the compounds of the instant invention is attached to the aminodiphenyl subunit to provide the instant compounds.

Thus, the aminodiphenyl subunit can be reductively alkylated with aldehydes such as 1-trityl-4-carboxaldehyde or 1-trityl-4-imidazolylacetaldehyde, to give products such as VIII (Reaction Scheme Q). The trityl protecting group can be removed from VIII to give IX, or alternatively, VIII can first be treated with an alkyl halide then subsequently deprotected to give the alkylated imidazole X. Alternatively, the aminomethylbenzamide subunit can be acylated or sulfonylated by standard techniques.

The imidazole acetic acid XI can be converted to the acetate XIII by standard procedures, and XIII can be first reacted with an alkyl halide, then treated with refluxing methanol to provide the regiospecifically alkylated imidazole acetic acid ester XIV. Hydrolysis and reaction with the aminodiphenyl subunit in the presence of condensing reagents such as 1-(3-dimethylaminopropyl)-3-ethylcarbodiimide (EDC) leads to acylated products such as XV. Coupling reactions with other suitably substituted aldehydes may be performed as illustrated in Schemes 3 and 6–9 hereinabove.

Reaction Scheme S illustrates a one pot synthesis of an instant compound wherein the N-terminus nitrogen is substituted with two different non-sulfhydryl-containing moieties. Thus, the aminodiphenyl subunit is treated with one equivalent of an appropriate aldehyde and, after the reductive adduct has been formed, the in situ intermediate is treated with an equivalent of a different aldehyde.

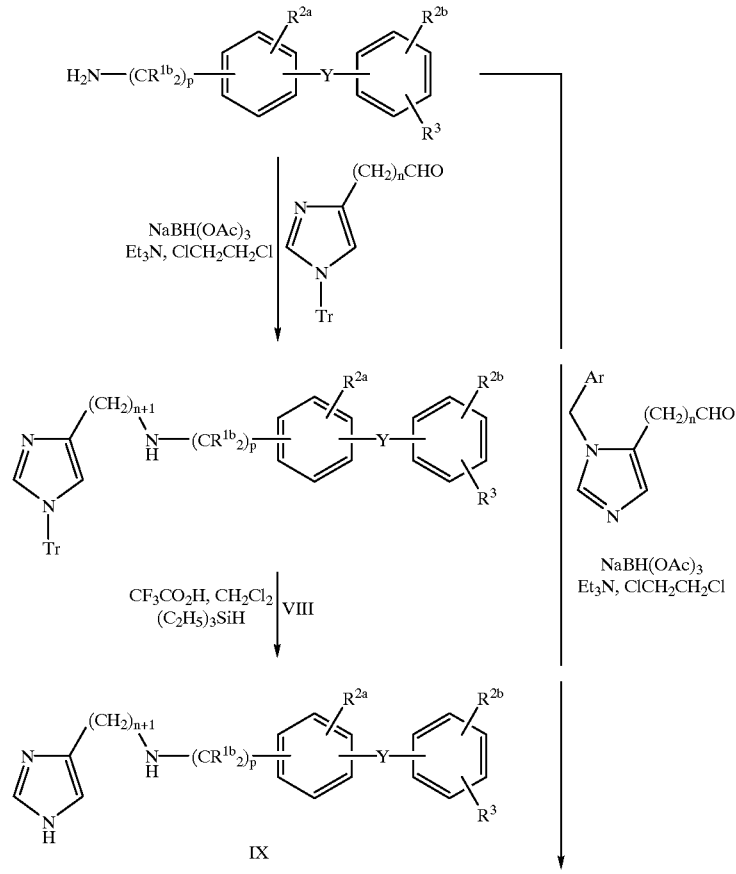

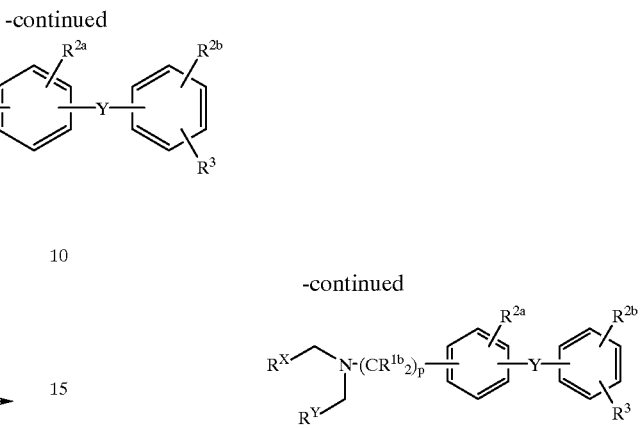

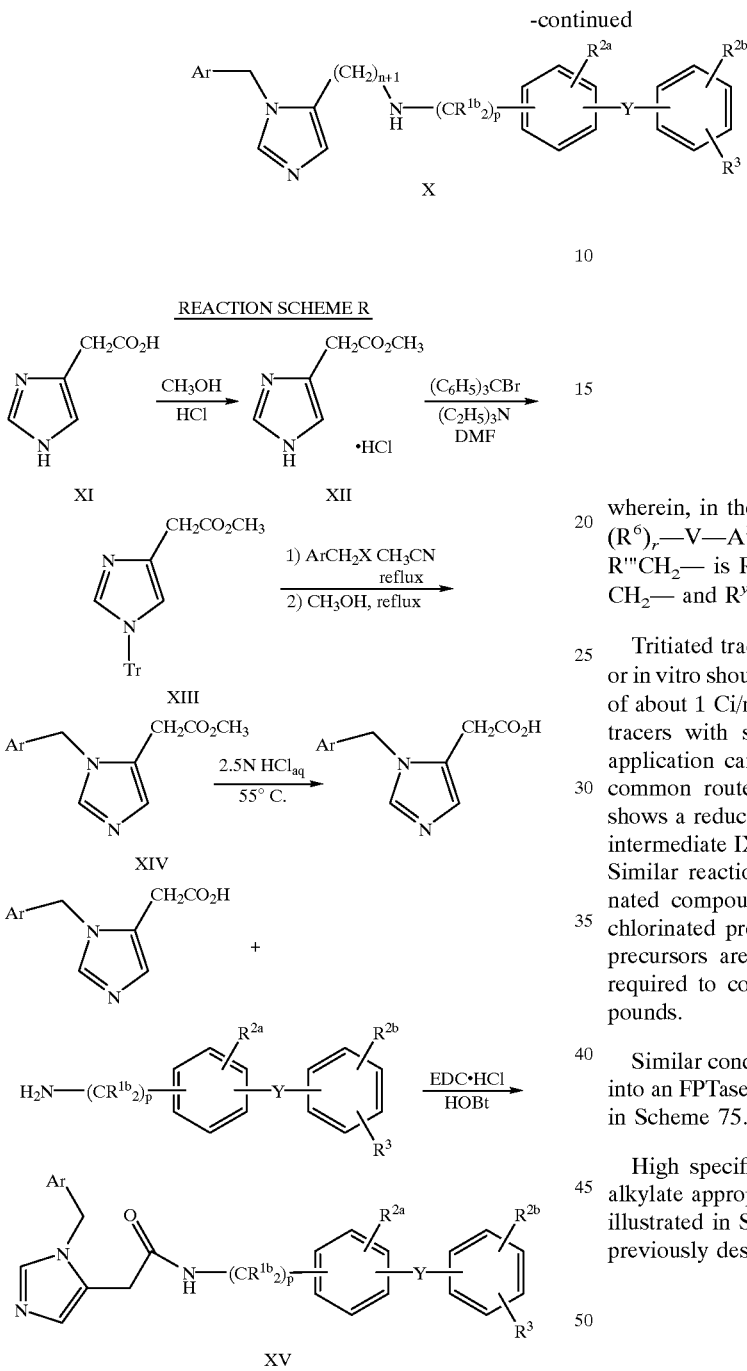

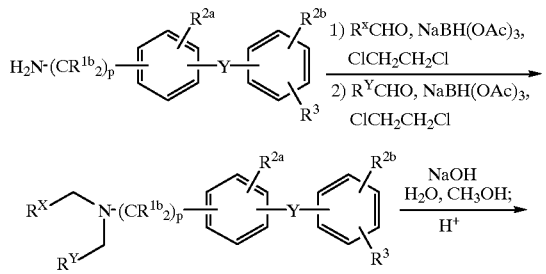

wherein, in the above Reaction Schemes, $R'$ is $R^{1a}$; $R''$ is $(R^6)_r$—V—$A^1$—$(CR^{1a})_n$—; $R'''$ is selected such that $R'''CH_2$— is $R^8$; and $R^x$ and $R^y$ are selected such that $R^x CH_2$— and $R^y CH_2$— are either $R^4$ or $R^5$.

Tritiated tracers for use in labeling FPTase either in vivo or in vitro should have specific activities that are on the order of about 1 Ci/mmol or above. Routes for preparing suitable tracers with sufficiently high specific activities for this application can be synthesized by several convenient and common routes which are illustrated below. Scheme 75 shows a reductive deiodination of the previously described intermediate IX-a (Scheme 1 hereinabove) with tritium gas. Similar reactions can be done with brominated or chlorinated compounds. Although this route can be used with chlorinated precursors, either the brominated or iodinated precursors are preferred because of the harsh conditions required to conduct the reaction on the chlorinated compounds.

Similar conditions can be used to incorporate two tritiums into an FPTase by reduction of a suitable olefin as illustrated in Scheme 75.

High specific activity [T]methyl iodide can be used to alkylate appropriate precursors such as phenols or thiols as illustrated in Schemes 76 and 77. Intermediate XVI-a was previously described in Scheme 3 hereinabove.

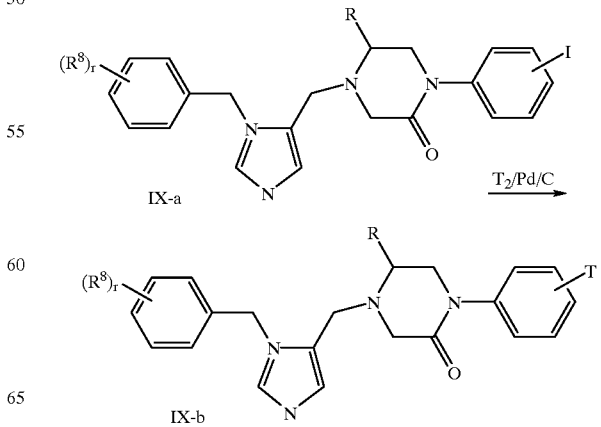

127
-continued
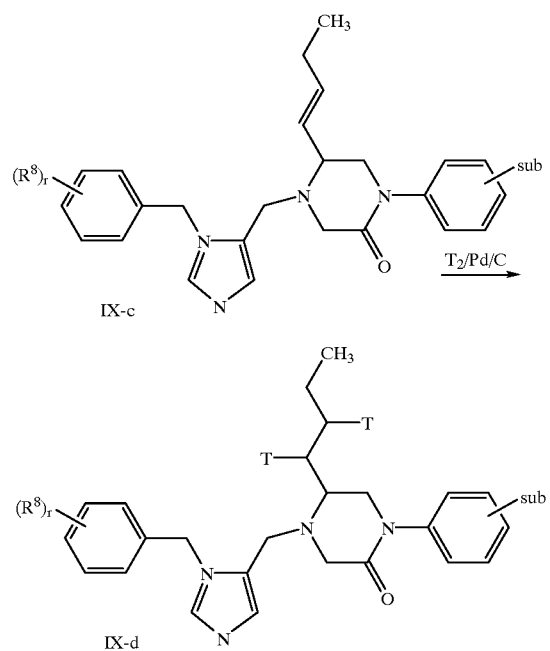
128
SCHEME 76
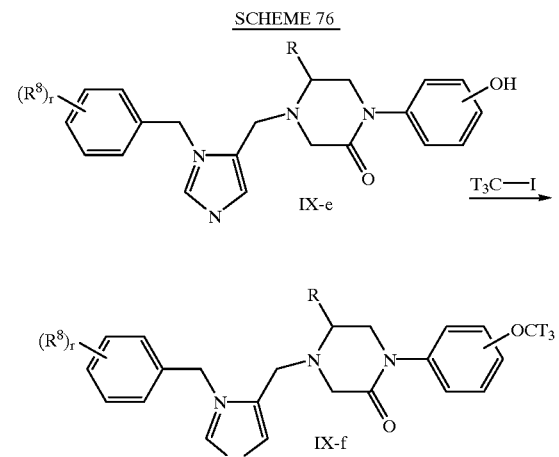
SCHEME 77
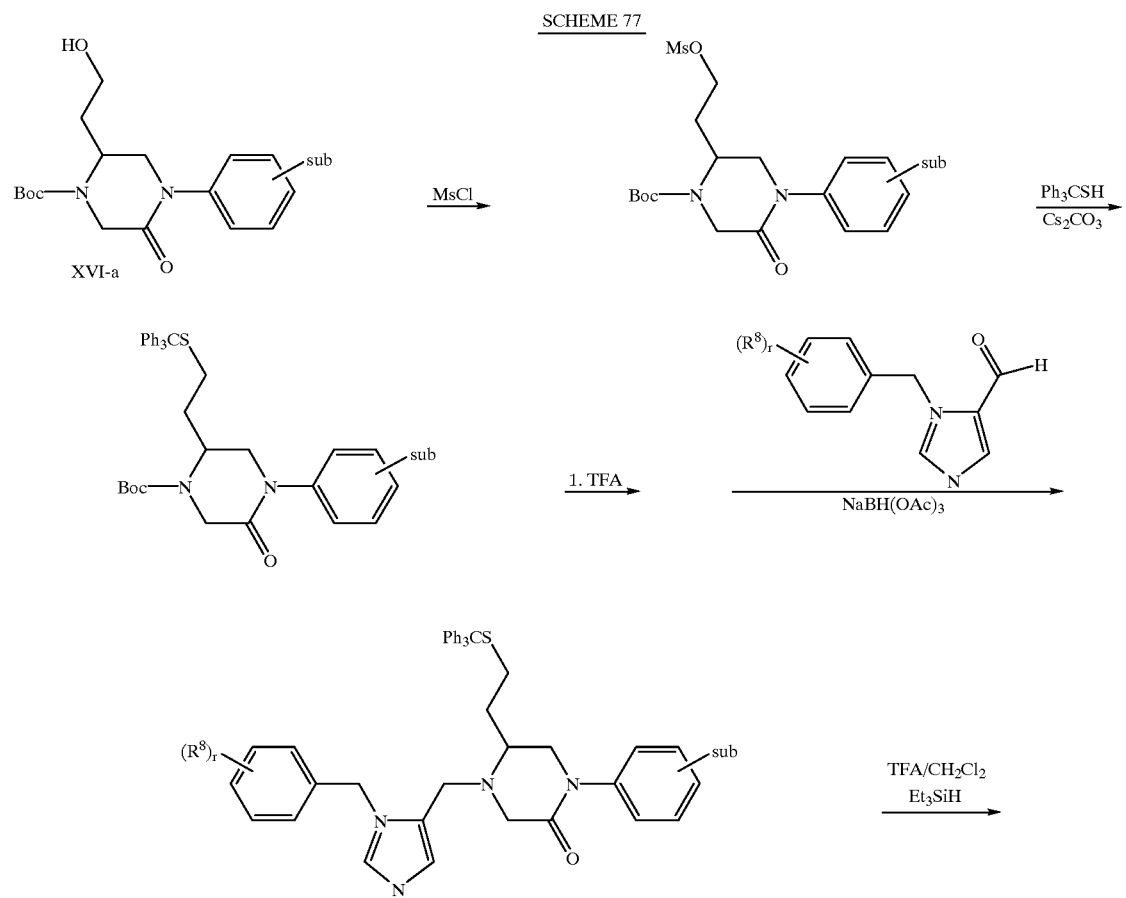

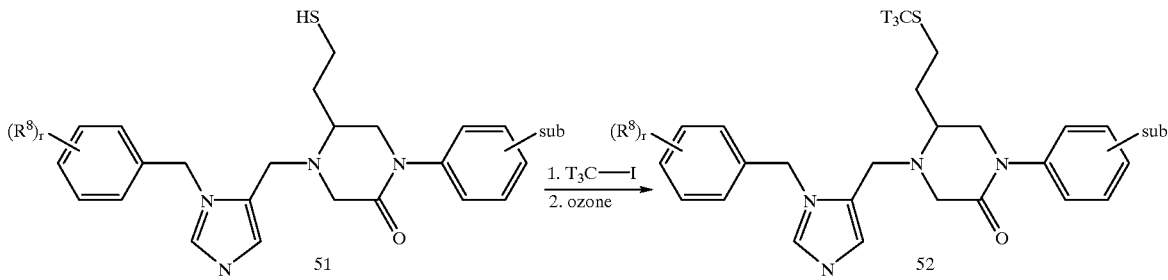

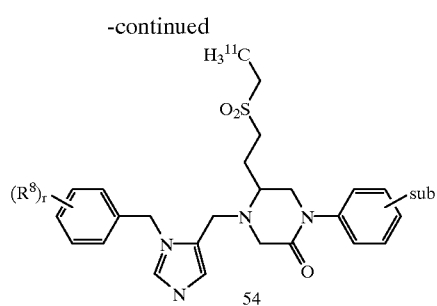

Scheme 78 illustrates incorporation of a $^{11}$C-methyl moiety into a piperazinone containing FPTase inhibitor. Thus, the previously described intermediate 51 is treated with $^{11}$C-methyl iodide, followed by ozonolysis to provide the radiolabeled compound analogous to compound 52 above. Synthesis of the homologous compound 54 is illustrated in Scheme 79.

Incorporation of a $^{11}$C-methoxy moiety is illustrated in Scheme 80.

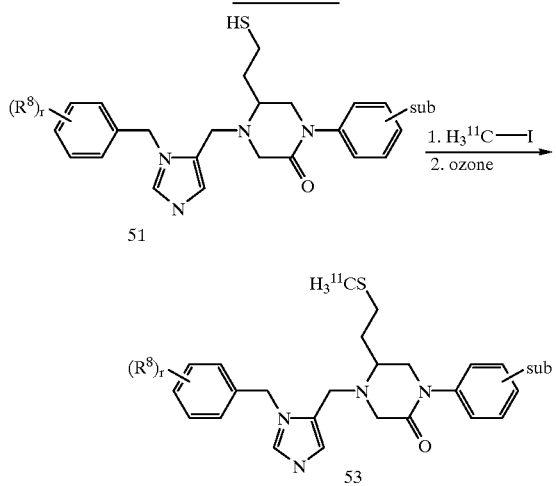

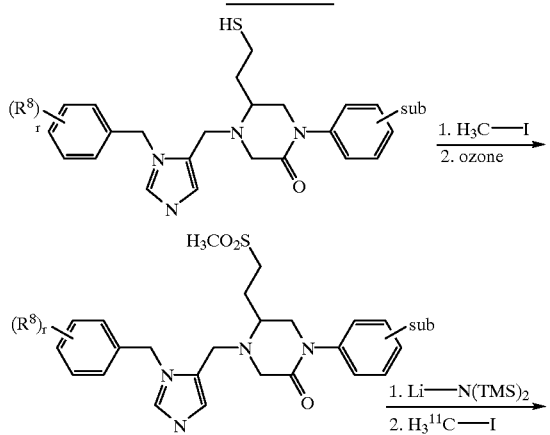

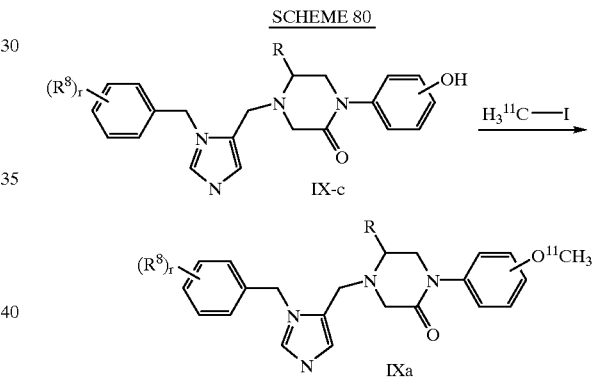

Synthesis of an $^{123}$I or $^{125}$I radiolabeled compound of the instant invention from the intermediates described hereinabove may be carried out by methods known in the art or described in the following Schemes. Thus as shown in Scheme 81, 127 in a compound such as IX-a may be exchanged with $^{123}$I or $^{125}$I by heating IX-a at 150°–200° C., preferably 180°–190° C., with a sodium hydroxide solution of Na$^{123}$I (or Na$^{125}$I) in the presence of cupric sulfate and ammonium sulfate under a stream of air for 0.5 to 10 hours, preferably 2 hours, to give the desired radiolabeled piperazinone IX-g bearing $^{123}$I or $^{125}$I in low specific activity (30–400 Ci/mmol).

Alternatively, $^{123}$I or $^{125}$I may be exchanged for $^{80}$Br under the same conditions to provide the piperazinone IX-g bearing $^{123}$I or $^{125}$I in high specific activity (approximately 2,000 Ci/mmol).

Another route to such a compound of the instant invention involves radioiododestannylation of an appropriate trialkyl tin derivative with Na$^{123}$I (or Na$^{125}$I) as illustrated in Scheme 82. Thus, the piperazinone 55 (prepared by reacting the previously described intermediate IX-a with hexamethylditin) is reacted with a sodium hydroxide solution of $Na^{123}I$ (or $Na^{125}I$) in the presence of TFA and either chloramine-T or an Iodobead at 100°–150° C., preferably about 130° C., for about 15 mins. to 5 hours, preferably 1 hour, to give the desired piperazinone bearing 123I or $^{125}I$ in high specific activity (approximately 2,000 Ci/mmol).

It is noted that salts of other radiohalogens (such as $Na^{122}I$, $Na^{131}I$, $Na^{75}Br$, $Na^{76}Br$, $Na^{77}Br$, $Na^{82}Br$ and $Na^{211}At$) may be utilized to prepare appropriately labeled inhibitor compounds.

The synthesis of an $^{18}F$ labeled farnesyl-protein transferase inhibitor is illustrated in Scheme 83. Thus the previously described intermediate XVI-a is selectively protected and deprotected to provide the piperazinone, which is then reductively alkylated with the preferred benzyl imidazolyl sidechain. The alcohol is subsequently deprotected, mesylated and reacted with $[^{18}F]$-tetrabutylammonium fluoride to provide the radiolabeled inhibitor compound 56.

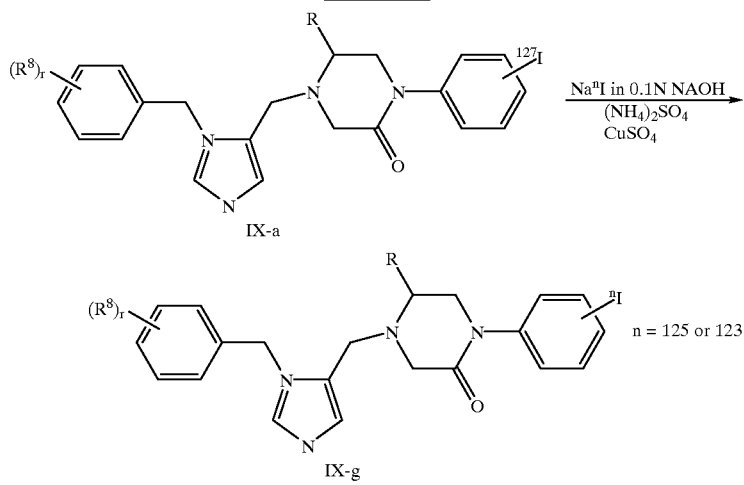

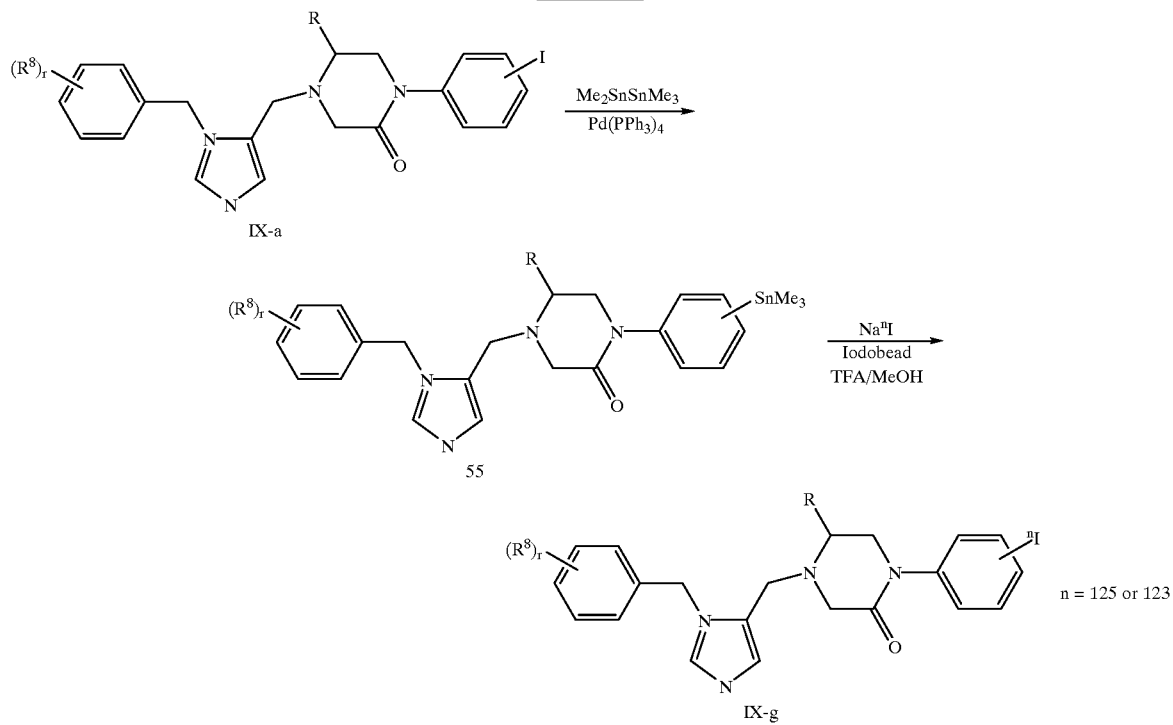

SCHEME 83

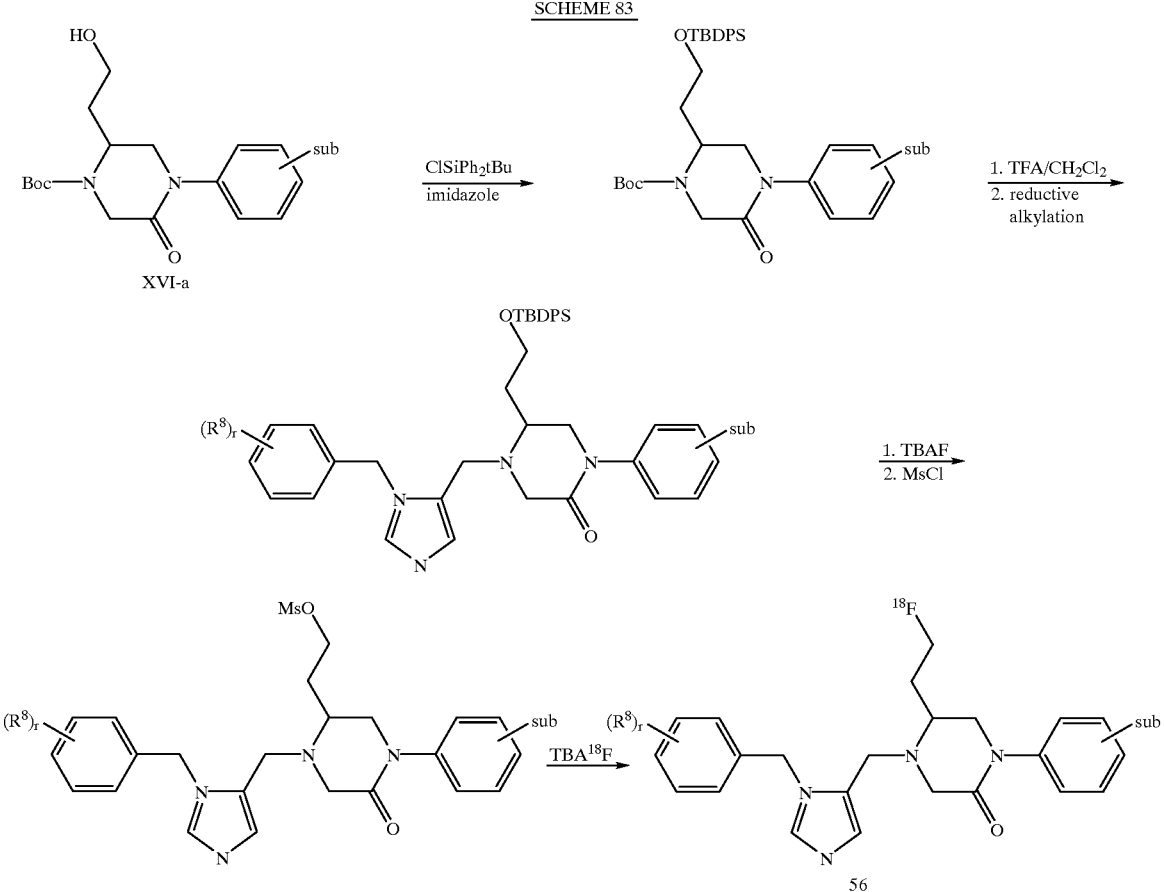

EXAMPLES

Examples provided are intended to assist in a further understanding of the invention. Particular materials employed, species and conditions are intended to be further illustrative of the invention and not limitative of the reasonable scope thereof.

EXAMPLE 1

Preparation of (S)-1-(3-iodo-5-fluoromethylphenyl)-4-[1-(4-cyanobenzyl)-5-imidazolylmethyl]-5-[2-(methanesulfonyl)ethyl]-2-piperazinone dihydrochloride (Compound 1)

Step A: 3-Amino-5-nitrobenzyl alcohol

A three neck flask fitted with a reflux condenser and an addition funnel was charged with 3,5-dinitrobenzyl alcohol (10 g, 50 mmol), 10% Pd/C (630 mg) and triethylamine (35 mL, 251 mmol). This was placed in a 70° C. oil bath and through the addition funnel was added 90% formic acid (10 mL, 234 mmol) dropwise. The reaction was heated for 30 minutes and cooled to room temperature. The clear yellow supernatant was filtered through celite and the lower layer containing the catalyst was treated with acetone, filtered through celite and rinsed with acetone. The filtered organic layers were combined and concentrated to give an orange oil. The oil was diluted in ethyl acetate which was washed with $H_2O$, dried ($MgSO_4$), filtered and concentrated to give crude 3-amino-5-nitrobenzyl alcohol as an orange solid.

Step B: 3-Iodo-5-nitrobenzyl alcohol

A mixture of crude 3-amino-5-nitrobenzyl alcohol (8.8 g, 52.3 mmol) described in Step A, in $H_2O$ (140 mL) was cooled to 0° C. and treated with $H_2SO_4$ (31.2 mL) followed by an aqueous solution of $NaNO_2$ (3.9 g, 56.5 mmol in 55 mL $H_2O$) added over approximately 10 minutes. After stirring this mixture for 35 minutes at 0° C., an aqueous solution of KI (7.6 g, 65.5 mmol in 55 mL of $H_2O$) was added via pipette over approximately 10 minutes. The resulting mixture was placed in a 60° C. oil bath and heated for 1.5 hours. HPLC analysis [$C_{18}$ μBondapak, 3.9×300 mm, 50:50 AcCN:$H_2O$ (0.1% TFA)@ 1 mL/min, 254 nm] showed the desired product at 6.5 minutes. The reaction was cooled to room temperature, placed in a separatory funnel and extracted with ethyl acetate. The organic layer was dried ($MgSO_4$), filtered and concentrated to give a purple oil. By TLC, the desired product has $R_f$=0.45 (3:1 hexane:ethyl acetate). Purification by flash chromatography (hexane, 10:1 hexane:ethyl acetate, 5:1 hexane:ethyl acetate) gave the 3-iodo-5-nitrobenzyl alcohol as a yellow solid: mp 85.5–86.5° C. NMR 14554-342-1

Step C: 3-Iodo-5-nitrobenzyl fluoride

A solution of 3-iodo-5-nitrobenzyl alcohol (7.2 g, 25.8 mmol) described in Step B, in $CH_2Cl_2$ (325 mL) was cooled to 0° C. and treated with $iPr_2NEt$ (6.57 mL, 37.7 mmol) and methane sulfonyl chloride (2.19 mL, 28.2 mmol). After stirring for 1.5 hours at 0° C, the reaction was poured into a separatory funnel containing aqueous 5% citric acid. The layers were separated and the aqueous layer was extracted with $CH_2Cl_2$. The organic layers were combined and dried ($MgSO_4$), filtered and concentrated to give an orange oil. This material was dissolved in acetonitrile (325 mL), cooled to 0° C. and treated with tetrabutylammonium fluoride (47 mL, 1 M in THF, 47 mmol) via an addition funnel over about 10 minutes giving a dark blue-green mixture. This was stirred overnight as the reaction warmed to room temperature. TLC analysis (1:1 hexane:ethyl acetate) showed the desired product ($R_f$=0.56). The reaction was diluted with $H_2O$, concentrated and then extracted with ethyl acetate. The ethyl acetate was dried ($MgSO_4$), filtered and concentrated to give a dark brown oil. This material was dissolved in methanol, treated with 7 g of silica gel, concentrated to a free flowing powder and purified by flash chromatography (hexane then 10:1 hexane:ethyl acetate) to give 3-iodo-5-nitrobenzyl fluoride as a tan solid: mp 50.5–51.5° C.

Step D: 3-Amino-5-ioodobenzyl fluoride

A solution of 3-iodo-5-nitrobenzyl fluoride (9.2 g, 32.7 mmol) described in Step C, in methanol (311 mL) was treated with $TiCl_3$ (311 mL, >10 wt. % in 20–30 wt % HCl) and stirred at room temperature for 20 minutes. The reaction was poured into a separatory funnel containing 95:5 $CH_2Cl_2$:MeOH and the aqueous layer was made basic with 15% aq. NaOH. The layers were separated and the aqueous layer was extracted with 95:5 $CH_2Cl_2$:MeOH. The organic layers were combined, dried ($MgSO_4$), filtered and concentrated to give an orange semi-solid. Purification by flash chromatography (3:1 to 1:1 hexane:methylene chloride) provided 3-amino-5-iodobenzyl fluoride as a tan solid: mp 48.5–50° C.

Step E: (S)-N-(tert-butoxycarbonyl)homoserine lactone

To a solution of (S)-homoserine lactone hydrochloride (11.0 g, 79.9 mmol) and di-tert-butylpyrocarbonate (19.2 g, 88.0 mmol) in 160 mL of dichloromethane at 0° C. was added diisopropyl-ethylamine (13.9 mL, 79.9 mmol) over 3 min. The solution was allowed to warm to room temperature. After 3 hours, another portion of di-tert-butylpyrocarbonate (1.75 g, 8.0 mmol) and diisopropylethylamine (0.70 mL, 4.0 mmol) were added, and the mixture was stirred for an additional 2.5 hours. The solution was washed with 10% citric acid, sat. $NaHCO_3$, and brine, dried ($Na_2SO_4$), filtered, and concentrated in vacuo. The resulting material was purified by silica gel chromatography (50% EtOAc/hexane) to provide pure titled compound.

Step F: (S)-N-(tert-butoxycarbonyl)homoserine lactol

To a solution of the lactone from Step E (7.0 g, 35 mmol) in 175 mL of THF at –78° C. was added diisobutylaluminum hydride (72.0 mL, 1M in THF, 72 mmol) dropwise, while maintaining the reaction temperature below –72° C. After 3 hours, another portion of diisobutylaluminum hydride (10.0 mL, 10 mmol) was added, followed by another after 1 hour (20.0 mL, 20 mmol). After an additional hour, the reaction was quenched with EtOAc at –78° C., followed by sat. Na—K-tartrate soln., then warmed to room temperature. The solution was poured into EtOAc, washed with brine, dried ($Na_2SO_4$), filtered, and concentrated in vacuo. The resulting material was purified by silica gel chromatography (50% EtOAc/hexane) to give the titled lactol.

Step G: (S)-1-N-(3-Fluoromethyl-5-iodophenyl)-2-N-t-butoxycarbonyl-1,2-diamino-4-butanol A solution of 3-amino-5-iodobenzyl fluoride from Step D (997 mg, 3.97 mmol) and aminolactol described in Step F (882 mg, 4.34 mmol) in 1,2-dichloroethane (10.4 mL) at room temperature was treated with acetic acid (0.23 mL), stirred for 10 minutes, and then was treated with NaBH(OAc)$_3$ (1.15 g, 5.43 mmol). After stirring at room temperature for 2.75 hours, the reaction was poured into a separatory funnel containing $CH_2Cl_2$, washed with aq. sat'd $NaHCO_3$. The organic layer was dried ($MgSO_4$), filtered and concentrated to give 1.71 g of a yellow foam. TLC analysis (3:1 hexane:ethyl acetate) showed unreacted benzyl fluoride (Re.27) along with an unknown spot ($R_f$=0.17) and the desired product ($R_f$=0.05). Purification by radial chromatography (10:1 to 1:2 hexane:ethyl acetate) gave the title benzyl diamine.

Step H: (S)-1-(3-Fluoromethyl-5-iodophenyl)-4-(t-butoxycarbonyl)-5-hydroxyethyl-2-piperazinone A mixture of the diamine described in Step G (630 mg, 1.44 mmol) in ethyl acetate (9.6 mL) and aq. sat'd $NaHCO_3$ (9.6 mL) was cooled to 0° C. and treated with chloroacetyl chloride (0.126 mL, 1.58 mmol). After stirring for 2.25 hours at 0° C., the reaction was diluted with ethyl acetate/$H_2O$. The layers were separated and the aqueous layer was extracted with ethyl acetate. The organic layers were combined, dried ($MgSO_4$), filtered and concentrated to give a foam. This material was dissolved in DMF (13 mL), cooled to 0° C. and treated with $Cs_2CO_3$ (3.1 g, 9.51 mmol). After stirring for 2.25 hours at 0° C., the reaction was diluted with ethyl acetate/brine/aq. sat'd $NH_4Cl$. The layers were separated and extracted with ethyl acetate. The organic layers were combined, washed with brine, dried ($MgSO_4$), filtered and concentrated to give a yellow oil.

TLC analysis (1:1 hexane:ethyl acetate) showed the main spot with $R_f$=0.12. Purification by radial chromatography (1:1 to 1:2 hexane:ethyl acetate) gave the title hydroxyethyl piperazinone as a yellow oil.

Step I: (S)-1-(3-Fluoromethyl-5-iodophenyl)-4-(t-butoxycarbonyl)-5-[(methanesulfonyl)ethyl]-2-piperazinone A solution of hydroxyethyl piperazinone described in Step H (52 mg, 0.11 mmol) in $CH_2Cl_2$ (1 mL) was cooled to 0° C. and treated with N,N-diisopropylethylamine (0.038 mL, 0.22 mmol) and methanesulfonyl chloride (0.012 mL, 0.15 mmol). After being stirred for 1.25 hours at 0° C., the reaction was poured into a separatory funnel containing 5% citric acid and the layers were separated. The aqueous layer was extracted with $CH_2Cl_2$, dried ($MgSO_4$), filtered and concentrated to give 66.4 mg of a white foam. The $^1$H NMR (CDCl$_3$) showed the mesylate singlet at d3.01. The mesylate was dissolved in DMF (1.5 mL), cooled to 0° C. and treated with sodium thiomethoxide (15.4 mg, 0.22 mmol) to give a clear magenta solution. The reaction was stirred for 30 minutes at 0° C., stored overnight in the freezer and stirred an additional hour at 0° C. The reaction was poured into a separatory funnel containing ethyl acetate and washed with aq. sat'd $NaHCO_3$ and brine. The organic layer was dried ($MgSO_4$), filtered and concentrated to give 59.5 mg of an orange oil. The $^1$H NMR (CDCl$_3$) showed the methyl singlet at d2.12. The methyl sulfide was dissolved in methanol (1 mL) at room temperature and treated with monoperoxyphthalic acid, magnesium salt (163 mg, 0.33 mmol) in methanol (1.5 mL) and stirred at room temperature for 1.75 hours. The reaction was quenched with 2N $Na_2S_2O_3$, poured into a separatory funnel containing ethyl acetate/aq. sat'd $NaHCO_3$ and the layers were separated. The organic layer was washed with brine, dried ($MgSO_4$), filtered and concentrated to give the crude product. TLC analysis (2:1 ethyl acetate:hexane) showed one main spot at $R_f$=0.25. Purification by radial chromatography (1:1 hexane:ethyl acetate) gave the title methyl sulfone as an oil.

Step J: Preparation of 1-triphenylmethyl-4-(hydroxymethyl)-imidazole

To a solution of 4-(hydroxymethyl)imidazole hydrochloride (35.0 g, 260 mmol) in 250 mL of dry DMF at room temperature was added triethylamine (90.6 mL, 650 mmol). A white solid precipitated from the solution. Chlorotriphenylmethane (76.1 g, 273 mmol) in 500 mL of DMF was added dropwise. The reaction mixture was stirred for 20 hours, poured over ice, filtered, and washed with ice water. The resulting product was slurried with cold dioxane, filtered, and dried in vacuo to provide the titled product as a white solid which was sufficiently pure for use in the next step.

Step K: Preparation of 1-triphenylmethyl-4-(acetoxymethyl)-imidazole

Alcohol described in Step J (260 mmol, prepared above) was suspended in 500 mL of pyridine. Acetic anhydride (74 mL, 780 mmol) was added dropwise, and the reaction was stirred for 48 hours during which it became homogeneous. The solution was poured into 2 L of EtOAc, washed with water (3×1 L), 5% aq. HCl soln. (2×1 L), sat. aq. NaHCO$_3$, and brine, then dried (Na$_2$SO$_4$), filtered, and concentrated in vacuo to provide the crude product. The acetate was isolated as a white powder which was sufficiently pure for use in the next reaction.

Step L: Preparation of 1-(4-cyanobenzyl)-5-(acetoxymethyl)-imidazole hydrobromide A solution of the product described in Step K (85.8 g, 225 mmol) and α-bromo-p-tolunitrile (50.1 g, 232 mmol) in 500 mL of EtOAc was stirred at 60° C. for 20 hours, during which a pale yellow precipitate formed. The reaction was cooled to room temperature and filtered to provide the solid imidazolium bromide salt. The filtrate was concentrated in vacuo to a volume 200 mL, reheated at 60° C. for two hours, cooled to room temperature, and filtered again. The filtrate was concentrated in vacuo to a volume 100 mL, reheated at 60° C. for another two hours, cooled to room temperature, and concentrated in vacuo to provide a pale yellow solid. All of the solid material was combined, dissolved in 500 mL of methanol, and warmed to 60° C. After two hours, the solution was reconcentrated in vacuo to provide a white solid which was triturated with hexane to remove soluble materials. Removal of residual solvents in vacuo provided the titled product hydrobromide as a white solid which was used in the next step without further purification.

Step M: Preparation of 1-(4-cyanobenzyl)-5-(hydroxymethyl)-imidazole

To a solution of the acetate described in Step L (50.4 g, 150 mmol) in 1.5 L of 3:1 THF/water at 0° C. was added lithium hydroxide monohydrate (18.9 g, 450 mmol). After one hour, the reaction was concentrated in vacuo, diluted with EtOAc (3 L), and washed with water, sat. aq. NaHCO$_3$ and brine. The solution was then dried (Na$_2$SO$_4$), filtered, and concentrated in vacuo to provide the crude product as a pale yellow fluffy solid which was sufficiently pure for use in the next step without further purification.

Step N: Preparation of 1-(4-cyanobenzyl)-5-imidazolecarboxaldehyde

To a solution of the alcohol described in Step M (21.5 g, 101 mmol) in 500 mL of DMSO at room temperature was added triethylamine (56 mL, 402 mmol), then SO$_3$-pyridine complex (40.5 g, 254 mmol). After 45 minutes, the reaction was poured into 2.5 L of EtOAc, washed with water (4×1 L) and brine, dried (Na$_2$SO$_4$), filtered, and concentrated in vacuo to provide the aldehyde as a white powder which was sufficiently pure for use in a next step without further purification.

Step O: (S)-1-(3-Fluoromethyl-5-iodophenyl)-4-[1-(4-cyanobenzyl)-5-imidazoylmethyl]-5-[(methanesulfonyl)ethyl]-2-piperazinone A solution of methyl sulfone described in Step I (48 mg, 0.094 mmol) in CH$_2$Cl$_2$ (1.2 mL) at room temperature was treated with TFA (0.33 mL, 4.28 mmol) and stirred for 30 minutes at room temperature. The reaction was concentrated, treated with 1,2-dichloroethane (1 mL), triethylamine (10–15 drops until pH>7.5), aldehyde describe in Step N (40 mg, 0.19 mmol), sodium triacetoxyborohydride (46 mg, 0.22 mmol) and molecular sieves. The reaction was stirred at room temperature and followed by HPLC [C$_{18}$ μBondapak, 3.9×300 mm, 10% AcCN:H$_2$O (0.1% TFA) to 90% AcCN over minutes with linear gradient, 1 mL/min, 220 and 254 nm] until product was maximized (retention time=21 minutes). Two additional portions of sodium triacetoxyborohydride had to be added. The reaction was stirred a total of 4 days. The reaction was diluted with CH$_2$Cl$_2$, washed with aq. sat'd NaHCO$_3$ (emulsion forms) and dried (MgSO$_4$), filtered and concentrated to give an oil. Purification by radial chromatography (2% MeOH:CHCl$_3$ until the aldehyde eluted and then 5% MeOH) gave the title compound (Compound 1).

EXAMPLE 2

Preparation of (S)-1-(3-iodophenyl)-4-[1-(4-cyanobenzyl)-5-imidazolylmethyl]-5-[2-(methanesulfonyl)ethyl]-2-piperazinone dihydrochloride (Compound 2)

The title compound was prepared using the procedure described in Example 1, Steps G–O, but replacing 3-amino-5-iodobenzyl fluoride with 3-iodoaniline in Step G.

EXAMPLE 3

Preparation of [$^{123}$I](S)-1-(3-iodo-5-fluoromethylphenyl)-4-[1-(4-cyanobenzyl)-5-imidazolylmethyl]-5-[2-(methanesulfonyl)ethyl]-2-piperazinone dihydrochloride ([$^{123}$I]-Compound 1)

Step A: (S)-1-(3-Fluoromethyl-5-trimethylstannyl)-4-[1-(4-cyanobenzyl)-5-imidazoylmethyl]-5-[(methanesulfonyl)ethyl]-2-piperazinone A solution of Compound 1 (12.9 mg, 0.02 mmol, described in Example 1) in dioxane (0.5 mL) at room temperature was treated with hexamethylditin (0.015 mL, 0.03 mmol), a catalytic amount of catalyst and placed in a 100° C. oil bath for 2 hours giving a black opaque mixture. The reaction was filtered through celite, rinsed with ethyl acetate and concentrated to give an oil. TLC analysis (5% MeOH:CH$_3$Cl) showed the desired product (R$_f$=0.06). Purification by radial chromatography (5% to 10% MeOH:CH$_3$Cl) gave the title compound as a clear colorless oil.

Step B: [$^{123}$I](S)-1-(3-Fluoromethyl-5-iodophenyl)-4-[1-(4-cyanobenzyl)-5-imidazoylmethyl]-5-[(methanesulfonyl)ethyl]-2-piperazinone A shipping vial of Na$^{123}$I (20 mCi, dry, Nordion) containing a stir bar was treated with an iodobead, MeOH (0.05 mL) and Na$^{127}$I solution (0.013 mg/mL H$_2$O) and stirred for 5 minutes at room temperature. A solution of trimethylstannane described in Step A (0.5 mg) in MeOH (0.05 mL) was treated with trifluoroacetic acid (0.02 mL) and immediately added to the Na$^{123}$I/iodobead vial. After stirring for 5 minutes at room temperature, the reaction was quenched with concentrated NH$_4$OH (0.02 mL) and aqueous Na$_2$S$_2$O$_5$ (0.01 mL of a 10 mg/mL solution). The reaction mixture was drawn into an HPLC syringe and injected for purification [Vydac C$_{18}$ Protein and Peptide column, 3.9×250 mm, 1 mL/min, 30:70 AcCN:H$_2$O (0.1% TFA), retention time=8 minutes]. A fraction collector was used to collect 0.5 mL fractions. The fractions containing the labeled product were pooled and partially concentrated to give a solution [$^{123}$,]-Compound 1. [$^{123}$I](S)-1-(3-iodo-phenyl)-4-[1-(4-cyanobenzyl)-5-imidazolylmethyl]-5-[2-(methanesulfonyl) ethyl]-2-piperazinone dihydrochloride ([1231]-Compound 2) was also prepared by this method but starting with Compound 2 instead of Compound 1.

EXAMPLE 4

Preparation of [$^{125}$I] (S)-1-(3-iodo-5-fluoromethylphenyl)-4-[1-(4-cyanobenzyl)-5-imidazolylmethyl]-5-[2-

(methanesulfonyl)ethyl]-2-piperazinone dihydrochloride ([$^{125}$I]-Compound 1)

Step A: [$^{125}$I](S)-1-(3-Fluoromethyl-5-iodophenyl)-4-[1-(4-cyanobenzyl)-5-imidazoylmethyl]-5-[(methanesulfonyl)ethyl]-2-piperazinone A shipping vial of Na$^{125}$I (10 mCi, 100 mCi/mL 10$^{-5}$M NaOH, pH 8–11, NEN) containing a stir bar was treated with an iodobead and stirred for 5 minutes at room temperature. A solution of the trimethylstannane described in Example 2, Step A (0.5 mg) in MeOH (0.05 mL) was treated with trifluoroacetic acid (0.02 mL) and immediately added to the Na$^{125}$I/iodobead vial. After being stirred for minutes at room temperature, the reaction was quenched with concentrated NH$_4$OH (0.02 mL) and aqueous Na$_2$S$_2$O$_5$ (0.02 mL of a 10 mg/mL solution). The reaction mixture was drawn into an HPLC syringe and injected for purification [Vydac C$_{18}$ Protein and Peptide column, 3.9×250 mm, 1 mL/min, 30:70 AcCN:H$_2$O (0.1% TFA), retention time=8 minutes]. A fraction collector was used to collect 0.2 mL fractions. The fractions containing the labeled product were pooled, concentrated almost to dryness and reconstituted in ethanol (1.0 mL) to give a solution of [$^{125}$I]-Compound 1.

EXAMPLE 5

Preparation of (S)-1-(3-iodo-5-fluoromethylphenyl)-4-[1-(4-cyanobenzyl)-5-imidazolylmethyl]-5-[2-($^{11}$C-methanesulfonyl)ethyl]-2-piperazinone dihydrochloride ([$^{11}$C]-Compound 1)

Step A: (S)-1-(3-Fluoromethyl-5-iodophenyl)-4-(t-butoxycarbonyl)-5-[(triphenylmethylthio)ethyl]-2-piperazinone A solution of hydroxyethylpiperazinone described in Example 1, Step H(576 mg, 1.21 mmol) in CH$_2$Cl$_2$ (11 mL) was cooled to 0° C. and treated with iPr$_2$NEt$_2$ (0.42 mL, 2.42 mmol) and methanesulfonyl chloride (0.133 mL, 1.72 mmol). The reaction was stirred at 0° C. for 1.25 hours, poured into a separatory funnel containing 5% citric acid (aqueous) and the layers were separated. The organic layer was dried (MgSO$_4$), filtered and concentrated to give the intermediate mesylate (83.01, 3H, s, CDCl$_3$) as a white foam. This material was dissolved in DMF (10 mL) at room temperature and treated with Cs$_2$CO$_3$ (1.97 g, 6.05 mmol) and triphenylmethyl mercaptan (669 mg, 2.42 mmol). After being stirred for 2 days at room temperature, TLC analysis (1:1 hexane:ethyl acetate) showed the product (R$_f$=0.49) with consumption of the mesylate (R$_f$=0.13). The reaction was diluted with ethyl acetate, brine and aqueous saturated NH$_4$Cl. The layers were separated and extracted with ethyl acetate. The organic layers were combined, dried (MgSO$_4$), filtered and concentrated to give an orange oil. Purification by radial chromatography (10:1 to 1:1 hexane:ethyl acetate) gave the title compound as a foam.

Step B: (S)-1-(3-Fluoromethyl-5-iodophenyl)-4-[1-(4-cyanobenzyl)-5-imidazolymethyl]-5-[(triphenylmethylthio)ethyl]-2-piperazinone A solution of tritylthioethylpiperazinone described in Step A (656 mg, 0.89 mmol) in CH$_2$Cl$_2$ (10.5 mL) at room temperature was treated with trifluoroacetic acid (2.38 mL) giving a clear orange solution. The reaction was quenched with H$_2$O after about 45 minutes. The reaction was concentrated on the rotary evaporator and placed in a separatory funnel containing CH$_2$Cl$_2$. Aqueous saturated NaHCO$_3$ was added until slightly basic and the aqueous layer was extracted with CH$_2$Cl$_2$. The organic layers were combined and dried (MgSO$_4$), filtered and concentrated to give 580 mg of a white foam. $^1$H NMR analysis indicated loss of the Boc protecting group and the presence of the trityl group. The white foam was treated with 1,2-dichloroethane (9.5 mL), molecular sieves, triethylamine (approx. 10 drops until about pH 7–7.5), NaBH(OAc)$_3$ (434 mg, 2.05 mmol) and aldehyde described in Example 1, Step N (376 mg, 1.78 mmol). After being stirred overnight at room temperature, the reaction was diluted with CH$_2$Cl$_2$ and rinsed with aqueous saturated NaHCO$_3$ (emulsion). The organic layer was dried (MgSO$_4$), filtered and concentrated to give a yellow semi-solid. Purification by radial chromatography (10% acetone:CH$_2$Cl$_2$ until the starting aldehyde eluted then 20% to 40% acetone:CH$_2$Cl$_2$ containing 5% MeOH) gave the title compound as a pale yellow oil.

Step C: (S)-1-(3-Fluoromethyl-5-iodophenyl)-4-[1-(4-cyanobenzyl)-5-imidazolymethyl]-5-thioethyl-2-piperazinone, bistrifluoroacetate A bright clear yellow solution of piperazinone described in Step B(247 mg, 0.297 mmol) in trifluoroacetic acid (5 mL) at room temperature was treated with triethylsilane (1 mL, 6.26 mmol) giving a pale yellow solution. The reaction was stirred for 30 minutes and was then concentrated on the rotary evaporator to give a white solid. A portion of this material was purified by semi-preparative HPLC [50:50 AcCN:H$_2$O (0.1% TFA), 2 mL/min, 254 nm, Alltech Econosil C-18, 10$\mu$, 10×250 mm, retention time=10 minutes] to provide the title compound.

Step D: (S)-1-(3-iodo-5-fluoromethylphenyl)-4-[1-(4-cyanobenzyl)-5-imidazolylmethyl]-5-[2-($^{11}$C-methanesulfonyl)ethyl]-2-piperazinone dihydrochloride The preparation of [$^{11}$C]methyl iodide has been described in detail by Langstrom et al. (J. Nucl. Med. 28:1037 (1987)). Two liters of ultra high purity nitrogen (Matheson Gas Products) are bombarded with protons accelerated by a small biomedical cyclotron (Scanditronix RNP-16). Carbon-11 in the form of carbon dioxide is formed by the reaction $^{14}$N(p,$\alpha$)$^{11}$C.

The target chamber is connected to the chemical processing by ⅛" stainless steel tubing.

The apparatus consists of the following: (1) a conical glass vessel (length=50 mm, i.d.=5 mm) connected to a reaction vessel equipped with a water-cooled reflux condenser (length=50 mm, i.d.=5 mm) via Teflon tubing (i.d. 1.5 mm) and electrovalves (General Valve Corp, Series 2) interfaced to a small computer (Hewlett Packard HP-85) for valve sequencing, (2) a heat gun (150° C.), (3) a 1 mL conical reaction vessel for trapping [$^{11}$C]methyl iodide, (4) a remote cooling t-78° C.) bath, (5) a high performance liquid chromatograph (sample equipment: Rheodyne Model 7126 injector, Waters Associates 6000A pump, Alltech Econosil C$_{18}$ 10 mm×725 cm column) equipped with a UV detector (Waters Associates Model 441) and a flow radioactivity detector, and (6) a rotary evaporator modified for remote addition and removal of solutions.

Ahead of this apparatus, there is a coil of stainless steel tubing (i.d.=2.2 mm) cooled by liquid nitrogen to retain $^{11}$CO$_2$ removed from the target under reduced pressure created by an oilless pump. Nitrogen is used as a sweep gas at a flow rate of 50 mL/min to sweep the radioactive gas through the above apparatus. This apparatus is evacuated and purged with argon prior to each synthesis to minimize carrier carbon contamination.

[$^{11}$C]CO$_2$ produced by 16 MeV proton irradiation of a nitrogen gas target is trapped in a cooled stainless steel coil at the end of bombardment. The cooling bath is removed and the trapped CO$_2$ is bubbled into the conical vessel containing 3.0 mg lithium aluminum hydride (Fluka Chemical Corp.) in 600 $\mu$L of tetra-hydrofuran. After the level of radioactivity in the vessel reaches a maximum, the vessel is heated by the heat gun to evaporate the tetrahydrofuran. Hydriodic acid (500 $\mu$L, 57% in water, Aldrich Chemical Co.) is then added to the hot vessel.

A presaturated solution of $Cs_2CO_3$ in DMF was prepare by heating 3.75 mg of $Cs_2CO_3$ 500 FL of dry DMF at 80° C. for 10 min. A solution containing 1 mg of the thioethylpiperazinone described in Step C in 200 μL of the presaturated solution of $Cs_2CO_3$ and an additional 1.36 mg of $Cs_2CO_3$ is added. This solution is cooled to −8° C. and [$^{11}$C]Methyl iodide is added via transfer from the production apparatus by a stream of nitrogen carrier gas. When the level of radioactivity reaches a plateau, the stream of gas is stopped. The mixture is heated at 80° C. for 3 minutes then 200 μL of Oxone solution (20 in 200 μl of $H_2O$) is added and the solution stirred for 1 min. A 400 μL aliquote of HPLC eluent (40:60 MeCN:$H_2O$ (0.1% TFA) is added. The resulting solution is then filtered and the filtrate injected onto the preparative HPLC and eluted with 40:60 (v:v) acetonitrile/water containing 0.1% trifluoroacetic acid. The radioactive peak corresponding to the desired product is collected in the rotary evaporator, and the solvent is evaporated under reduced pressure.

The residue is dissolved in sterile, normal saline (7 mL, sample label: Saline 0.9% injectable, U.S.P., Injection USP 0.9% sterile, nonpyrogenic; Abbott Laboratories, N. Chicago, Ill. 60064), filtered through a sterile, 0.22 μM filter (Sample label: Gelman Acrodisc, disposable filter assembly, sterile, nonpyrogenic) into a sterile, pyrogen free bottle (Sample label: 20 cc EVACUATED VIAL—sterile, pyrogen free; Medi-Physics/Amersham Company, Arlington Heights, Ill. 60005), and diluted with sterile, sodium bicarbonate (3 mL, 8.4%) (Sample label: 8.4% Sodium Bicarbonate Inj., U.S.P.; Abbott Laboratories, N. Chicago, Ill. 60064).

The container used for the drug is described above. It consists of a sterile, pyrogen free glass vial with a crimp-sealed aluminum cap surrounding a rubber stopper. Samples of the radiotracer have been stored for up to 90 minutes and analyzed for radiochemical decomposition. No decomposition has been observed over this time period.

EXAMPLE 6

5(S)-n-Butyl-4-[1-(4-cyanobenzyl)imidazol-5-ylmethyl]-1-(2,3-dimethylphenyl)piperazin-2-one ditrifluoroacetic acid salt (Compound 3)

Step A: N-Methoxy-N-methyl 2(S)-(tert-butoxycarbonylamino)-hexanamide

2(S)-(tert-Butoxycarbonylamino)hexanoic acid (24.6 g, 0.106 mol), N,O-dimethylhydroxylamine hydrochloride (15.5 g, 0.15 mol), EDC hydrochloride (22.3 g, 0.117 mol) and HOBT (14.3 g, 0.106 mol) were stirred in dry, degassed DMF (300 mL) at 20° C. under nitrogen. N-Methylmorpholine was added to obtain pH 7. The reaction was stirred overnight, the DMF distilled under high vacuum, and the residue partitioned between ethyl acetate and 2% potassium hydrogen sulfate. The organic phase was washed with saturated sodium bicarbonate, water, and saturated brine, and dried with magnesium sulfate. The solvent was removed in vacuo to give the title compound.

Step B: 2(S)-(tert-Butoxycarbonylamino)hexanal

A mechanically stirred suspension of lithium aluminum hydride (5.00 g, 0.131 mol) in ether (250 mL) was cooled to −45° C. under nitrogen. A solution of the product from Step A (28.3 g, 0.103 mol) in ether (125 mL) was added, maintaining the temperature below −35° C. When the addition was complete, the reaction was warmed to 5° C., then recooled to −45° C. A solution of potassium hydrogen sulfate (27.3 g, 0.200 mol) in water was slowly added, maintaining the temperature below −5° C. After quenching, the reaction was stirred at room temperature for 1 h. The mixture was filtered through Celite, the ether evaporated, and the remainder partitioned between ethyl acetate and 2% potassium hydrogen sulfate. After washing with saturated brine, drying over magnesium sulfate and solvent removal, the title compound was obtained.

Step C: N-(2,3-Dimethylphenyl)-2(S)-(tert-butoxycarbonylamino)-hexanamine 2,3-Dimethylaniline (8.32 mL, 68.3 mmol) was dissolved in dichloroethane under nitrogen. Acetic acid was added to obtain pH 5, and sodium triacetoxyborohydride (17.2 g, 80.8 mmol) and crushed molecular sieves (4 g) were added. A solution of the product from Step B (13.3 g, 62.1 mmol) in dichloroethane (80 mL) was added slowly dropwise at 20° C. The reaction was stirred overnight, then quenched with saturated sodium bicarbonate solution. The aqueous layer was removed, the organic phase washed with saturated brine and dried over magnesium sulfate. Crystallization from hexane gave the title compound.

Step D: 4-tert-Butoxycarbonyl-5(S)-n-butyl-1-(2,3-dimethylphenyl)piperazin-2-one A solution of the product from Step C 98.50 g, 26.5 mmol) in ethyl acetate (250 mL) was vigorously stirred at 0° C. with saturated sodium bicarbonate (150 mL). Chloroacetyl chloride (2.33 mL, 29.1 mmol) was added, and the reaction stirred at ) 0° C. for 1 h. The layers were separated, and the ethyl acetate phase was washed with saturated brine, and dried over magnesium sulfate. The crude product was dissolved in DMF (300 mL) and cooled to 0° C. under nitrogen. Sodium hydride (1.79 g, 60% dispersion in oil, 44.9 mmol) was added portionwise to maintain moderate hydrogen evolution. After 30 min, an additional amount of sodium hydride was added (0.8 g). The reaction was stirred another 30 min, then quenched with saturated ammonium chloride. The DMF was distilled in vacuo, and the residue partitioned between ethyl acetate and water. The organic phase was washed with water, saturated brine, and dried over magnesium sulfate. The crude product was chromatographed on silica gel with 20–30% ethyl acetate in hexane to obtain the title compound.

Step E: 5(S)-n-Butyl-1-(2,3-dimethylphenyl)-4-[4-(1-triphenylmethylimidazolyl)methyl]piperazin-2-one A solution of the product from Step D (0.570 g, 1.58 mmol) in ethyl acetate (50 mL) was cooled to −15° C. under nitrogen. HCl gas was bubbled through for 15 min, and the reaction solution warmed to 0° C. for 2 h. The solvent was removed in vacuo, and the resulting solid was dissolved in dichloroethane (20 mL). Sodium triacetoxyborohydride (0.502 g, 2.37 mmol) and 1-triphenylmethyl-4-imidazolyl carboxaldehyde (0.534 g, 1.58 mmol) was added. The reaction was stirred overnight at 20° C. then poured into saturated sodium bicarbonate solution. The organic phase was washed with saturated brine and dried over magnesium sulfate. Silica gel chromatography using 4% methanol in dichloromethane as eluant yielded the title compound.

Step F: 5(S)-n-Butyl-4-[1-(4-cyanobenzyl)imidazol-5-ylmethyl]-1-(2,3-dimethylphenyl)piperazin-2-one ditrifluoroacetic acid salt 4-cyanobenzylbromide (0.043 g, 0.22 mmol) was added at 20° C. to a solution of 5(S)-n-butyl-1-(2,3-dimethylphenyl)-4-[4-(1-triphenylmethylimidazolyl) methyl]piperazin-2-one (0.120 g, 0.21 mmol) described in Step E, in acetonitrile (10 mL). After 48 h, the solvent was removed in vacuo, and the crude product dissolved in dichloromethane (6 mL). Triethylsilane (0.13 mL) and trifluoroacetic acid (2 mL) were added, and the reaction stirred at 20° C. for 2 h. The volatiles were removed in vacuo, and the residue partitioned between hexane and water-methanol. The aqueous phase was injected onto a reverse phase preparative HPLC column and purified with a mixed gradient of 30%–60% acetonitrile/0.1% TFA; 70%–40% 0.1% aqueous TFA over 50 min. The title compound was isolated after lyophilization from water-acetonitrile solution. FAB ms (m+1) 456.

Anal. Calc. for $C_{28}H_{33}N_5O$·0.7 $H_2O$·2.0 TFA: C, 55.28; H, 5.13; N, 10.07. Found: C, 55.27; H, 5.20; N, 10.41.

Biological Assays.

The ability of compounds of the present invention to inhibit cancer can be demonstrated using the following assays.

In vitro inhibition of farnesyl-protein transferase

Transferase Assays. Isoprenyl-protein transferase activity assays were carried out at 30° C. unless noted otherwise. A typical reaction contained (in a final volume of 50 μL): [$^3$H]farnesyl diphosphate or [$^3$H]geranylgeranyl diphosphate, Ras protein, 50 mM HEPES, pH 7.5, 5 mM $MgCl_2$, 5 mM dithiothreitol and isoprenyl-protein transferase. The FPTase employed in the assay was prepared by recombinant expression as described in Omer, C. A., Kral, A. M., Diehl, R. E., Prendergast, G. C., Powers, S., Allen, C. M., Gibbs, J. B. and Kohl, N. E. (1993) *Biochemistry* 32:5167–5176. The geranylgeranyl-protein transferase-type I employed in the assay was prepared as described in U.S. Pat. No. 5,470,832, incorporated by reference. After thermally pre-equilibrating the assay mixture in the absence of enzyme, reactions were initiated by the addition of isoprenyl-protein transferase and stopped at timed intervals (typically 15 min) by the addition of 1 M HCl in ethanol (1 mL). The quenched reactions were allowed to stand for 15 m (to complete the precipitation process). After adding 2 mL of 100% ethanol, the reactions were vacuum-filtered through Whatman GF/C filters. Filters were washed four times with 2 mL aliquots of 100% ethanol, mixed with scintillation fluid (10 mL) and then counted in a Beckman LS3801scintillation counter.

For inhibition studies, assays were run as described above, except inhibitors were prepared as concentrated solutions in 100% dimethyl sulfoxide and then diluted 20-fold into the enzyme assay mixture. $IC_{50}$ values were determined with both transferase substrates near KM concentrations. Nonsaturating substrate conditions for inhibitor $IC_{50}$ determinations were as follows: FTase, 650 nM Ras-CVLS, 100 nM farnesyl diphosphate; GGPTase-I, 500 nM Ras-CAIL, 100 nM geranylgeranyl diphosphate.

In vivo ras prenylation assay

The cell lines used in this assay consist of either Rat1 or NIH3T3 cells transformed by either viral Ha-ras; an N-ras chimeric gene in which the C-terminal hypervariable region of v-Ha-ras was substituted with the corresponding region from the N-ras gene; or ras-CVLL, a v-Ha-ras mutant in which the C-terminal exon encodes leucine instead of serine, making the encoded protein a substrate for geranylgeranylation by GGPTase I. The assay can also be performed using cell lines transformed with human Ha-ras, N-ras or Ki4B-ras. The assay is performed essentially as described in DeClue, J. E. et al., Cancer Research 51:712–717, (1991). Cells in 10 cm dishes at 50–75% confluency are treated with the test compound(s) (final concentration of solvent, methanol or dimethyl sulfoxide, is 0.1%). After 4 hours at 37° C., the cells are labelled in 3 ml methionine-free DMEM supplemented with 10% regular DMEM, 2% fetal bovine serum, 400 μCi[$^{35}$S]methionine (1000 Ci/mmol) and test compound(s). Cells treated with lovastatin, a compound that blocks Ras processing in cells by inhibiting the rate-limiting step in the isoprenoid biosynthetic pathway (Hancock, J. F. et al. Cell, 57:1167 (1989); DeClue, J. E. et al. *Cancer Res.,* 51:712 (1991); Sinensky, M. et al. *J. Biol. Chem.,* 265:19937 (1990)), serve as a positive control in this assay. After an additional 20 hours, the cells are lysed in 1 ml lysis buffer (1% NP40/20 mM HEPES, pH 7.5/5 mM $MgCl_2$/1 mM DTT/10 mg/ml aprotinen/2 mg/ml leupeptin/2 mg/ml antipain/0.5 mM PMSF) and the lysates cleared by centrifugation at 100,000×g for 45 min. Alternatively, four hours after the additon of the labelling media, the media is removed, the cells washed, and 3 ml of media containing the same or a different test compound added. Following an additional 16 hour incubation, the lysis is carried out as above. Aliquots of lysates containing equal numbers of acid-precipitable counts are bought to 1 ml with IP buffer (lysis buffer lacking DTT) and immunoprecipitated with the ras-specific monoclonal antibody Y13–259 (Furth, M. E. et al., J. Virol. 43:294–304, (1982)). Following a 2 hour antibody incubation at 4° C., 200 μl of a 25% suspension of protein A-Sepharose coated with rabbit anti rat IgG is added for 45 min. The immunoprecipitates are washed four times with IP buffer (20 nM HEPES, pH 7.5/1 mM EDTA/1% Triton X-100.0.5% deoxycholate/0.1%/SDS/0.1 M NaCl) boiled in SDS-PAGE sample buffer and loaded on 13% acrylamide gels. When the dye front reached the bottom, the gel is fixed, soaked in Enlightening, dried and autoradiographed. The intensities of the bands corresponding to prenylated and nonprenylated Ras proteins are compared to determine the percent inhibition of prenyl transfer to protein.

Partition Coefficient Protocol

Prior to assay, equal volumes of 1-octanol and pH 7.4 buffer are mutually saturated, allowed to settle, and separated into individual containers until use.

Standard solutions are prepared by dissolving an accurately weighed amount (1–2 mg) of the compound under study in a suitable solvent. Sample is dissolved in 10.00 ml spectral grade methanol although ethanol, acetonitrile or water may also be used provided the compound is completely soluble in that solvent. The solutions or appropriate dilutions are scanned by UV (HP 8452A Diode Array Spectrophotometer) to determine the wavelength of maximum absorbance (λmax). The scan can also be obtained from the HPLC chromatogram of the methanol standard.

Partition sample solutions are prepared by placing an accurately weighed 1–2 mg of sample into a 20 ml scintillation vial and adding 10.00 ml of pH 7.4 buffer and 10.00 ml of 1-octanol which have been mutually saturated with each other. Vials are placed in the ultrasonic bath for 5 min. and then onto a flatbed shaker for at least 2 to 4 hrs. After agitation, vials are centrifuged at 1500 rpm for 10 min. and approximately 1 ml of each layer is removed to separate HPLC vials for analysis.

Measurement of concentration of the standard, octanol, and buffer solutions can be conducted either by absorbance in ultraviolet spectroscopy (UV) or by peak areas in high performance liquid chromatography (HPLC) with the detector set at the compound's % max. Currently, HPLC measurement is the method of choice. Appropriate dilutions, if necessary, should be made into the appropriate solvent.

Standard conditions of analysis are as follows:

Instrument—HP 1090 HPLC using either the diode array (DAD) or the variable wavelength detectors (VWD) set at the compound's λmax.

Column—Vydac Protein/Peptide C-18

Solvent system—Gradient from 5–95% Acetonitrile/ $H_3PO_4$ Buffer over 10 min.; flow rate—3.0 m/min.

Sample size—5 μl injection; larger injections (50, 100, 200 μl) can be used subsequently should no detectable peak result from the smaller injection.

Temperature—Ambient conditions.
Partition coefficients (lipophiliciies) are calculated by the following equation:

$$(a) \text{Partition Coefficient (PC)} = \frac{\text{(Octanol HPLC Area) (Octanol Dilution)}}{\text{(Buffer HPLC Area) (Buffer Dilution)}}$$

In vivo Enzyme Binding Studies

To determine the biodistribution of a radiotracer compound, 3–5 µCi of radiotracer is injected (i.v. in 30% PEG/10% EtOH/H$_2$O) in male Sprague-Dawley rats (200–250 g). The animals are euthanized at 30 min., 120 min. and 360 min. after radiotracer injection. To determine the extent of specific binding to FPTase, an unlabeled FPTase inhibitor, such as compound 3 of Example 6, (10 mpk or 5 mpk) is injected 30 min. prior to injection of the radiotracer, then the animals are euthanized at the times provided above. After euthanasia by cervical dislocation under light anesthesia, the thoratic aorta are cut and 1 ml of blood collected in heparinized syringes. Centrifugation for 2.5 minutes at 5000 rpm provides the plasma samples. The left ventricular muscle, left upper lobe of the lung, liver, kidney (cortex), both adrenals, spleen, pancreas, descending colan and prostate are removed, placed on ice and two 50 mg samples biopsied. For radiotracers with $^{125}$I labels, samples are counted, without further treatment, in an autogamma counter for 2 min. each. For tritium-containing radiotracers, tissues are dissolved by shaking in Biosolv (New England Nuclear) overnight. After neutralization of base with 0.5 N HCl, scintillation cocktail is added (in subdued light), samples dark adapted for several hours, then counted in a scintillation counter through several cycles to insure chemiluminescene is not significant. Data are expressed as %-injected dose/gm wet weight tissue.

To determine in vivo dissociation rates of radiotracer compound, 3–5 µCi of radiotracer is injected (i.v. in 30% PEG/10% EtOH/H20) in male Sprague-Dawley rats (200–250 g). One hour after radiotracer injection, an unlabeled FPTase is injected i.v., and the animals are euthanized 60 min. after this "chase." For comparison, uninhibited binding is also determined at 60 and 120 min. post-injection of radiotracer (corresponds to 0 and 60 min. post-chase). Total enzyme signal is examined by preinjection of unlabeled FPTase inhibitor (5 mpk) 30 min. prior to radiotracer injection. After euthanasia, tissues samples are obtained and processed as described above.

Gamma Camera Imaging

Two rats are anesthetized (ketamine/ace-promazine), positioned on the camera head, and their tail veins canulated for ease of injection. One rat is preinjected with an unlabeled FPTase inhibitor (10% EtOH/27% PEG/63% H$_2$O) 30 min. prior to injection of radiotracer to demonstrate non-specific binding. 150 mCi/rat of an $^{123}$I labeled FPTase inhibitor is injected via its tail vein, and the catheters flushed with several mls of normal saline. Acquisition of images is started as the radiotracer was injected. Sixty, one minute images were acquired and the rats are subsequently euthanized with sodium pentobarbital. The images acquired during the first minute are dominated by blood flow, and as a result, provide good depiction of the heart, liver and kidneys. Regions of interest (ROIs) are drawn on the first image which includes a region defined as soft tissue (upper left chest), then used to analyze the count rates in subsequent images. The ROIs do not include the entire liver since radioactivity in adjacent tissues partially obscures these structures. Therefore, ROIs are defined to remain fairly clear during the course of the study, and are assumed to be representative of the entire organ. Radioactivity in the bladder was obtained from the final image. Count-rates are converted to %-dose/ROI by dividing the count-rate in the ROI by that of the whole rat, which is then multiplied by 100.

In vivo Occupancy Studies

Kinetics of enzyme occupancy by an unlabeled FPTase inhibitor (test compound) is determined by this assay. Thus, FVB mice are injected the test compound at either 40 mpk or 10 mpk subcutaneously (0.1 mls). Thirty minutes prior to euthanasia, 3 nCi of tritiated farnesyl protein transferase inhibitor (radiotracer) was injected i.p. (0.2 mls 10% EtOH in 0.9% saline). Uninhibited binding of the radiotracer is determined by injection of the radiotracer in mice which have not received injection of the test compound. The mice are euthanized either 2 hours of 14 hours after injection of the test compound and lung, spleen, pancrease and blood are removed and processed as described above. Data are plotted as %-dose/g of tissue (wet weight). PET Imaging in Dogs Female beagle dogs weighing 7.7–14.6 kg (11.0±2.3 kg) are fasted for at least 12 hours allowing water intake ad libitum, and are premedicated with 0.3–0.4 mL Acepromazine injected i.m. on the day of the experiment. A 20 G two inch venous catheter is placed into the right front leg ulnar vein through which anesthesia is introduced by sodium pentobarbital 25–30 mg/kg in 3–4 ml and maintained with additional pentobarbital at an average dose of 3 mg/kg/hr. Another catheter is inserted into the contralateral ulnar vein for radiotracer administration.

Oxygen saturation of circulating blood is measured with a pulse oximeter (Nellcor Inc., Hayward, Calif.) placed on the tongue of the animal. Circulatory volume is maintained by intravenous infusion of isotonic saline. A 22 G cannula is inserted into the anterior tibial or distal femoral artery for continuous pressure monitoring (Spacelabs™, model 90603A). EKG, heart rate, and core temperature are monitored continuously. In particular, EKG is observed for ST segment changes and arrhythmias.

The animal is positioned in the PET camera and a tracer dose of [$^{15}$O]H$_2$O administered via i.v. catheter. The image thus obtained is used to insure that the dog is positioned correctly to include liver, kidneys and pancreas. Subsequently [$^{11}$C]-Compound 1 (<20 mCi) is administered via i.v. catheter. Following the acquisition of the total radiotracer image, an infusion is begun of the unlabeled FTI (test compound) at one of three dose rates (0.1, 1 or 10 mpk/day). After infusion for 2.5 hrs, [$^{11}$C]-Compound 1 is again injected via the catheter. Images are again acquired for up to 90 min. Within ten minutes of the injection of radiotracer and at the end of the imaging session, 1 ml blood samples are obtained for determining the plasma concentration of test compound. In one imaging session, a dose of 10 mpk Compound 3 (described in Example 6) is infused over 5 minutes. This dose has been determined to completely block radiotracer binding and thus is used to determine the maximum enzyme-specific signal obtained with the PET radiotracer. At the conclusion of the study, animals are recovered and returned to animal housing.

For uninhibited distribution of radiotracer, regions of interest (ROIs) are drawn on the reconstructed image includes the kidney cortex and a region of liver which is removed from the gallbladder images. These regions are used to generate time activity curves obtained in the absence of test compound or in the presence of test compound at the various infusion doses examined. Data are expressed as radioactivity per unit time per unit volume (µCi/cc/mCi injected dose). Inhibition curves are generated from the data obtained in a region of interest obtained starting at 70 min. post-injection of radiotracer. At this time, clearance of non-specific binding has reached steady state. The $ID_{50}$ values were obtained by curve fitting the dose-rate/inhibition curves with equation iii, hereinabove.

Cell Radiotracer Assay of Farnesyl Transferase Inhibitors (CRAFTI)

This assay measures the competition between a farnesyl transferase inhibitor (FTI) and a radiolabeled FTI for binding to high affinity sites (presumably farnesyl transferase) in living cells.

Fresh radiotracer ($[^{123}I]$-Compound 2, described in Example 3) is synthesized monthly, with a specific activity of ~350–1400 Ci/mmole. CRAFTI is run routinely using a Rat1 fibroblast line transformed by v-Ha-ras (Hras/rat1). CRAFTI is performed by growing cells under anchorage-dependent conditions in 24-well tissue culture plates overnight, to achieve near confluent monolayers of cells. Radiotracer is diluted in cell growth media to a concentration of ~1 nM (~1 mCi/ml), and vehicle or test FTI (in log dilutions, 6 point titration) is added to the diluted tracer. The growth media is removed from the cell monolayers, and 0.65 ml of the diluted radiotracer/test FTI mixture is applied. After 4 hr incubation, the tracer is removed by aspiration, the monolayers are rinsed quickly with 2 ml PBS, and the cells are trypsinized and transferred to tubes for gamma counting. Dose-inhibition curves and $IC_{50}$'s are determined by curve-fitting the equation: Radiotracer Bound=$A_0-A_0*[I_0]/([I_0]+IC_{50})$+NS, where $A_0$ is the count-rate of radiotracer in the absence of inhibitor, $I_0$ is the concentration of added FTI, $IC_{50}$ is the concentration of FTI that inhibits 50% of radiotracer binding and NS is the extent of non-specific binding.

What is claimed is:
1. A radiolabeled compound which is selected from:

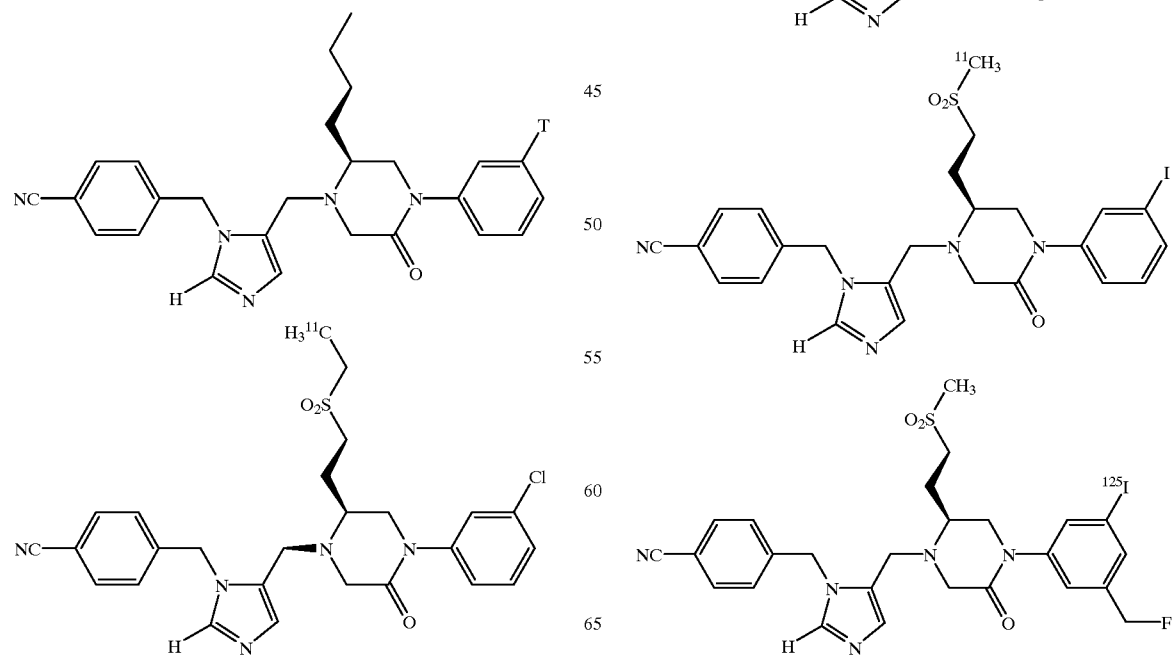

-continued

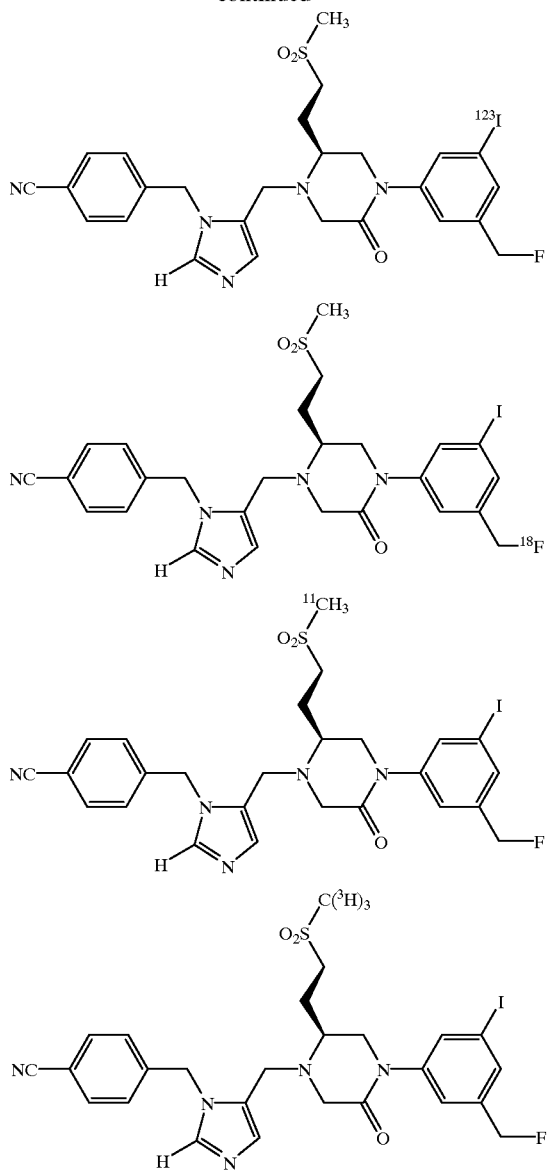

or a pharmaceutically acceptable salt thereof.

2. A radiolabeled compound of the formula

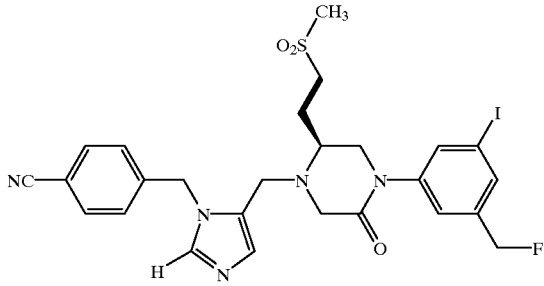

or pharmaceutically acceptable salt thereof, which has been radiolabeled with a radionuclide selected from $^3$H, $^{11}$C, $^{18}$F, $^{125}$I and $^{123}$I, provided that if $^3$H or $^{11}$C is selected, the radionuclide is incorporated at the terminal methyl moiety of the side chain attached to the C5 position of the piperazinone ring.

3. A pharmaceutical composition comprising a pharmaceutical carrier, and dispersed therein, a therapeutically effective amount of a compound of claim 1.

4. A method of diagnostic imaging of farnesyl-protein transferase binding sites in tissues of a mammalian species which comprises administering to the mammalian species in need of such diagnostic imaging an effective amount of the compound according to claim 1 and performing a radioactive scan to obtain an image.

5. A method of diagnostic imaging of farnesyl-protein transferase binding sites in tissues of a mammalian species which comprises administering to the mammalian species in need of such diagnostic imaging an effective amount of the compound according to claim 2 and performing a radioactive scan to obtain an image.

6. A method of evaluation of cancer in tissues of a mammalian species which comprises administering to the mammalian species in need of such evaluation an effective amount of the compound according to claim 1 and performing a radioactive scan to obtain an image.

7. A method of evaluation of cancer in tissues of a mammalian species which comprises administering to the mammalian species in need of such evaluation an effective amount of the compound according to claim 2 and performing a radioactive scan to obtain an image.

8. The method according to claim 6 wherein the cancer arises by mutation in the ras gene or mutation in a protein that can regulate Ras activity.

* * * * *